(12) United States Patent
Park et al.

(10) Patent No.: US 10,717,744 B2
(45) Date of Patent: Jul. 21, 2020

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si, Chungcheongnam-do (KR)

(72) Inventors: Junghwan Park, Hwaseong-si (KR); Jeongkeun Park, Seoul (KR); Hoyoung Jung, Cheonan-si (KR); Moonsung Kang, Cheonan-si (KR); Jong-jin Ha, Cheonan-si (KR); Wonsam Kim, Hwaseong-si (KR); Seul-gi Kim, Daejeon (KR); Munjae Lee, Cheonan-si, Chungcheongnam-do (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 382 days.

(21) Appl. No.: 15/555,450

(22) PCT Filed: Mar. 2, 2016

(86) PCT No.: PCT/KR2016/002056
§ 371 (c)(1),
(2) Date: Dec. 1, 2017

(87) PCT Pub. No.: WO2016/140497
PCT Pub. Date: Sep. 9, 2016

(65) Prior Publication Data
US 2018/0141957 A1 May 24, 2018

(30) Foreign Application Priority Data
Mar. 3, 2015 (KR) .................... 10-2015-0029762

(51) Int. Cl.
*H01L 51/50* (2006.01)
*C07D 495/04* (2006.01)
(Continued)

(52) U.S. Cl.
CPC ......... *C07D 495/04* (2013.01); *C07D 209/82* (2013.01); *C07D 409/04* (2013.01);
(Continued)

(58) Field of Classification Search
None
See application file for complete search history.

(56) References Cited

U.S. PATENT DOCUMENTS 6,465,115 B2  10/2002  Shi et al.
6,596,415 B2   7/2003  Shi et al.
(Continued)

FOREIGN PATENT DOCUMENTS

KR  10-2011-0120994 A  11/2011
KR  10-2013-0004925 A   1/2013
(Continued)

OTHER PUBLICATIONS

Extended European Search Report for corresponding EP Application 16759133.8, dated Jul. 6, 2018.
(Continued)

*Primary Examiner* — Gregory D Clark
(74) *Attorney, Agent, or Firm* — Vorys, Sater, Seymour & Pease LLP; Mih Suhn Koh

(57) ABSTRACT

Provided are a compound represented by Formula 1, and an organic electric element comprising a first electrode, a second electrode, and an organic material layer formed between the first electrode and the second electrode, wherein the organic material layer comprised the compound represented by Formula 1, and the driving voltage of an organic electronic device can be lowered, and the luminous effi-
(Continued)

ciency, color purity, and life span can be improved by comprising the compound represented by Formula 1 in the organic material layer.

14 Claims, 2 Drawing Sheets

(51) Int. Cl.
*C09K 11/06* (2006.01)
*C07D 209/82* (2006.01)
*C07D 409/04* (2006.01)
*C07D 491/048* (2006.01)
*H01L 51/00* (2006.01)

(52) U.S. Cl.
CPC .......... *C07D 491/048* (2013.01); *C09K 11/06* (2013.01); *H01L 51/0052* (2013.01); *H01L 51/0071* (2013.01); *H01L 51/0072* (2013.01); *H01L 51/0073* (2013.01); *H01L 51/0074* (2013.01); *H01L 51/50* (2013.01); *C09K 2211/1018* (2013.01); *H01L 51/0003* (2013.01); *H01L 51/0004* (2013.01); *H01L 51/0005* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 2251/552* (2013.01)

(56) References Cited

U.S. PATENT DOCUMENTS

| | | | | |
|---|---|---|---|---|
| 2014/0009453 A1* | 1/2014 | Liu | ........................ | H01L 27/288 345/211 |
| 2014/0332793 A1 | 11/2014 | Park et al. | | |

FOREIGN PATENT DOCUMENTS

| | | | | |
|---|---|---|---|---|
| KR | 10-2013-0049275 A | 5/2013 | | |
| KR | 10-2013-0083817 A | 7/2013 | | |
| KR | 10-2013-0084963 A | 7/2013 | | |
| KR | 10-2013-0132226 A | 12/2013 | | |
| KR | 10-2014-0011093 A | 1/2014 | | |
| KR | 2014011093 | * 1/2014 | ............ | H01L 51/50 |
| KR | 10-2014-0099082 A | 8/2014 | | |
| KR | 10-2015-0003658 A | 1/2015 | | |
| TW | 201331208 A | 8/2013 | | |
| WO | 2009/148015 A1 | 12/2009 | | |
| WO | 2013/105747 A1 | 7/2013 | | |
| WO | 2013/108997 A1 | 7/2013 | | |

OTHER PUBLICATIONS

Chinese Office Action for corresponding Chinese Application No. 201680013567.X, dated Sep. 2, 2019, 8 pages.

Japanese Office Action for Japanese Patent Application No. 2018-188579, dated Aug. 27, 2019, 2 pages.

* cited by examiner

| | Comparative compound 4 | The present invention Com. 2-1 |
|---|---|---|
| Structure |  |  |
| HOMO (electron cloud) |  |  |
| LUMO (electron cloud) |  |  |
| HOMO (eV) | -4.88 | -5.13 |
| LUMO (eV) | -0.71 | -0.91 |
| Eg (eV) | 4.17 | 4.23 |
| T1 (nm) | 2.92 | 2.88 |

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0029762, filed on Mar. 3, 2015, which is hereby incorporated by reference for all purposes as if fully set forth herein. Further, this application claims the benefit of priority in countries other than U. S, which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given. In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. Therefore, there is a continuous need to develop new materials, in particular, there are strong needs to develop host material for a light emitting layer.

SUMMARY

In order to solve one or more of the above-mentioned problems in prior art, an aspect of the present invention is to provide a compound which allows an organic electric element to have high luminous efficiency, low driving voltage, high heat-resistance, improved color purity and life span, an organic electric element comprising the compound, and an electronic device including the organic electric element.

In accordance with an aspect of the present invention, compound represented by the following formula is provided:

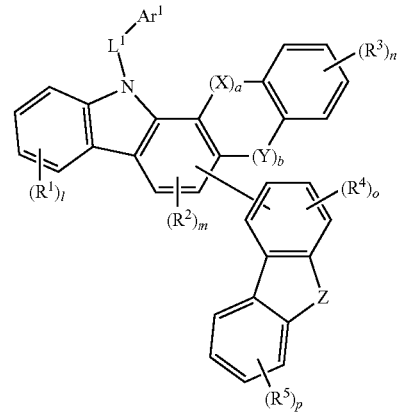

In another aspect of the present invention, organic electric elements comprising the compound represented by the above formula and electronic devices including the organic electric element are provided.

By using the compounds according to the embodiments of the present invention, the organic electric elements according to one or more embodiments of the present invention not only have high luminous efficiency, low driving voltage, high heat-resistance, but can also be significantly improved in color purity, and life span.

DETAILED DESCRIPTION

Figure 1:
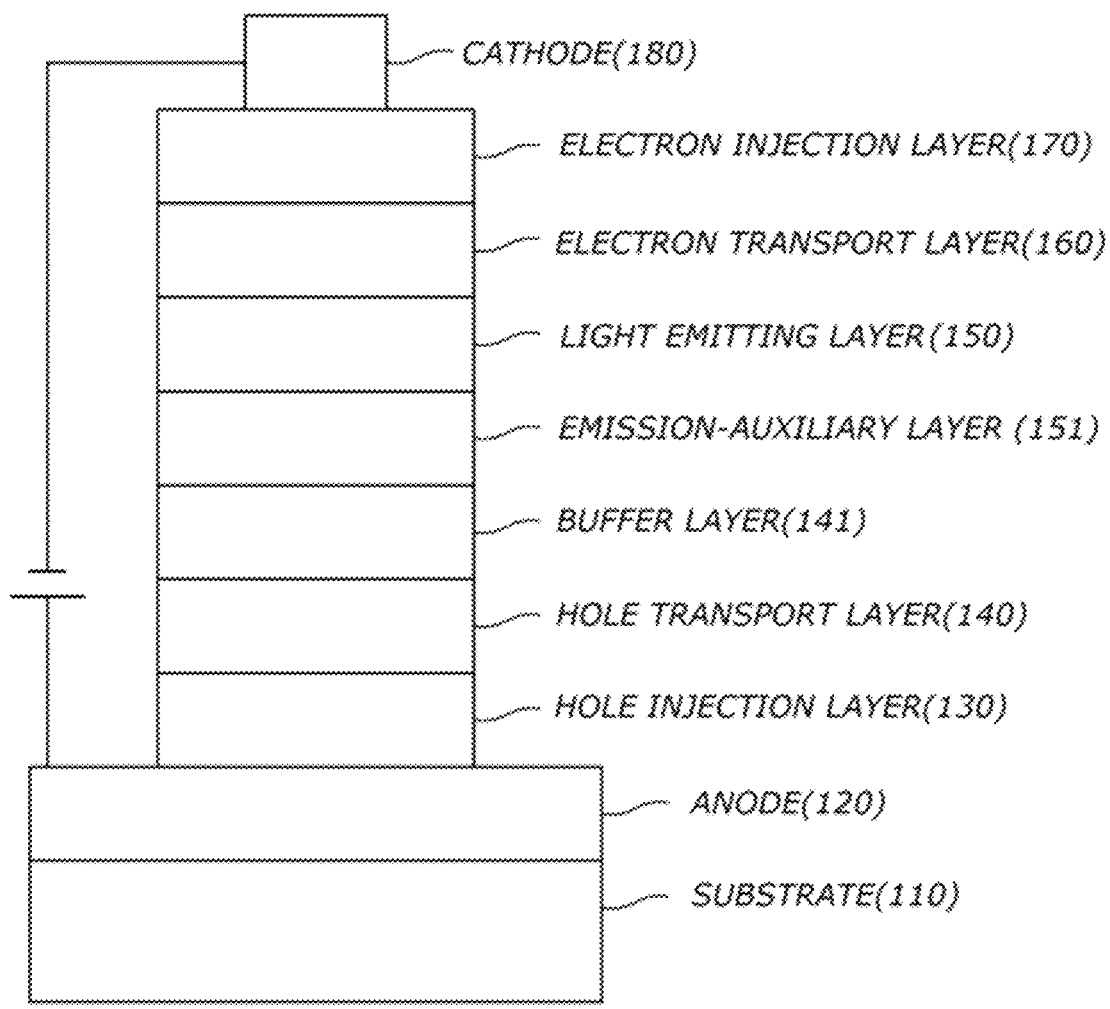
FIG. 1 illustrates an example of an organic light emitting diode according to an embodiment of the present invention.

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R'' are all hydrogen in the structural formula below, "substituted fluorenyl group" or "substituted fluorenylene group" means, functional group which at least any one of R, R' and R'' is a functional group other than hydrogen, and fluorenyl group" or "fluorenylene group" comprises spiro compound which is formed by linking R and R' together with the carbon bonded to them.

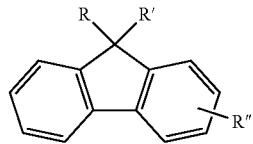

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

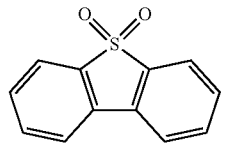 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a fluorenyl group, a $C_8$-$C_{20}$ arylalkenyl group, a silane group, a boron group, a germanium group, and a $C_5$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene, which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

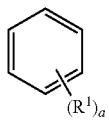

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

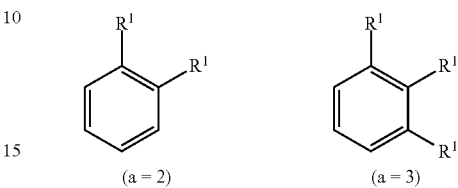

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include a protective layer or a capping layer formed on at least one of the sides the first and second electrodes, which is a side opposite to the organic material layer.

The inventive compound employed in the organic material layer may be used as materials of the hole injection layer 130, the hole transport layer 140, the electron transport-auxiliary layer, the electron transport layer 160, the electron injection layer 170, the light emitting layer 150, the capping layer, the emission-auxiliary layer 151 and so on. For example, the inventive compound may be used as materials of the light emitting layer 150.

On the other hand, even if the core is the same core, the band gap, the electrical characteristics, the interface characteristics, and the like may be different depending on which substituent is bonded at which position. Therefore, a selection of core and the combination of the core and the sub-substituent attached to it are very important. Specially, long life span and high efficiency can be simultaneously achieved when the optimal combination of energy levels and T1 values, inherent material properties (mobility, interfacial properties, etc.), and the like among the respective layers of an organic material layer is achieved.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R(Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

A compound according to an aspect of the present invention is represented by Formula 1 below.

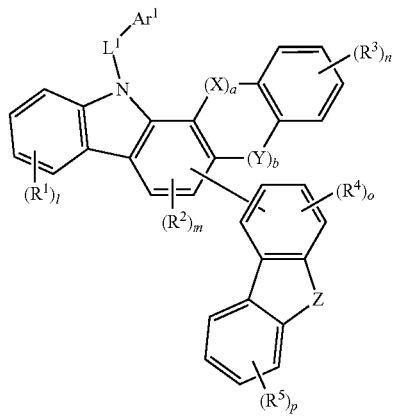

[Formula 1]

In formula 1 above, each of symbols may be defined as follows.

$Ar^1$ may be selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, and -L'-N(R')(R").

Preferably, $Ar^1$ may be a $C_6$-$C_{30}$ aryl group, a $C_2$-$C_{30}$ heterocyclic group, a fluorenyl group, a $C_1$-$C_{10}$ alkyl group, a $C_2$-$C_{10}$ alkenyl group and so on, more preferably, $Ar^1$ may be a $C_6$-$C_{12}$ aryl group, a $C_2$-$C_{12}$ heterocyclic group and so on, for example, $Ar^1$ may be phenyl, naphthyl, biphenyl, dimethylfluorene, diphenylfluorene, dimethylbenzofluorene, spirobifluorene, a heterocyclic group comprising N such as pyridine, pyrimidine, triazine, triazole, 1,10-phenanthroline, 1,5-naphthyridine, quinazoline, benzoquinazoline, indole and so on, a heterocyclic group comprising S such as dibenzothiophene and so on, a heterocyclic group comprising N and S such as benzothienopyrimidine, a heterocyclic group comprising N and O such as benzofuropyrimidine, benzofuropyridine and so on, propenyl, tert-butyl, ethenyl and so on.

In formula 1 above, $L^1$ may be selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_3$-$C_{60}$ aliphatic ring or a $C_6$-$C_{60}$ aromatic ring, an aliphatic hydrocarbon group, and the combinations thereof.

$L^1$, preferably, may be a $C_6$-$C_{30}$ arylene group, a fluorenylene group, a $C_2$-$C_{30}$ heterocyclic group and so on, more preferably, may be a $C_6$-$C_{12}$ arylene group, a $C_2$-$C_{12}$ heterocyclic group and so on, for example, may be phenylene, naphthalene, biphenylene, a heterocyclic group comprising N such as pyridine, pyrimidine, triazine, triazole, 1,10-phenanthroline, 1,5-naphthyridine, quinazoline, benzoquinazoline, indole and so on, a heterocyclic group comprising N and S such as dibenzothiophene and so on, a heterocyclic group comprising N and O such as benzofuropyridine, benzofuropyrimidine and so on.

In formula 1 above, $R^1$ to $R^5$ may be each independently selected from the group consisting of deuterium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, -L'-N(R')(R''), and combinations thereof, neighboring $R^1$s, $R^3$s, $R^4$s or $R^5$s may be optionally linked each other to form a ring, l, n, and p are each an integer of 0 to 4, m is an integer of 0 or 1, and o is an integer of 0 to 3. When l, n, p and o are each an integer of 2 or more, the plurality of $R^1$s, $R^3$s, $R^4$s, and $R^5$s on may be each the same or different from each other.

$R^1$ to $R^5$, preferably, may be a $C_6$-$C_{30}$ aryl group, a $C_2$-$C_{30}$ heterocyclic group, a $C_2$-$C_{10}$ alkenyl group, halogen, a cyano group, a nitro group, a $C_1$-$C_{10}$ alkoxyl group, -L'-N(R')(R'') or the like, more preferably, may be a $C_6$-$C_{14}$ aryl group, a $C_2$-$C_{12}$ heterocyclic group, halogen, a cyano group, a nitro group, a $C_1$-$C_4$ alkoxyl group, a $C_2$-$C_4$ alkenyl group, -L'-N(R')(R''), or the like, for example, may be phenyl, phenanthryl, a heterocyclic group comprising N such as pyridyl, carbazoly or the like, propenyl, fluorine, diphenylamine, cyano group, methoxy group, nitro group or the like.

Also, when neighboring $R^1$s, $R^3$s, $R^4$s and/or $R^5$s are/is linked each other to form a ring, preferably, one or two benzene ring, a ring such as naphthalene, phenanthrene and or the like together with a benzene ring which $R^1$s, $R^3$s, $R^4$s and/or $R^5$s are/is bonded to may be formed.

X and Y are each independently O, S, C($R^6$)($R^7$), Si($R^8$)($R^9$) or Se, and "a" and "b" are each an integer of 0 or 1, with the proviso that, at least one of "a" and "b" is an integer of 1. That is, a+b is equal to or greater than 1. Here, when the index of "a" and "b" are '0', X and Y do not exist, as a result, the carbons of both benzene rings are not bonded via X and Y but directly bonded to each other.

Z is N-($L^2$-$Ar^2$), O, S, C($R^{10}$)($R^{11}$), Si($R^{12}$)($R^{13}$), or Se.

When Z is N-($L^2$-$Ar^2$), $L^2$ may be selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_3$-$C_{60}$ aliphatic ring or a $C_6$-$C_{60}$ aromatic ring, an aliphatic hydrocarbon group, and the combinations thereof.

$L^2$, preferably, may be a $C_6$-$C_{30}$ arylene group, a $C_2$-$C_{30}$ heterocyclic group and so on, more preferably, may be a $C_6$-$C_{18}$ arylene group, a $C_2$-$C_{10}$ heterocyclic group and so on, for example, may be phenylene, naphthalene, biphenylene, pyrene, a heterocyclic group comprising N such as pyridine, pyrimidine, triazine, triazole, quinazoline, benzoquinazoline, dibenzoquinazoline and so on, a heterocyclic group comprising N and S such as dibenzothiophene and so on, a heterocyclic group comprising N and O such as benzofuropyrimidine and so on.

$Ar^2$ may be selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, and -L'-N(R')(R'').

$Ar^2$, preferably, may be a $C_6$-$C_{30}$ aryl group, a $C_2$-$C_{30}$ heterocyclic group, a $C_1$-$C_{10}$ alkoxyl group, halogen and so on, more preferably, may be a $C_6$-$C_{18}$ aryl group, a $C_2$-$C_{10}$ heterocyclic group and so on, for example, may be phenyl, naphthyl, biphenyl, pyrene, phenanthrene, triphenylene, a heterocyclic group comprising N such as pyridine, pyrimidine, triazine, carbazole, quinazoline, benzoquinazoline, dibenzoquinazoline, triazole or the like, a heterocyclic group comprising O such as dibenzofuran or the like, a heterocyclic group comprising N and O such as benzofuropyrimidine, naphthofuropyrimidine or the like, a heterocyclic group comprising N and S such as benzothienopyridine, benzothienopyrimidine or the like, methoxyl group, fluorine or the like.

In X, Y and Z, $R^6$ to $R^{13}$ may be each independently selected from the group consisting of hydrogen, deuterium, a $C_6$-$C_{24}$ aryl group, a $C_1$-$C_{50}$ alkyl group, a $C_2$-$C_{20}$ alkenyl group, a $C_1$-$C_{30}$ alkoxyl group, and the combinations thereof. Preferably, $R^6$ to $R^{13}$ may be each a $C_6$-$C_{12}$ aryl group, or a $C_1$-$C_{10}$ alkyl group, for example, methyl, ethyl, phenyl or the like.

Also, neighboring $R^6$s to $R^{13}$s may be optionally linked to form a ring. For example, $R^6$ and $R^7$, $R^8$ and $R^9$, $R^{10}$ and $R^{11}$, or $R^{12}$ and $R^{13}$ may be each optionally linked to form a spiro compound, preferably, $R^{10}$ and $R^{11}$, or $R^{12}$ and $R^{13}$ may be each optionally linked to form a spirobifluorene.

L' may be selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_3$-$C_{60}$ aliphatic ring or a $C_6$-$C_{60}$ aromatic ring, an aliphatic hydrocarbon group, and the combinations thereof. That is, when $Ar^1$, $Ar^2$, and $R^1$ to $R^5$ are -L'-N(R')(R''), L' may be each independently defined as the same above.

R' and R'' may be each independently selected from the group consisting of a $C_6$-$C_{30}$ aryl group, a fluorenyl group, a $C_2$-$C_{30}$ heterocyclic group containing at least one heteroatom selected from the group consisting of O, N, S, Si, and P, a fused ring group of a $C_3$-$C_{30}$ aliphatic ring and a $C_6$-$C_{30}$ aromatic ring, a $C_1$-$C_{50}$ alkyl group, a $C_2$-$C_{20}$ alkenyl group, and the combinations thereof. That is, when $Ar^1$, $Ar^2$, and $R^1$ to $R^5$ are -L'-N(R')(R''), R' and R'' may be each independently defined as the same above.

In formula 1 above, when the symbols are each the aryl group, fluorenyl group, heterocyclic group, fused ring group, alkyl group, alkenyl group, alkoxyl group, aryloxy group, arylene group, fluorenylen group or aliphatic hydrocarbon group, each of these may be optionally further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group, arylamine group and heteroarylamine group.

Specifically, Formula 1 may be represented by the following formula 2 or formula 3. The formula 1 may be represented by formula 2 when "b" is '0' in the formula 1, and the formula 1 may be represented by formula 3 when "a" is '0' in the formula 1.

[Formula 2]

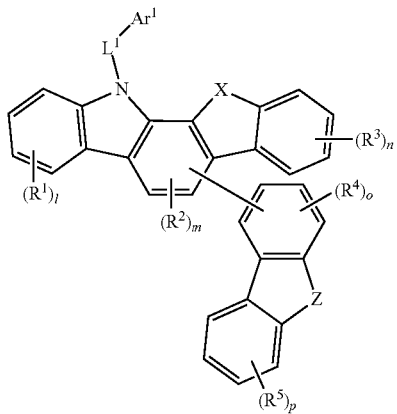

[Formula 3]

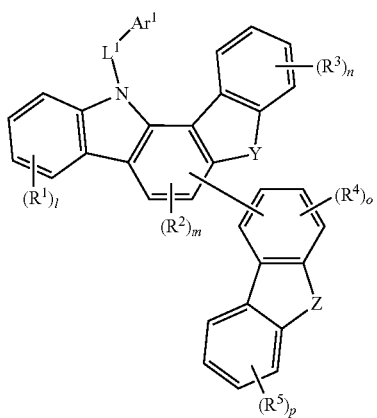

In Formulas 2 and 3, each of symbols may be defined as in Formula 1.

Also, Formula 1 may be represented by any one of the following formula 4 to formula 9, and each of symbols in these formulas may be defined as in Formula 1.

[Formula 4]

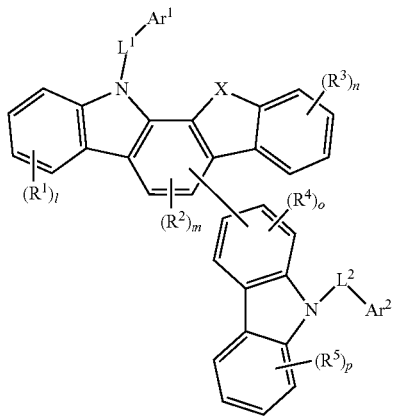

[Formula 5]

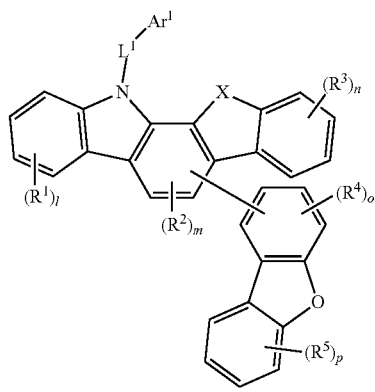

[Formula 6]

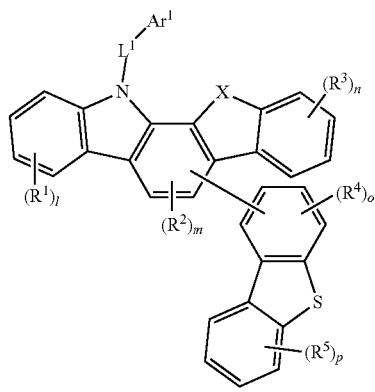

[Formula 7]

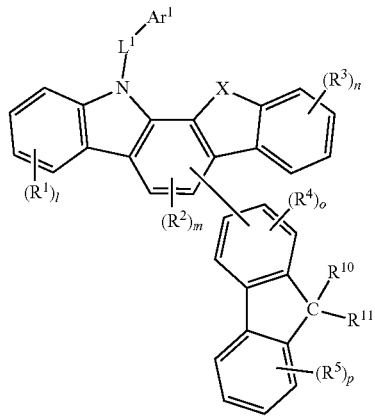

[Formula 8]

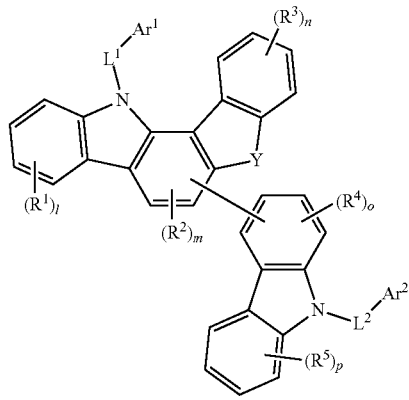

[Formula 9]

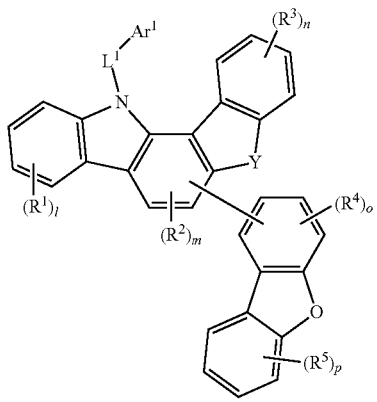

[Formula 10]

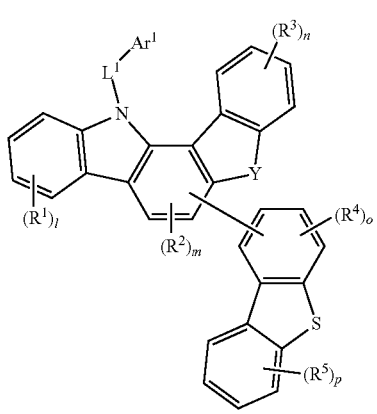

[Formula 11]

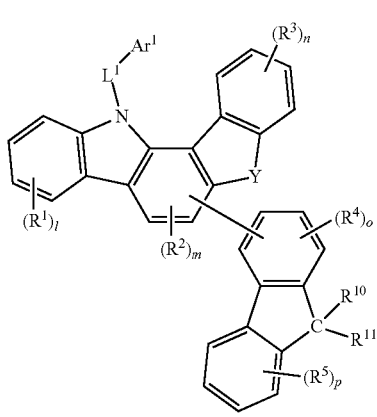

Preferably, in formulas 1 to formula 9, all of l, m and n may be "0". Also, in formulas 1 to formula 9, both R⁴ and R⁵ may be hydrogen, and neighboring R⁴ or neighboring R⁵ may be linked each other to form a ring when o and p are each 2 and more. Also, preferably, in formulas 1 to formula 9, X or Y may be S or O.

More specifically, the compound represented by Formula 1 above may be one of the compounds below.

1-1

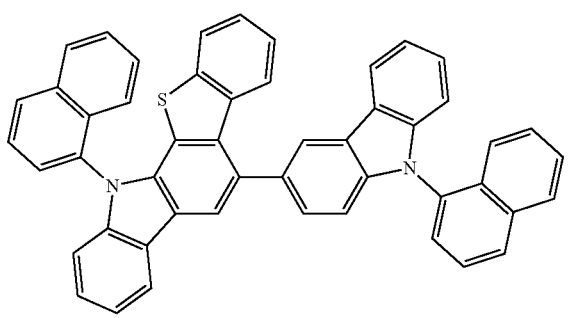

1-2

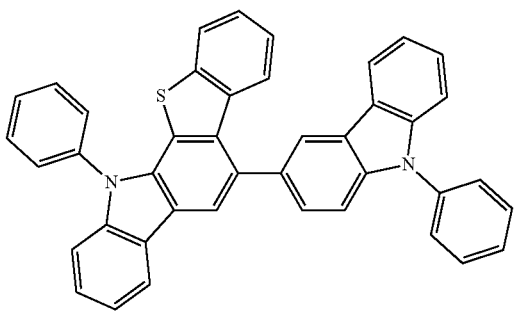

1-3

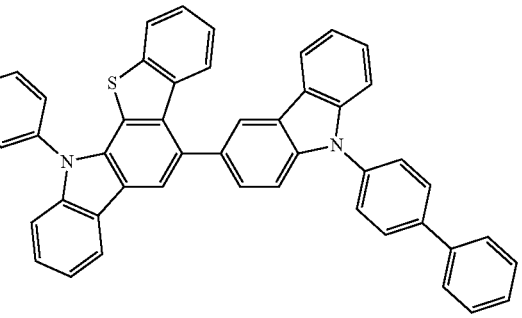

1-4

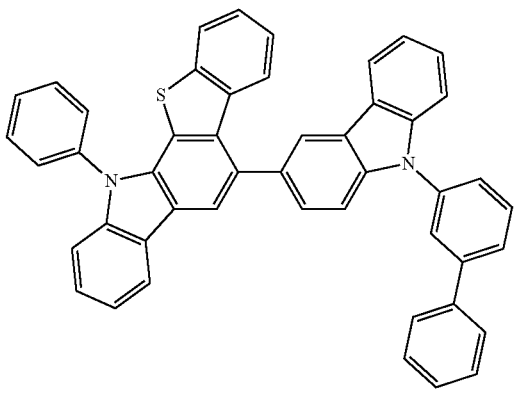

1-5
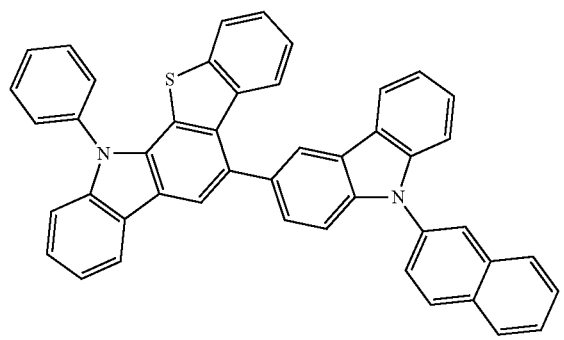
1-6
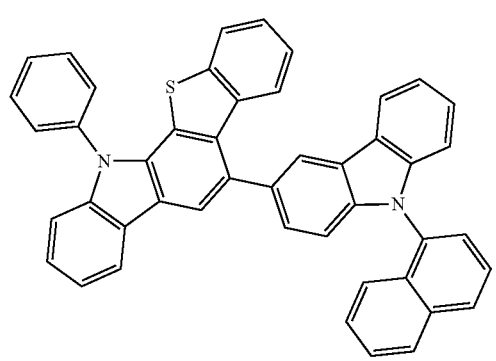
1-7
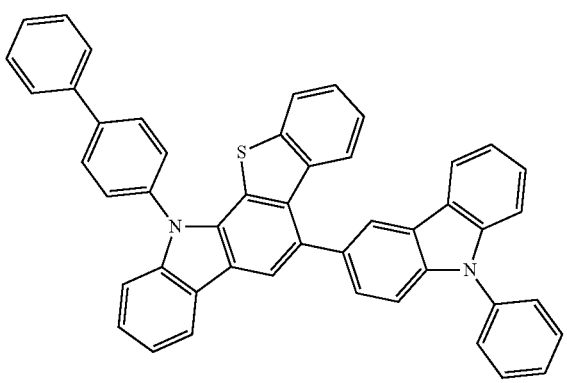
1-8
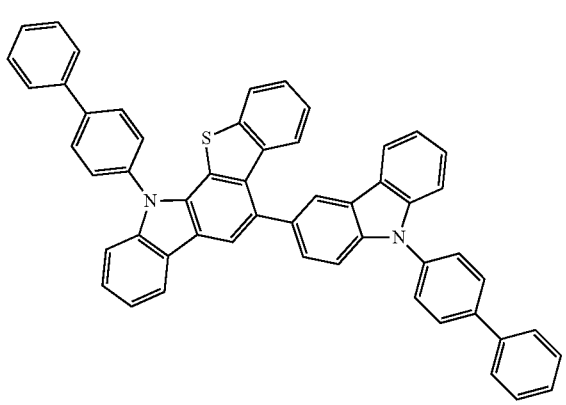
1-9
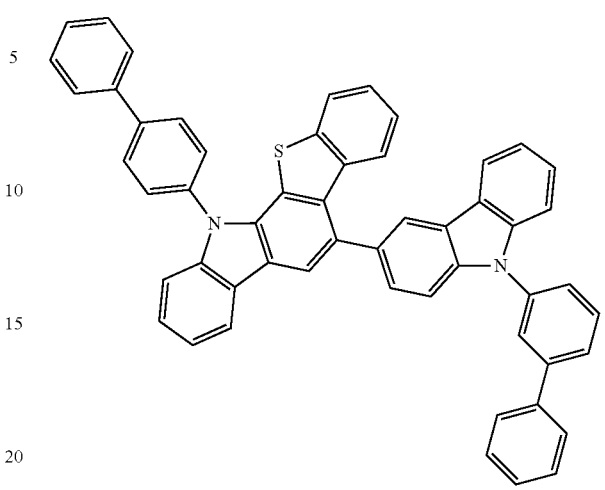
1-10
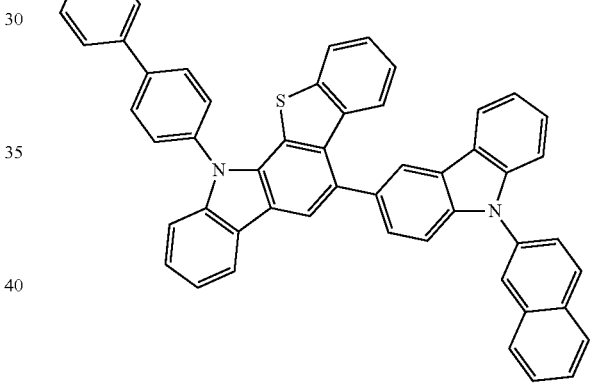
1-11
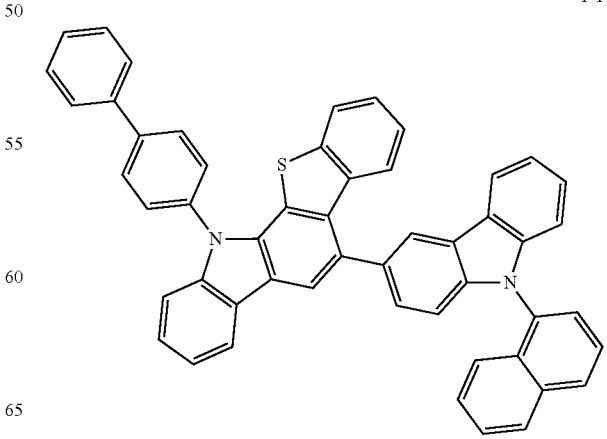

1-12
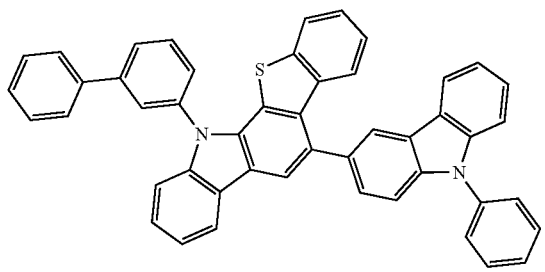
1-13
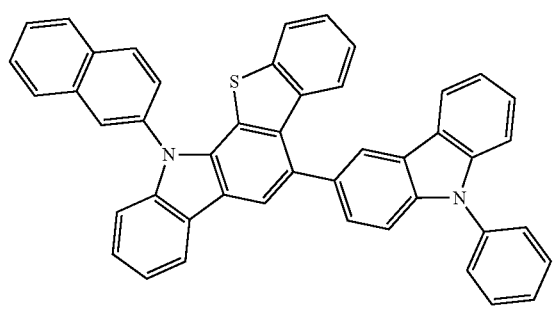
1-14
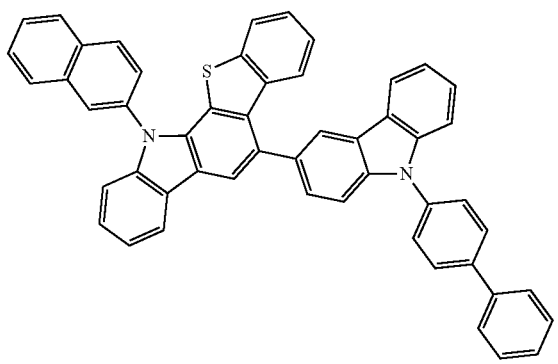
1-15
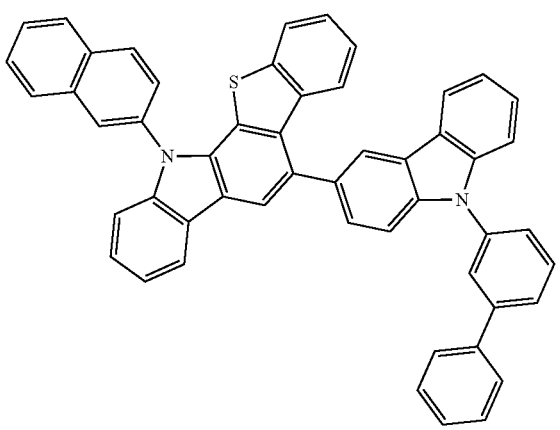
1-16
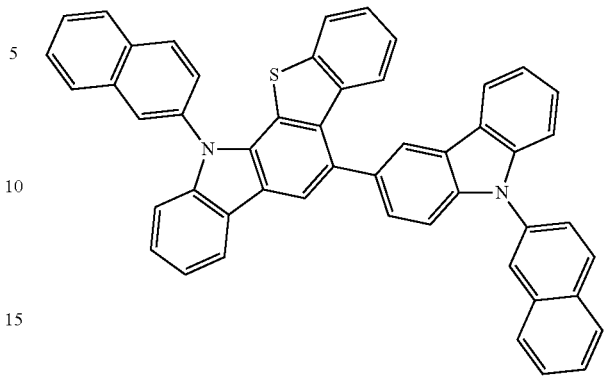
1-17
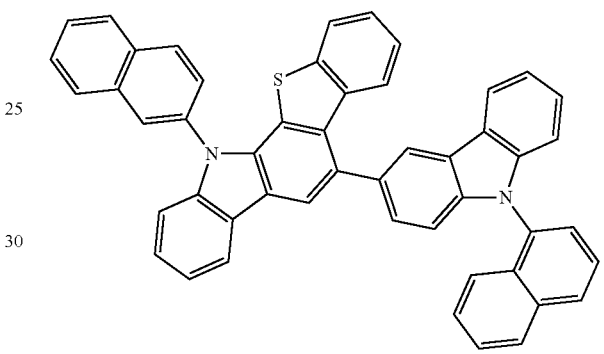
1-18
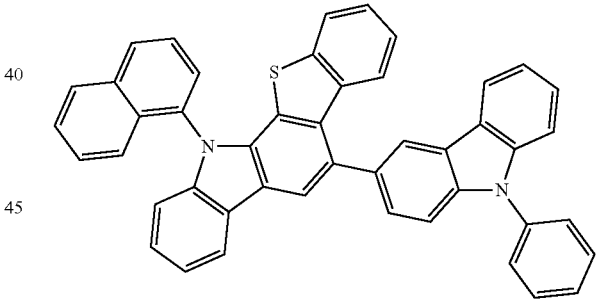
1-19
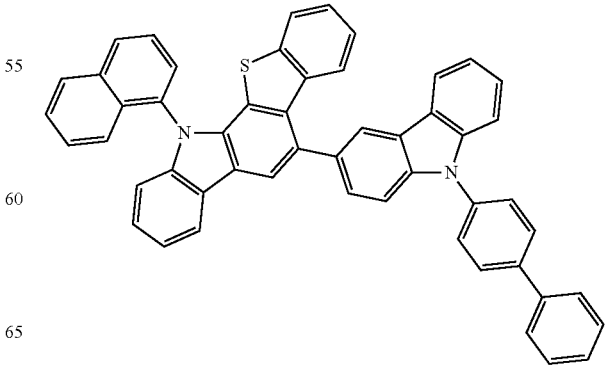

1-20
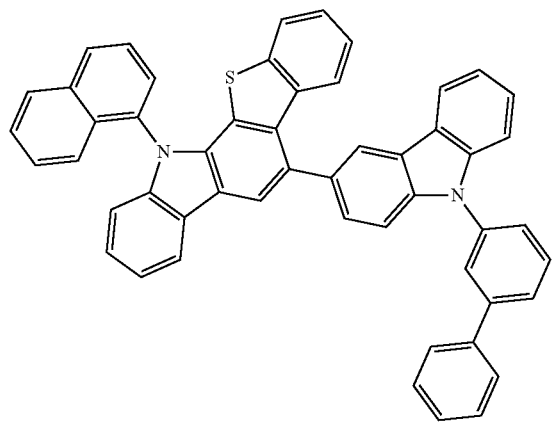
1-21
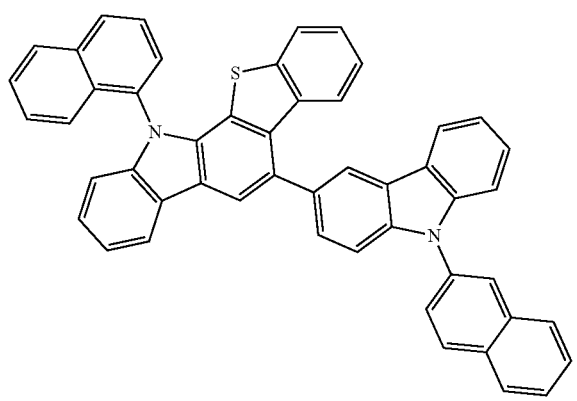
1-22
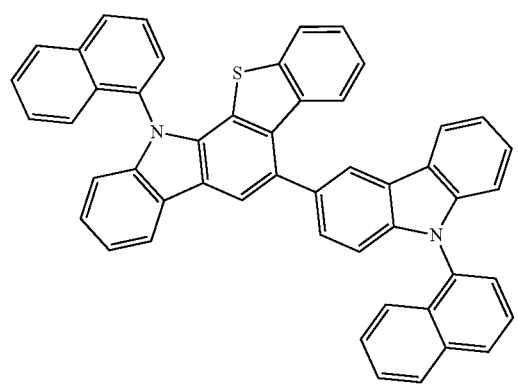
1-23
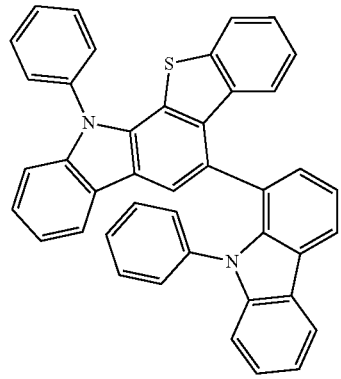
1-24
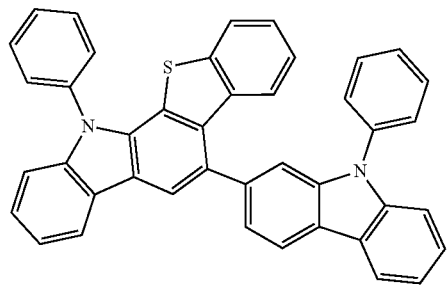
1-25
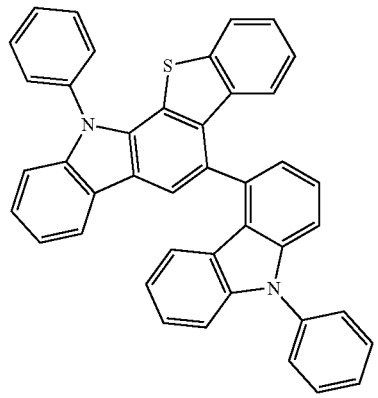
1-26
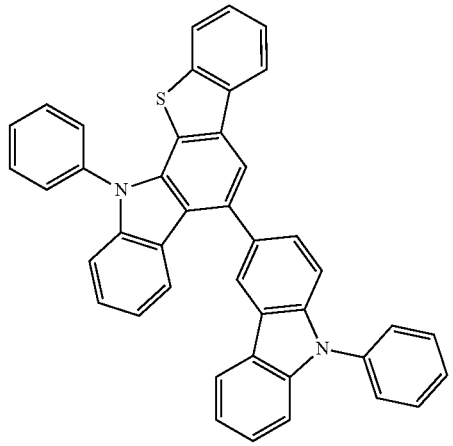
1-27
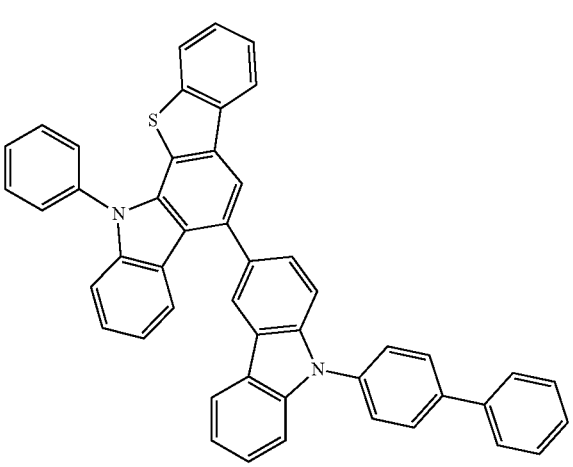

1-28
1-31
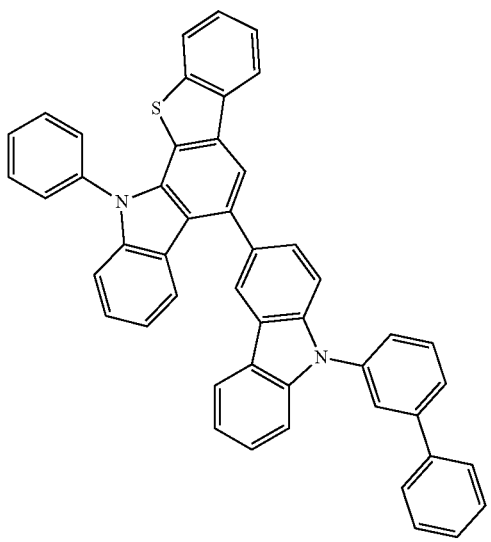
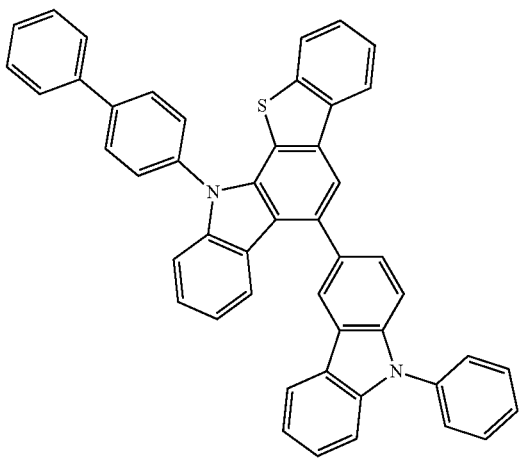
1-29
1-32
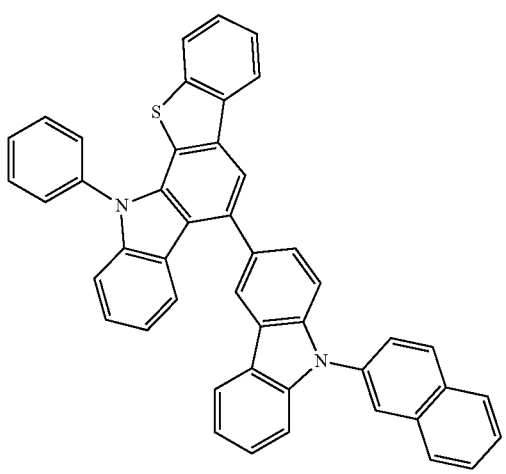
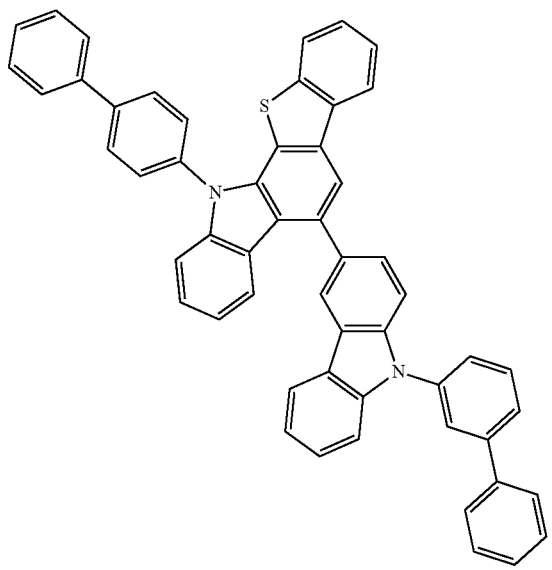
1-30
1-33

1-34
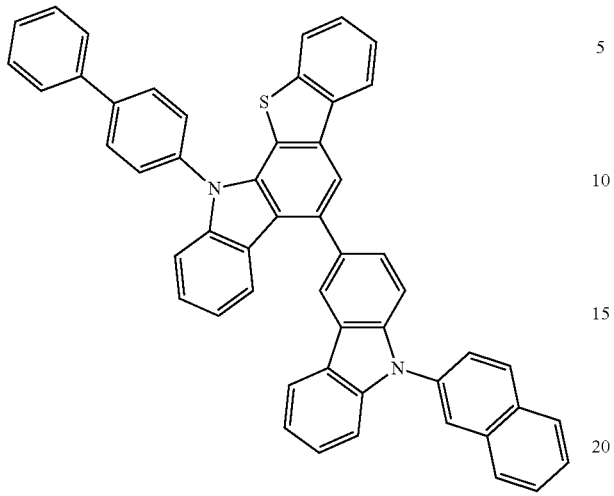
1-35
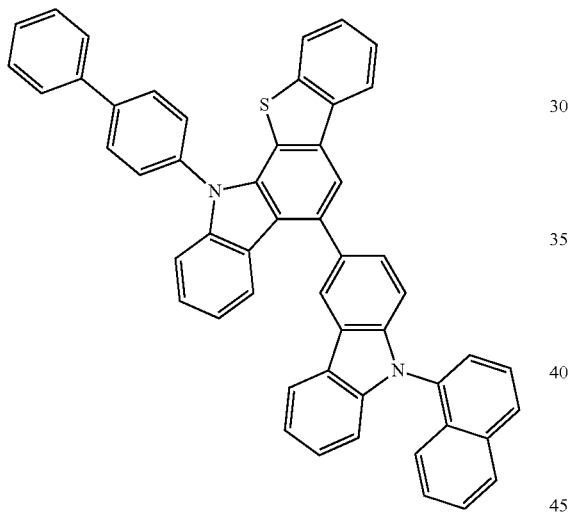
1-36
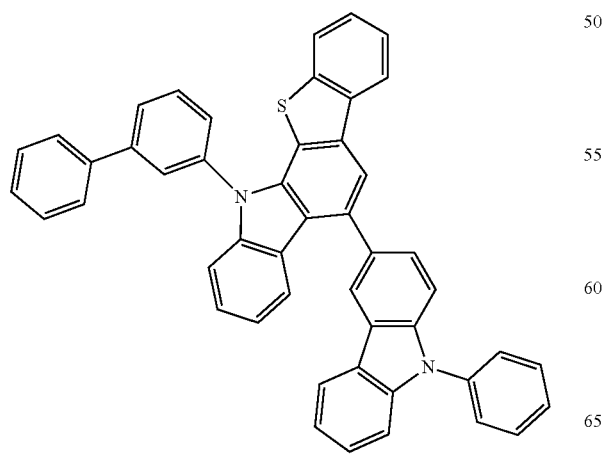
1-37
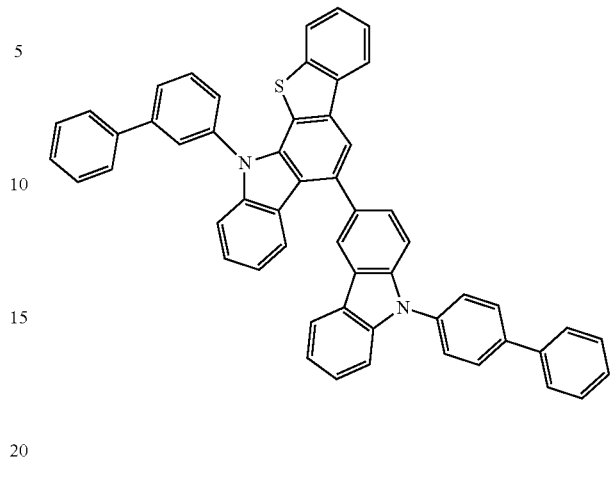
1-38
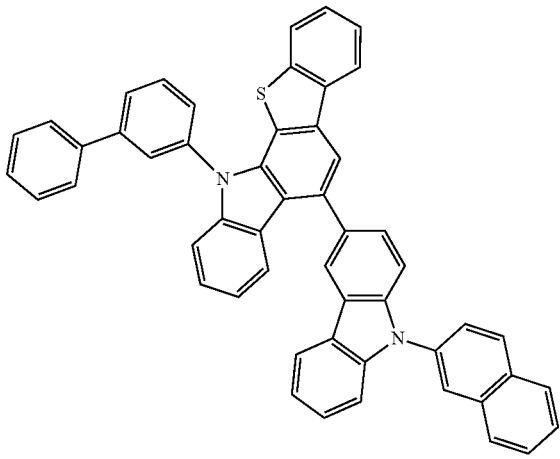
1-39

1-40
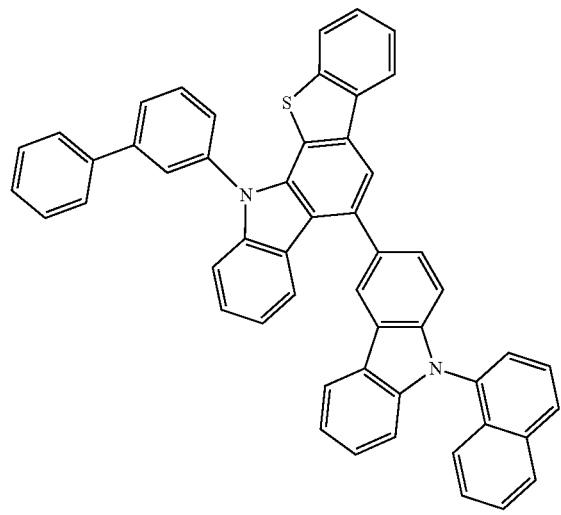
1-41
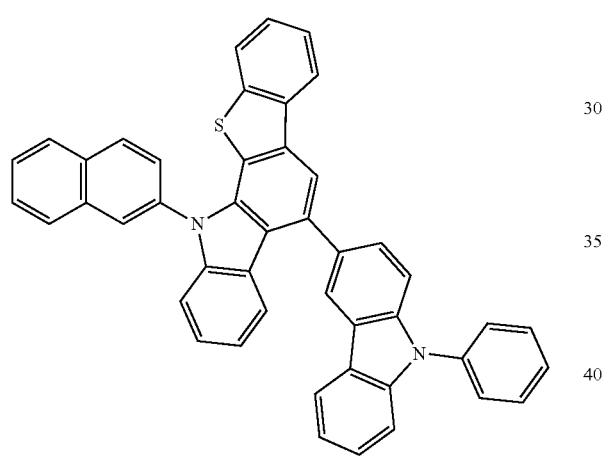
1-42
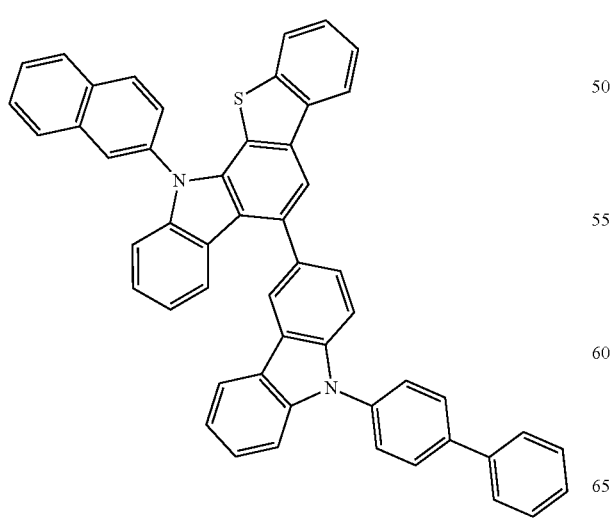
1-43
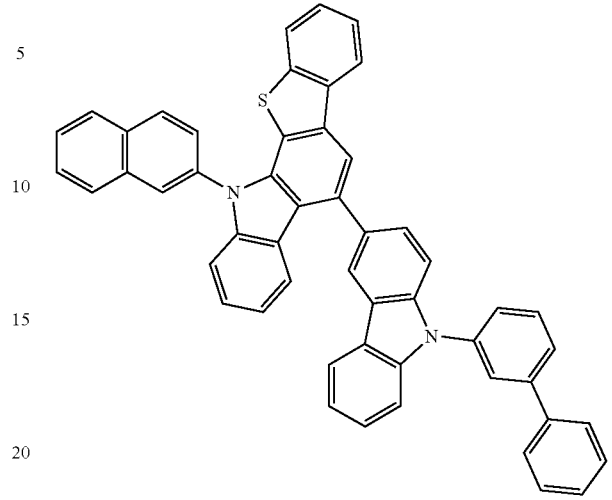
1-44
1-45
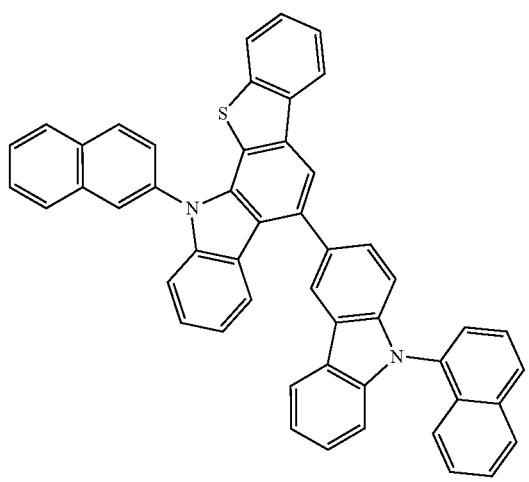

1-46
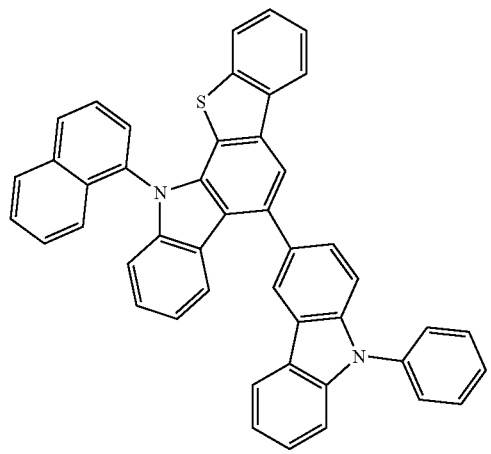
1-49
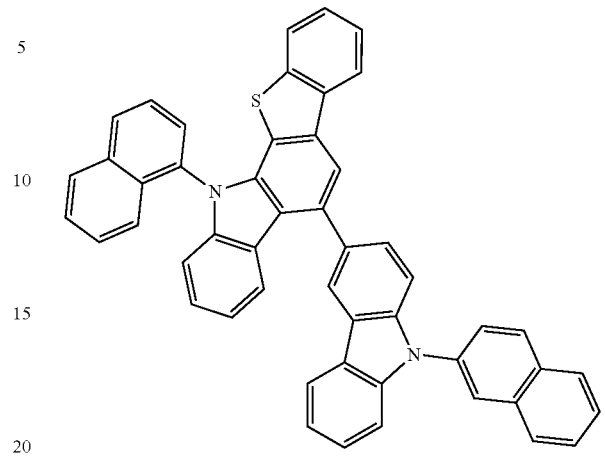
1-47
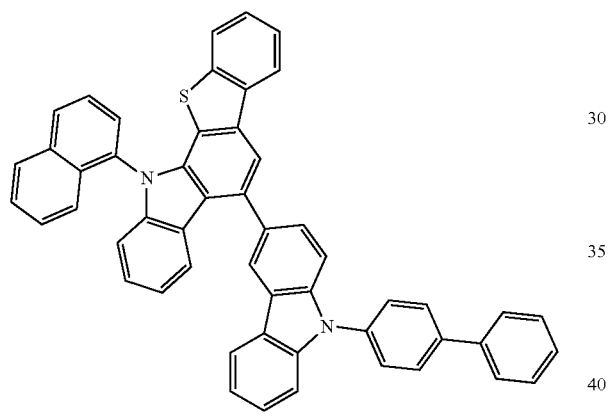
1-50
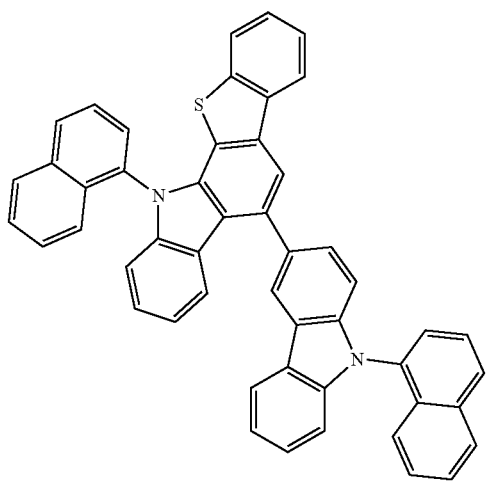
1-48
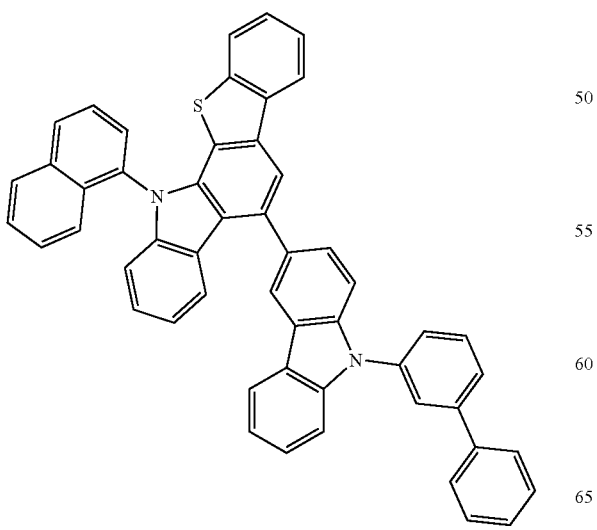
1-51
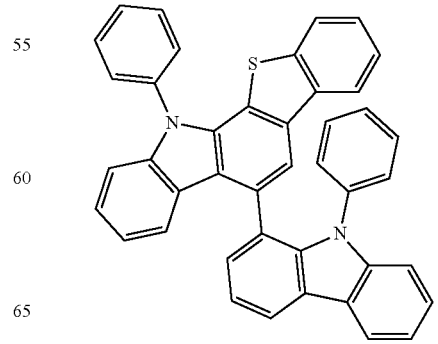

1-52
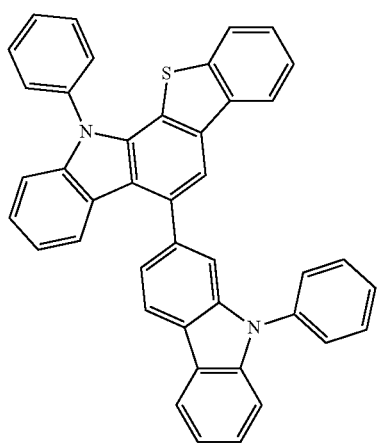
1-53
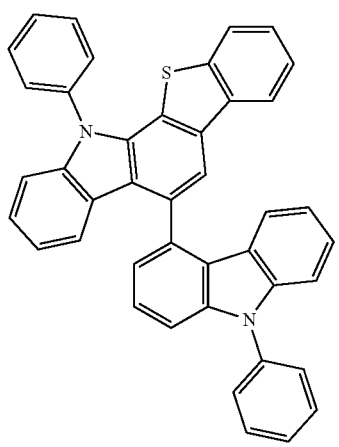
1-54
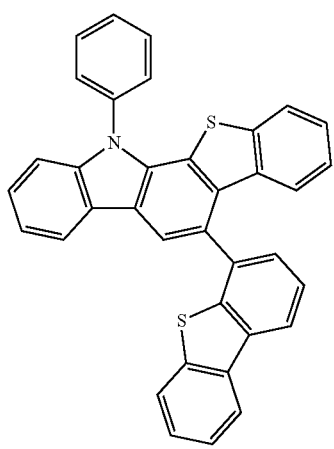
1-55
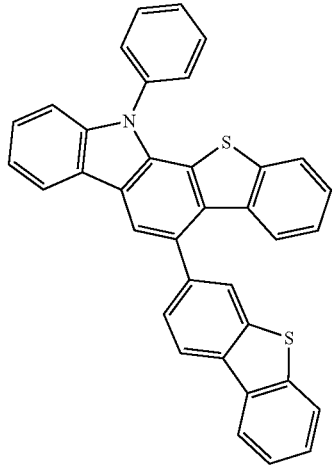
1-56
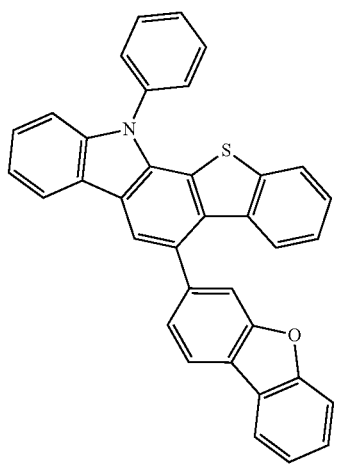
1-57
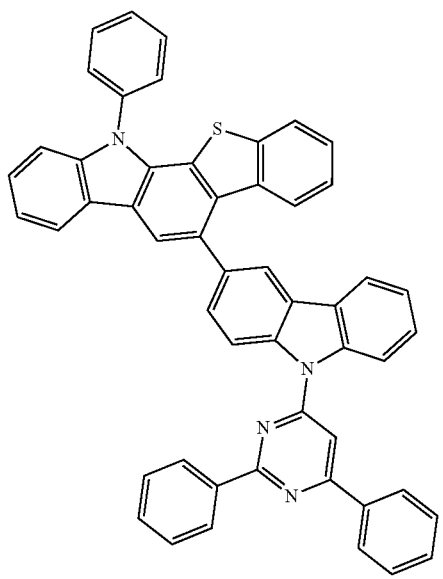

1-58
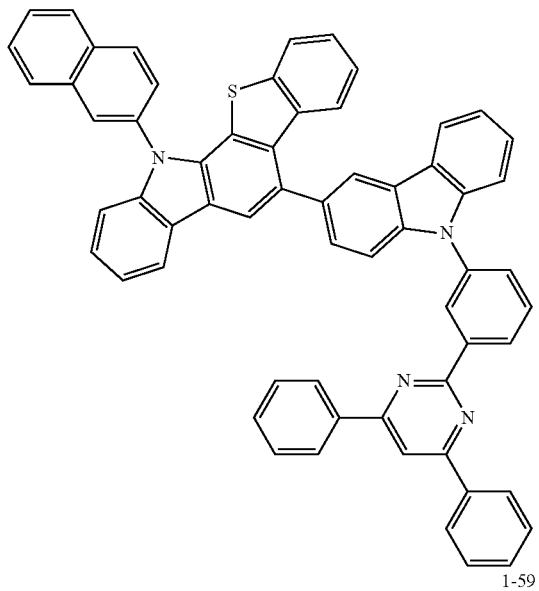
1-59
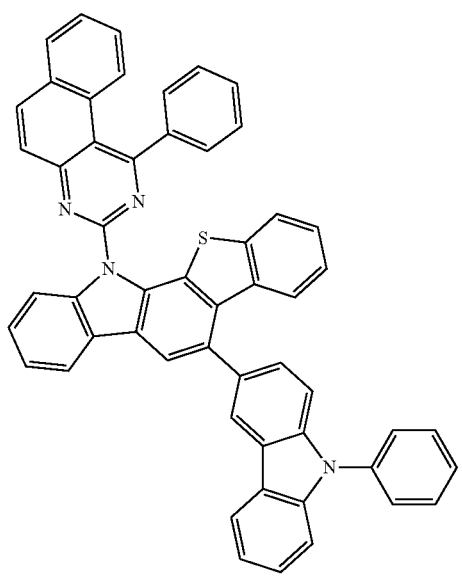
1-60
1-61
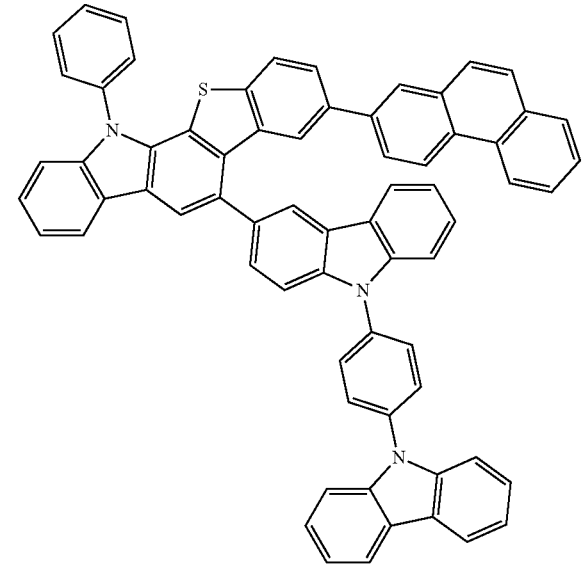
1-62
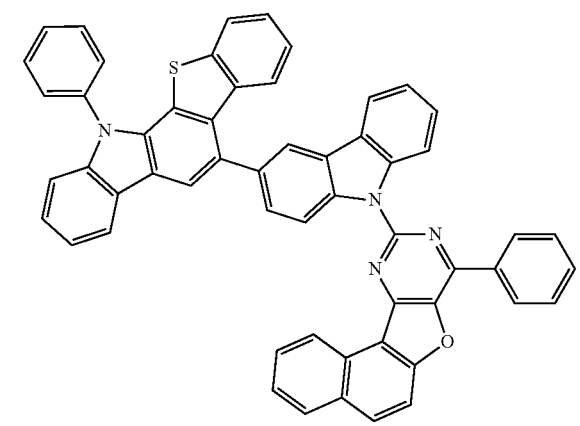
1-63
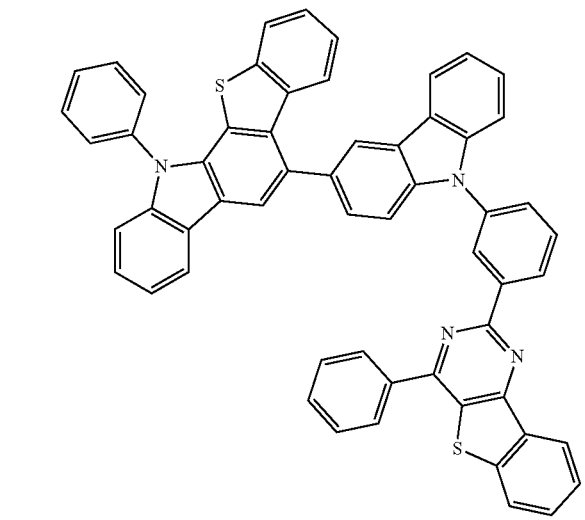

-continued
1-64
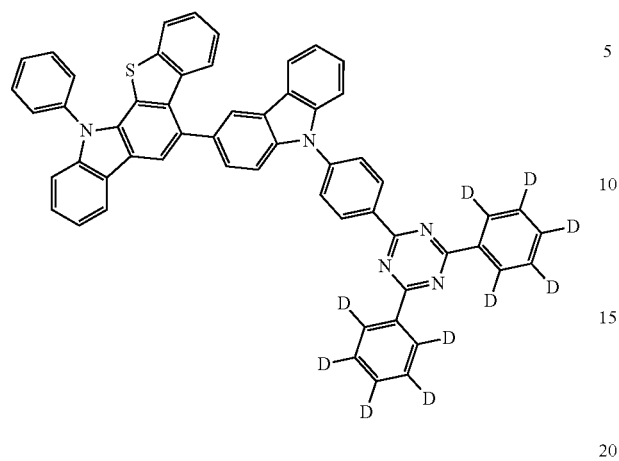
1-67
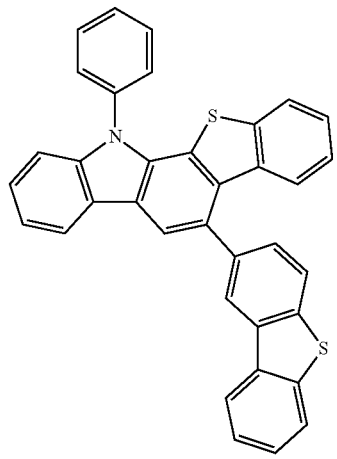
1-65
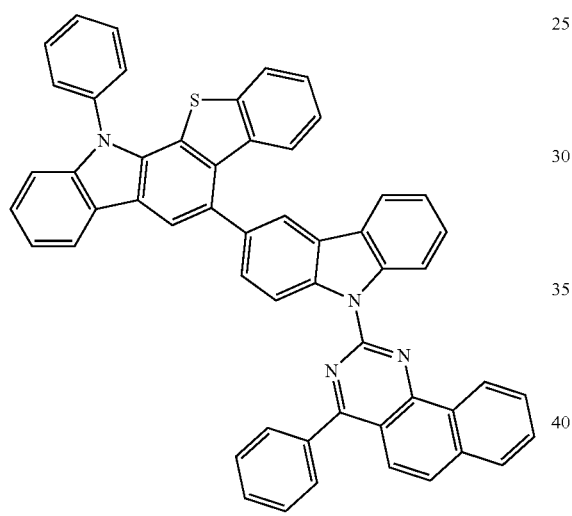
1-68
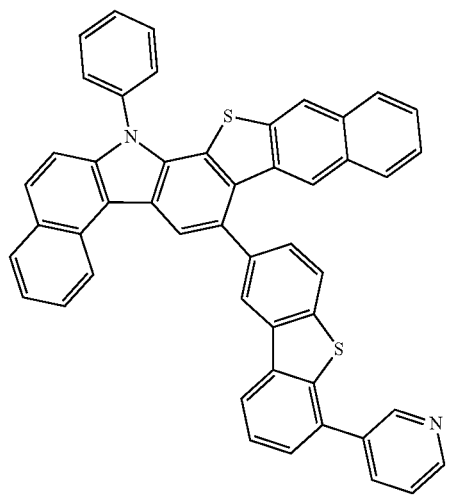
1-66
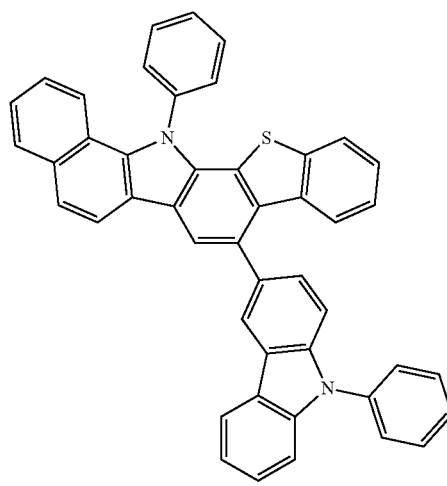
1-69
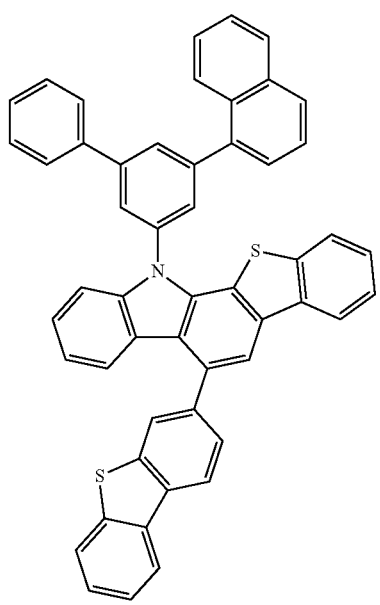

1-70
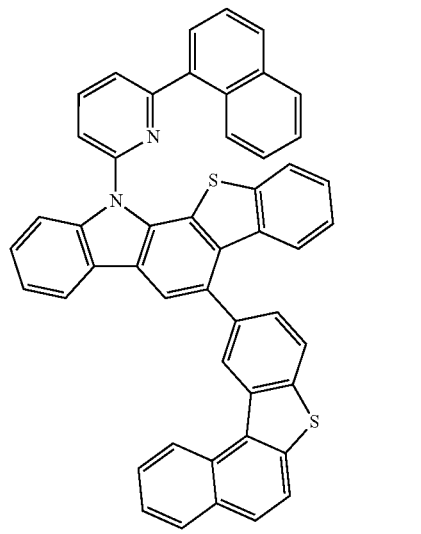
1-71
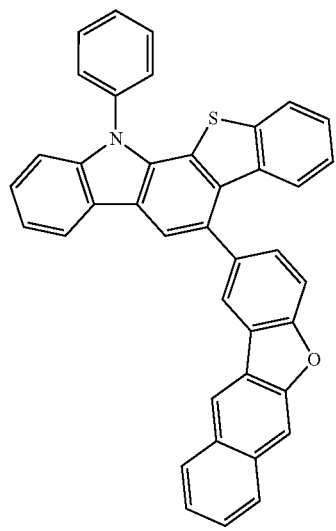
1-72
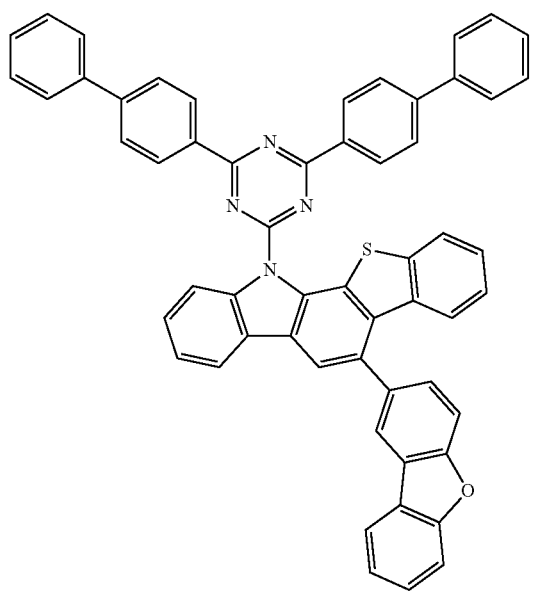
1-73
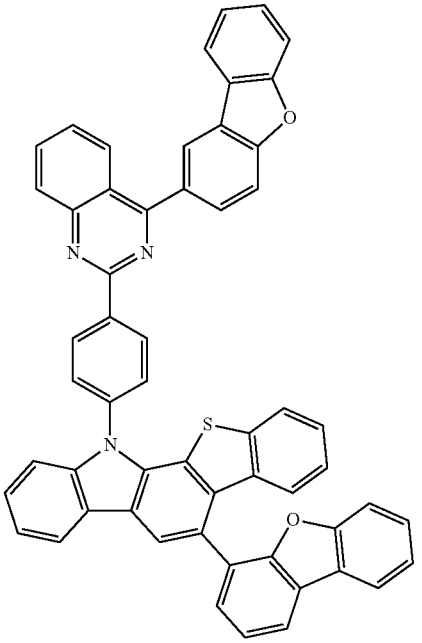
1-74
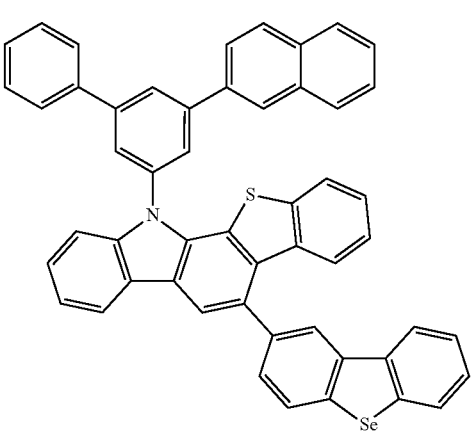
1-75
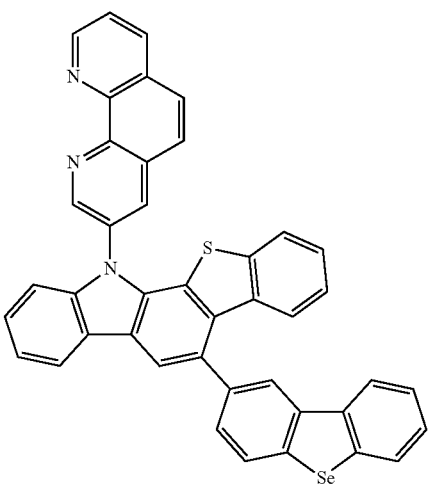

1-76
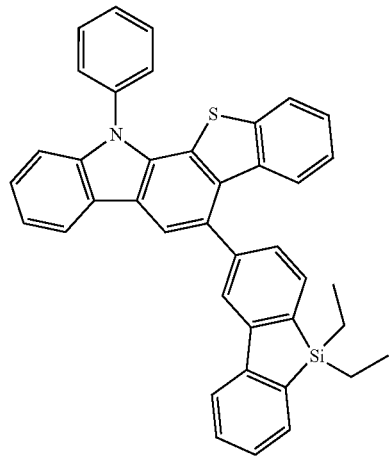
1-77
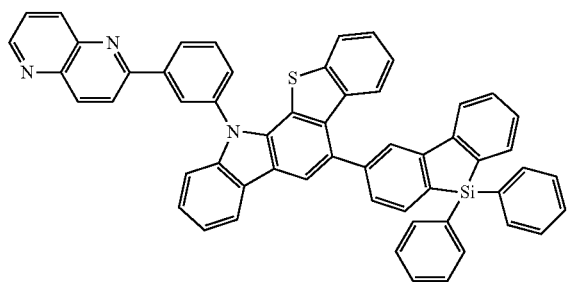
1-78
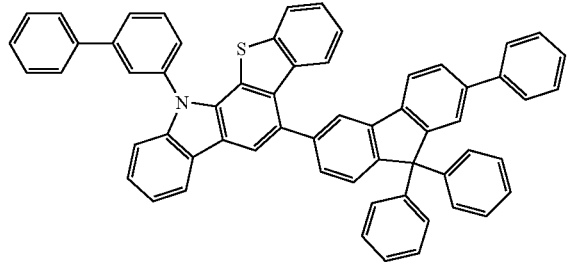
1-79
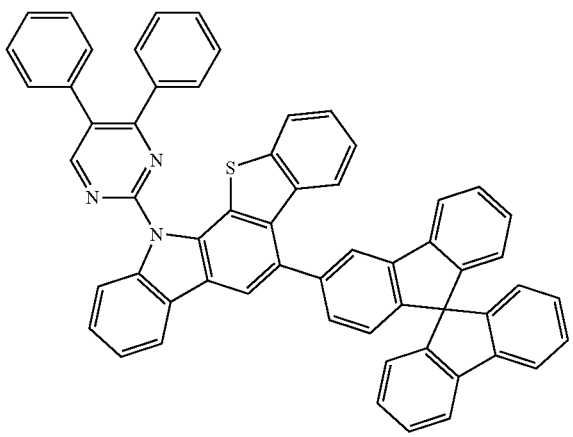
1-80
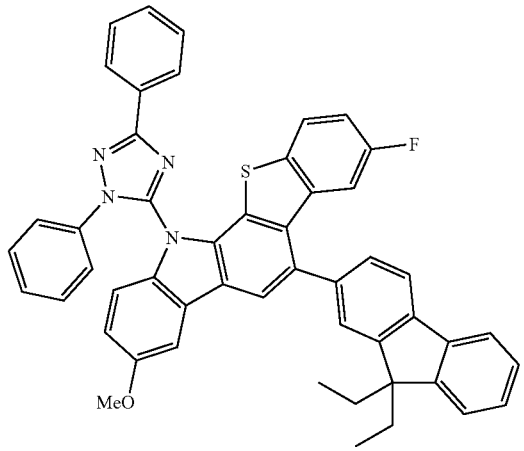
1-81
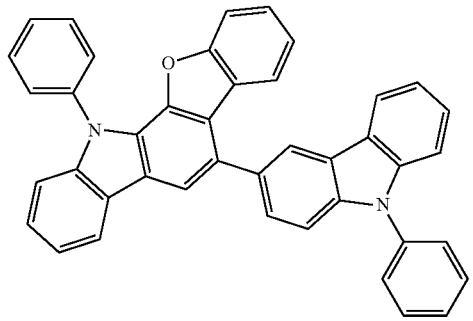
1-82
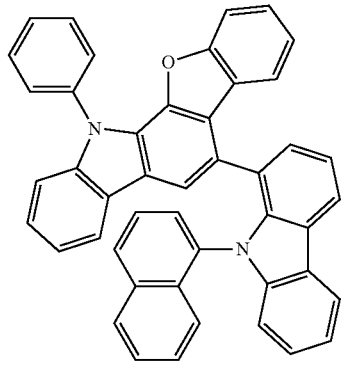
1-83
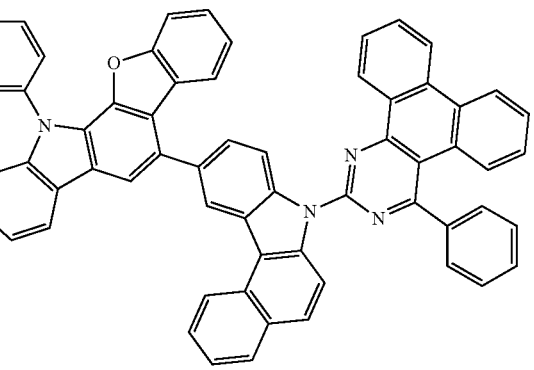

1-84
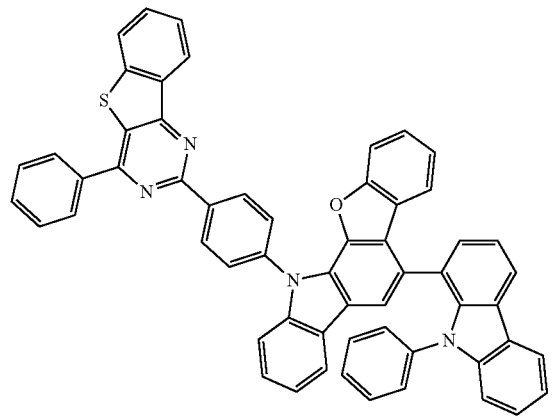
1-85
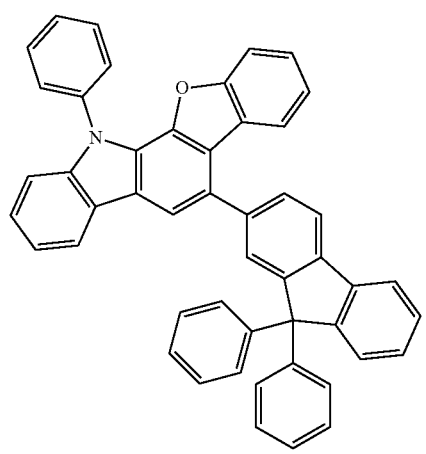
1-86
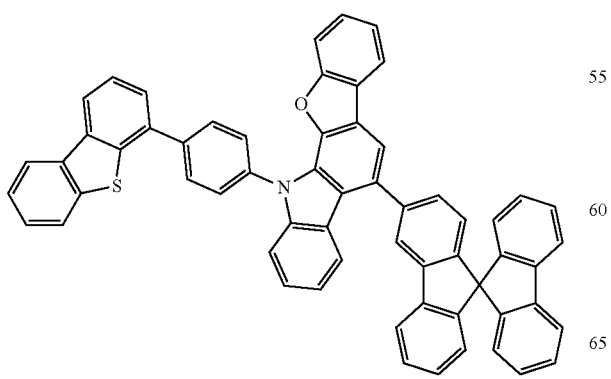
1-87
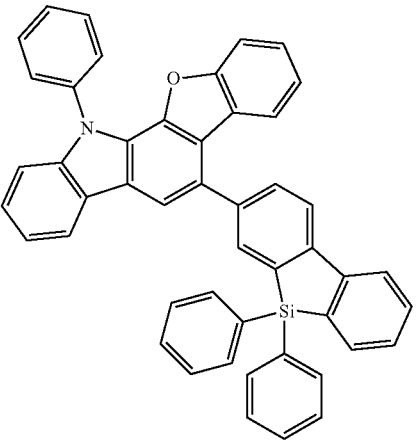
1-88
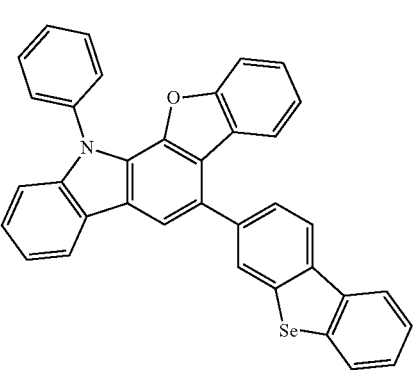
1-89
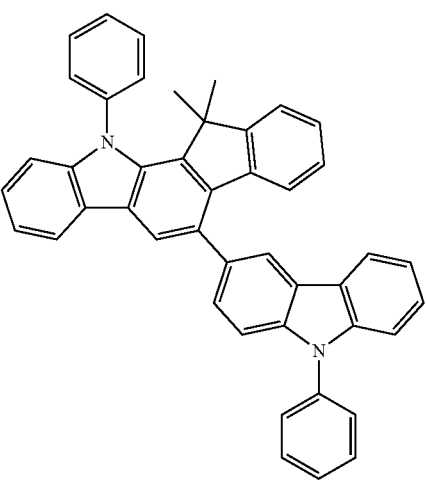
1-90
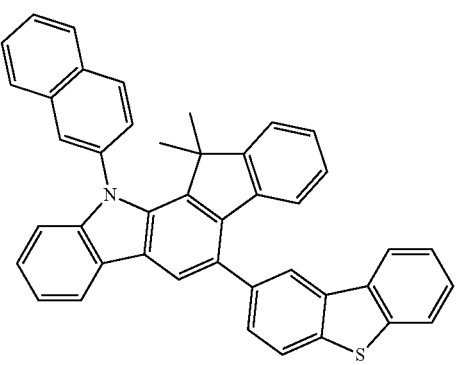

1-91
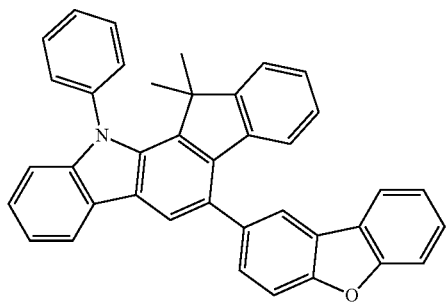
1-92
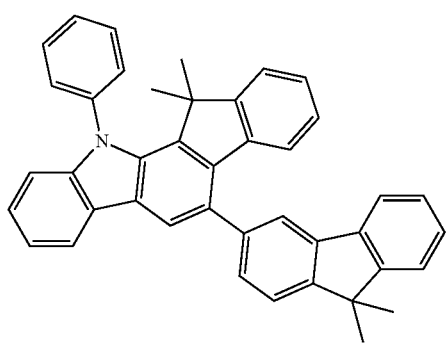
1-93
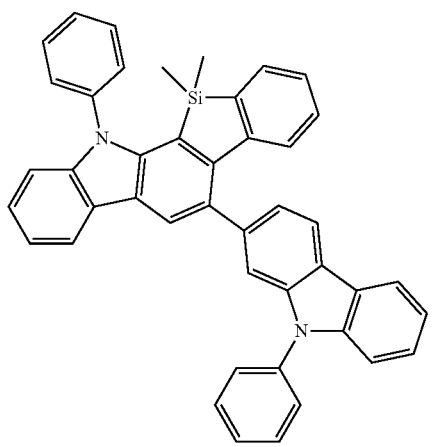
1-94
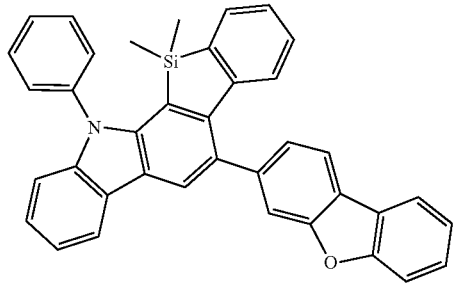
1-95
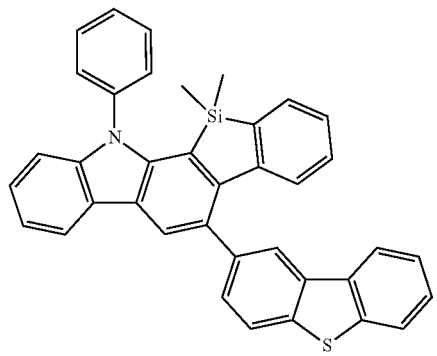
1-96
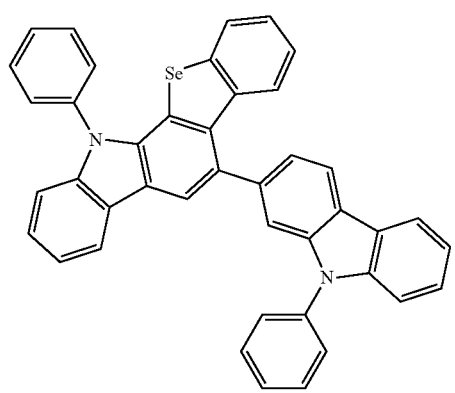
1-97
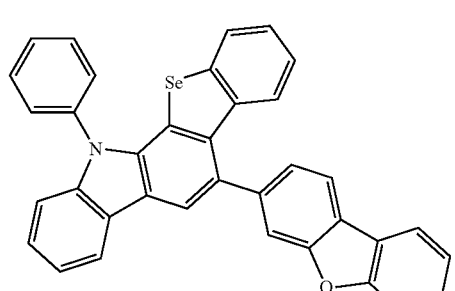
1-98
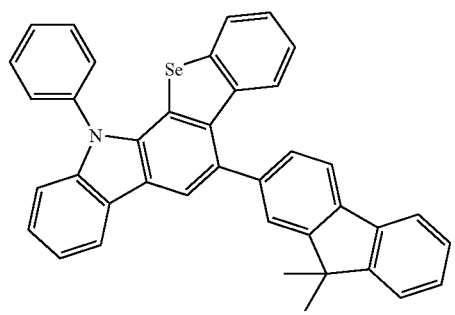

2-1
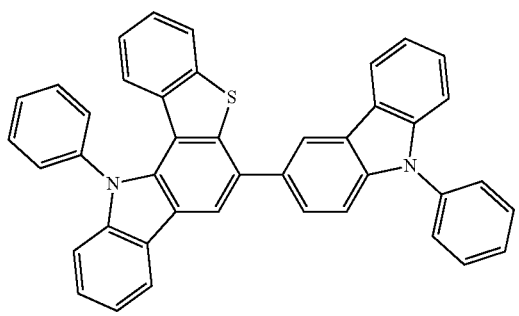
2-5
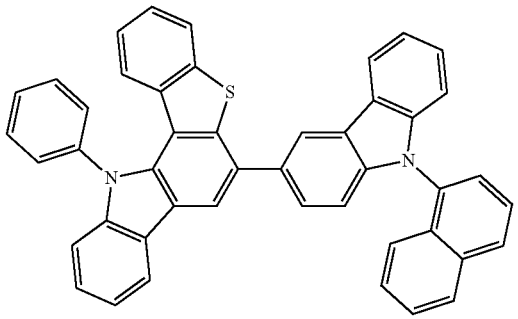
2-2
2-6
2-3
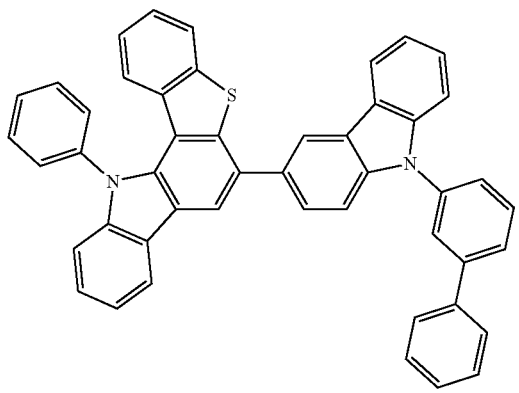
2-7
2-4
2-8
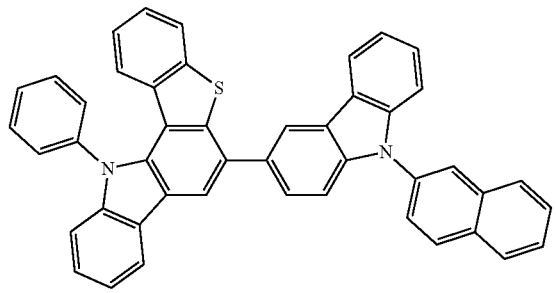

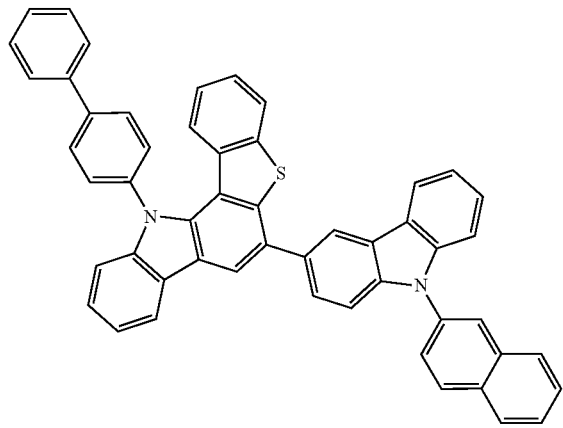
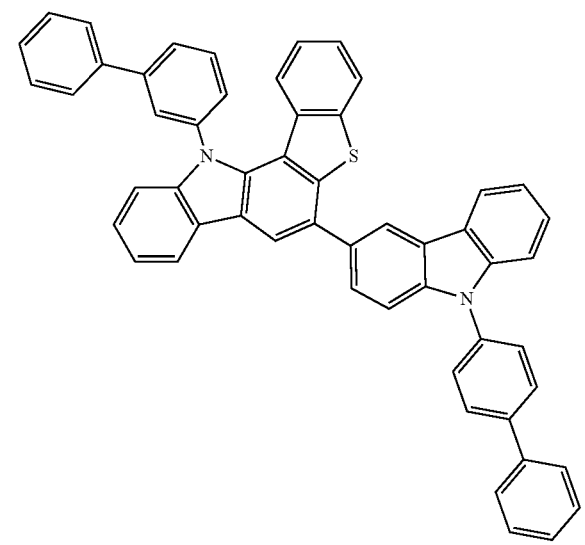
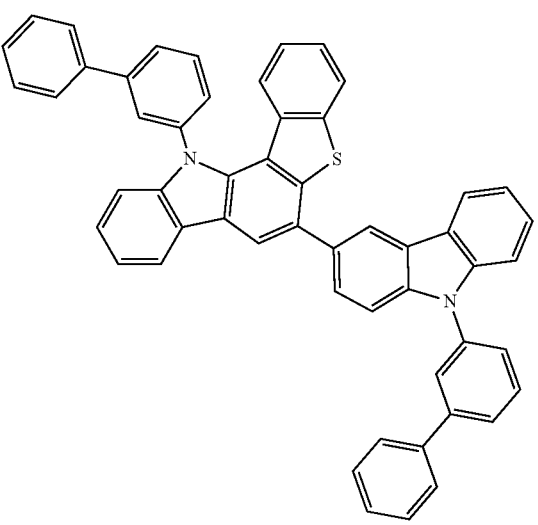

2-15
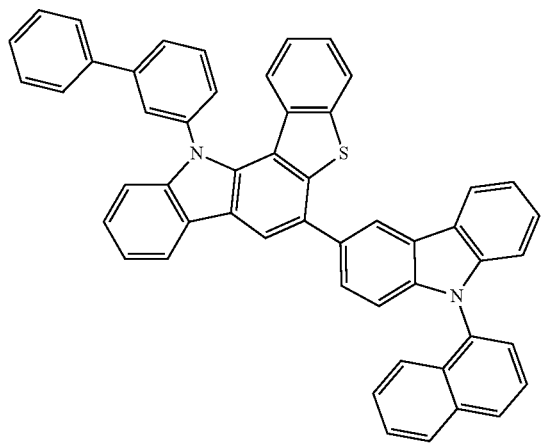
2-16
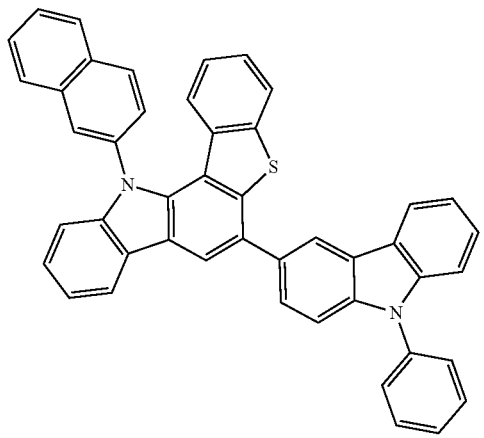
2-17
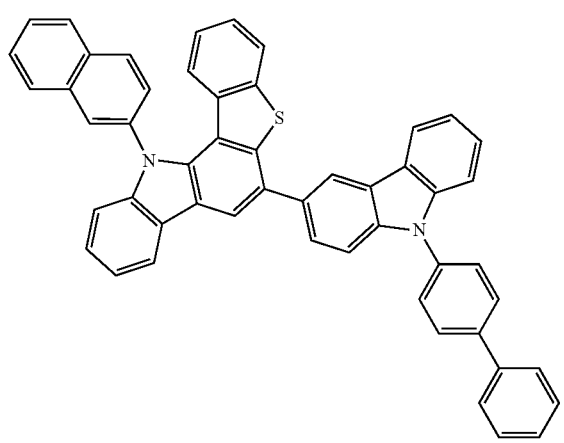
2-18
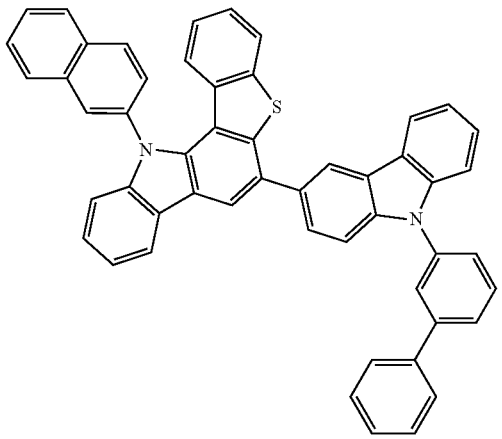
2-19
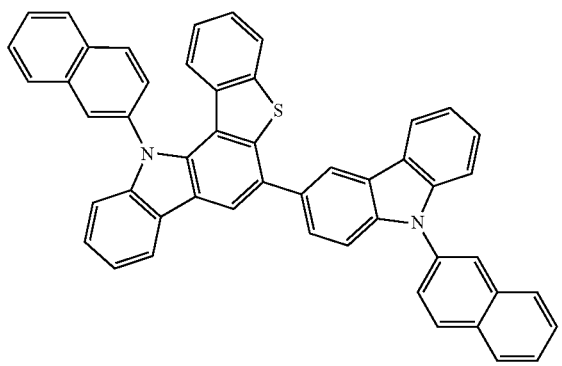
2-20
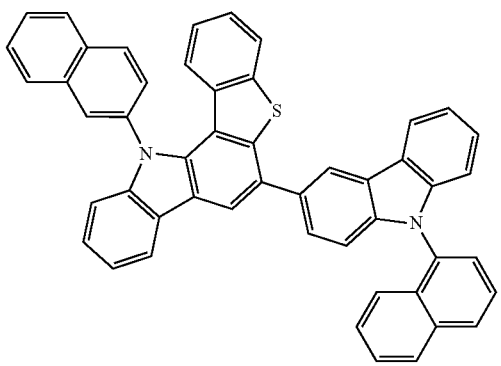
2-21
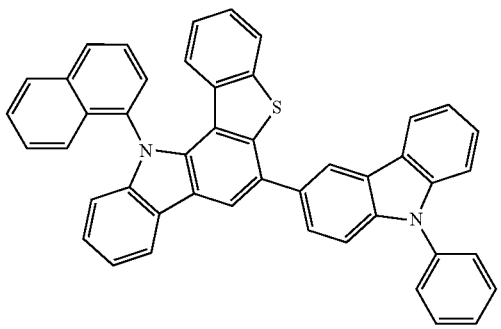

2-22
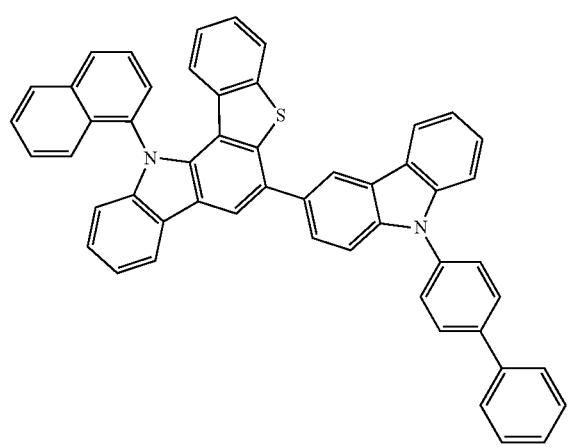
2-25
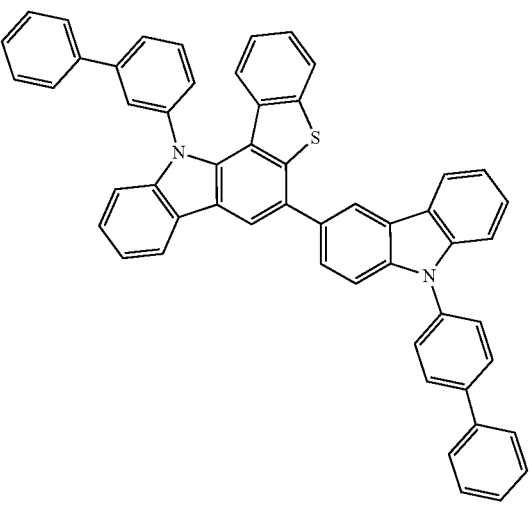
2-23
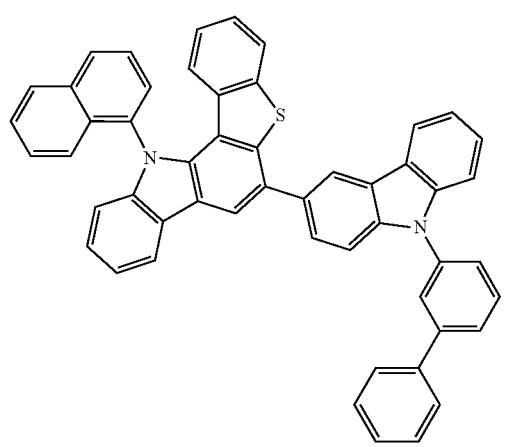
2-26
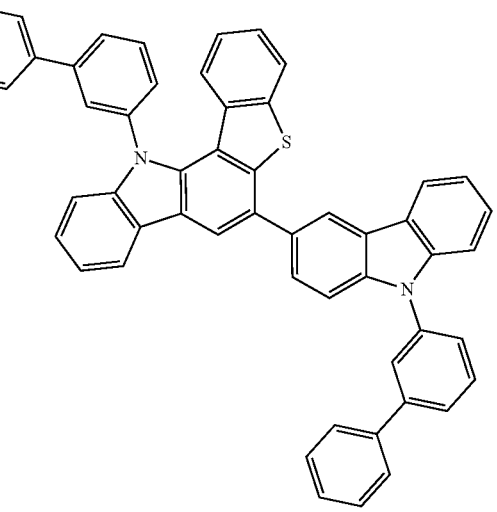
2-24
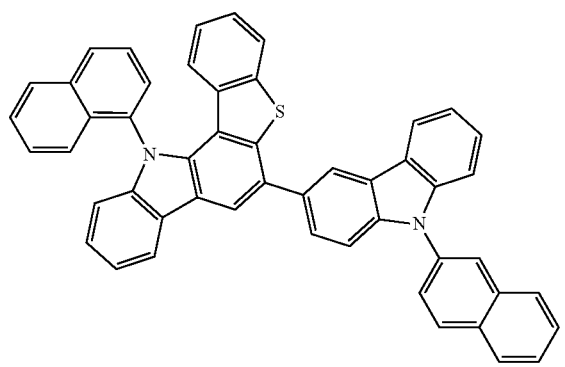
2-27
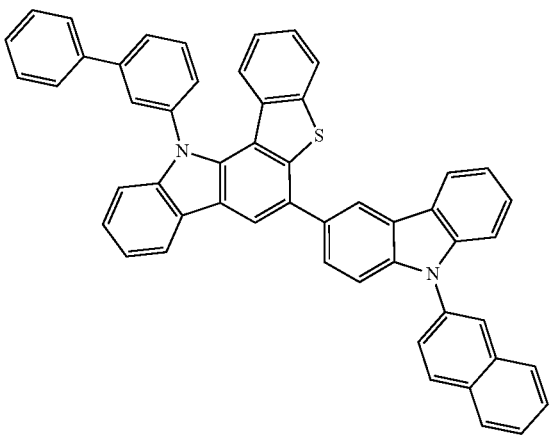

2-28
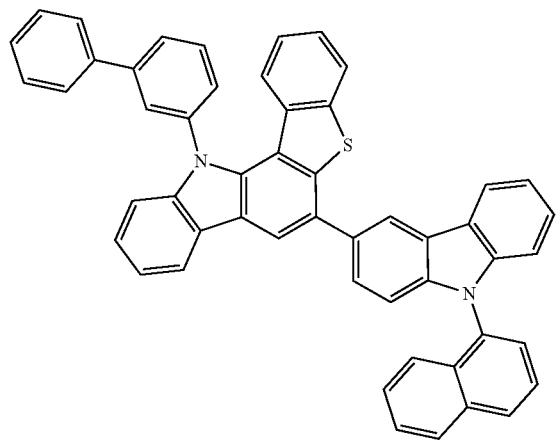
2-29
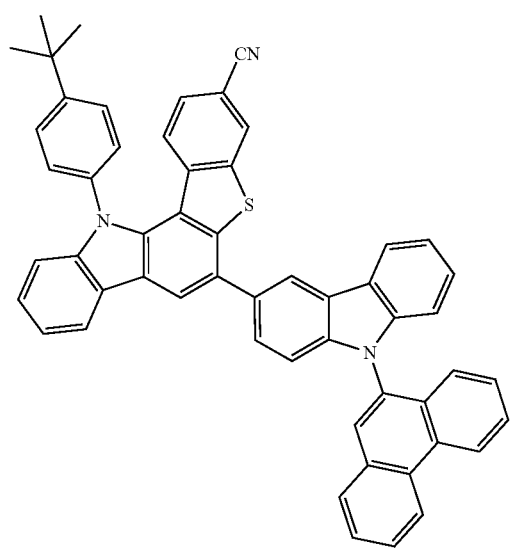
2-30
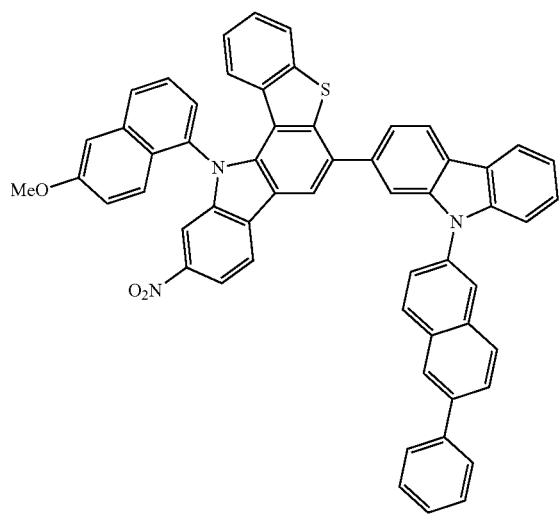
2-31
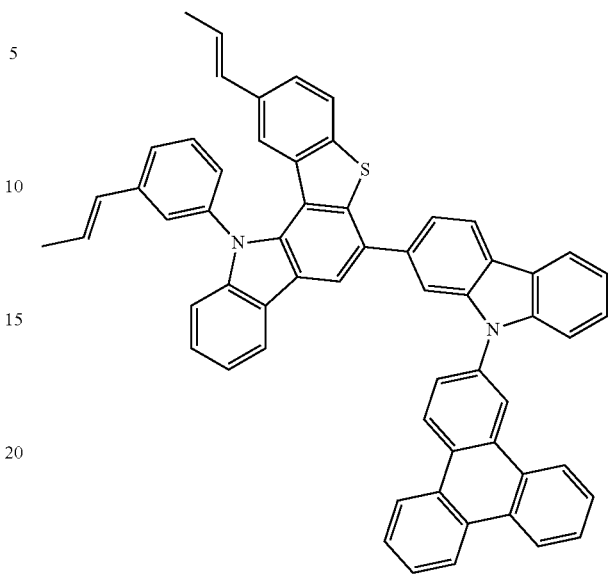
2-32
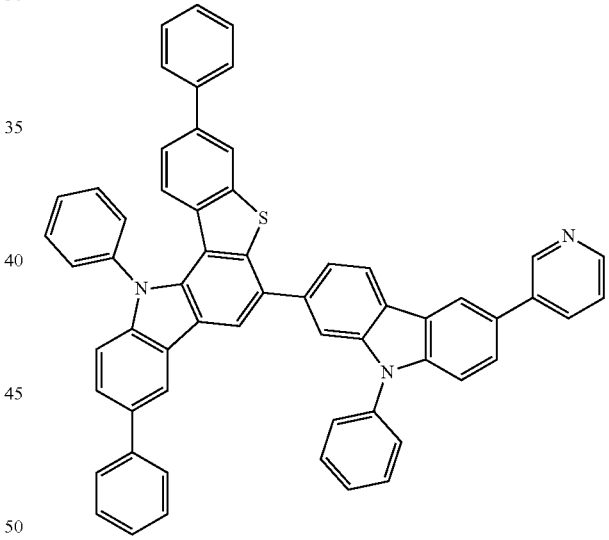
2-33
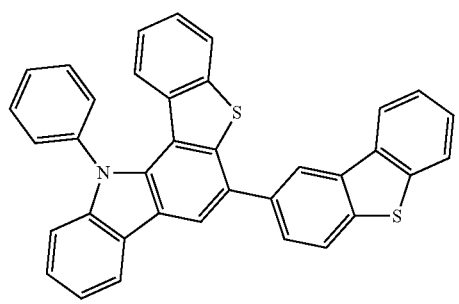

2-34
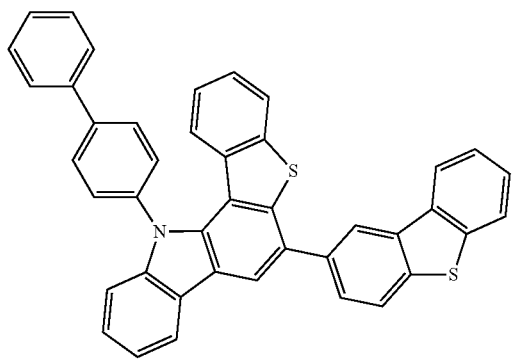
2-35
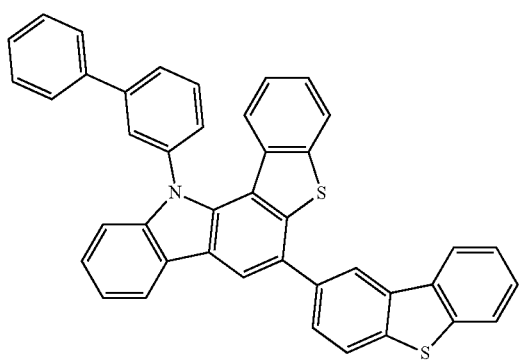
2-36
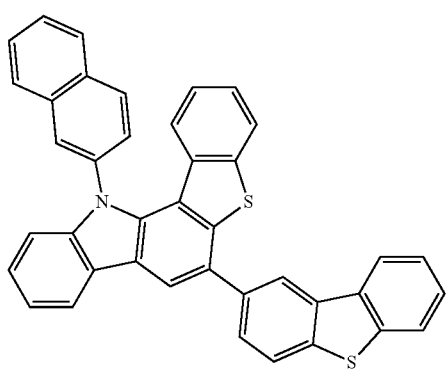
2-37
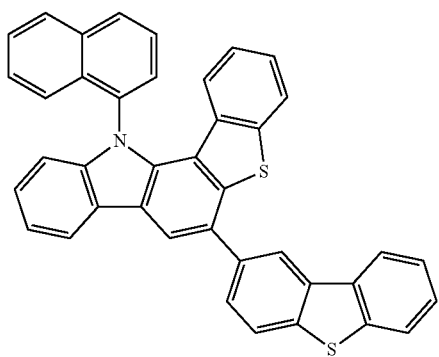
2-38
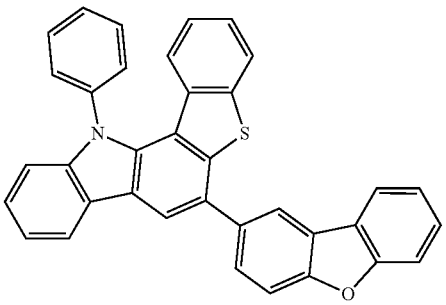
2-39
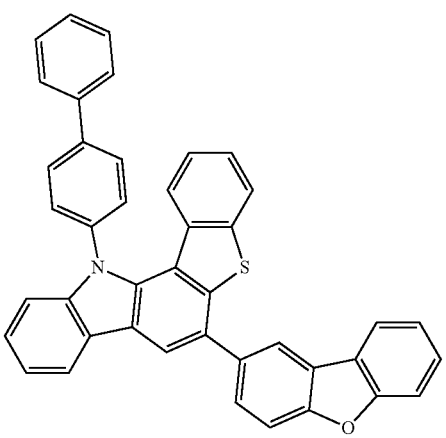
2-40
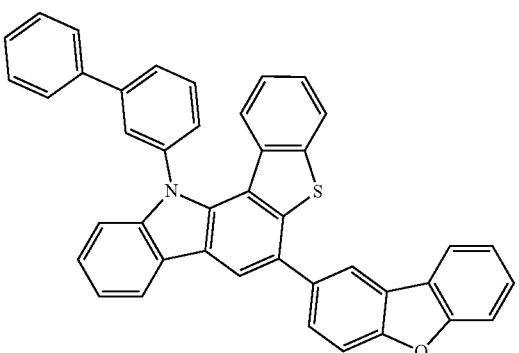
2-41
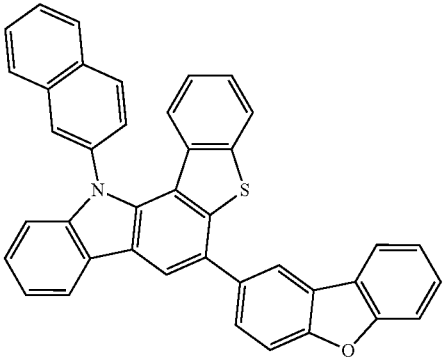

2-42
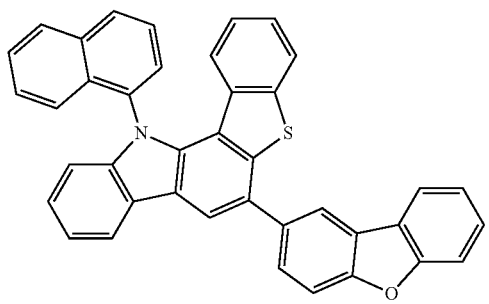
2-43
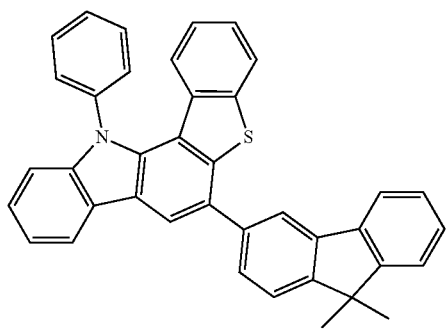
2-44
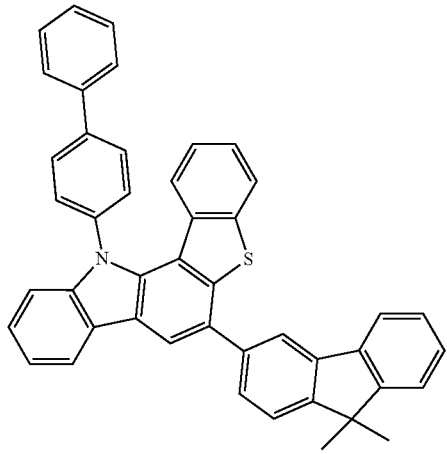
2-45
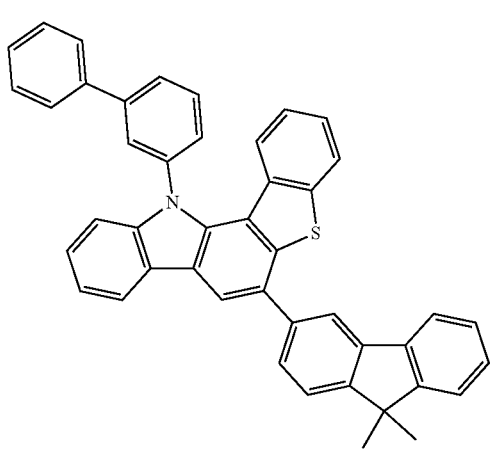
2-46
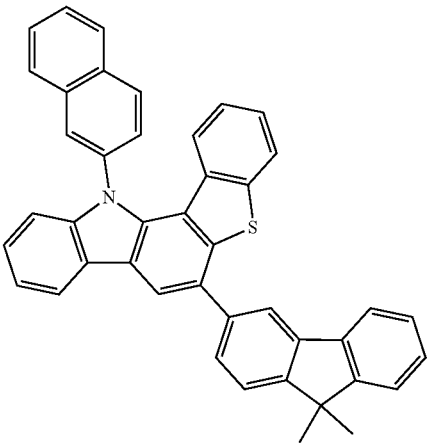
2-47
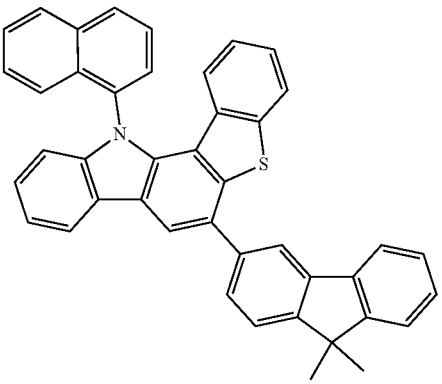
2-48
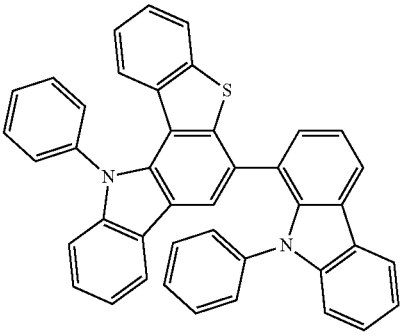
2-49
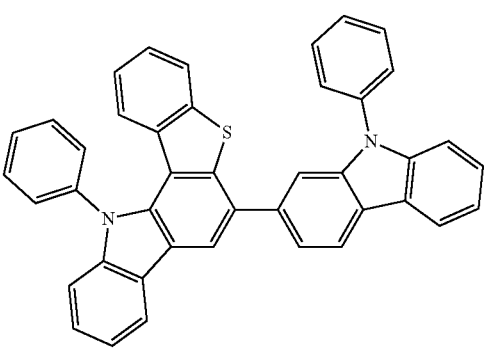

2-50
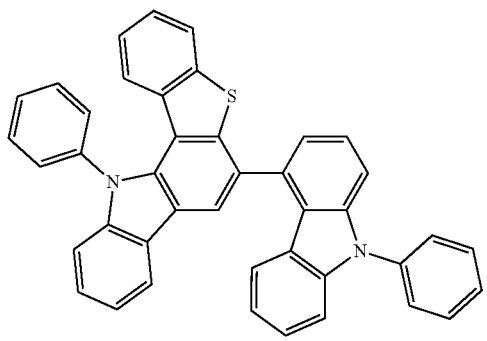
2-54
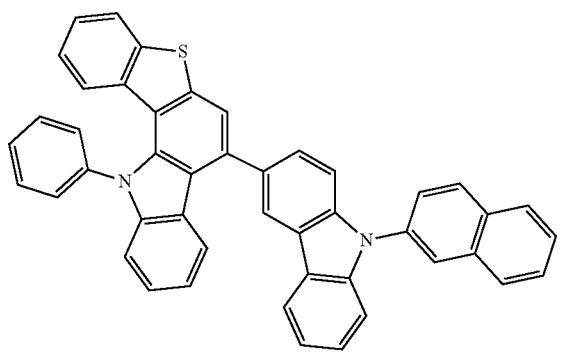
2-51
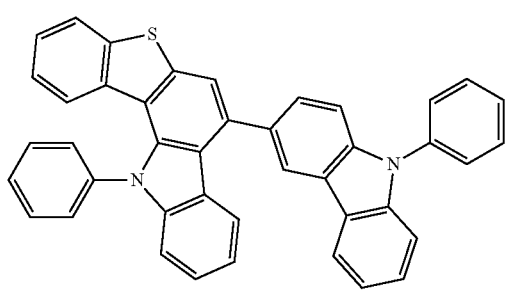
2-55
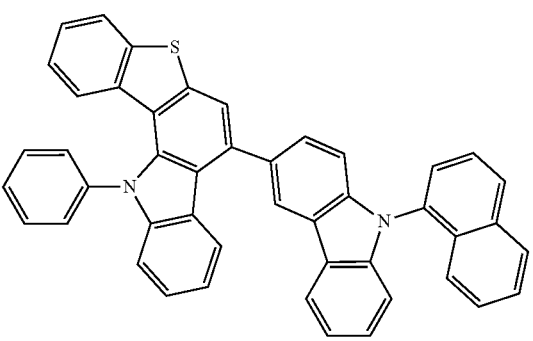
2-52
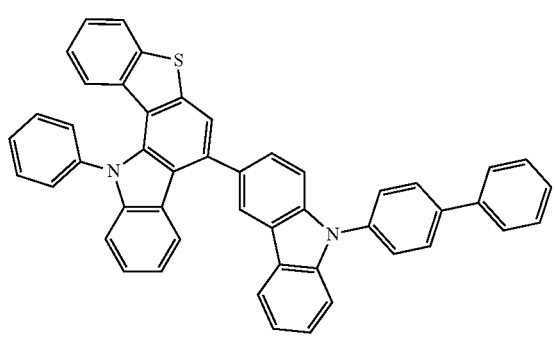
2-56
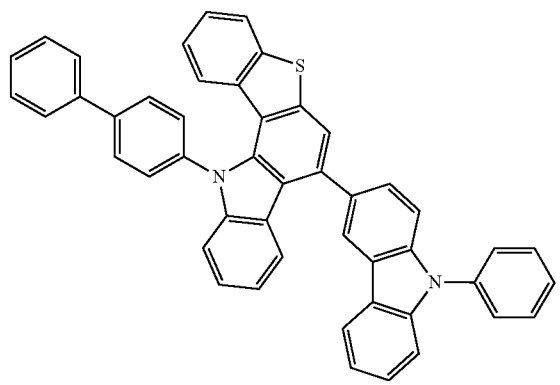
2-53
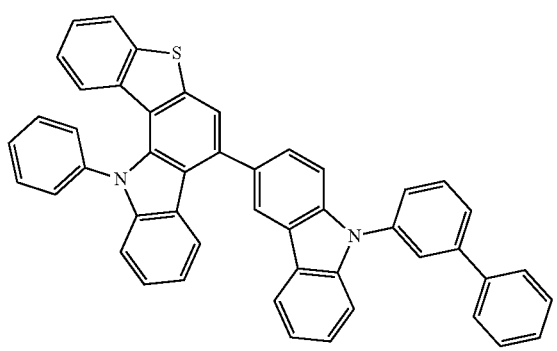
2-57
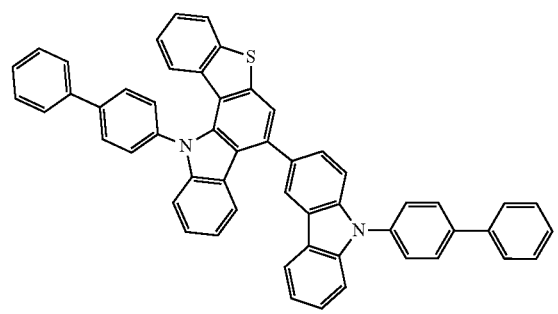

2-58
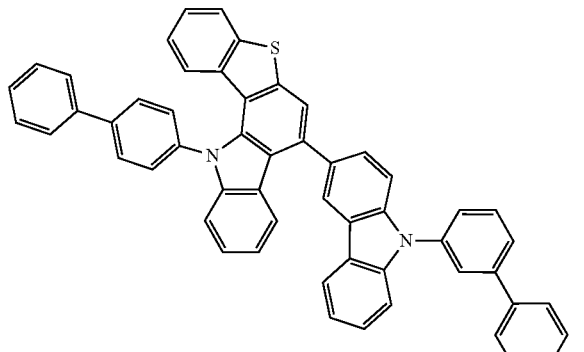
2-59
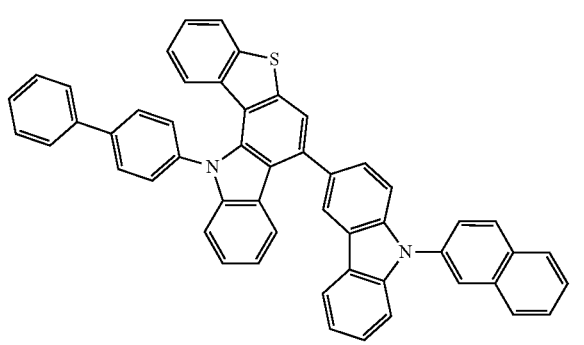
2-60
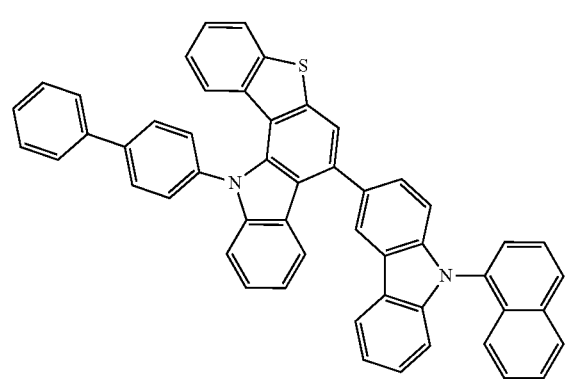
2-61
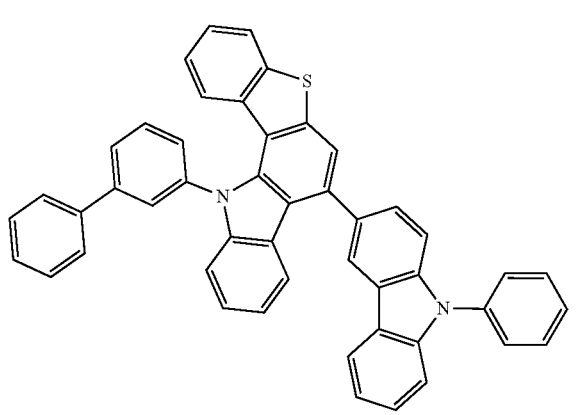
2-62
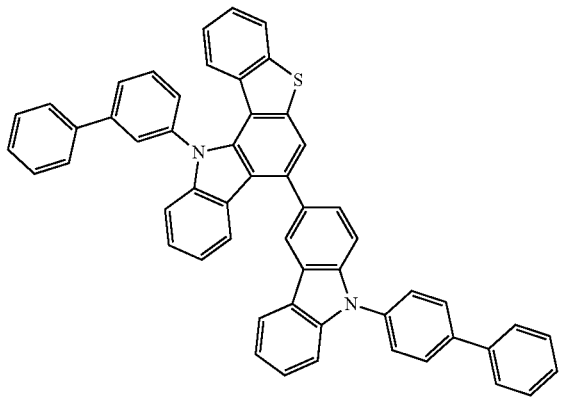
2-63
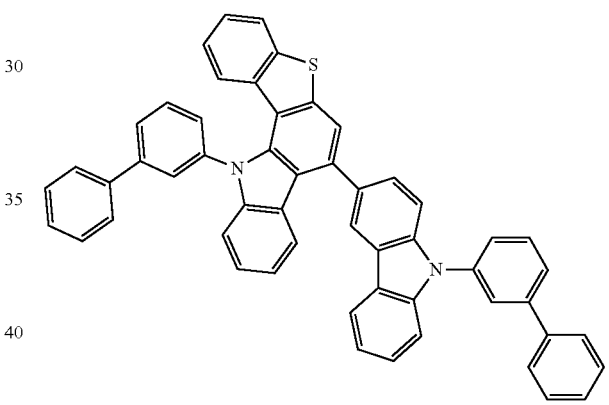
2-64

2-65
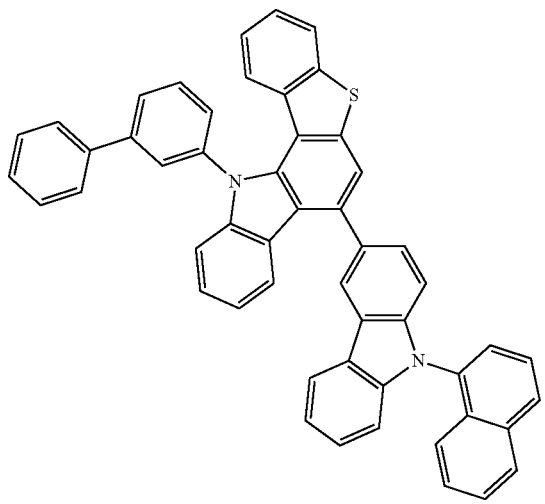
2-66
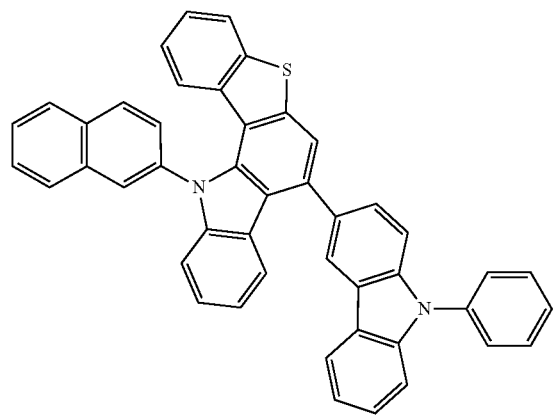
2-67
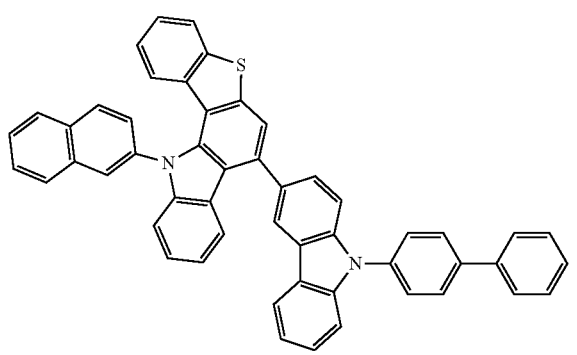
2-68
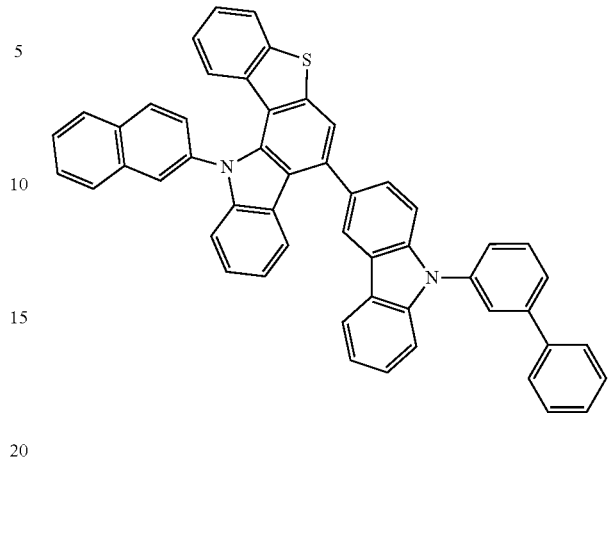
2-69
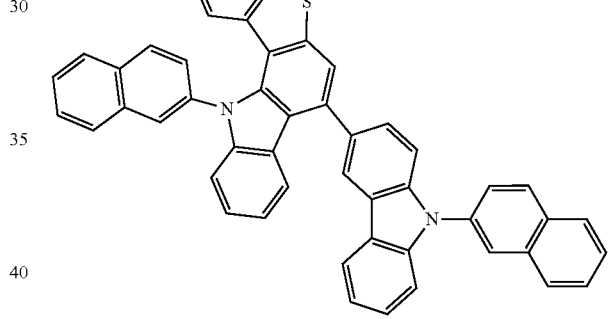
2-70
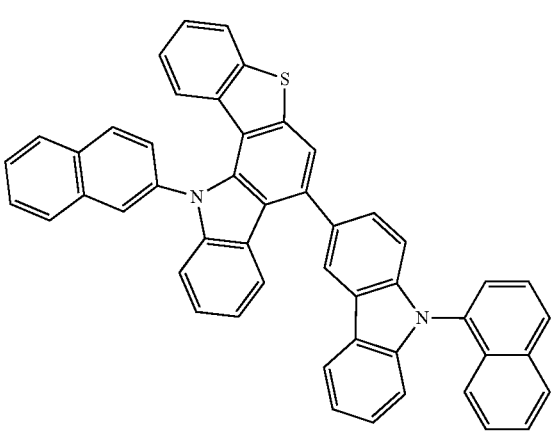

2-71
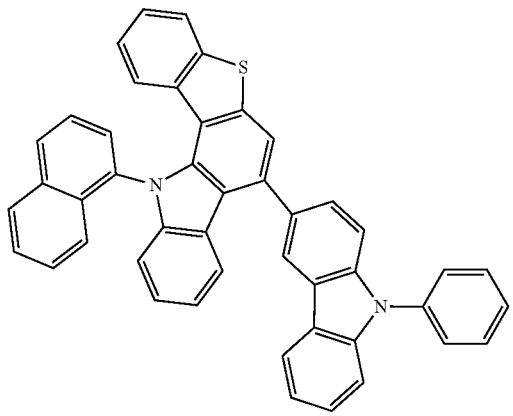
2-72
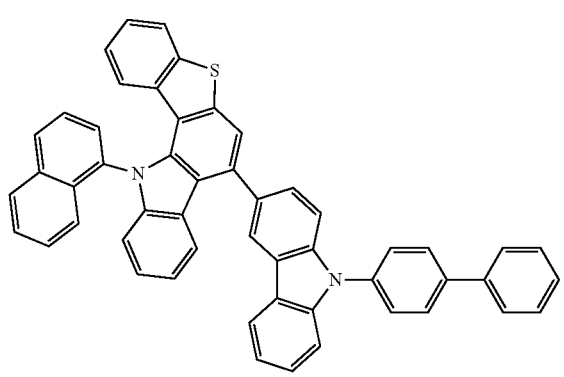
2-73
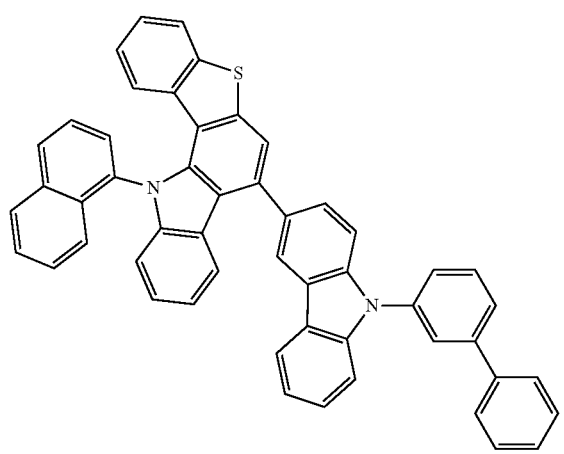
2-74
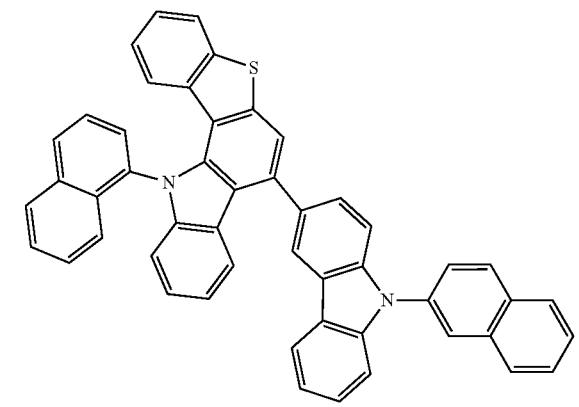
2-75
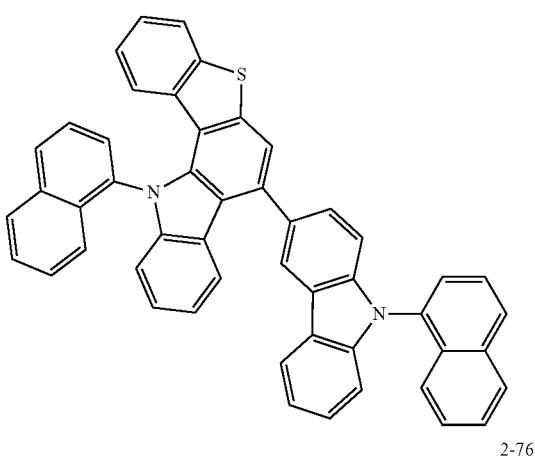
2-76
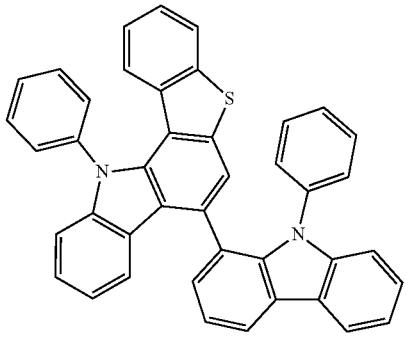
2-77
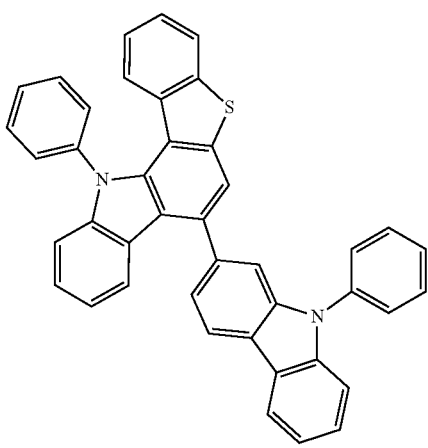

2-78
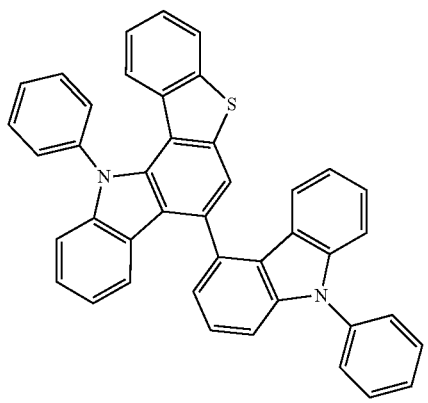
2-79
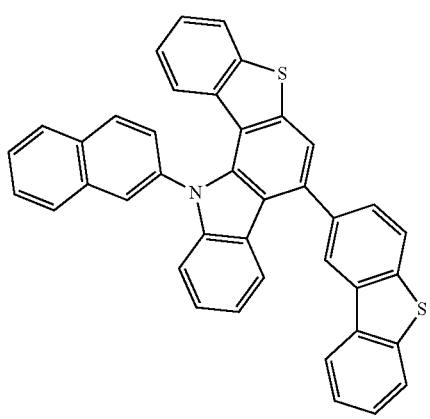
2-80
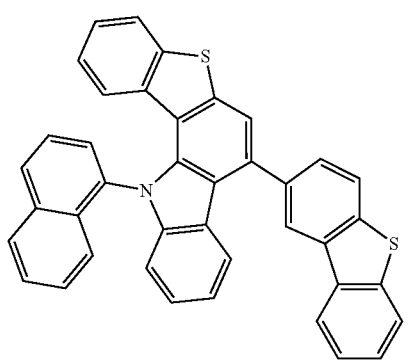
2-81
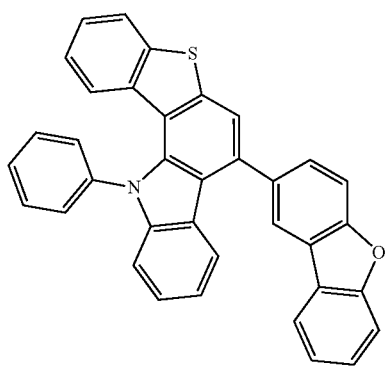
2-82
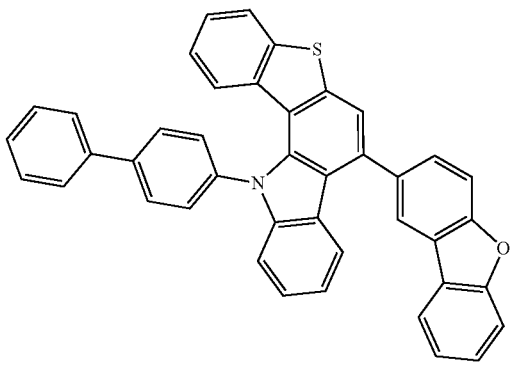
2-83
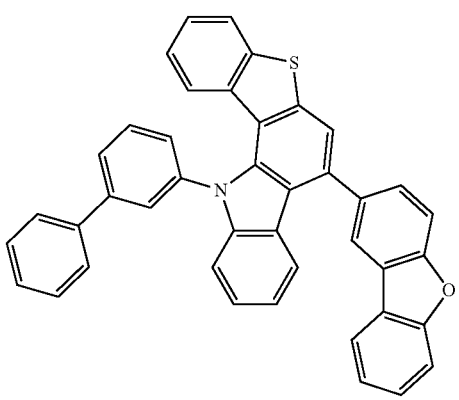
2-84
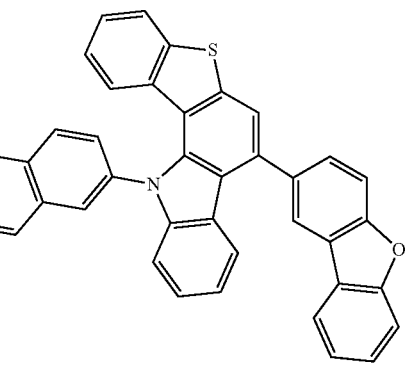
2-85
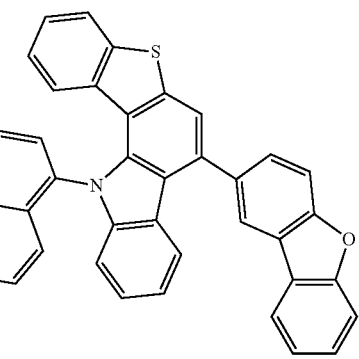

-continued
2-86
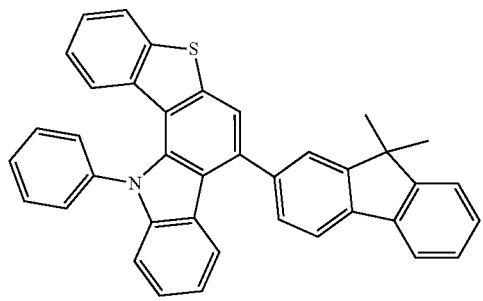
2-87
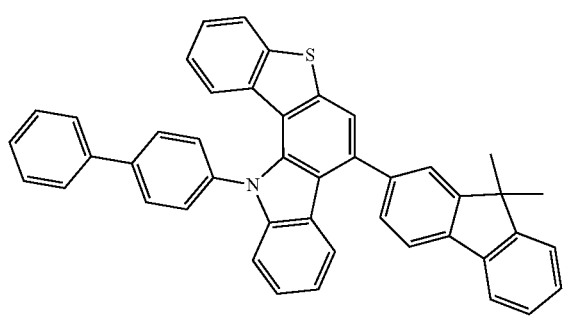
2-88
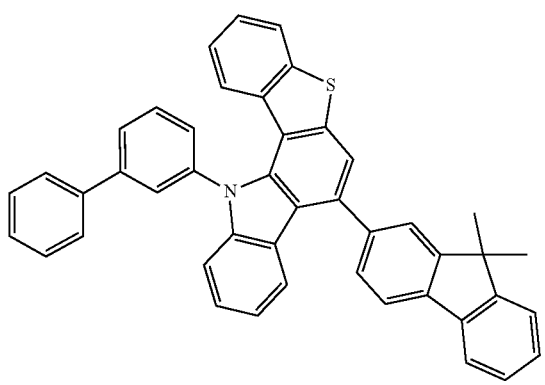
2-89
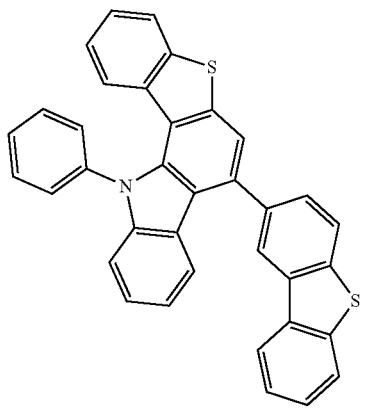
-continued
2-90
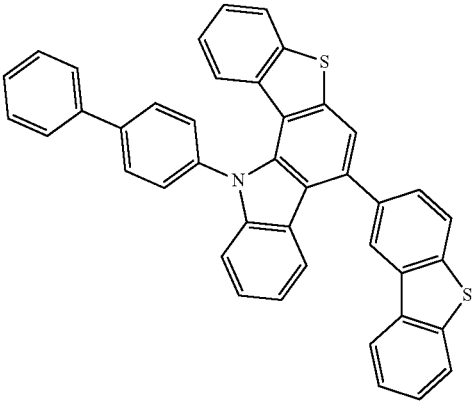
2-91
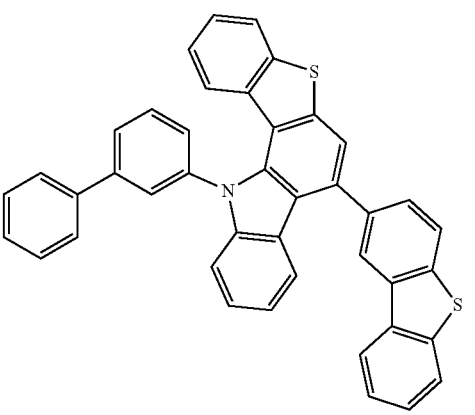
2-92
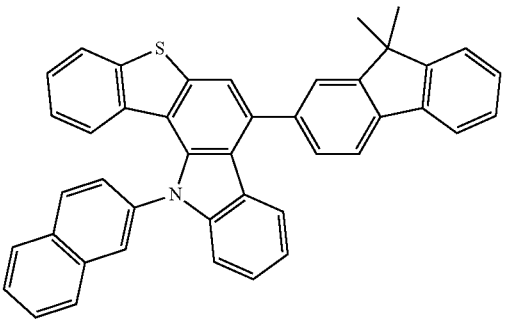
2-93
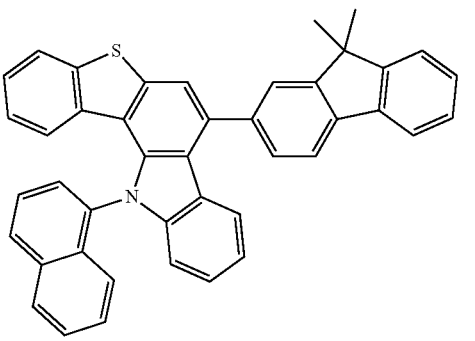

2-94
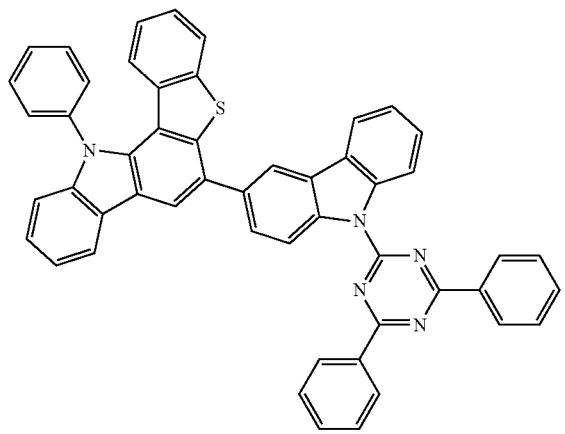
2-95
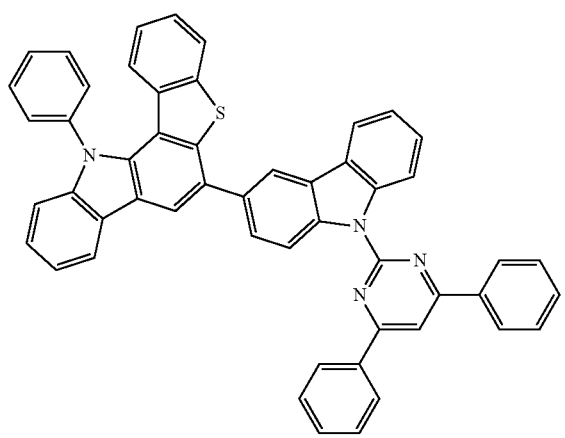
2-96
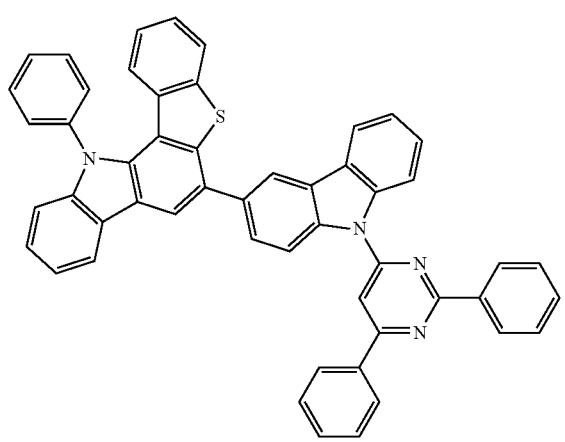
2-97
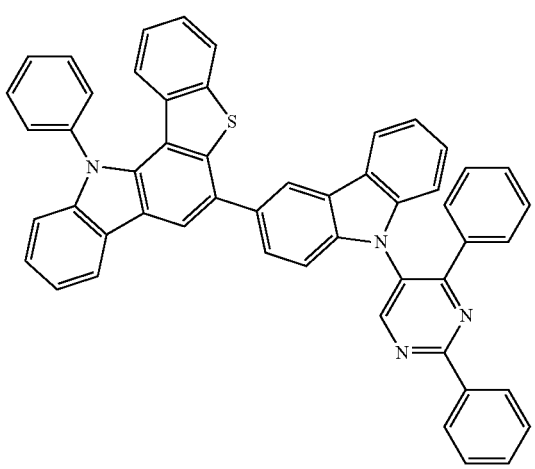
2-98
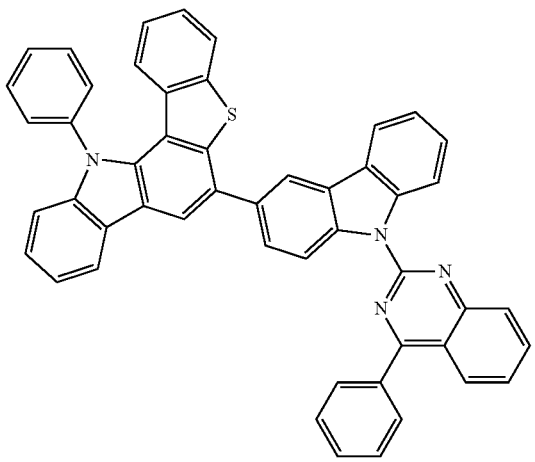
2-99
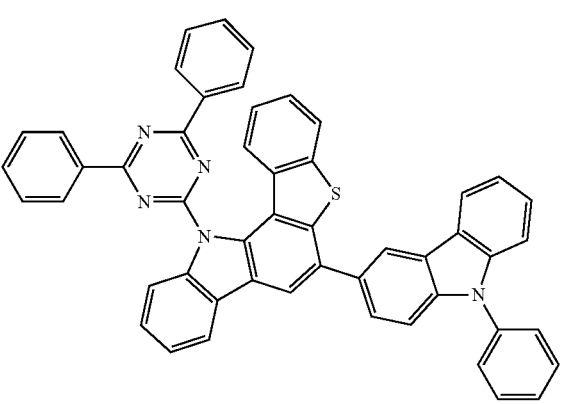

2-100
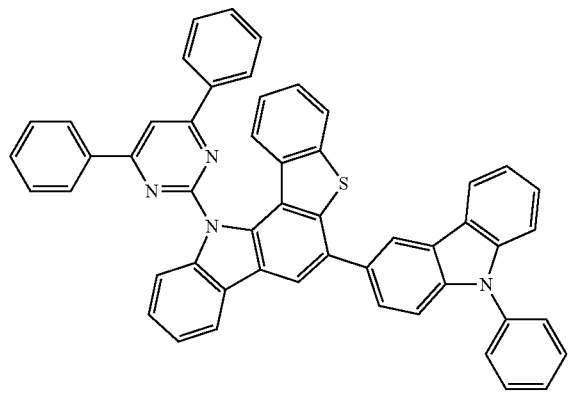
2-101
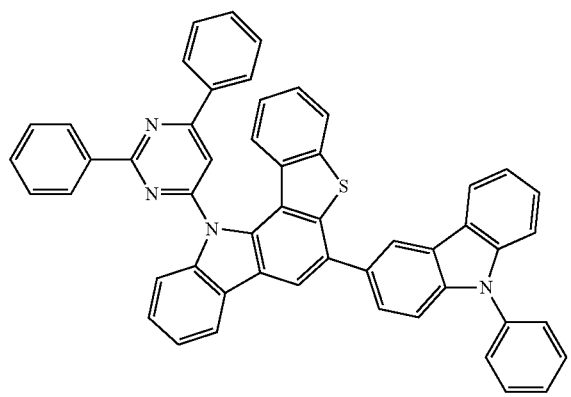
2-102
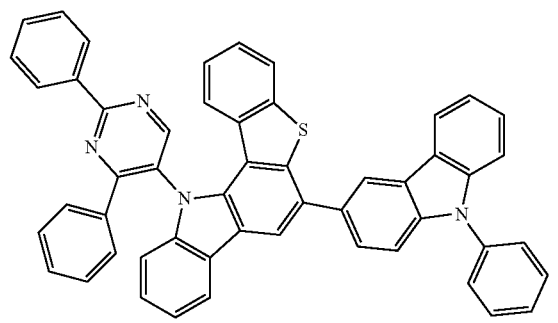
2-103
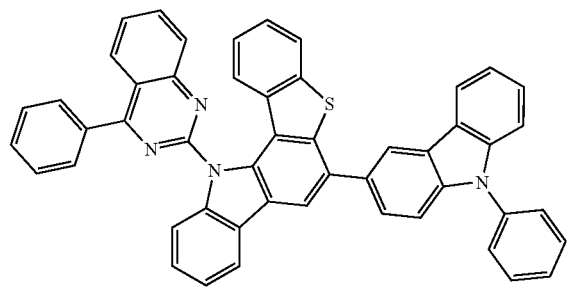
2-104
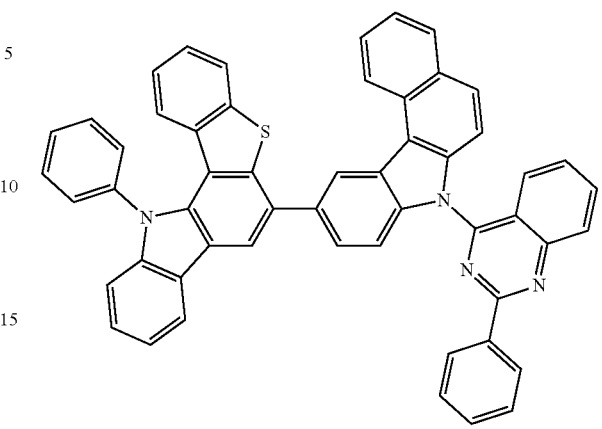
2-105
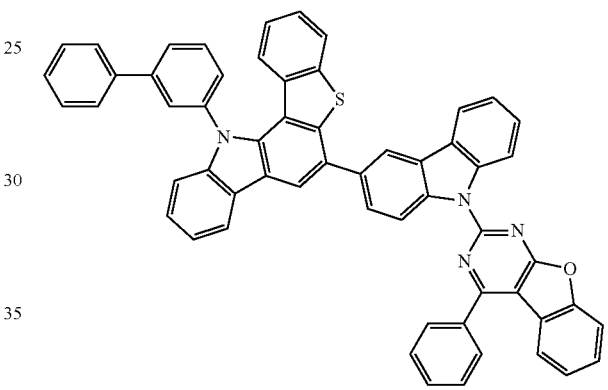
2-106
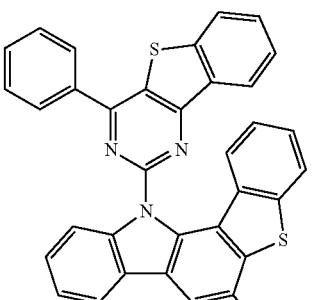
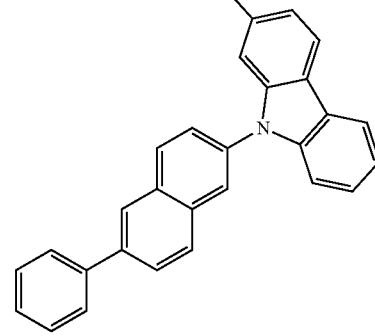

-continued
2-107
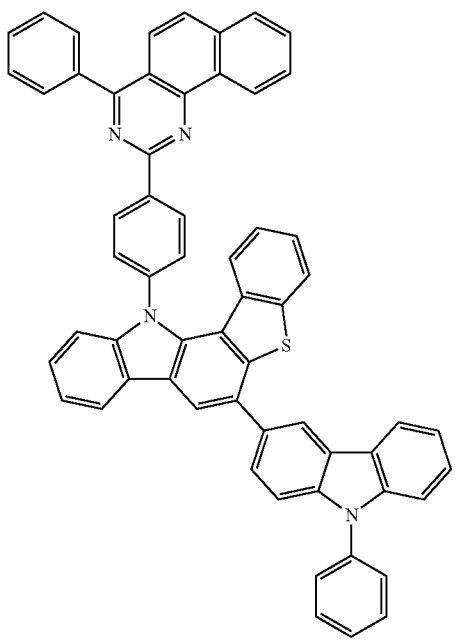
2-109
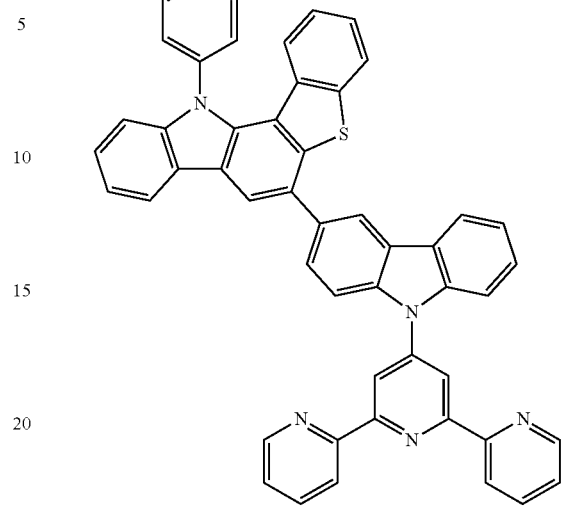
2-108
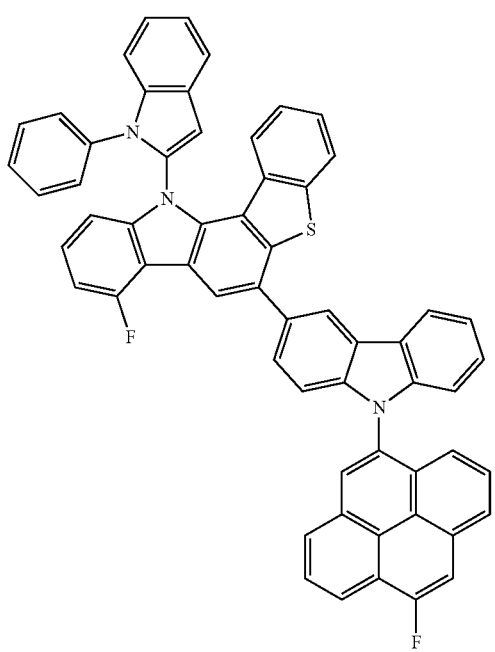
2-110
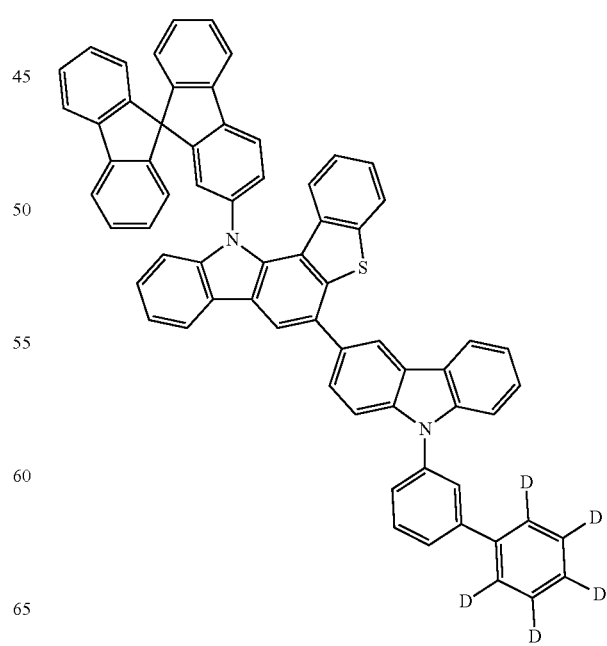

-continued
2-111
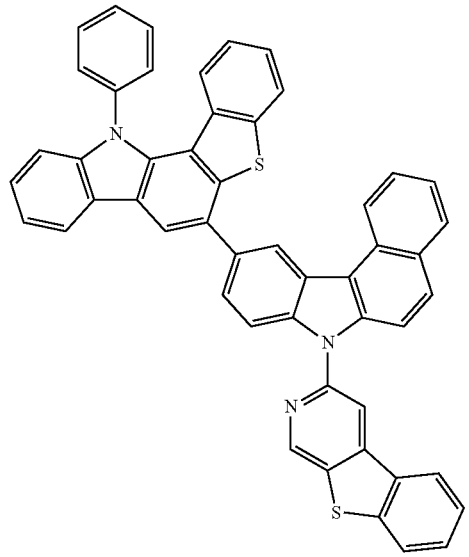
2-114
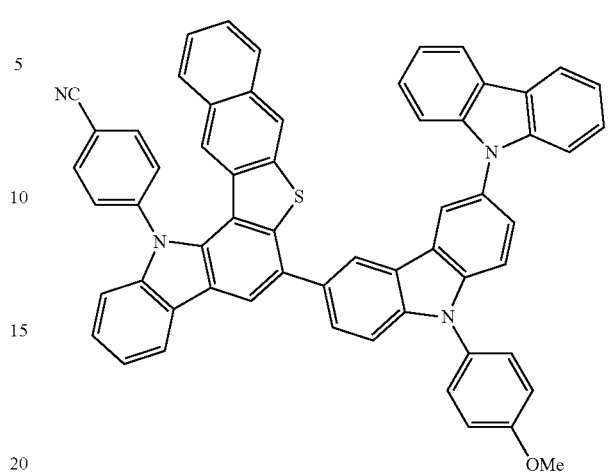
2-112
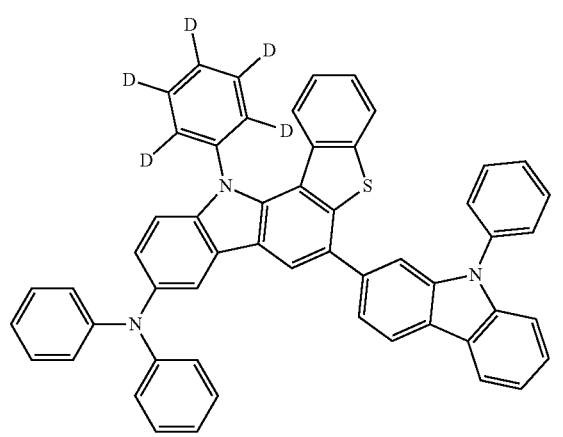
2-115
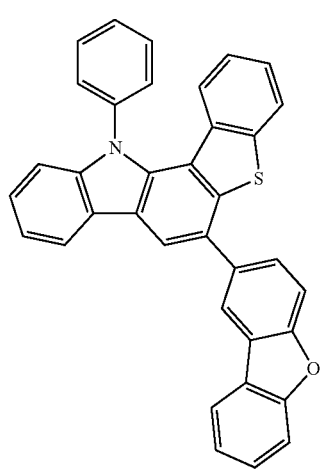
2-113
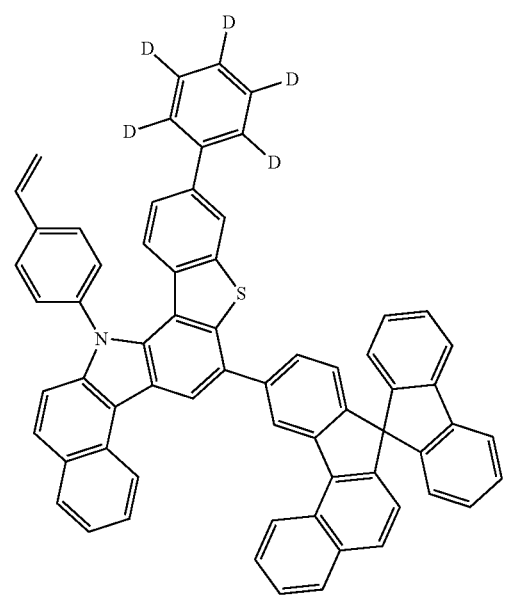
2-116
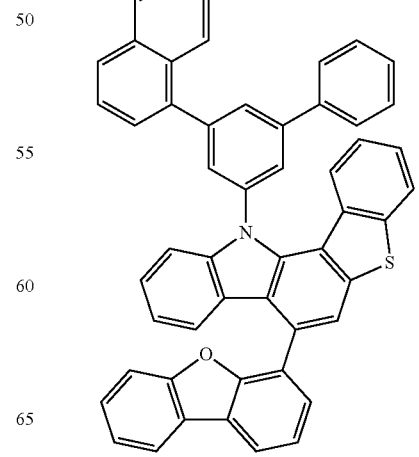

2-117
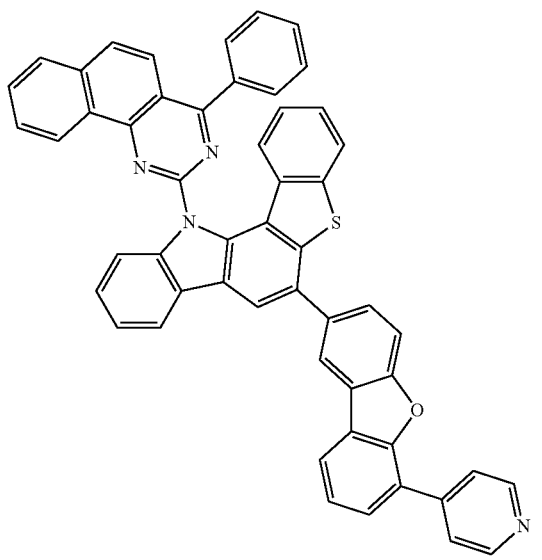
2-118
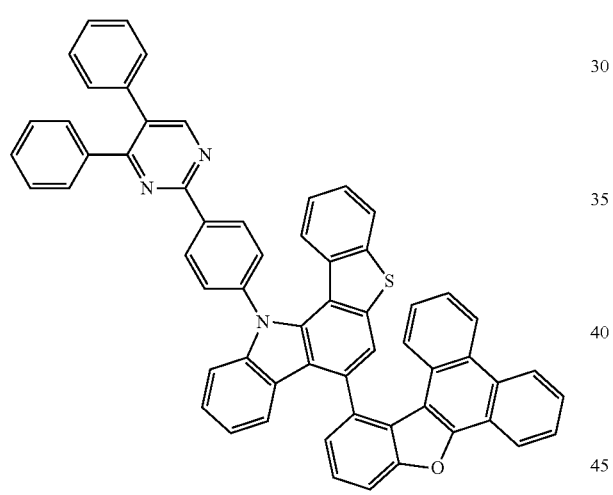
2-119
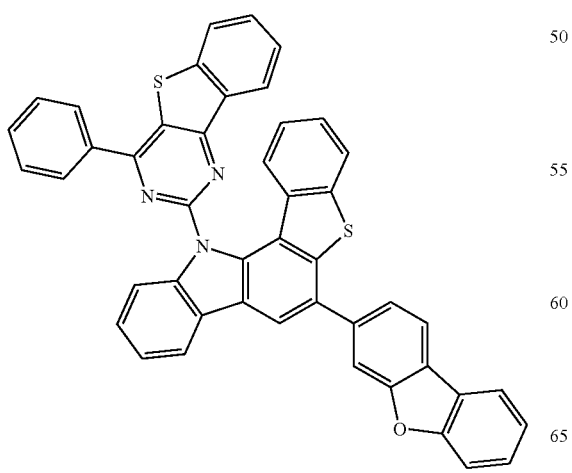
2-120
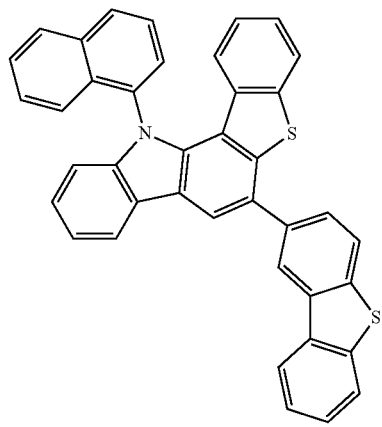
2-121
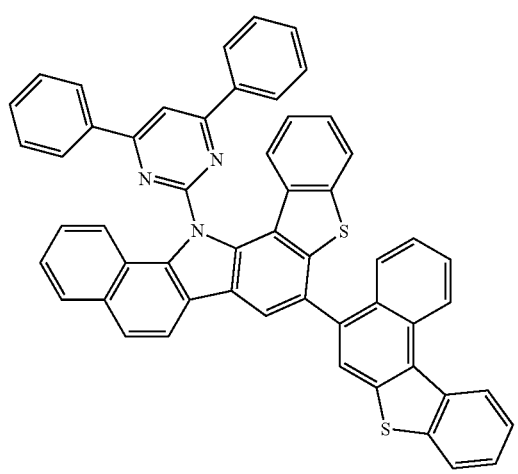
2-122
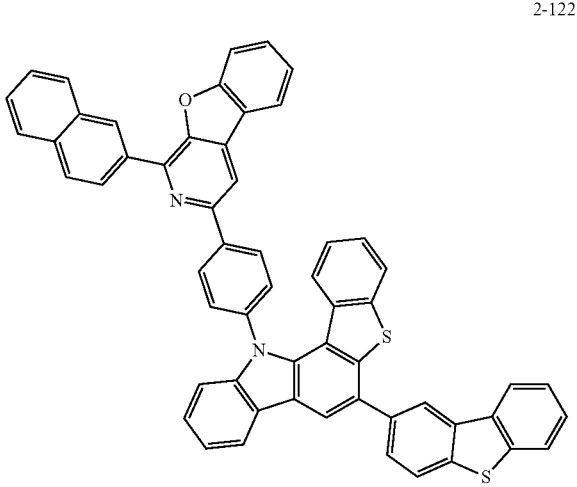

2-123
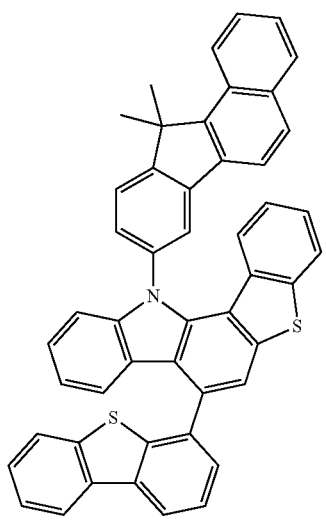
2-124
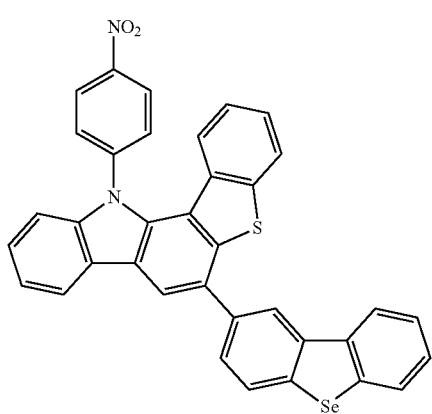
2-125
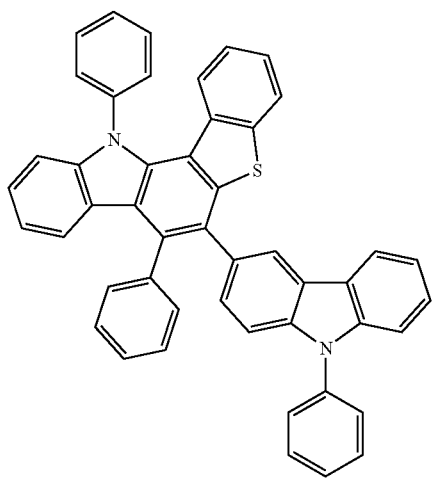
2-126
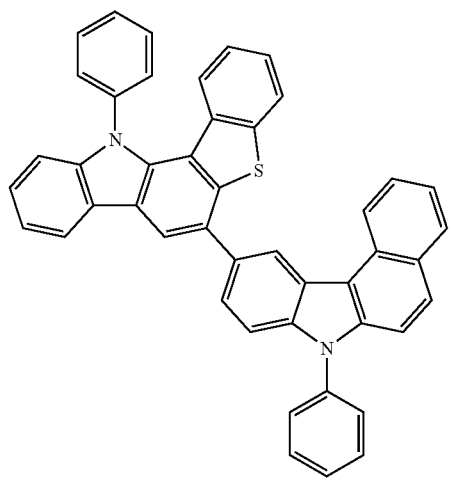
2-127
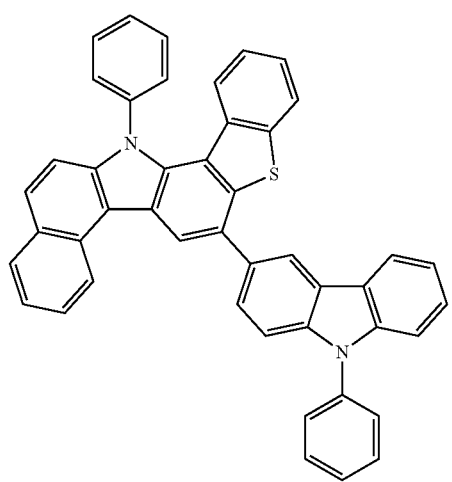
2-128
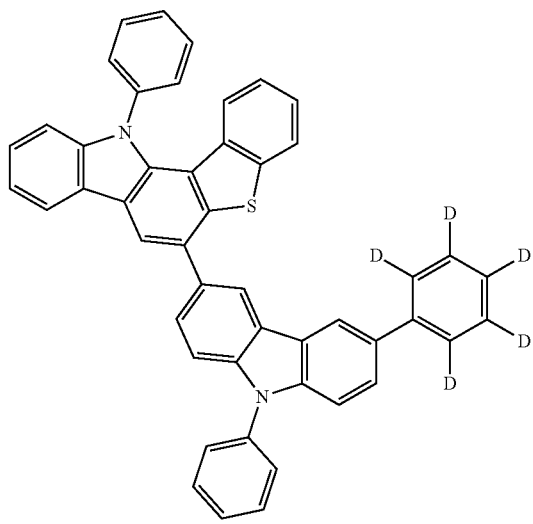

2-129
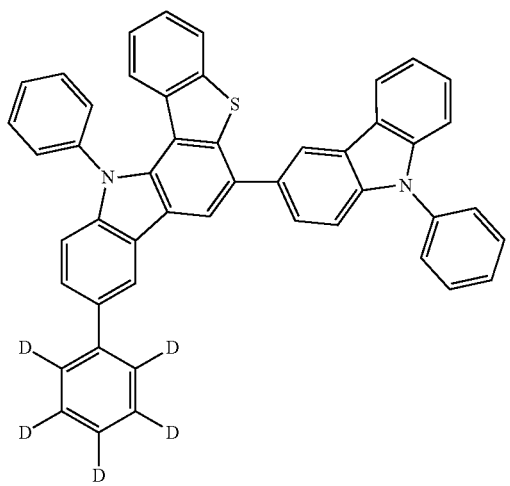
2-133
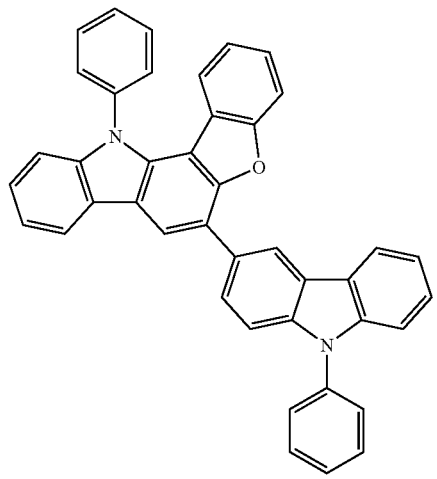
2-130
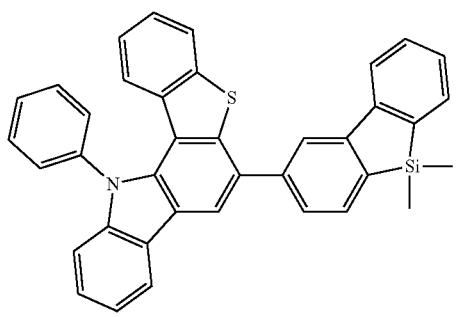
2-134
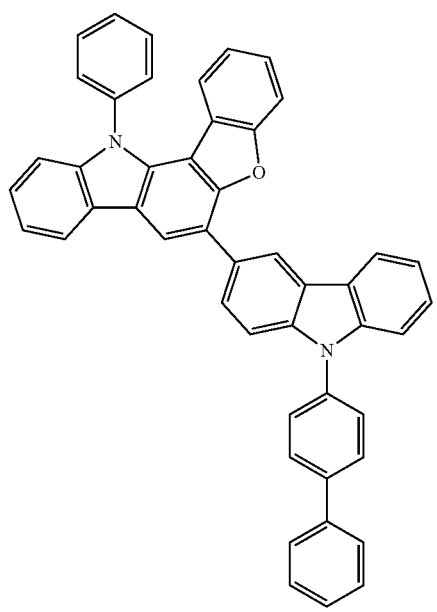
2-131
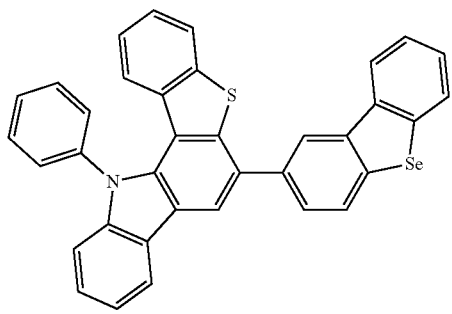
2-132
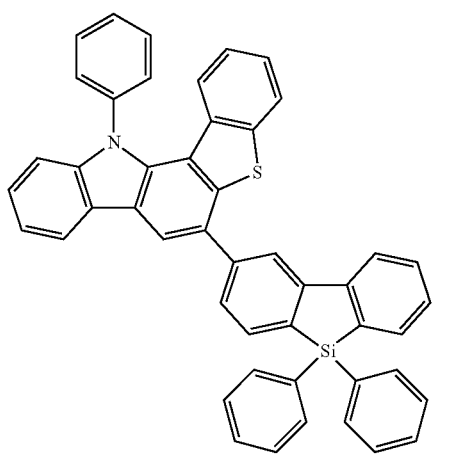
2-135
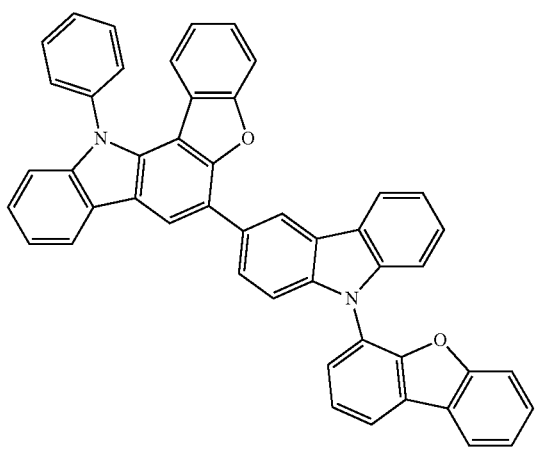

-continued
2-136
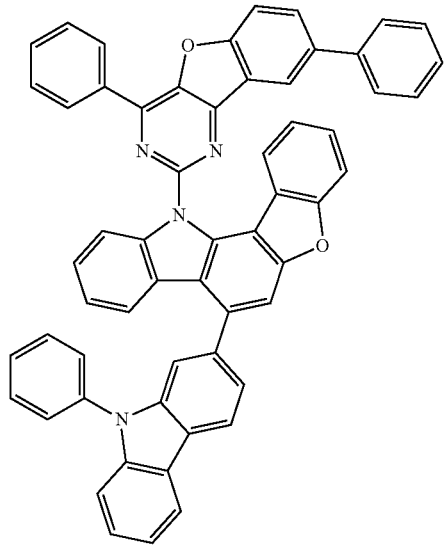
2-137
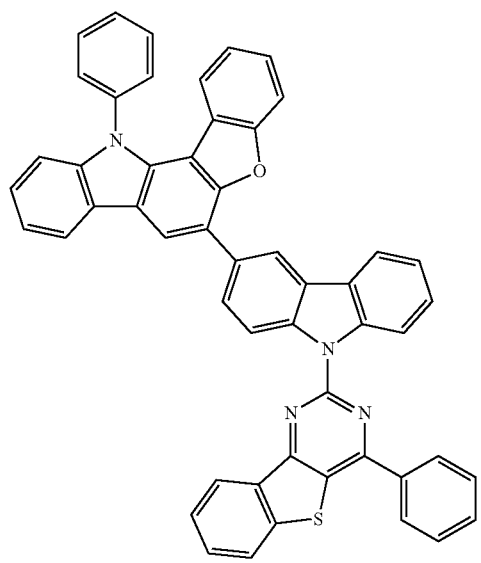
2-138
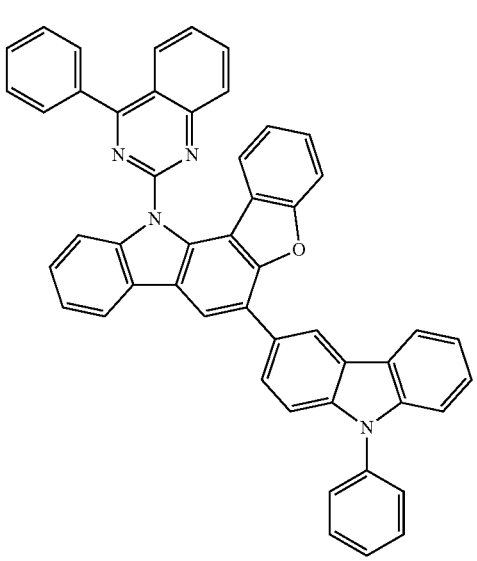
2-139
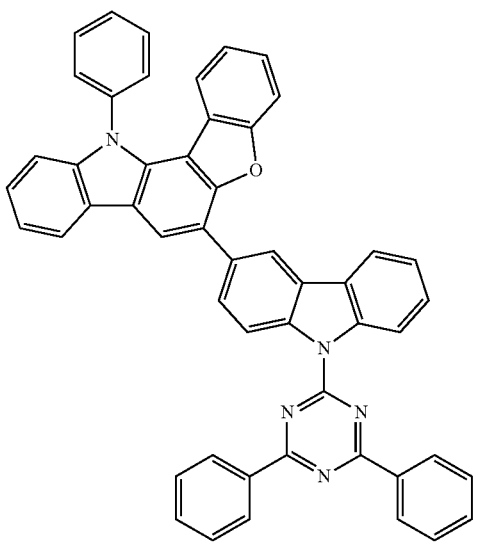

2-140
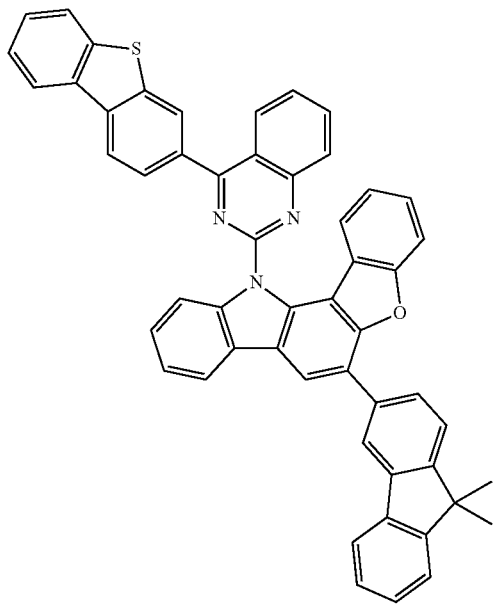
2-141
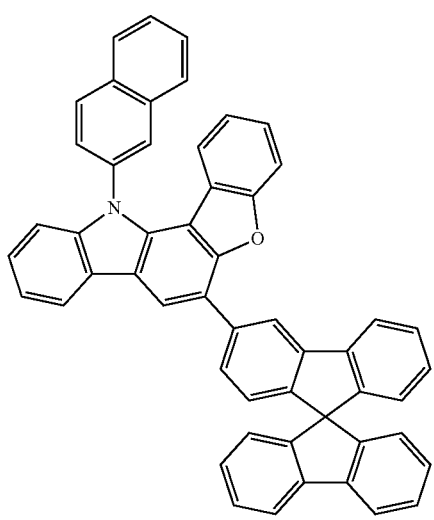
2-142
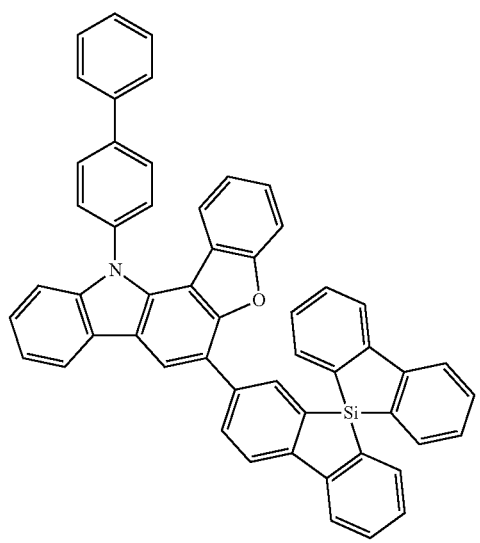
2-143
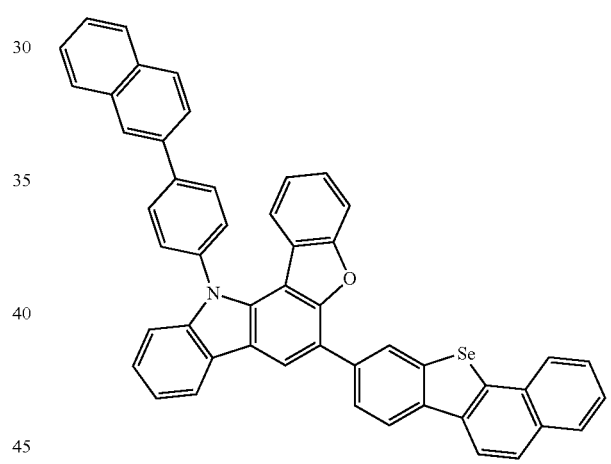
2-144
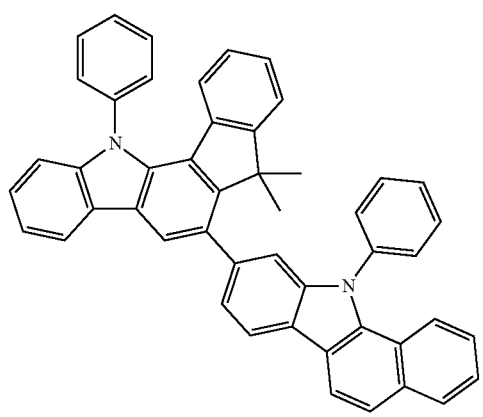

2-145
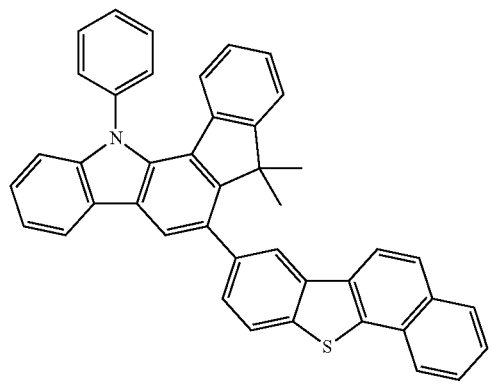
2-146
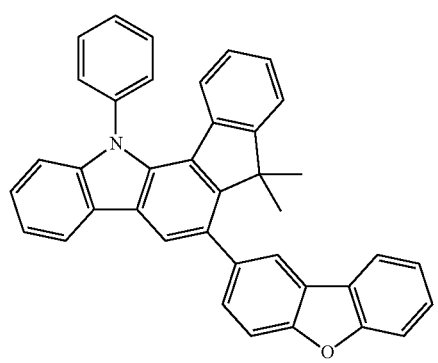
2-147
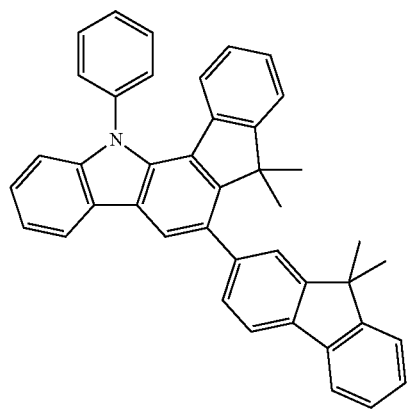
2-148
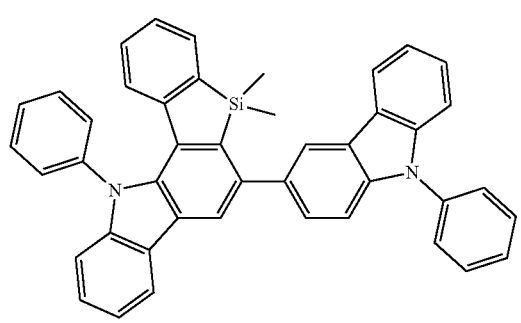
2-149
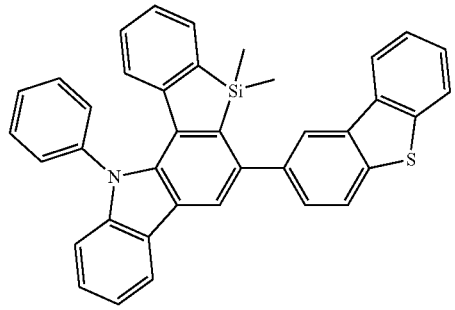
2-150
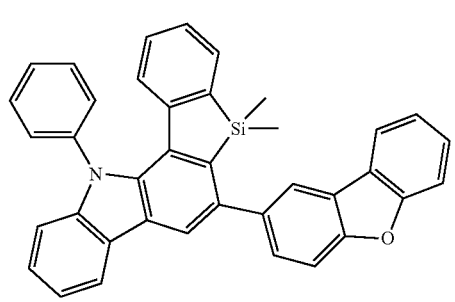
2-151
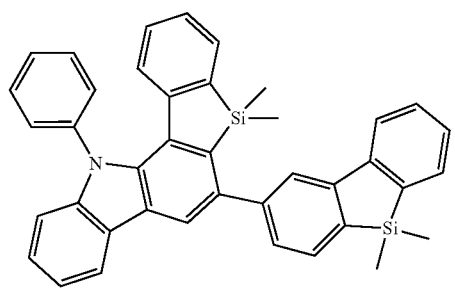
2-152
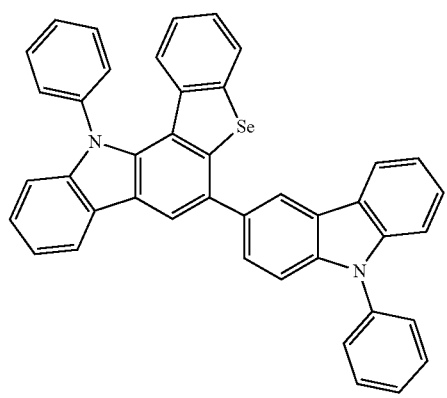
2-153
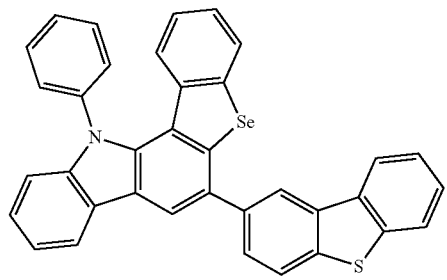

2-154

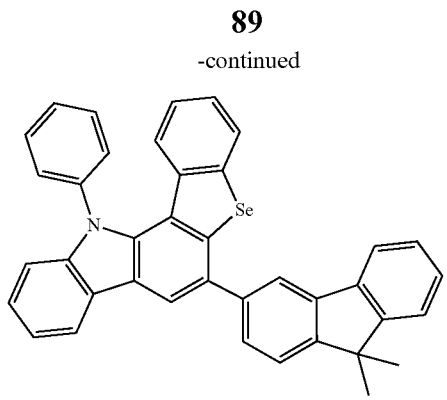

In another aspect of the present invention, the present invention provides an organic electric element comprising a first electrode, a second electrode, and an organic material layer formed between the first electrode and the second electrode. Here, the organic material layer may comprise at least one layer of a hole injection layer, a hole transport layer, an emission-auxiliary layer, a light emitting layer, an electron transport-auxiliary layer, a electron transport layer and a electron injection layer, the compound is comprised in at least one layer of the organic material layer, preferably, in the light emitting layer. The compound comprised in the organic material layer is a single compound or a mixture of two or more kinds represented by Formulas 1 to 9. Also, a layer for improving luminous efficiency is further formed on at least one sides of the first and second electrodes, which is opposite to the organic material layer. The organic material layer may be formed by a spin coating process, a nozzle printing process, an inkjet printing process, a slot coating process, a dip coating process, or a roll-to-roll process.

In another aspect of the present invention, the present invention provides an electronic device comprising a display device, wherein a display device comprises an organic electric element according to the present invention, and a control unit for controlling the display device. The organic electric element may be any one of an organic light emitting diode, an organic solar cell, an organic photo conductor, an organic transistor, and an element for monochromatic or white illumination.

Hereinafter, Synthesis Examples of the compounds represented by Formula 1 and Formula 2 according to the present invention and Preparation Examples of an organic electric element, wherein the compounds are used as materials of the organic layer of the present invention, will be described in detail by way of example. However, the following examples are only for illustrative purposes and are not intended to limit the scope of the invention.

Synthesis Example of Formula 1

The final product of the present invention, represented by Formula 1, can be synthesized by reaction between Sub 1 or Sub 2 and Sub 3 as illustrated in, but not limited to, the following Reaction Scheme 1.

<Reaction Scheme 1>

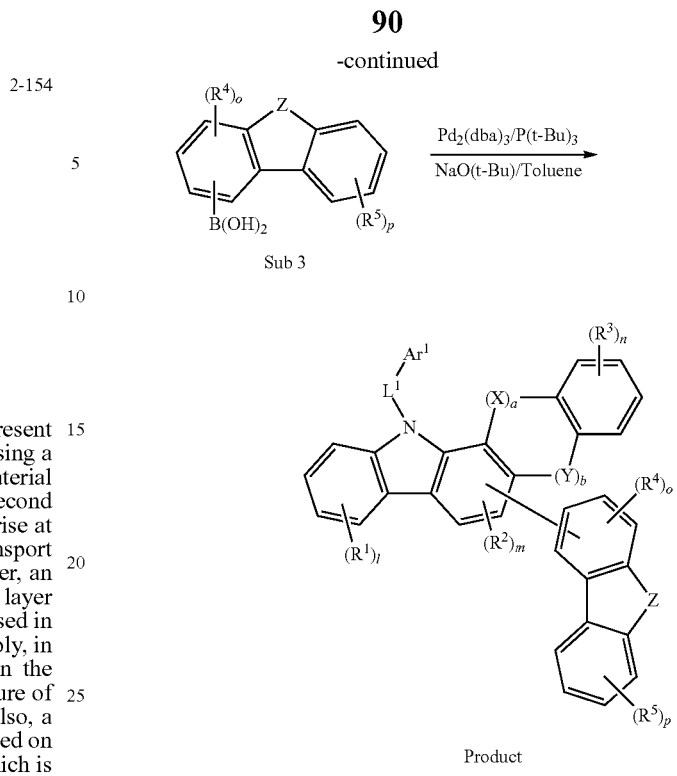

Synthesis Example of Sub 1

Sub 1 of the Reaction Scheme 1 can be synthesized according to, but not limited to, the following Reaction Scheme 2.

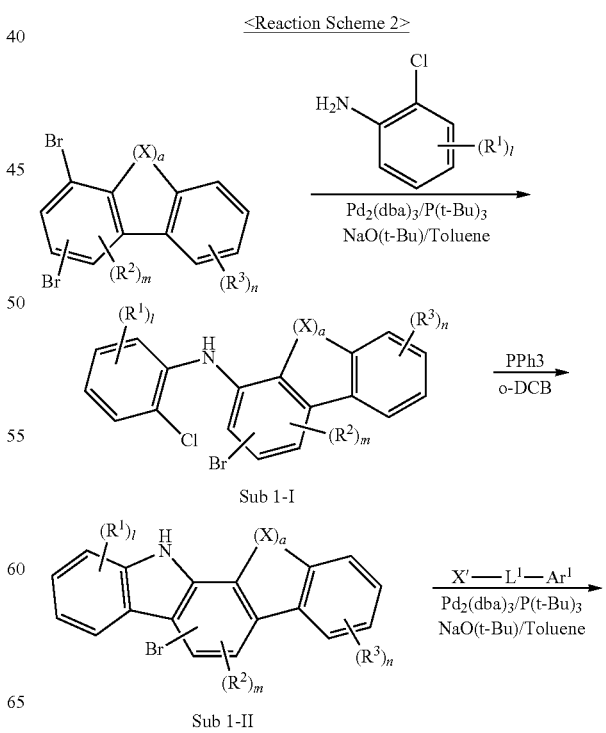

-continued

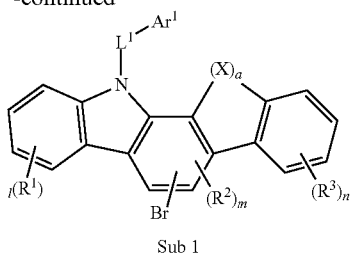

Sub 1

(where X' = I, Br or Cl)

Synthesis Example of compounds comprised in Sub 1 of the reaction scheme 2 is as follows.

1. Synthesis Example of Sub 1-1 (where a=1, b=0, X=S)

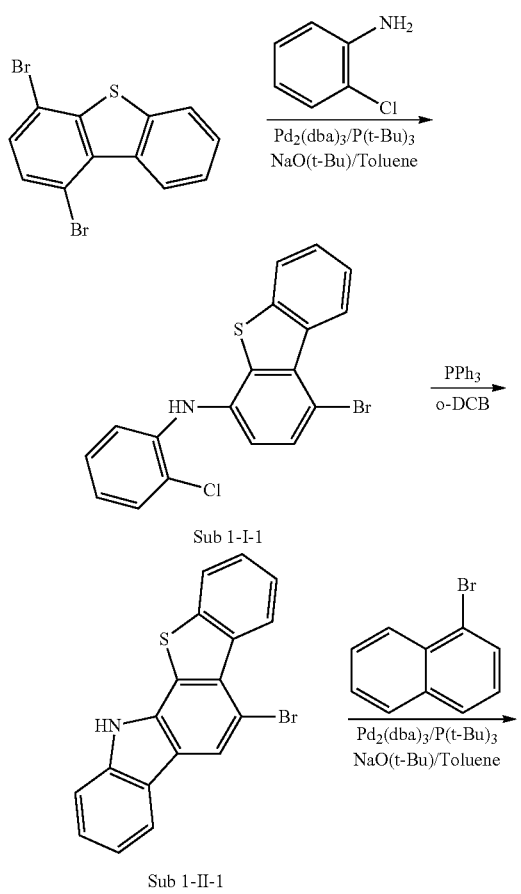

Sub 1-1

Synthesis Method of Sub 1-I-1

To a round bottom flask were added 2-Chloroaniline (67.2 g, 525 mmol), 1,4-Dibromodibenzothiophene (150 g, 438 mmol), $Pd_2(dba)_3$ (16.2 g, 17.4 mmol), $P(t-Bu)_3$ (15 g, 43.8 mmol), NaO(t-Bu) (126 g, 1317 mmol) and Toluene (1.5 L). Then, the mixture was heated and refluxed at 70° C. for 4 hours. When the reaction was completed, the reaction product was diluted with distilled water at room temperature and extracted with methylene chloride and water. The organic layer was dried over $MgSO_4$ and concentrated. The resulting compound was recrystallized with methylene chloride and hexane to obtain the product Sub 1-I-1 (135 g, 79%).

Synthesis Method of Sub 1-II-1

To a round bottom flask were added Sub 1-I-1 (135 g, 348 mmol), $PPh_3$ (228 g, 867 mmol) and o-Dichlorobenzene (900 mL). Then, the mixture was heated and refluxed at 180° C. for 24 hours. When the reaction was completed, the reaction product was cooled to room temperature and concentrated. The resulting compound was purified by column chromatography on silica gel and recrystallized to obtain the product Sub 1-II-1 (91.8 g, 75%).

Synthesis Method of Sub 1-1

To a round bottom flask were added Sub 1-II-1 (30.6 g 87 mmol), 1-Bromonaphthalene (21.5 g, 104 mmol), $Pd_2(dba)_3$ (3.2 g, 3.5 mmol), $P(t-Bu)_3$ (1.8 g, 8.7 mmol), NaO(t-Bu) (25 g, 261 mmol), and Toluene (300 mL). Then, the mixture was heated and refluxed at 110° C. for 8 hours. When the reaction was completed, the reaction product was diluted with distilled water at room temperature and extracted with methylene chloride and water. The organic layer was dried over $MgSO_4$ and concentrated. The resulting compound was recrystallized with methylene chloride and hexane to obtain the product Sub 1-1 (31.6 g, 74%).

2. Synthesis Example of Sub 1-2 (where a=1, b=0, X=S)

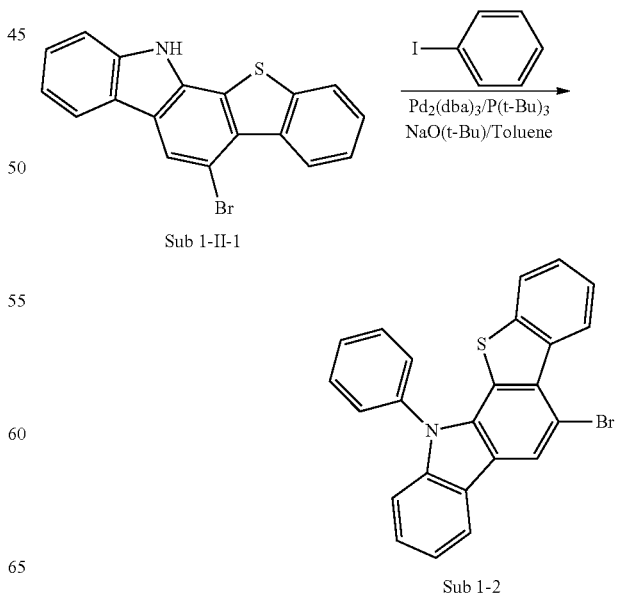

Sub 1-2

To a round bottom flask were added Sub 1-II-1 (30 g, 84 mmol), Iodobenzene (20.7 g, 102 mmol), Pd₂(dba)₃ (3 g, 3.3 mmol), P(t-Bu)₃ (1.8 g, 8.4 mmol), NaO(t-Bu) (24.6 g, 255 mmol) and Toluene (240 mL), and then the product Sub 1-2 (28 g, 76%) was obtained by using the same manner as described above for the synthesis of compound Sub 1-1.

3. Synthesis Example of Sub 1-3 (where a=1, b=0, X=S)

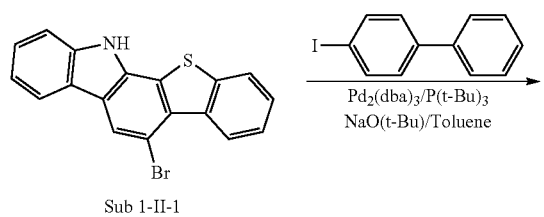

To a round bottom flask were added Sub 1-II-1 (30.6 g 87 mmol), 4-Iodo-1,1'-biphenyl (29.2 g, 104 mmol), Pd₂(dba)₃ (3.2 g, 3.5 mmol), P(t-Bu)₃ (1.8 g, 8.7 mmol), NaO(t-Bu) (25 g, 261 mmol), and Toluene (300 mL), and then the product Sub 1-3 (32 g, 74%) was obtained by using the same manner as described above for the synthesis of compound Sub 1-1.

Synthesis Example of Sub 1-5 (where a=1, b=0, X=S)

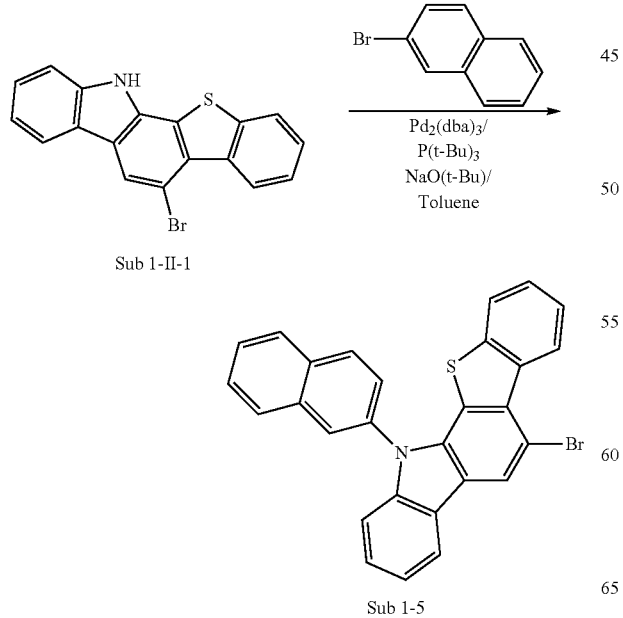

To a round bottom flask were added Sub 1-II-1 (30.6 g 87 mmol), 2-Bromonaphthalene (21.5 g, 104 mmol), Pd₂(dba)₃ (3.2 g, 3.5 mmol), P(t-Bu)₃ (1.8 g, 8.7 mmol), NaO(t-Bu) (25 g, 261 mmol) and Toluene (300 mL), and then the product Sub 1-5 (29.1 g, 70%) was obtained by using the same manner as described above for the synthesis of compound Sub 1-1.

Synthesis Example of Sub 1-6 (where a=1, b=0, X=S)

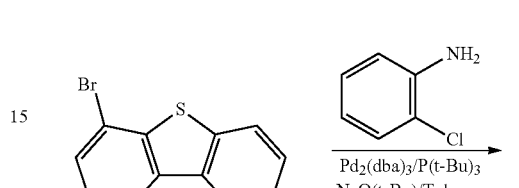

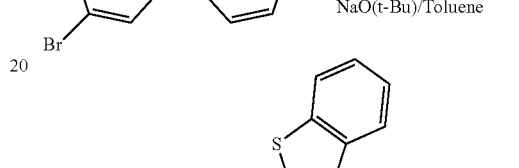

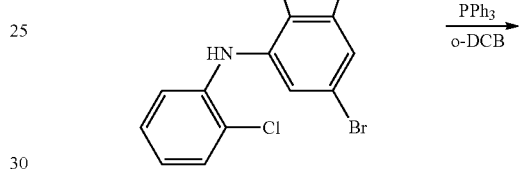

Synthesis Method of Sub 1-I-6 (where a=1, b=0, X=S)

To a round bottom flask were added 2-Chloroaniline (22.4 g, 175 mmol), 2,4-Dibromodibenzothiophene (50 g, 146 mmol), Pd₂(dba)₃ (5.4 g, 5.8 mmol), P(t-Bu)₃ (5 g, 14.6 mmol), NaO(t-Bu) (42 g, 439 mmol) and Toluene (500 mL), and then the product Sub 1-I-6 (46 g, 90%) was obtained by using the same manner as described above for the synthesis of compound Sub 1-I-1.

Synthesis Method of Sub 1-II-6

To a round bottom flask were added Sub 1-I-6 (45 g, 116 mmol), PPh₃ (76 g, 289 mmol), and o-Dichlorobenzene (300 mL), and then the product Sub 1-II-6 (32.6 g, 80%) was obtained by using the same manner as described above for the synthesis of compound Sub 1-II-1.

Synthesis Method of Sub 1-6

To a round bottom flask were added Sub 1-II-6 (10 g, 28 mmol), Iodobenzene (6.9 g, 34 mmol), Pd₂(dba)₃ (1 g, 1.1 mmol), P(t-Bu)₃ (0.6 g, 2.8 mmol), NaO(t-Bu) (8.2 g, 85 mmol), and Toluene (80 mL), and then the product Sub 1-6 (10 g, 84%) was obtained by using the same manner as described above for the synthesis of compound Sub 1-1.

Synthesis Example of Sub 1-7 (where a=1, b=0, X=S)

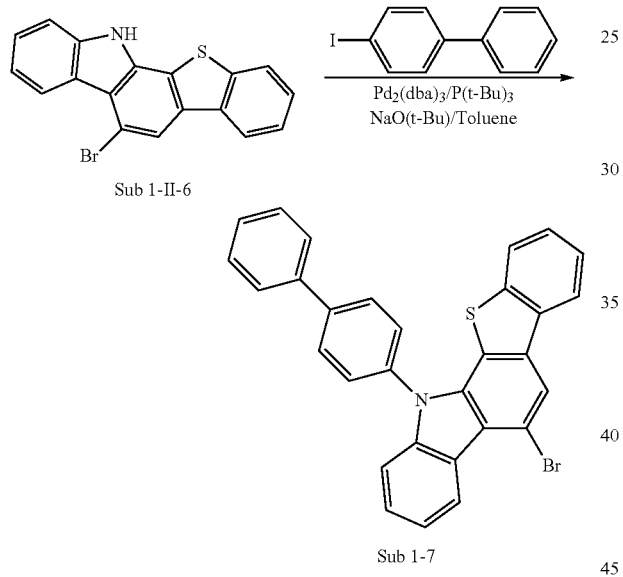

To a round bottom flask were added Sub 1-II-6 (10 g, 28 mmol), 4-Iodo-1,1'-biphenyl (9.5 g, 34 mmol), Pd₂(dba)₃ (1 g, 1.1 mmol), P(t-Bu)₃ (0.6 g, 2.8 mmol), NaO(t-Bu) (8.2 g, 85 mmol) and Toluene (80 mL), and then the product Sub 1-7 (10 g, 71%) was obtained by using the same manner as described above for the synthesis of compound Sub 1-1.

Synthesis Example of Sub 1-14 (where a=1, b=0, X=S)

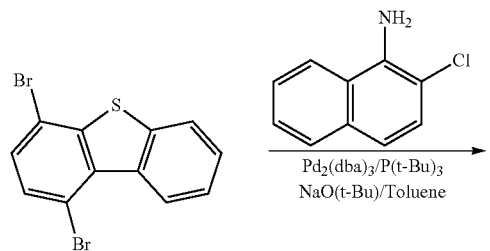

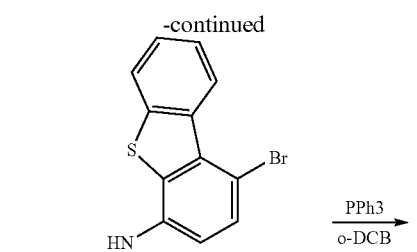

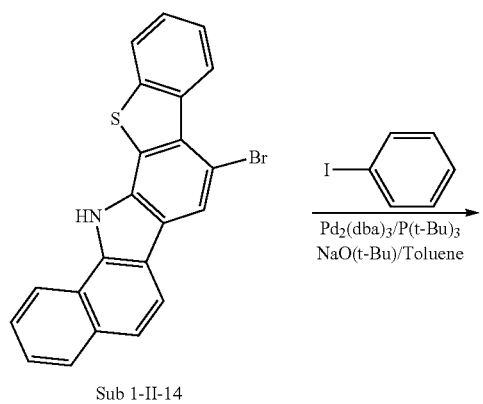

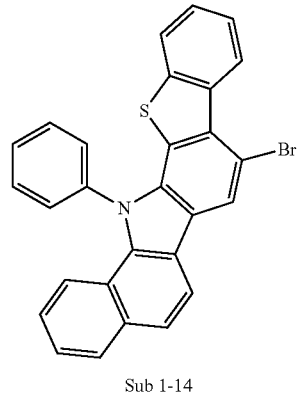

Synthesis Method of Sub 1-I-14

To a round bottom flask were added 2-Chloronaphthalen-1-amine (31 g, 175 mmol), 2,4-Dibromodibenzothiophene (50 g, 146 mmol), Pd₂(dba)₃ (5.4 g, 5.8 mmol), P(t-Bu)₃ (5 g, 14.6 mmol), NaO(t-Bu) (42 g, 439 mmol) and Toluene (500 mL), and then the product Sub 1-I-14 (48 g, 75%) was obtained by using the same manner as described above for the synthesis of compound Sub 1-I-1.

Synthesis Method of Sub 1-II-14

To a round bottom flask were added Sub 1-I-14 (30 g, 68 mmol), PPh₃ (45 g, 171 mmol) and o-Dichlorobenzene (150 mL). Then, the mixture was heated and refluxed at 180° C. for 24 hours. When the reaction was completed, the reaction product was cooled to room temperature and concentrated. The resulting compound was purified by column chromatography on silica gel and recrystallized to obtain the product Sub 1-II-14 (25 g, 93%).

Synthesis Method of Sub 1-14

To a round bottom flask were added Sub 1-II-14 (25 g, 62 mmol), Iodobenzene (15 g 75 mmo), Pd$_2$(dba)$_3$ (2. g, 2.5 mmol), P(t-Bu)$_3$ (1.3 g (6.2 mmol), NaO(t-Bu) (18 g, 186 mmol) and Toluene (300 mL). Then, the mixture was heated and refluxed at 110° C. for 8 hours. When the reaction was completed, the reaction product was diluted with distilled water at room temperature and extracted with methylene chloride and water. The organic layer was dried over MgSO$_4$ and concentrated. The resulting compound was recrystallized with methylene chloride and hexane to obtain the product Sub 1-14 (20 g, 67%).

Synthesis Example of Sub 1-25 (where a=1, b=0, X=O)

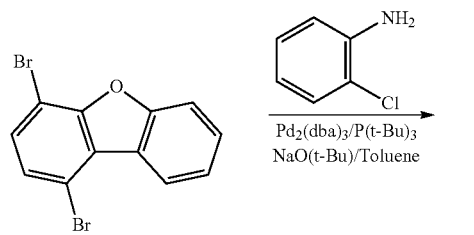

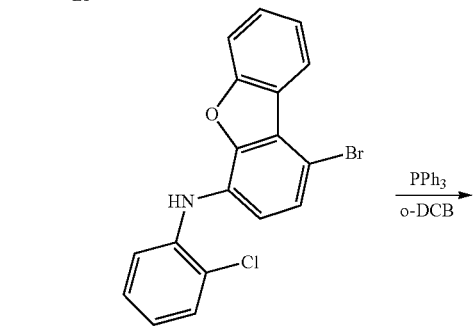

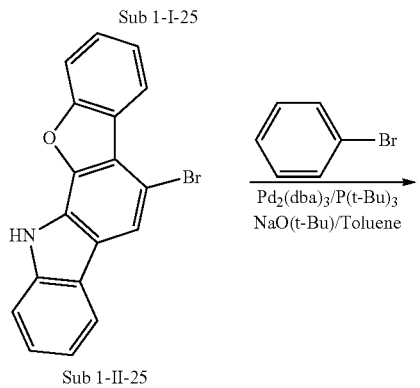

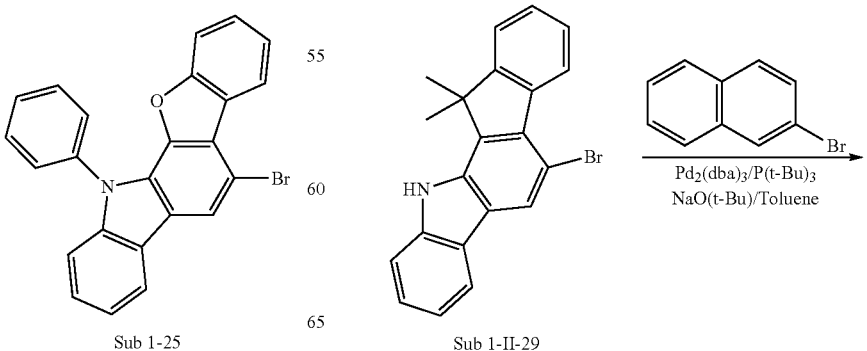

Synthesis Method of Sub 1-I-25

To a round bottom flask were added 2-Chloronaphthalen-1-amine (23.45 g, 183.85 mmol), 1,4-dibromodibenzo[b,d]furan (50 g, 153.4 mmol), Pd$_2$(dba)$_3$ (5.58 g, 6.1 mmol), P(t-Bu)$_3$ (3.1 g, 15.34 mmol), NaO(t-Bu) (44.32 g, 461.2 mmol) and Toluene (340 mL), and then the product Sub 1-I-25 (41.7 g, 73%) was obtained by using the same manner as described above for the synthesis of compound Sub 1-I-1.

Synthesis Method of Sub 1-II-25

To a round bottom flask were added Sub 1-I-25 (47 g, 126.1 mmol), PPh$_3$ (82.7 g, 315.3 mmol) and o-Dichlorobenzene (505 mL), and then the product Sub 1-II-25 (35.62 g, 84%) was obtained by using the same manner as described above for the synthesis of compound Sub 1-II-1.

Synthesis Method of Sub 1-25

To a round bottom flask were added Sub 1-II-25 (47 g, 126.13 mmol), Bromobenzene (19.59 g 124.79 mmol), Pd$_2$(dba)$_3$ (3.79 g, 4.14 mmol), P(t-Bu)$_3$ (2.11 g, 10.4 mmol), NaO(t-Bu) (30.08 g, 313.045 mmol) and Toluene (230 mL), and then the product Sub 1-25 (34.77 g, 82%) was obtained by using the same manner as described above for the synthesis of compound Sub 1-1.

Synthesis Example of Sub 1-29

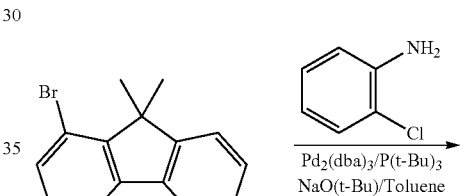

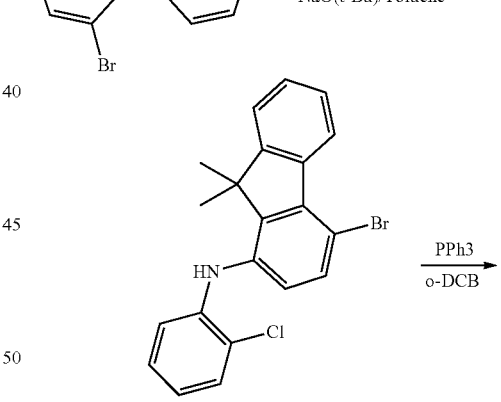

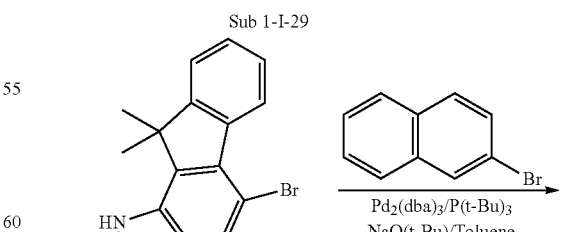

-continued

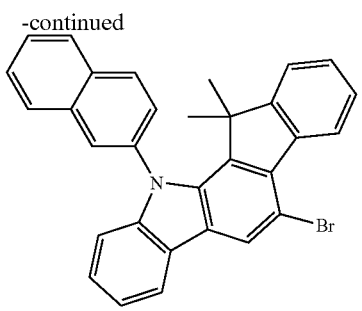

Sub 1-29

Synthesis Method of Sub 1-I-29

To a round bottom flask were added 2-Chloronaphthalen-1-amine (31 g, 175 mmol), 1,4-dibromo-9,9-dimethyl-9H-fluorene (51 g, 146 mmol), $Pd_2(dba)_3$ (5.4 g, 5.8 mmol), $P(t-Bu)_3$ (5 g, 14.6 mmol), NaO(t-Bu) (42 g, 439 mmol) and Toluene (500 mL), and then the product Sub 1-I-29 (36 g, 63%) was obtained by using the same manner as described above for the synthesis of compound Sub 1-I-1.

Synthesis Method of Sub 1-II-29

To a round bottom flask were added Sub 1-I-29 (27 g, 68 mmol), $PPh_3$ (45 g, 171 mmol) and o-Dichlorobenzene (150 mL), and then the product Sub 1-II-29 (22 g, 92%) was obtained by using the same manner as described above for the synthesis of compound Sub 1-II-1.

Synthesis Method of Sub 1-29

To a round bottom flask were added Sub 1-II-29 (22 g, 62 mmol), 2-Bromonaphthalene (15 g 74 mmo), $Pd_2(dba)_3$ (2. g, 2.5 mmol), $P(t-Bu)_3$ (1.3 g (6.2 mmol), NaO(t-Bu) (18 g, 186 mmol) and Toluene (300 mL), and then the product Sub 1-29 (20 g, 67%) was obtained by using the same manner as described above for the synthesis of compound Sub 1-1.

Example of Sub 1

The compound comprised in Sub 1 may be, but not limited to, the following compounds, and Table 1 shows FD-MS (Field Desorption-Mass Spectrometry) values thereof.

Sub 1-1

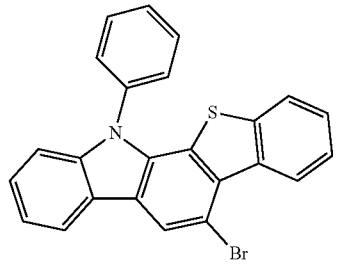

Sub 1-2

Sub 1-3

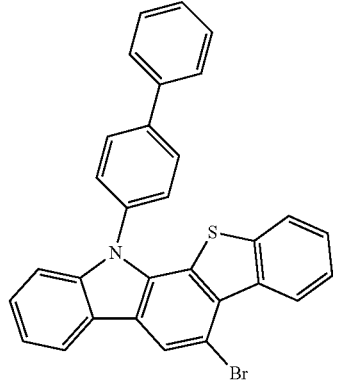

Sub 1-4

Sub 1-5

Sub 1-6

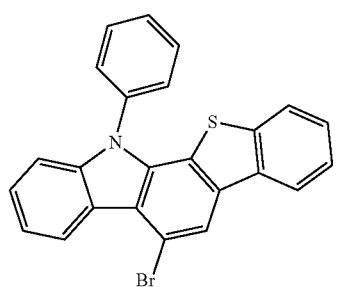

-continued
Sub 1-7
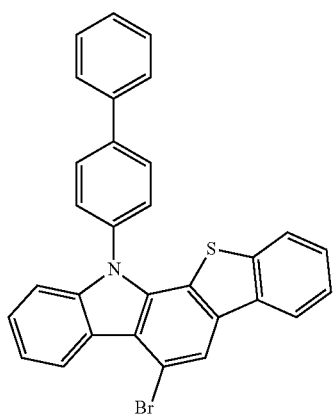
Sub 1-8
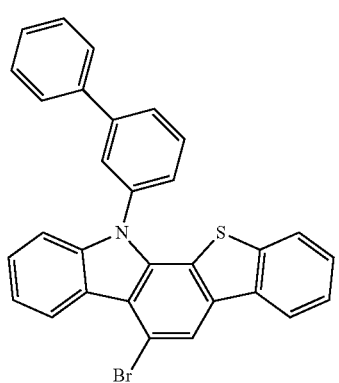
Sub 1-9
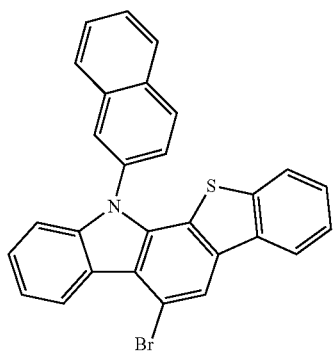
Sub 1-10
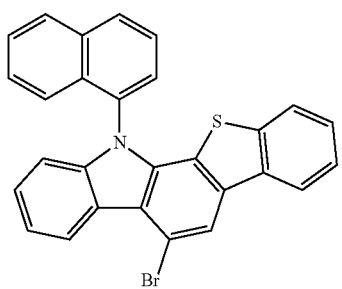
-continued
Sub1-11
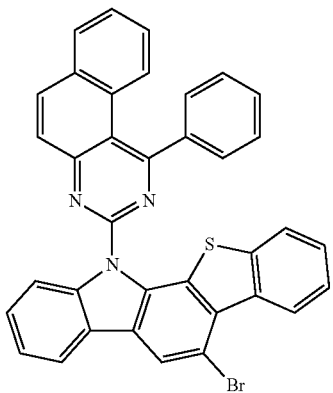
Sub1-12
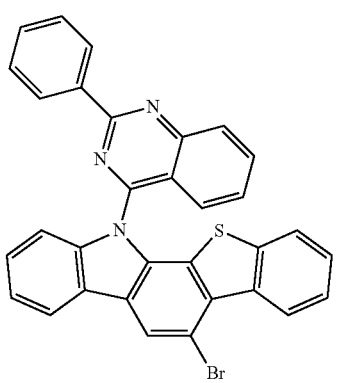
Sub1-13
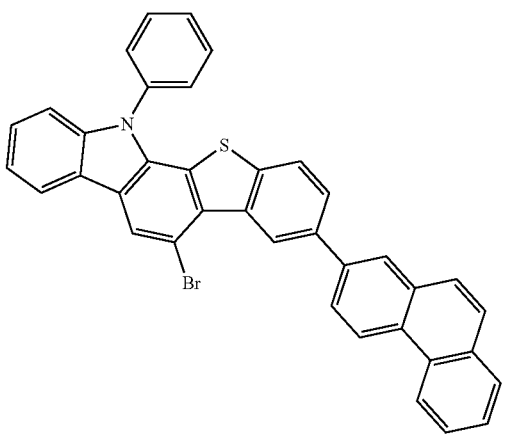
Sub1-14
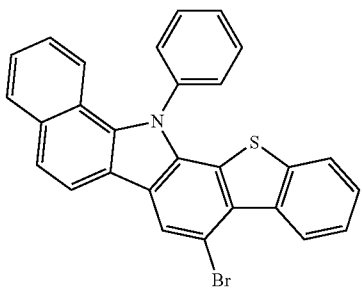

Sub1-15
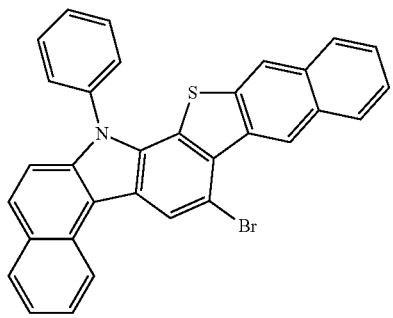
Sub1-16
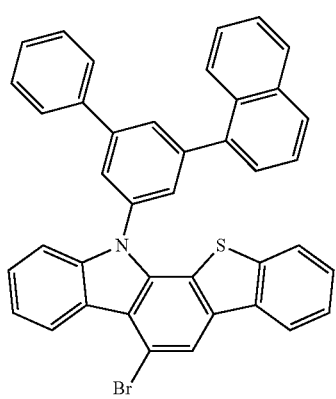
Sub1-17
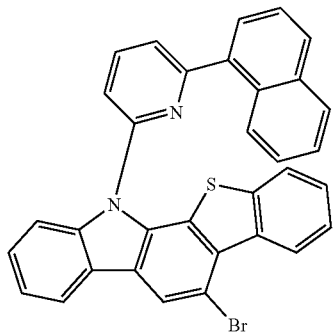
Sub1-18
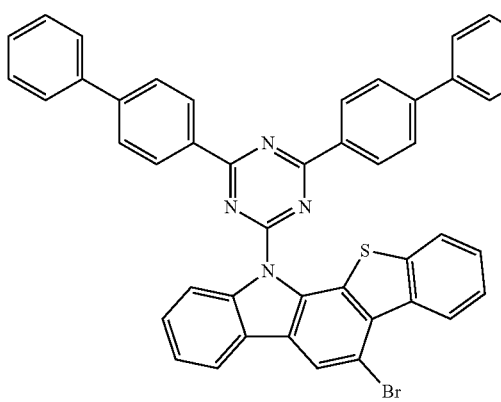
Sub1-19
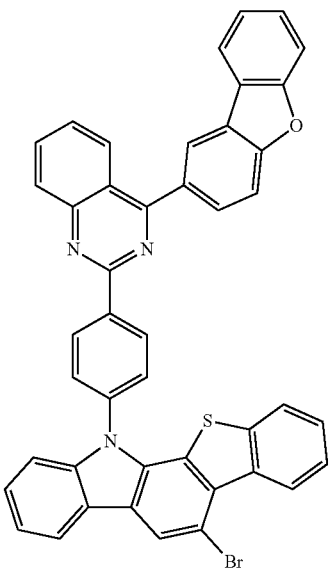
Sub1-20
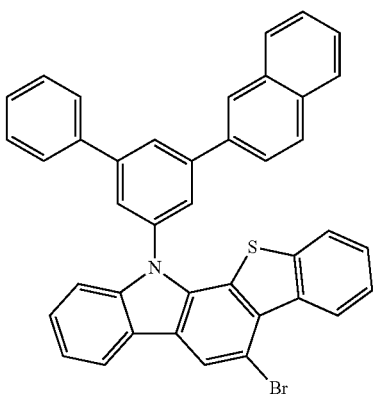
Sub1-21
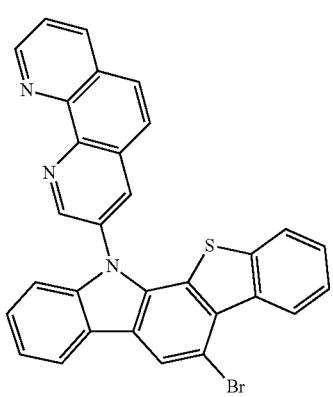

Sub1-22
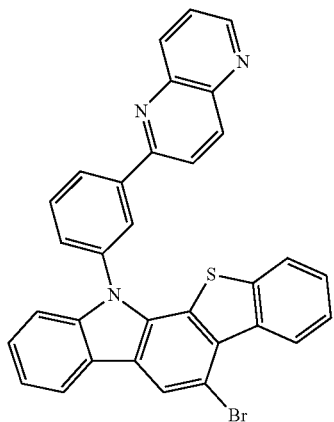
Sub1-23
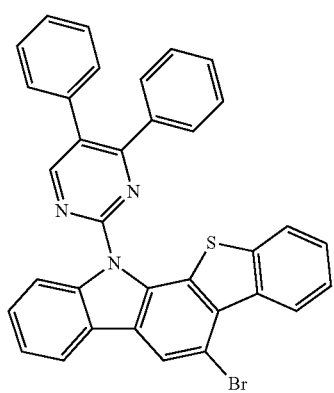
Sub1-24
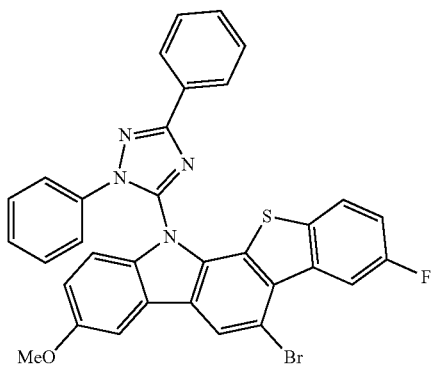
Sub1-25
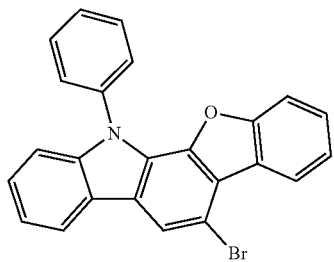
Sub1-26
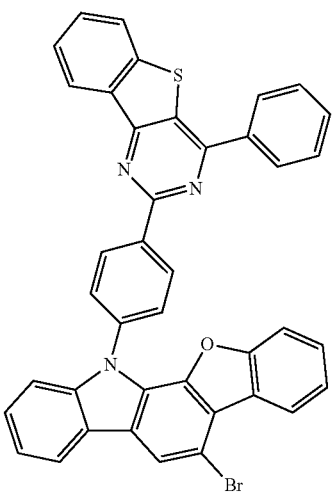
Sub1-27
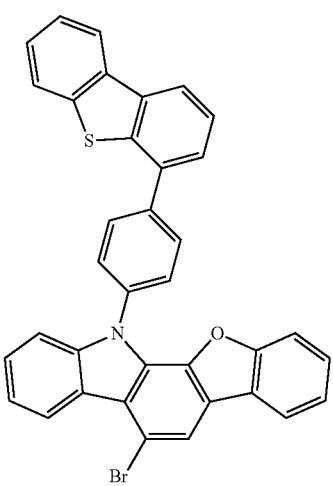
Sub1-28
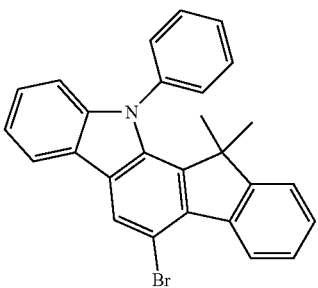
Sub1-29
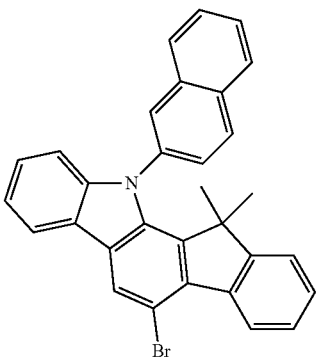

-continued

Sub1-30

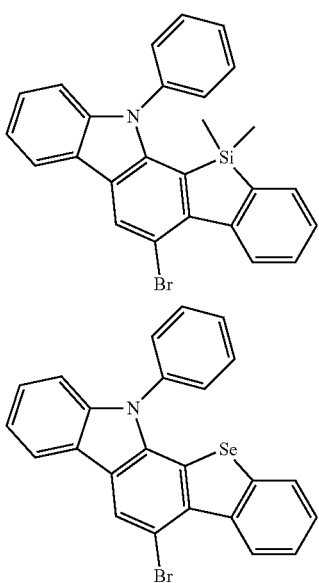

Sub1-31

-continued

Sub 2-II

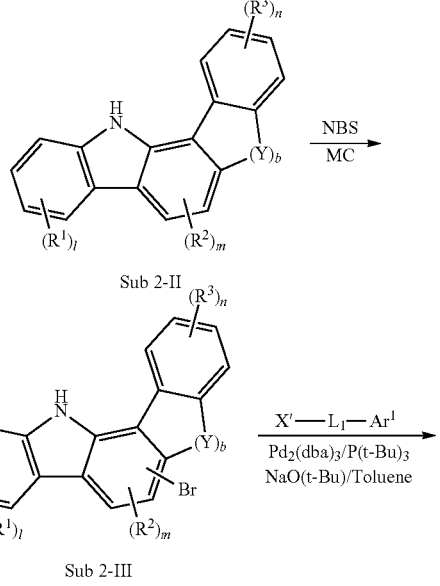

Sub 2-III

TABLE 1

| compound | FD-MS | compound | FD-MS |
| --- | --- | --- | --- |
| Sub 1-1 | m/z = 477.02($C_{28}H_{16}BrNS$ = 478.40) | Sub 1-2 | m/z = 427.00(C24HBrNS = 428.34) |
| Sub 1-3 | m/z = 503.03($C_{30}H_{18}BrNS$ = 504.44) | Sub 1-4 | m/z = 503.03($C_{30}H_{18}BrNS$ = 504.44) |
| Sub 1-5 | m/z = 477.02($C_{28}H_{16}BrNS$ = 478.40) | Sub 1-6 | m/z = 427.00(C24HBrNS = 428.34) |
| Sub 1-7 | m/z = 503.03($C_{30}H_{18}BrNS$ = 504.44) | Sub 1-8 | m/z = 503.03($C_{30}H_{18}BrNS$ = 504.44) |
| Sub 1-9 | m/z = 477.02($C_{28}H_{16}BrNS$ = 478.40)) | Sub 1-10 | m/z = 477.02($C_{28}H_{16}BrNS$ = 478.40) |
| Sub 1-11 | m/z = 605.06($C_{36}H_{20}BrN_3S$ = 606.53) | Sub 1-12 | m/z = 555.04($C_{32}H_{18}BrN_3S$ = 556.47) |
| Sub 1-13 | m/z = 603.07($C_{38}H_{22}BrNS$ = 604.56) | Sub 1-14 | m/z = 477.02($C_{28}H_{16}BrNS$ = 478.40) |
| Sub 1-15 | m/z = 527.03($C_{32}H_{18}BrNS$ = 528.46) | Sub 1-16 | m/z = 629.08($C_{40}H_{24}BrNS$ = 630.59) |
| Sub 1-17 | m/z = 554.05$C_{33}H_{19}BrN_2S$ = 555.49) | Sub 1-18 | m/z = 734.11($C_{45}H_{27}BrN_4S$ = 735.69) |
| Sub 1-19 | m/z = 721.08($C_{44}H_{24}BrN_3OS$ = 722.65) | Sub 1-20 | m/z = 629.08($C_{40}H_{24}BrNS$ = 630.59) |
| Sub 1-21 | m/z = 529.02($C_{30}H_{16}BrN_3S$ = 530.44) | Sub 1-22 | m/z = 555.04($C_{32}H_{18}BrN_3S$ = 556.47) |
| Sub 1-23 | m/z = 581.06($C_{34}H_{20}BrN_3S$ = 582.51) | Sub 1-24 | m/z = 600.06($C_{33}H_{21}BrN_4OS$ = 601.52) |
| Sub 1-25 | m/z = 411.03($C_{24}H_{14}BrNO$ = 412.28) | Sub 1-26 | m/z = 671.07($C_{40}H_{22}BrN_3OS$ = 672.59) |
| Sub 1-27 | m/z = 593.04($C_{36}H_{20}BrNOS$ = 594.52) | Sub 1-28 | m/z = 437.08($C_{27}H_{20}BrN$ = 438.36) |
| Sub 1-29 | m/z = 487.09($C_{31}H_{22}BrN$ = 488.42) | Sub 1-30 | m/z = 453.05($C_{26}H_{20}BrNSi$ = 454.43) |
| Sub 1-31 | m/z = 474.95($C_{24}H_{14}BrNSe$ = 475.24) | | |

2. Synthesis Example of Sub 2

Sub 2 of the above Reaction Scheme 1 may be synthesized by the reaction route of Reaction Scheme 3, but is not limited thereto.

<Reaction Scheme 3>

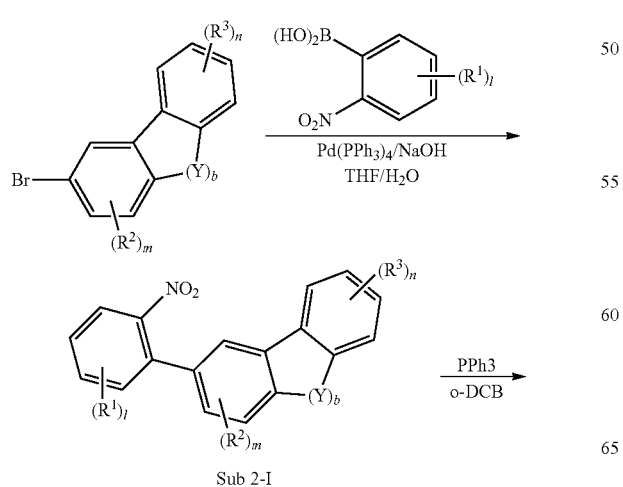

Sub 2-I

-continued

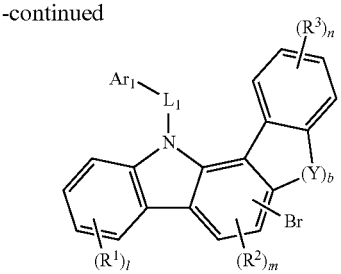

Sub 2

(X' = I, Br, Cl)

Synthesis Examples of Compounds comprised in Sub 2 are as follows.

Synthesis Example of Sub 2-1 (where a=0, b=1, Y=S)

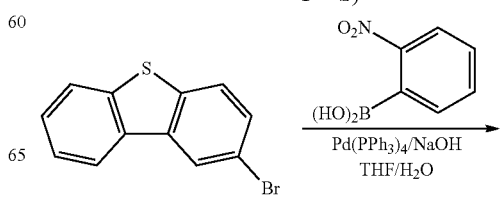

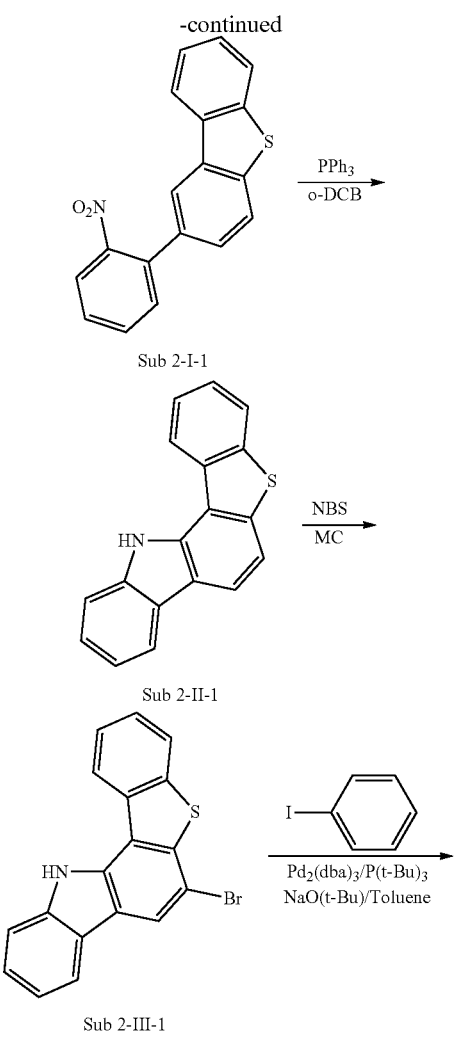

Synthesis Method of Sub 2-II-1

To a round bottom flask were added Sub 2-I-1 (99 g, 323 mmol), PPh$_3$ (218 g, 808 mmol) and o-Dichlorobenzene (1.0 L). Then, the mixture was heated and refluxed at 180° C. for 24 hours. When the reaction was completed, the reaction product was cooled to room temperature and concentrated. The resulting compound was purified by column chromatography on silica gel and recrystallized to obtain the product Sub 2-II-1 (70 g, 80%).

Synthesis Method of Sub 2-III-1

To a round bottom flask were added Sub 2-II-1 (70 g, 293 mmol) and N-Bromosuccinimide (52 g, 293 mmol), Methylene chloride (1 L). Then, the mixture was mixed for 4 hours. When the reaction was completed, the reaction product was extracted with methylene chloride and water. The organic layer was dried over MgSO$_4$ and concentrated. The resulting compound was recrystallized with methylene chloride and hexane to obtain the product Sub 2-III-1 (86 g, 83%).

Synthesis Method of Sub 2-1

To a round bottom flask were added Sub 2-III-1 (30 g, 84 mmol), Iodobenzene (20.7 g, 102 mmol), Pd$_2$(dba)$_3$ (3 g, 3.3 mmol), P(t-Bu)$_3$ (1.8 g, 8.4 mmol), NaO(t-Bu) (24.6 g, 255 mmol) and Toluene (240 mL). Then, the mixture was heated and refluxed at 110° C. for 8 hours. When the reaction was completed, the reaction product was diluted with distilled water at room temperature and extracted with methylene chloride and water. The organic layer was dried over MgSO$_4$ and concentrated. The resulting compound was recrystallized with methylene chloride and hexane to obtain the product Sub 2-1 (28 g, 76%).

Synthesis Example of Sub 2-2 (where a=0, b=1, Y=S)

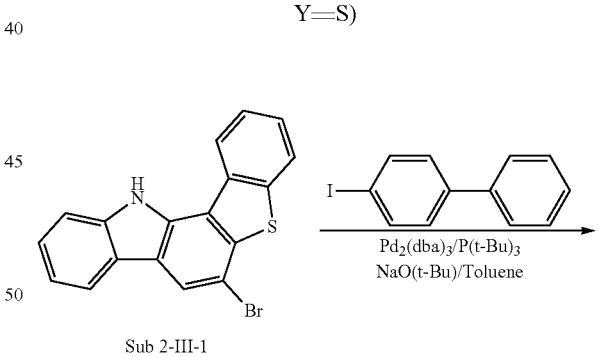

Synthesis Method of Sub 2-I-1

To a round bottom flask were added 2-Bromodibenzothiophene (100 g, 380 mmol), 2-Nitrophenyl boronic acid (76 g, 456 mmol), Pd(PPh$_3$)$_4$ (18 g, 15 mmol), NaOH (46 g, 1140 mmol) and THF (1.2 L)/H$_2$O (0.6 L). Then, the mixture was heated and refluxed at 70° C. for 4 hours. When the reaction was completed, the reaction product was diluted with distilled water at room temperature and extracted with methylene chloride and water. The organic layer was dried over MgSO$_4$ and concentrated. The resulting compound was recrystallized with methylene chloride and hexane to obtain the product Sub 2-I-1 (99 g, 85%).

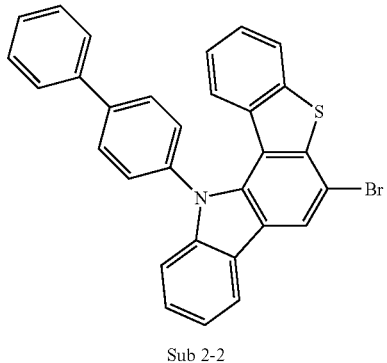

Sub 2-2

To a round bottom flask were added Sub 2-III-1 (30 g, 84 mmol), 4-Iodo-1,1'-biphenyl (28.6 g, 102 mmol), Pd₂(dba)₃ (3 g, 3.3 mmol), P(t-Bu)₃ (1.8 g, 8.4 mmol), NaO(t-Bu) (24.6 g, 255 mmol) and Toluene (240 mL), and then the product Sub 2-2 (32 g, 76%) was obtained by using the same manner as described above for the synthesis of compound Sub 2-1.

Synthesis Example of Sub 2-3 (where a=0, b=1, Y=S)

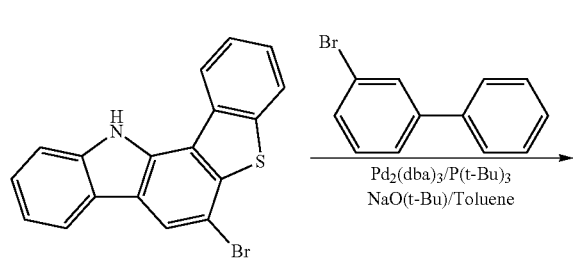

Sub 2-III-1

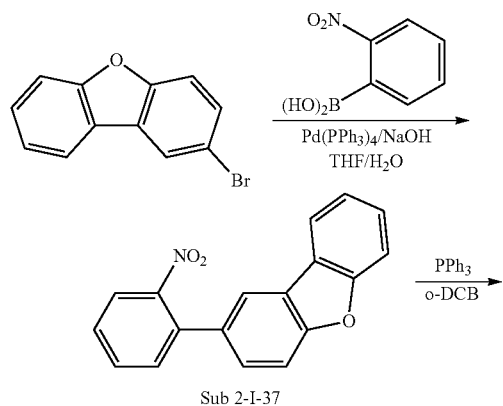

Sub 2-3

To a round bottom flask were added Sub 2-III-1 (30 g, 84 mmol), 3-Bromo-1,1'-biphenyl (23.8 g, 102 mmol), Pd₂(dba)₃ (3 g, 3.3 mmol), P(t-Bu)₃ (1.8 g, 8.4 mmol), NaO(t-Bu) (24.6 g, 255 mmol) and Toluene (240 mL), and then the product Sub 2-3 (34 g, 80%) was obtained by using the same manner as described above for the synthesis of compound Sub 2-1.

Synthesis Example of Sub 2-37 (where a=0, b=1, Y=O)

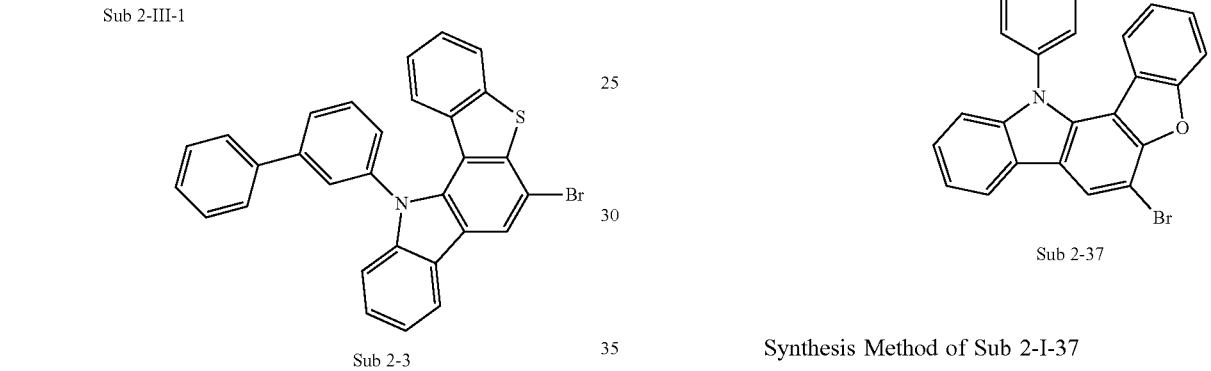

Sub 2-I-37

Sub 2-II-37

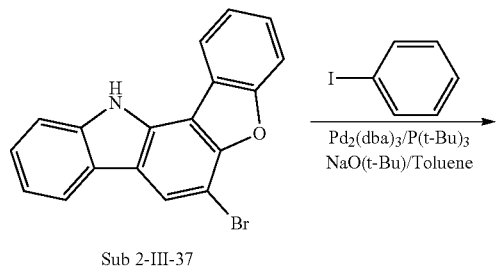

Sub 2-III-37

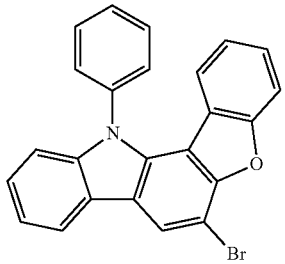

Sub 2-37

Synthesis Method of Sub 2-I-37

To a round bottom flask were added 2-Bromodibenzofuran (50 g, 202 mmol), 2-Nitrophenyl boronic acid (40.5 g, 242 mmol), Pd(PPh₃)₄ (9.3 g, 8 mmol), NaOH (24 g, 606 mmol) and THF (600 mL)/H₂O (300 mL), and then the product Sub 2-I-37 (43 g, 74%) was obtained by using the same manner as described above for the synthesis of compound Sub 2-I-1.

Synthesis Method of Sub 2-II-37

To a round bottom flask were added Sub 2-I-37 (43 g, 110 mmol), PPh₃ (72 g, 276 mmol) and o-Dichlorobenzene (350 mL), and then the product Sub 2-II-37 (23 g, 82%) was obtained by using the same manner as described above for the synthesis of compound Sub 2-II-1.

Synthesis Method of Sub 2-III-37

To a round bottom flask were added Sub 2-II-37 (23 g, 89 mmol), N-Bromosuccinimide (16 g, 89 mmol) and Methylene chloride (300 mL), and then the product Sub 2-III-37 (21 g, 70%) was obtained by using the same manner as described above for the synthesis of compound Sub 2-III-1.

Synthesis Method of Sub 2-37

To a round bottom flask were added Sub 2-III-37 (21 g, 62 mmol), Iodobenzene (15.3 g, 75 mmol), Pd₂(dba)₃ (2.3 g, 2.5 mmol), P(t-Bu)₃ (1.3 g, 6.2 mmol), NaO(t-Bu) (18 g, 187 mmol) and Toluene (200 mL), and then the product Sub 2-37

(16 g, 63%) was obtained by using the same manner as described above for the synthesis of compound Sub 2-1.

Synthesis Example of Sub 2-144 (where a=0, b=1, Y=C)

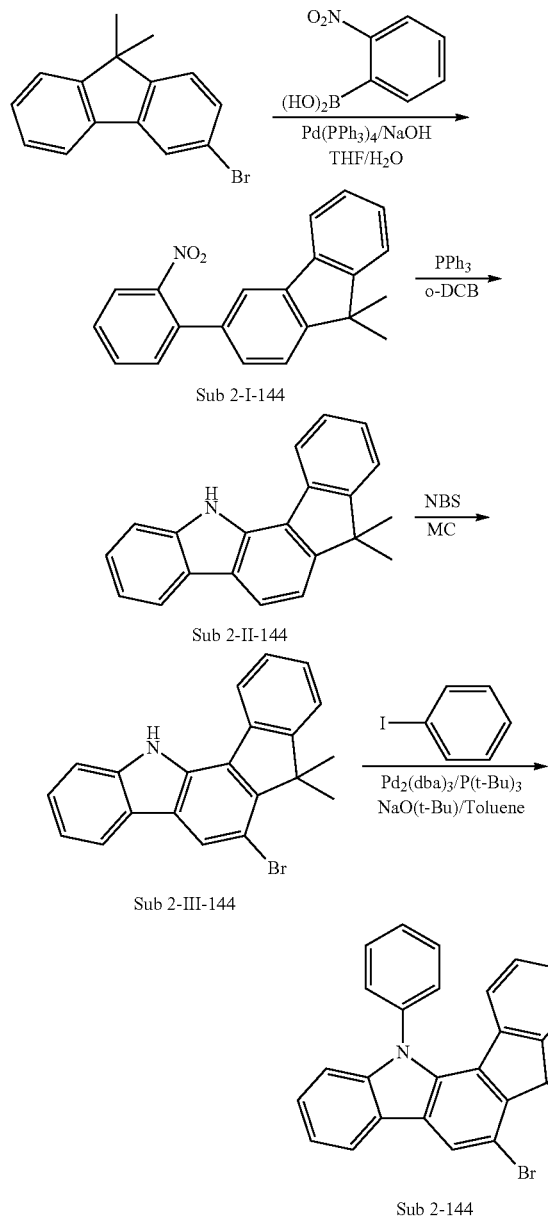

Synthesis Method of Sub 2-I-144

To a round bottom flask were added 3-bromo-9,9-dimethyl-9H-fluorene (50 g, 183.04 mmol), 2-Nitrophenyl boronic acid (36.6 g, 219.28 mmol), Pd(PPh$_3$)$_4$ (8.4 g, 7.25 mmol), NaOH (22 g, 549.11 mmol) and THF (805 mL)/H$_2$O (402 mL), and then the product Sub 2-I-144 (47.72 g, 69%) was obtained by using the same manner as described above for the synthesis of compound Sub 2-I-1.

Synthesis Method of Sub 2-II-144

To a round bottom flask were added Sub 2-I-144 (47 g, 149 mmol), PPh$_3$ (97.7 g, 372.48 mmol) and o-Dichlorobenzene (596 mL), and then the product Sub 2-II-144 (30.41 g, 72%) was obtained by using the same manner as described above for the synthesis of compound Sub 2-II-1.

Synthesis Method of Sub 2-III-144

To a round bottom flask were added Sub 2-II-144 (30 g, 89 mmol), N-Bromosuccinimide (18.8 g, 105.9 mmol) and Methylene chloride (318 mL), and then the product Sub 2-III-144 (18.24 g, 53%) was obtained by using the same manner as described above for the synthesis of compound Sub 2-III-1.

Synthesis Method of Sub 2-144

To a round bottom flask were added Sub 2-III-144 (18 g, 49.7 mmol), Iodobenzene (12.26 g, 60.1 mmol), Pd$_2$(dba)$_3$ (1.83 g, 2 mmol), P(t-Bu)$_3$ (1.01 g, 4.97 mmol), NaO(t-Bu) (14.4 g, 149.9 mmol) and Toluene (109 mL), and then the product Sub 2-144 (15.03 g, 69%) was obtained by using the same manner as described above for the synthesis of compound Sub 2-1.

Example of Sub 2

The compound comprised in Sub 2 may be, but not limited to, the following compounds, and Table 2 shows FD-MS values thereof.

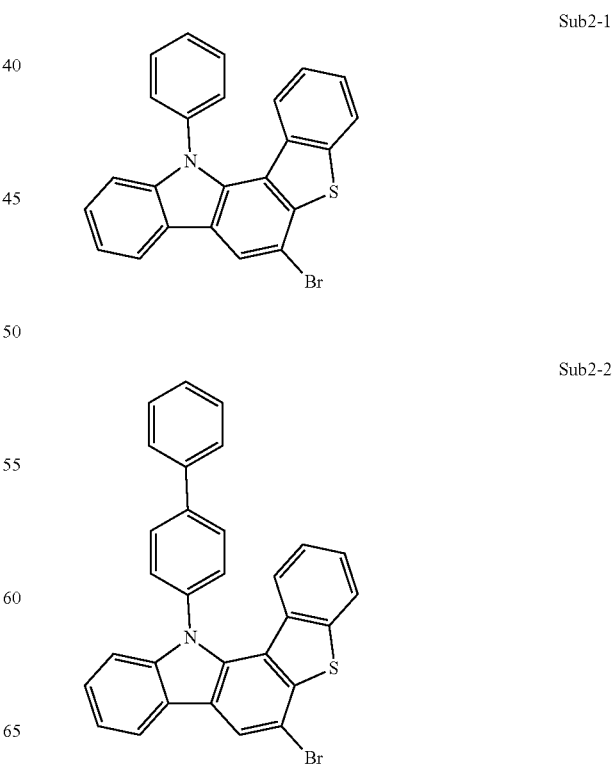

-continued
Sub2-3
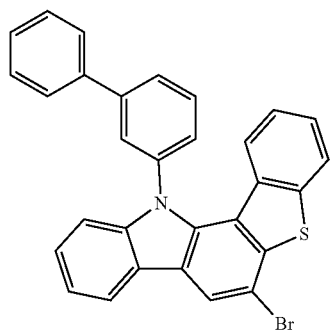
Sub2-4
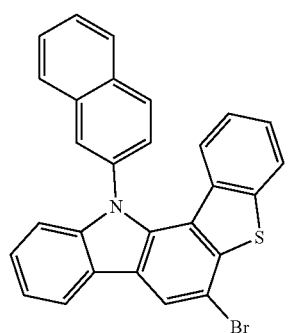
Sub2-5
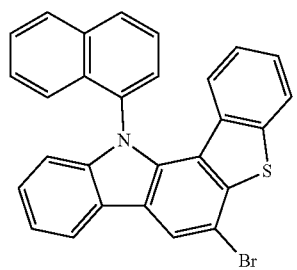
Sub2-6
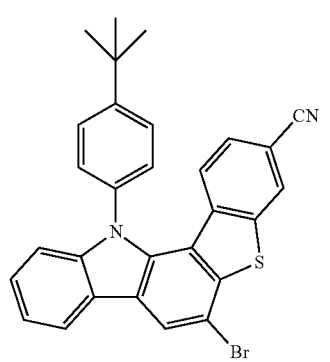
Sub2-7
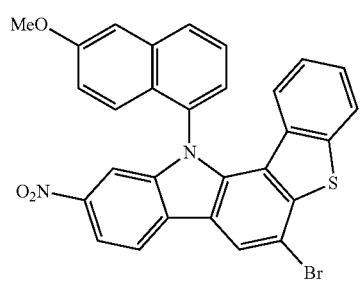
-continued
Sub2-8
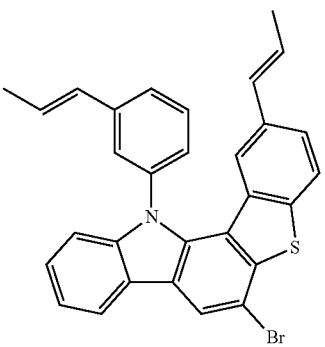
Sub2-9
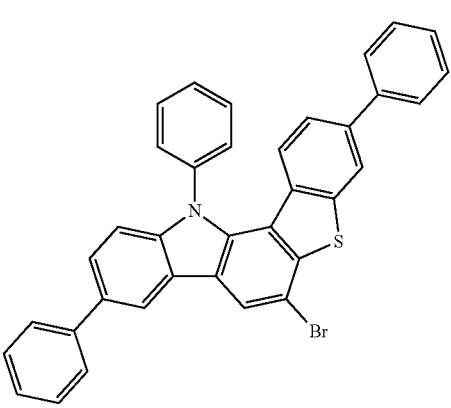
Sub2-10
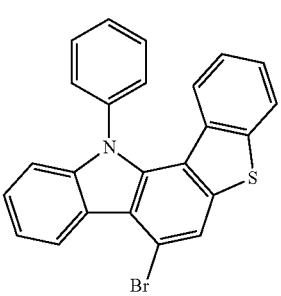
Sub2-11
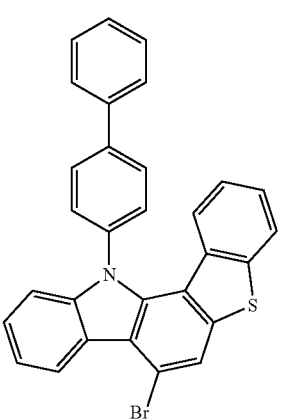

Sub2-12
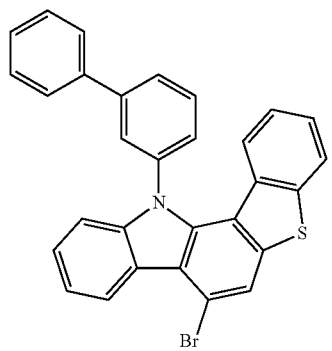
Sub2-13
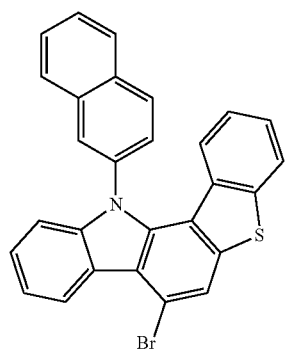
Sub2-14
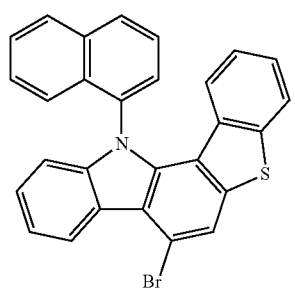
Sub2-15
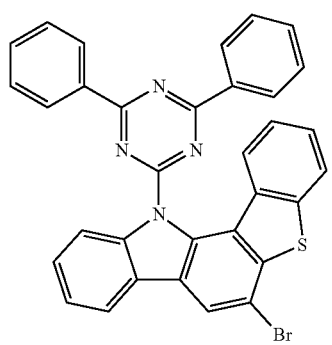
Sub2-16
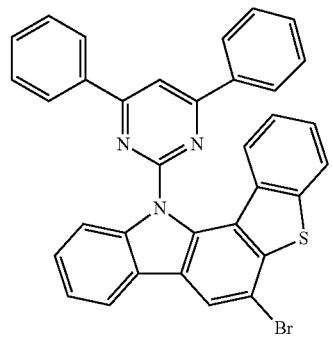
Sub2-17
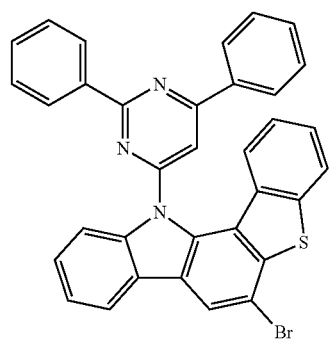
Sub2-18
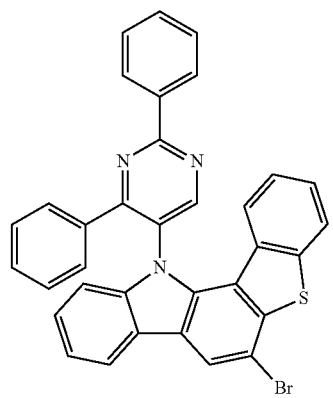
Sub2-19
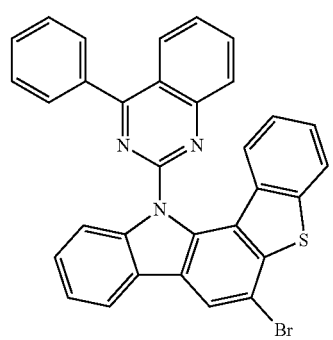

Sub2-20
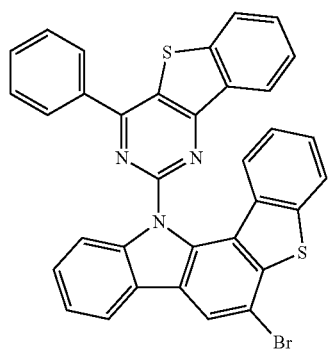
Sub2-21
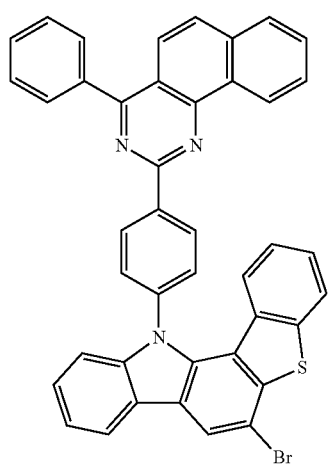
Sub2-22
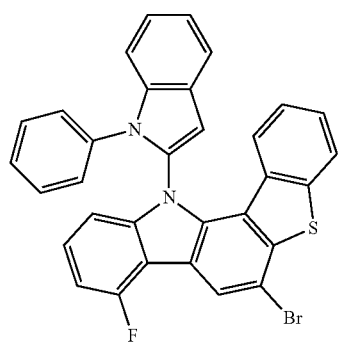
Sub2-23
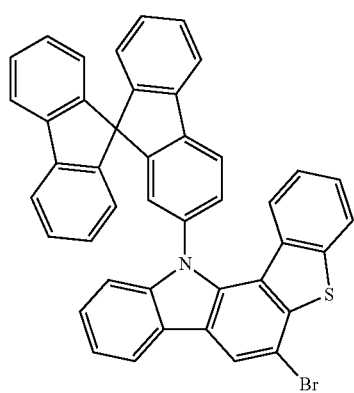
Sub2-24
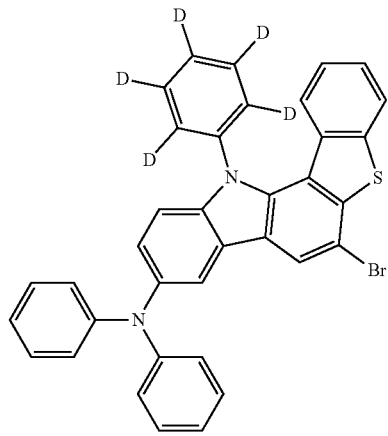
Sub2-25
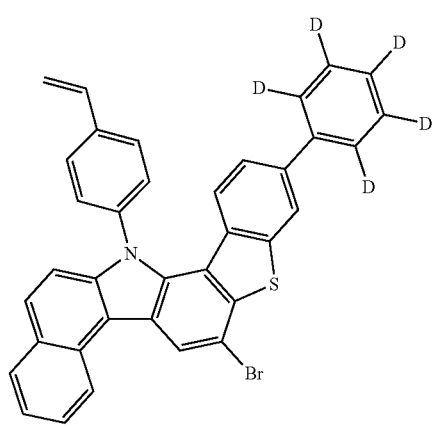
Sub2-26
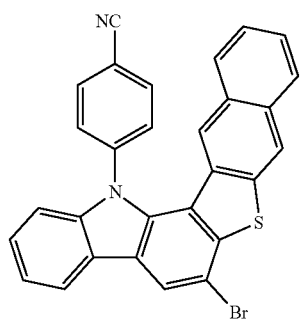
Sub2-27
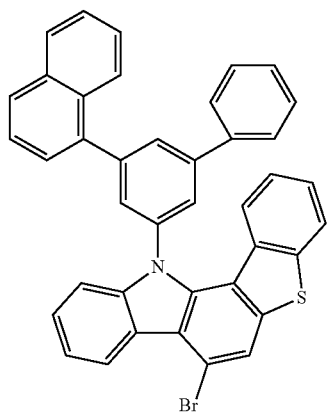

| Sub2-28 | Sub2-31 |
|---|---|
| 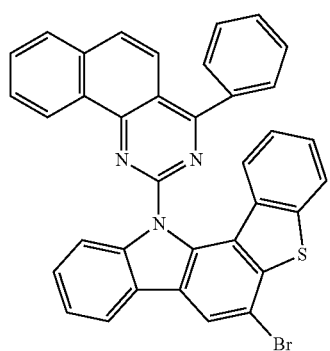 | 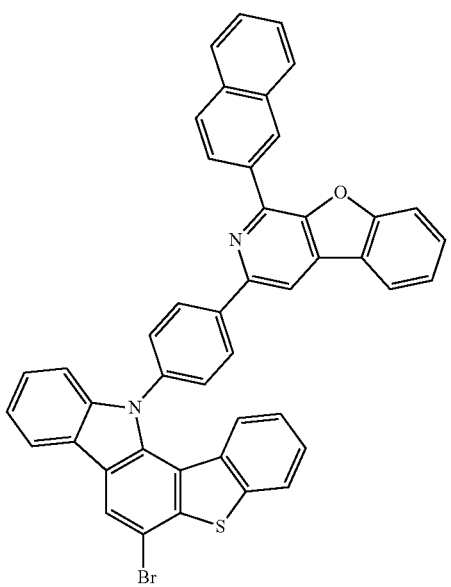 |
| Sub2-29 | |
|---|---|
| 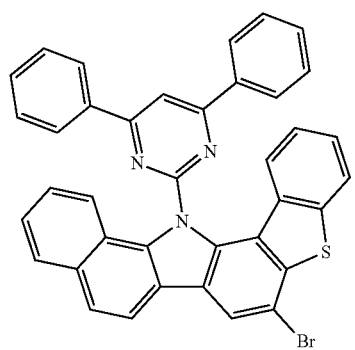 | Sub2-32 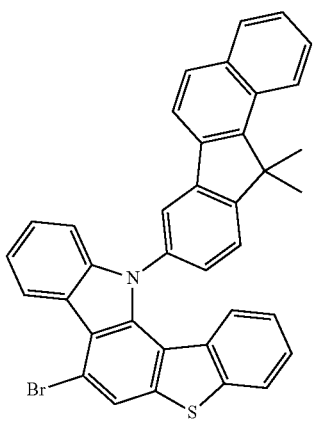 |
| Sub2-30 | Sub2-33 |
|---|---|
| | 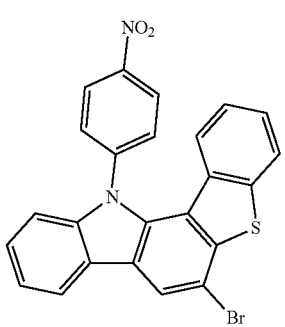 |

Sub2-34
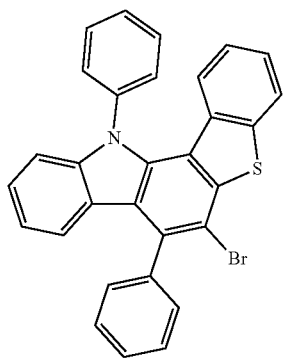
Sub2-38
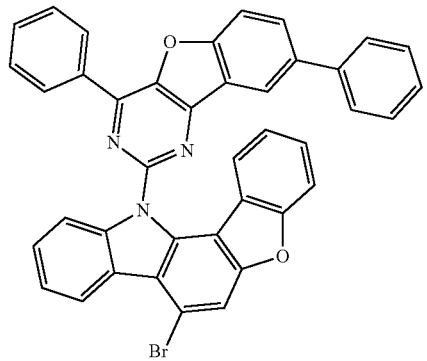
Sub2-35
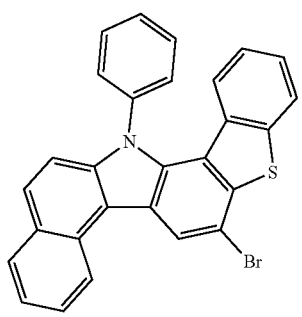
Sub2-39
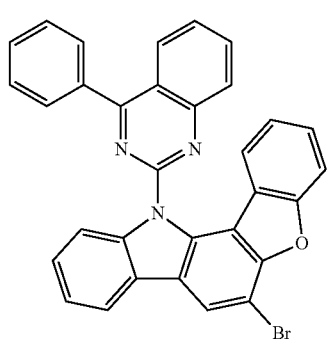
Sub2-36
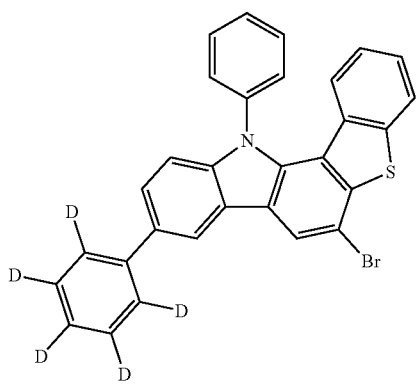
Sub2-40
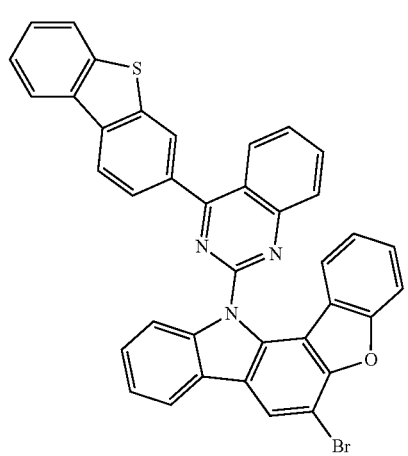
Sub2-37
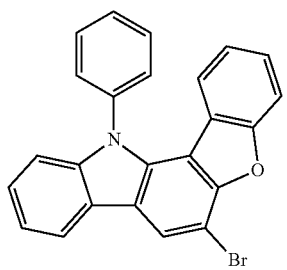
Sub2-41
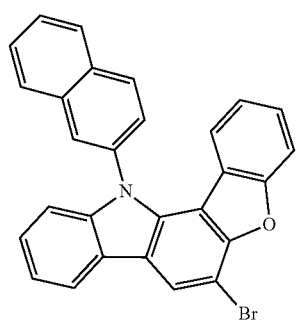

-continued

Sub2-42

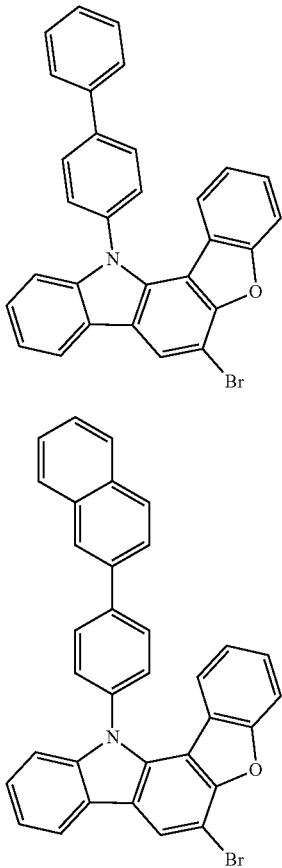

Sub2-43

Sub2-44

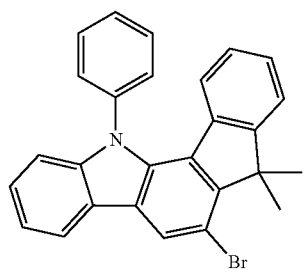

Sub2-45

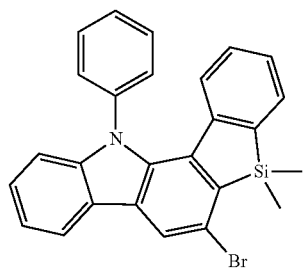

Sub2-46

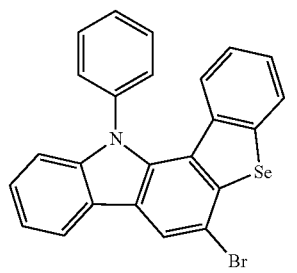

TABLE 2

| compound | FD-MS | compound | FD-MS |
|---|---|---|---|
| Sub 2-1 | m/z = 427.00($C_{24}$HBrNS = 428.34) | Sub 2-2 | m/z = 503.03($C_{30}H_{18}$BrNS = 504.44) |
| Sub 2-3 | m/z = 503.03($C_{30}H_{18}$BrNS = 504.44) | Sub 2-4 | m/z = 477.02($C_{28}H_{16}$BrNS = 478.40) |
| Sub 2-5 | m/z = 477.02($C_{28}H_{16}$BrNS = 478.40) | Sub 2-6 | m/z = 483.07($C_{28}H_{22}$BrNS = 484.45) |
| Sub 2-7 | m/z = 507.03($C_{29}H_{18}$BrNOS = 508.43) | Sub 2-8 | m/z = 467.03($C_{27}H_{18}$BrNS = 468.41) |
| Sub 2-9 | m/z = 503.03($C_{30}H_{18}$BrNS = 504.44) | Sub 2-10 | m/z = 427.00($C_{24}$HBrNS = 428.34) |
| Sub 2-11 | m/z = 503.03($C_{30}H_{18}$BrNS = 504.44) | Sub 2-12 | m/z = 503.03($C_{30}H_{18}$BrNS = 504.44) |
| Sub 2-13 | m/z = 477.02($C_{28}H_{16}$BrNS = 478.40) | Sub 2-14 | m/z = 477.02($C_{28}H_{16}$BrNS = 478.40) |
| Sub 2-15 | m/z = 582.05($C_{33}H_{19}BrN_4S$ = 583.50) | Sub 2-16 | m/z = 581.06($C_{34}H_{20}BrN_3S$ = 582.51) |
| Sub 2-17 | m/z = 581.06($C_{34}H_{20}BrN_3S$ = 582.51) | Sub 2-18 | m/z = 581.06($C_{34}H_{20}BrN_3S$ = 582.51) |
| Sub 2-19 | m/z = 555.04($C_{32}H_{18}BrN_3S$ = 556.47) | Sub 2-20 | m/z = 611.01($C_{34}H_{18}BrN_3S_2$ = 612.56) |
| Sub 2-21 | m/z = 681.09($C_{42}H_{24}BrN_3S$ = 682.63) | Sub 2-22 | m/z = 542.05($C_{32}H_{19}BrN_2S$ = 543.48) |
| Sub 2-23 | m/z = 665.08($C_{43}H_{24}$BrNS = 666.63) | Sub 2-24 | m/z = 599.11($C_{36}H_{18}D_5BrN_2S$ = 600.58) |
| Sub 2-25 | m/z = 503.03($C_{30}H_{18}$BrNS = 504.44) | Sub 2-26 | m/z = 502.01($C_{29}H_{15}BrN_2S$ = 503.41) |
| Sub 2-27 | m/z = 629.08($C_{40}H_{24}$BrNS = 630.59) | Sub 2-28 | m/z = 605.06($C_{36}H_{20}BrN_3S$ = 606.53) |
| Sub 2-29 | m/z = 657.09($C_{40}H_{24}BrN_3S$ = 658.61) | Sub 2-30 | m/z = 631.07($C_{38}H_{22}BrN_3S$ = 632.57) |
| Sub 2-31 | m/z = 720.09($C_{45}H_{25}BrN_2OS$ = 721.66) | Sub 2-32 | m/z = 593.08($C_{37}H_{24}$BrNS = 594.56) |
| Sub 2-33 | m/z = 471.99($C_{24}H_{13}BrN_2O_2S$ = 473.34) | Sub 2-34 | m/z = 503.03($C_{30}H_{18}$BrNS = 504.44) |
| Sub 2-35 | m/z = 477.02($C_{28}H_{16}$BrNS = 478.40) | Sub 2-36 | m/z = 508.07($C_{30}H_{13}D_5$BrNS = 509.47) |
| Sub 2-37 | m/z = 411.03($C_{24}H_{14}$BrNO = 412.28) | Sub 2-38 | m/z = 655.09($C_{40}H_{22}BrN_3O_2$ = 656.53) |
| Sub 2-39 | m/z = 539.06($C_{32}H_{18}BrN_3O$ = 540.41) | Sub 2-40 | m/z = 645.05($C_{38}H_{20}BrN_3OS$ = 646.55) |
| Sub 2-41 | m/z = 461.04($C_{28}H_{16}$BrNO = 462.34) | Sub 2-42 | m/z = 487.06($C_{30}H_{18}$BrNO = 488.37) |
| Sub 2-43 | m/z = 537.07($C_{34}H_{20}$BrNO = 538.43) | Sub 2-44 | m/z = 437.08($C_{27}H_{20}$BrN = 438.36) |
| Sub 2-45 | m/z = 453.05($C_{20}H_{20}$BrNSi = 453.43) | Sub 2-46 | m/z = 474.95($C_{24}H_{14}$BrNSi = 478.24) |

Example of Sub 3
The compound comprised in Sub 3 may be, but not limited to, the following compounds, and Table 3 shows FD-MS (Field Desorption-Mass Spectrometry) values thereof.
Sub 3-1
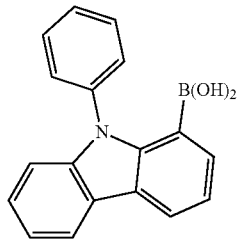
Sub 3-2
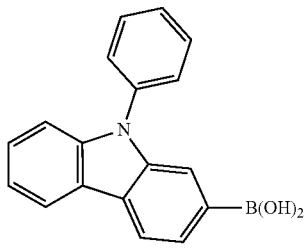
Sub 3-3
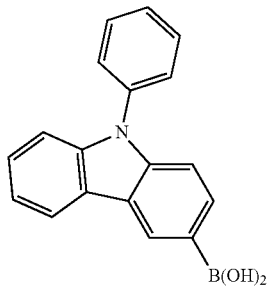
Sub 3-4
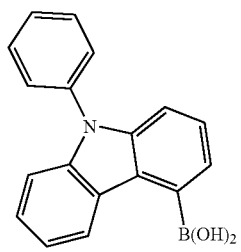
Sub 3-5
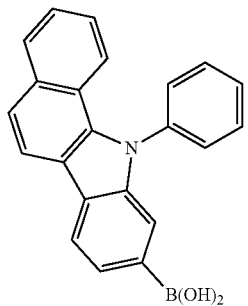
Sub 3-6
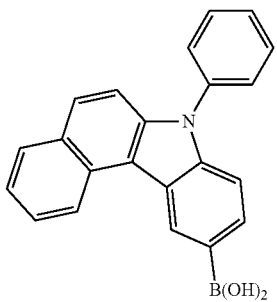
Sub 3-7
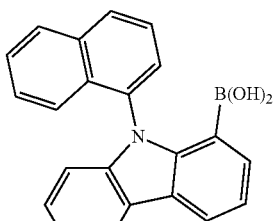
Sub 3-8
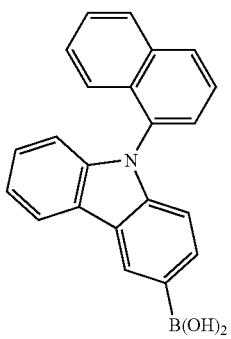
Sub 3-9
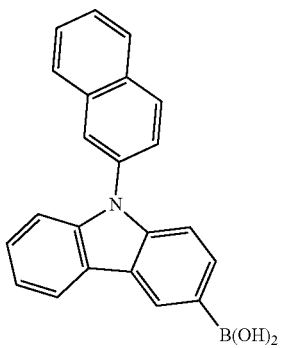
Sub 3-10
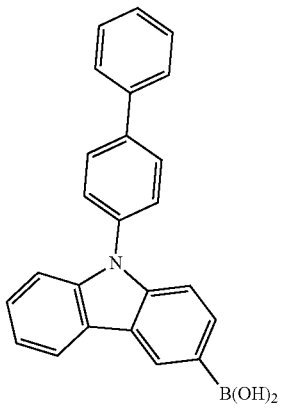

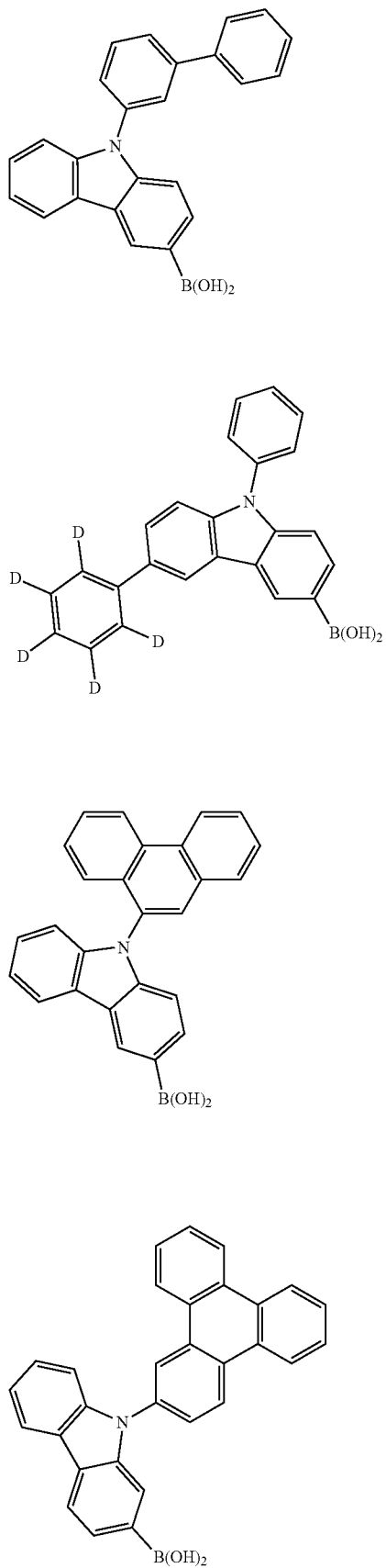
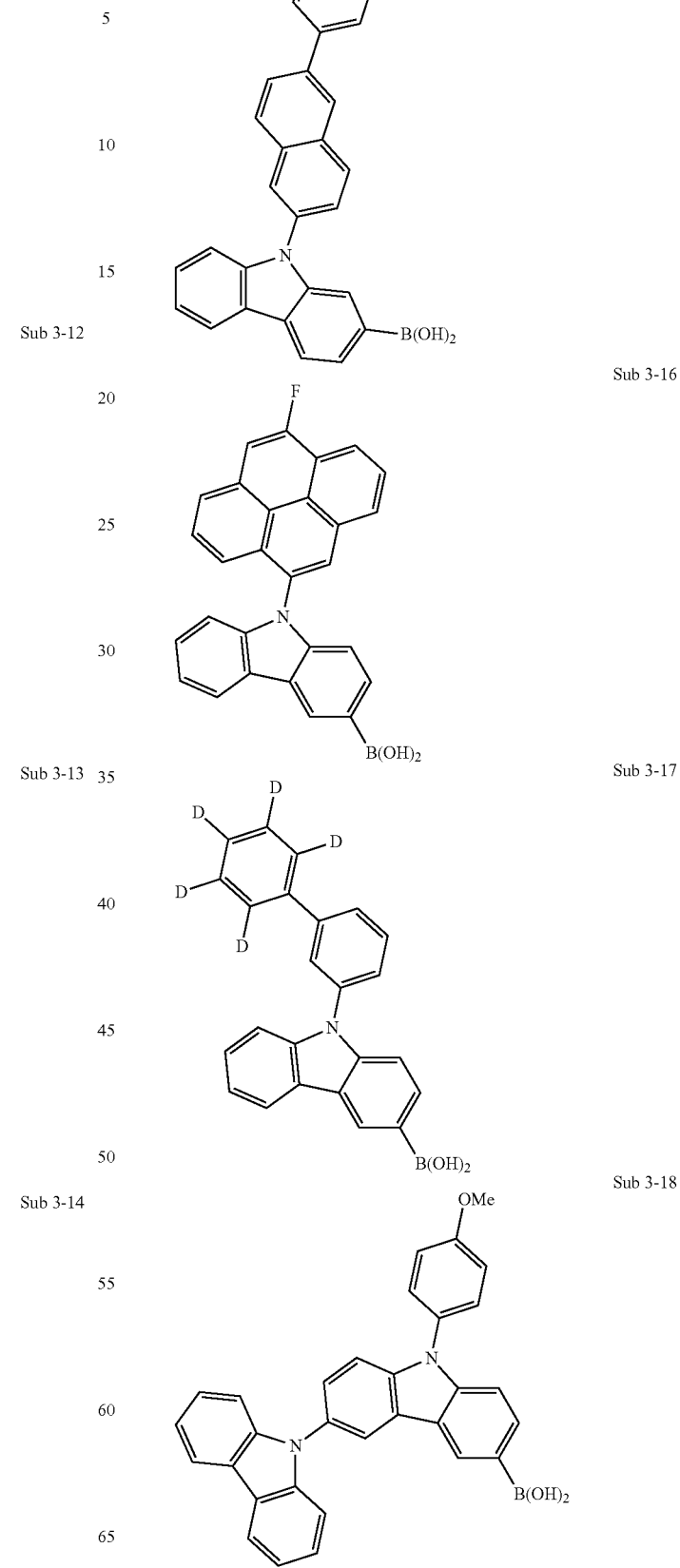

-continued
Sub 3-19
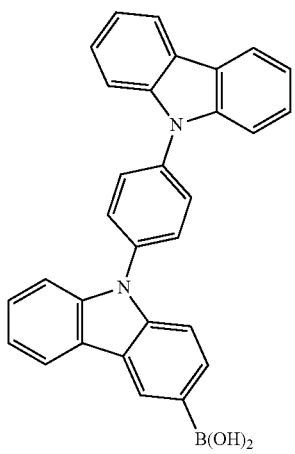
Sub 3-20
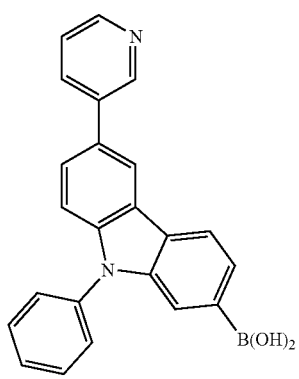
Sub 3-21
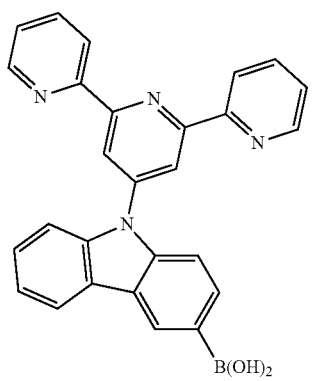
Sub 3-22
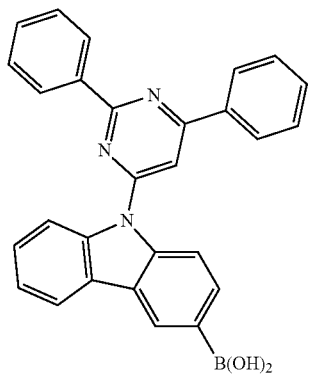
-continued
Sub 3-23
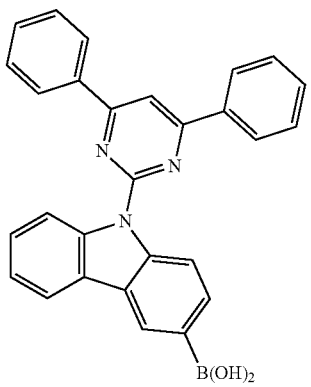
Sub 3-24
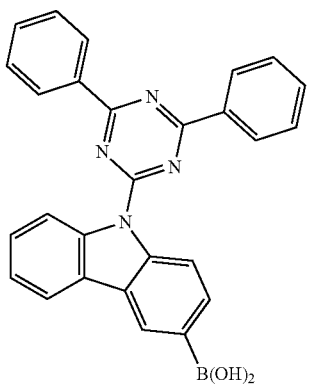
Sub 3-25
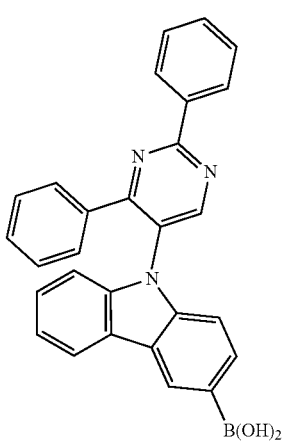
Sub 3-26
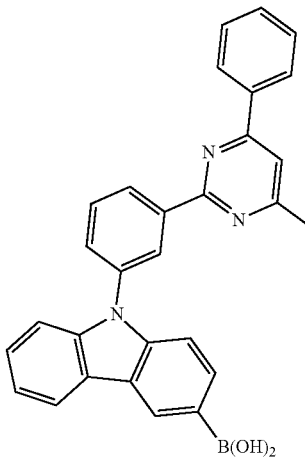

Sub 3-27
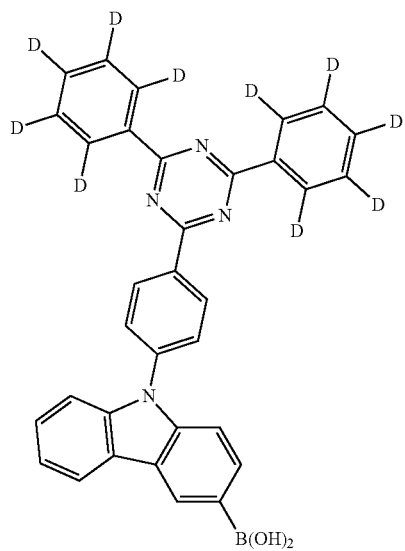
Sub 3-28
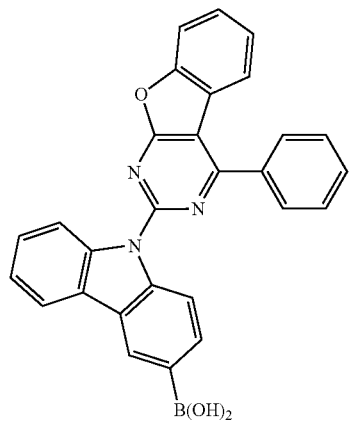
Sub 3-29
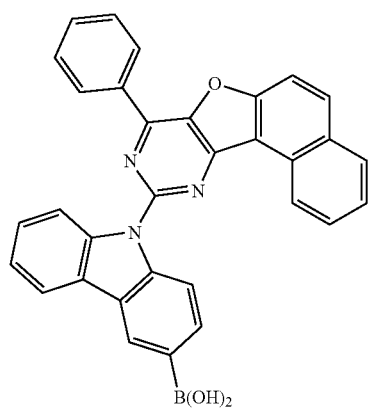
Sub 3-30
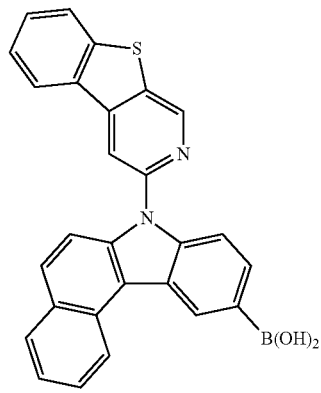
Sub 3-31
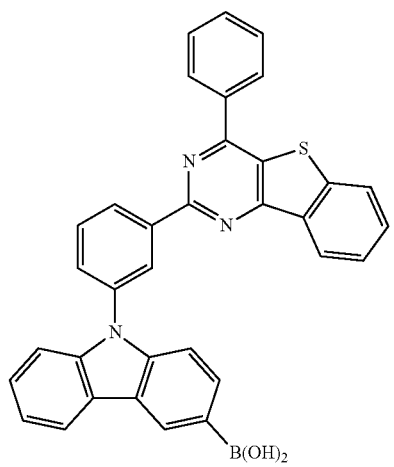
Sub 3-32
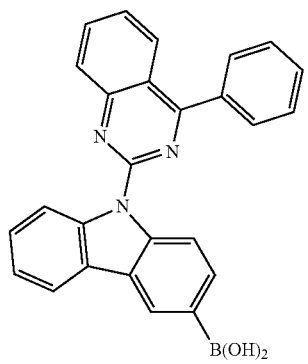
Sub 3-33
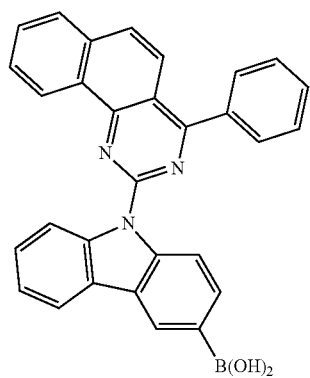

Sub 3-34
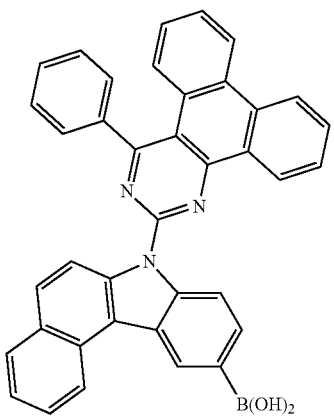
Sub 3-35
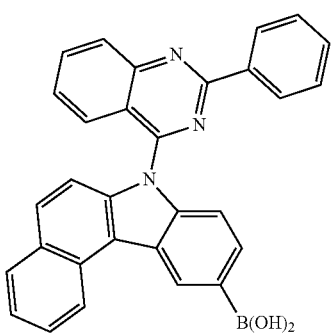
Sub 3-36
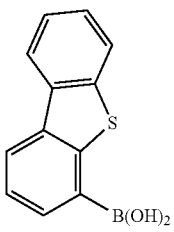
Sub 3-37
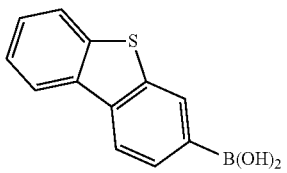
Sub 3-38
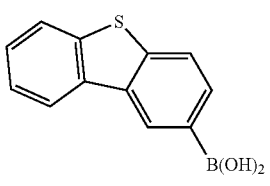
Sub 3-39
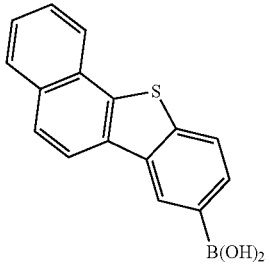
Sub 3-40
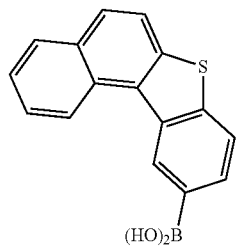
Sub 3-41
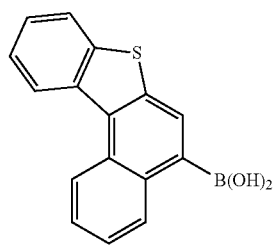
Sub 3-42
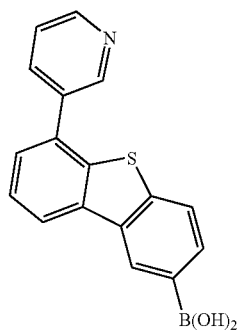
Sub 3-43
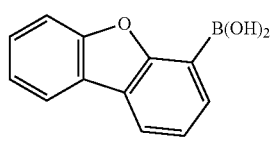
Sub 3-44
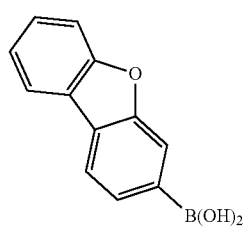
Sub 3-45
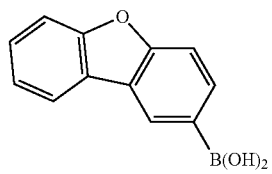
Sub 3-46

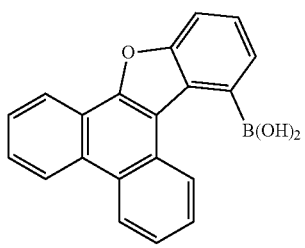
Sub 3-47
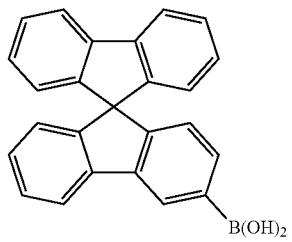
Sub 3-54
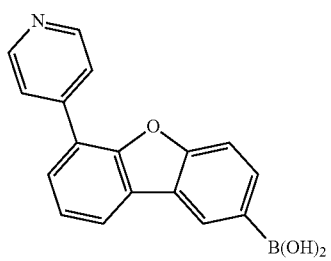
Sub 3-48
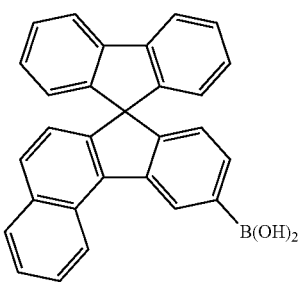
Sub 3-55
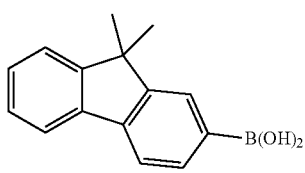
Sub 3-49
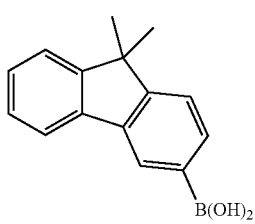
Sub 3-50
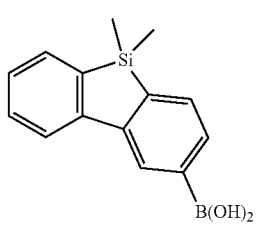
Sub 3-56
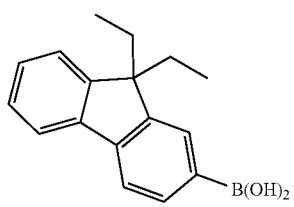
Sub 3-51
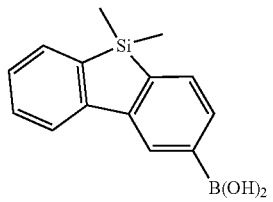
Sub 3-57
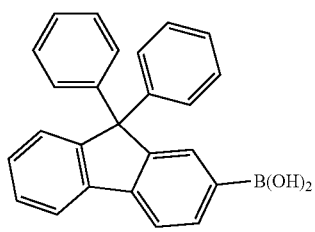
Sub 3-52
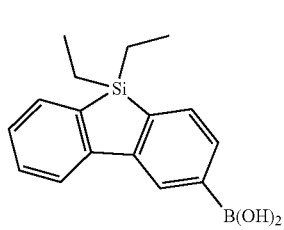
Sub 3-58
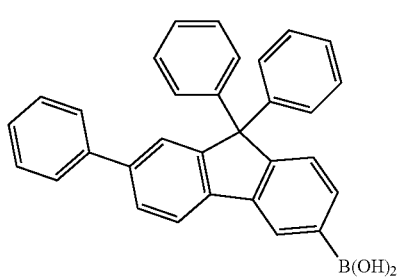
Sub 3-53
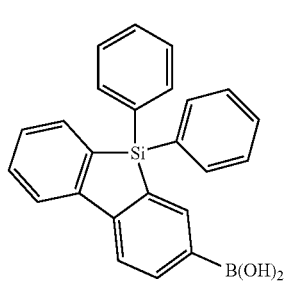
Sub 3-59

Sub 3-60

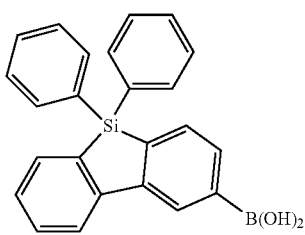

Sub 3-61

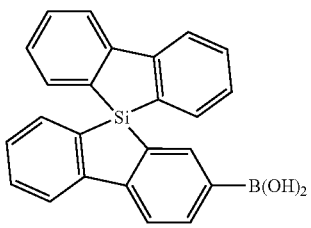

Sub 3-62

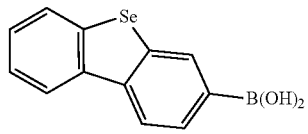

Sub 3-63

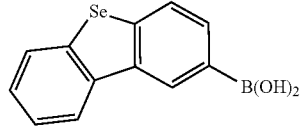

Sub 3-64

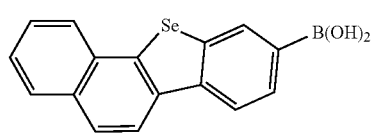

TABLE 3

| compound | FD-MS | compound | FD-MS |
| --- | --- | --- | --- |
| Sub 3-1 | m/z = 287.11($C_{18}H_{14}BNO_2$ = 287.12) | Sub 3-2 | m/z = 287.11($C_{18}H_{14}BNO_2$ = 287.12) |
| Sub 3-3 | m/z = 287.11($C_{18}H_{14}BNO_2$ = 287.12) | Sub 3-4 | m/z = 287.11($C_{18}H_{14}BNO_2$ = 287.12) |
| Sub 3-5 | m/z = 337.13($C_{22}H_{16}BNO_2$ = 337.18) | Sub 3-6 | m/z = 337.13($C_{22}H_{16}BNO_2$ = 337.18) |
| Sub 3-7 | m/z = 337.13($C_{22}H_{16}BNO_2$ = 337.18) | Sub 3-8 | m/z = 337.13($C_{22}H_{16}BNO_2$ = 337.18) |
| Sub 3-9 | m/z = 337.13($C_{22}H_{16}BNO_2$ = 337.18) | Sub 3-10 | m/z = 363.14($C_{24}H_{18}BNO_2$ = 363.22) |
| Sub 3-11 | m/z = 363.14($C_{24}H_{18}BNO_2$ = 363.22) | Sub 3-12 | m/z = 368.17($C_{24}H_{13}D_5BNO_2$ = 368.25) |
| Sub 3-13 | m/z = 387.14($C_{26}H_{18}BNO_2$ = 387.24) | Sub 3-14 | m/z = 437.16($C_{30}H_{20}BNO_2$ = 437.30) |
| Sub 3-15 | m/z = 413.16($C_{28}H_{20}BNO_2$ = 413.27) | Sub 3-16 | m/z = 429.13($C_{28}H_{17}BFNO_2$ = 429.25) |
| Sub 3-17 | m/z = 368.17($C_{24}H_{13}D_5BNO_2$ = 368.25) | Sub 3-18 | m/z = 482.18($C_{31}H_{23}BNO_3$ = 482.34) |
| Sub 3-19 | m/z = 452.17($C_{30}H_{21}BN_2O_2$ = 452.31) | Sub 3-20 | m/z = 364.14($C_{23}H_{17}BN_2O_2$ = 364.20) |
| Sub 3-21 | m/z = 442.16($C_{27}H_{19}BN_4O_2$ = 442.28) | Sub 3-22 | m/z = 441.16($C_{28}H_{20}BN_3O_2$ = 441.29) |
| Sub 3-23 | m/z = 441.26($C_{28}H_{20}BN_3O_2$ = 441.29) | Sub 3-24 | m/z = 442.16($C_{27}H_{19}BN_4O_2$ = 442.28) |
| Sub 3-25 | m/z = 441.16($C_{28}H_{20}BN_3O_2$ = 441.29) | Sub 3-26 | m/z = 517.20($C_{34}H_{24}BN_3O_2$ = 517.38) |
| Sub 3-27 | m/z = 528.25($C_{33}H_{13}D_{10}BN_4O_2$ = 528.43) | Sub 3-28 | m/z = 455.14($C_{28}H_{18}BN_3O_3$ = 455.27) |
| Sub 3-29 | m/z = 505.16($C_{32}H_{20}BN_3O_3$ = 505.33) | Sub 3-30 | m/z = 444.11($C_{27}H_{17}BN_2O_2S$ = 444.31) |
| Sub 3-31 | m/z = 547.15($C_{34}H_{22}BN_3O_2S$ = 547.43) | Sub 3-32 | m/z = 415.15($C_{26}H_{18}BN_3O_2$ = 415.25) |
| Sub 3-33 | m/z = 465.16($C_{30}H_{20}BN_3O_2$ = 465.31) | Sub 3-34 | m/z = 565.20($C_{38}H_{24}BN_3O_2$ = 565.43) |
| Sub 3-35 | m/z = 465.16($C_{30}H_{20}BN_3O_2$ = 465.31) | Sub 3-36 | m/z = 228.04($C_{12}H_9BO_2S$ = 228.07) |
| Sub 3-37 | m/z = 228.04($C_{12}H_9BO_2S$ = 228.07) | Sub 3-38 | m/z = 228.04($C_{12}H_9BO_2S$ = 228.07) |
| Sub 3-39 | m/z = 278.06($C_{16}H_{11}BN_2S$ = 278.13) | Sub 3-40 | m/z = 278.06($C_{16}H_{11}BO_2S$ = 278.13) |
| Sub 3-41 | m/z = 278.06($C_{16}H_{11}BO_2S$ = 278.13) | Sub 3-42 | m/z = 305.07($C_{17}H_{12}BNO_2S$ = 305.16) |
| Sub 3-43 | m/z = 212.06($C_{12}H_9BO_3$ = 212.01) | Sub 3-44 | m/z = 212.06($C_{12}H_9BO_3$ = 212.01) |
| Sub 3-45 | m/z = 212.06($C_{12}H_9BO_3$ = 212.01) | Sub 3-46 | m/z = 262.08($C_{16}H_{11}BO_3$ = 262.07) |
| Sub 3-47 | m/z = 312.10($C_{20}H_{13}BO_3$ = 312.13) | Sub 3-48 | m/z = 289.09($C_{17}H_{12}BNO_3$ = 289.09) |
| Sub 3-49 | m/z = 238.12($C_{15}H_{15}BO_2$ = 238.09) | Sub 3-50 | m/z = 238.12($C_{15}H_{15}BO_2$ = 238.09) |
| Sub 3-51 | m/z = 266.15($C_{17}H_{19}BO_2$ = 266.14) | Sub 3-52 | m/z = 362.15($C_{25}H_{19}BO_2$ = 362.23) |
| Sub 3-53 | m/z = 438.18($C_{31}H_{23}BO_2$ = 438.32) | Sub 3-54 | m/z = 360.13($C_{24}H_{17}BO_2$ = 360.21) |
| Sub 3-55 | m/z = 410.15($C_{29}H_{19}BO_2$ = 410.27) | Sub 3-56 | m/z = 254.09($C_{14}H_{15}BO_2Si$ = 254.16) |
| Sub 3-57 | m/z = 254.09($C_{14}H_{15}BO_2Si$ = 254.16) | Sub 3-58 | m/z = 282.12($C_{16}H_{19}BO_2Si$ = 282.22) |
| Sub 3-59 | m/z = 378.12($C_{24}H_{19}BO_2Si$ = 387.30) | Sub 3-60 | m/z = 378.12($C_{24}H_{19}BO_2Si$ = 378.30) |
| Sub 3-61 | m/z = 376.11($C_{24}H_{17}BO_2Si$ = 376.29) | Sub 3-62 | m/z = 275.99($C_{12}H_9BO_2Se$ = 274.97) |
| Sub 3-63 | m/z = 275.99($C_{12}H_9BO_2Se$ = 274.97) | Sub 3-64 | m/z = 326.00($C_{16}H_{11}BO_2Se$ = 325.03) |

141

Synthesis Method of the Products Represented by Formula 1

To a round bottom flask were added compound Sub 1 or Sub 2 (1 eq.), compound Sub3 (1 eq.), Pd(PPh₃)₄ (0.03~0.05 eq.), NaOH (3 eq.), THF (3 mL/1 mmol), water (1.5 mL/1 mmol). Then, the mixture was heated and refluxed at 80° C. When the reaction was completed, the reaction product was diluted with distilled water at room temperature and extracted with methylene chloride and water. The organic layer was dried over MgSO₄ and concentrated. The resulting compound was recrystallized with toluene and acetone to obtain the product.

Synthesis of Compound 1-2

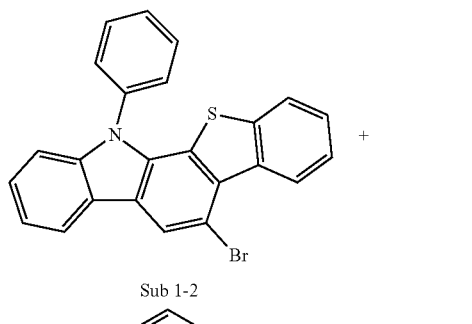

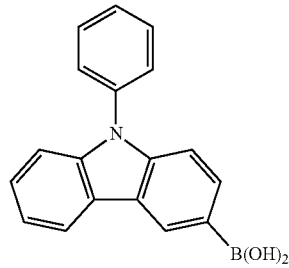

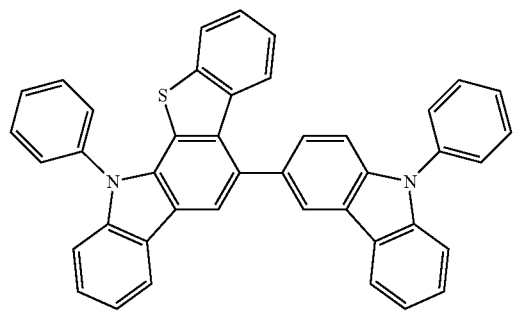

To a round bottom flask were added Sub 1-2 (5 g, 11.5 mmol), Sub 3-3 (3.9 g, 11.5 mmol), Pd(PPh₃)₄ (0.5 g, 0.5 mmol), NaOH (1.4 g, 35 mmol), THF (30 mL)/H₂O (15 mL). Then, the mixture was heated and refluxed at 80° C. for 8 hours. When the reaction was completed, the reaction product was diluted with distilled water at room temperature and extracted with methylene chloride and water. The organic layer was dried over MgSO₄ and concentrated. The resulting compound was recrystallized with toluene and acetone to obtain the product 1-2 (5.4 g, 80%).

142

Synthesis of Compound 1-7

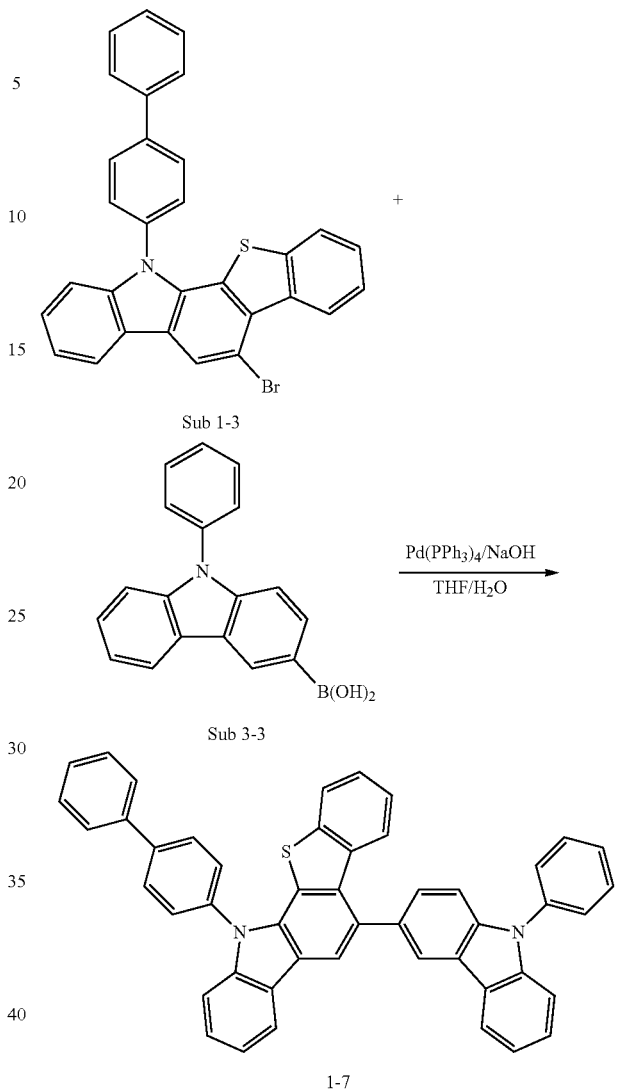

Sub 1-3 (10 g, 20 mmol), Sub 3-3 (5.7 g, 20 mmol), Pd(PPh₃)₄ (0.9 g, 0.8 mmol), NaOH (2.4 g, 59 mmol) and THF (40 mL)/H₂O (20 mL) were used in the same manner as described above for the synthesis of compound 1-2 to obtain the product 1-7 (11.3 g, 85%).

Synthesis of Compound 1-14

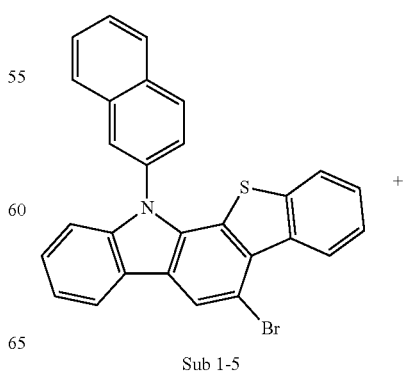

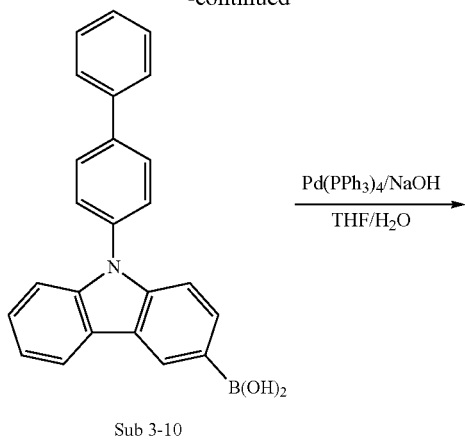

Sub 3-10

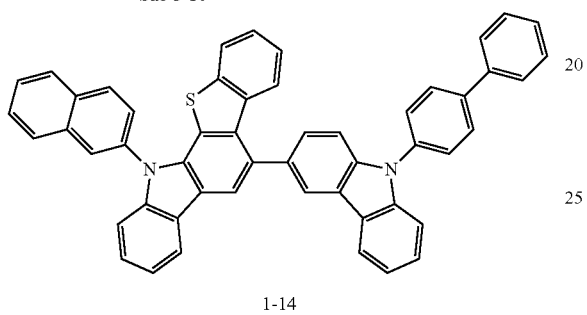

1-14

Sub 1-5 (10 g, 21 mmol), Sub 3-10 (7.6 g, 21 mmol), Pd(PPh₃)₄ (1 g, 0.8 mmol), NaOH (2.5 g, 63 mmol) and THF (40 mL)/H₂O (20 mL) were used in the same manner as described above for the synthesis of compound 1-2 to obtain the product 1-14 (12.3 g, 82%).

Synthesis of Compound 1-20

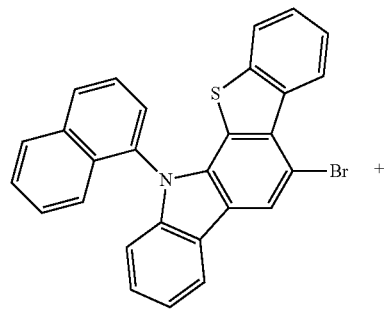

Sub 1-1

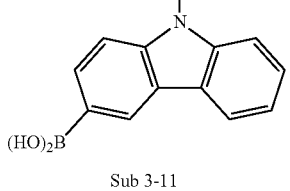

Sub 3-11

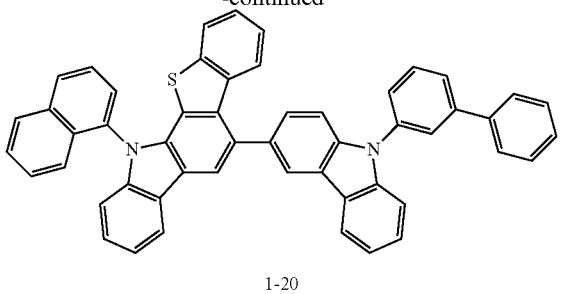

1-20

Sub 1-1 (10 g, 21 mmol), Sub 3-11 (7.6 g, 21 mmol), Pd(PPh₃)₄ (1 g, 0.8 mmol), NaOH (2.5 g, 63 mmol) and THF (40 mL)/H₂O (20 mL) were used in the same manner as described above for the synthesis of compound 1-2 to obtain the product 1-20 (12.5 g, 83%).

Synthesis of Compound 1-26

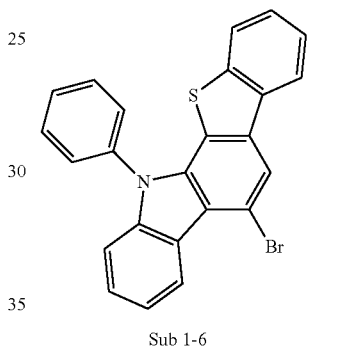

Sub 1-6

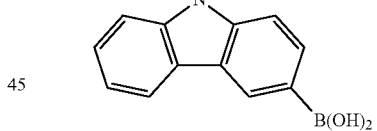

Sub 3-3

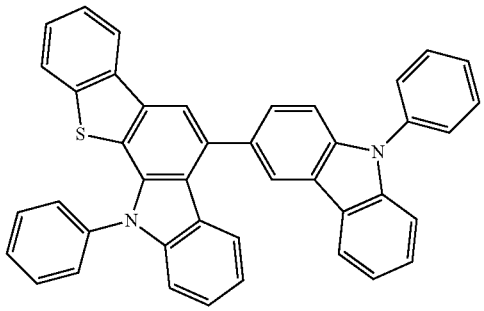

1-26

Sub 1-6 (5 g, 11.5 mmol), Sub 3-3 (3.9 g, 11.5 mmol), Pd(PPh₃)₄ (0.5 g, 0.5 mmol), NaOH (1.4 g, 35 mmol), THF (30 mL)/H₂O (15 mL) were used in the same manner as described above for the synthesis of compound 1-2 to obtain the product 1-26 (4.9 g, 72%).

Synthesis of Compound 1-27

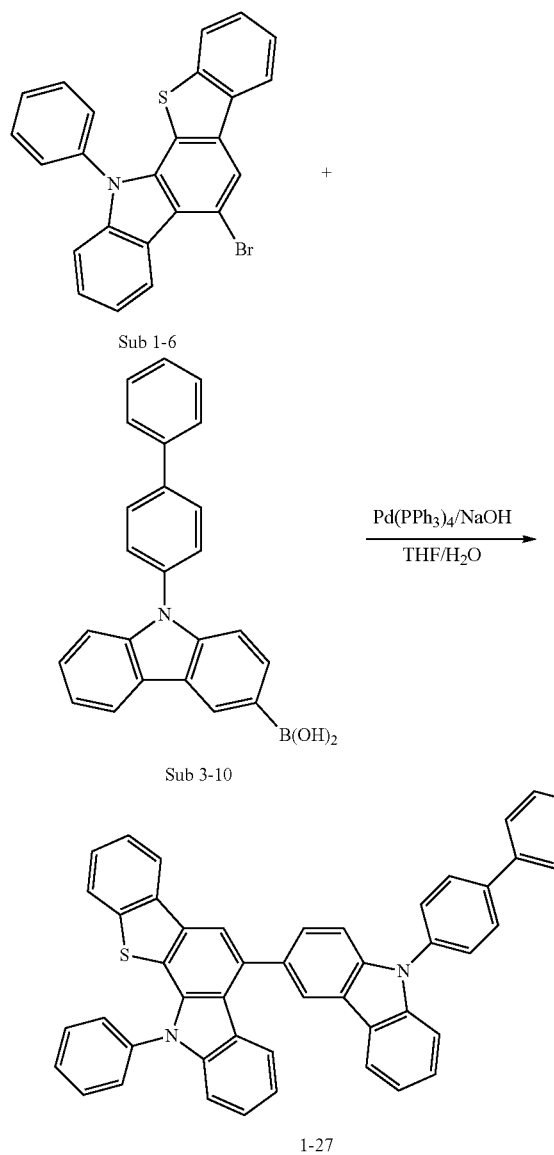

Sub 1-6 (5 g, 11.5 mmol), Sub 3-10 (4.2 g, 11.5 mmol), Pd(PPh$_3$)$_4$ (0.5 g, 0.5 mmol), NaOH (1.4 g, 35 mmol) and THF (30 mL)/H$_2$O (15 mL) were used in the same manner as described above for the synthesis of compound 1-2 to obtain the product 1-27 (6.5 g, 85%).

Synthesis of Compound 1-33

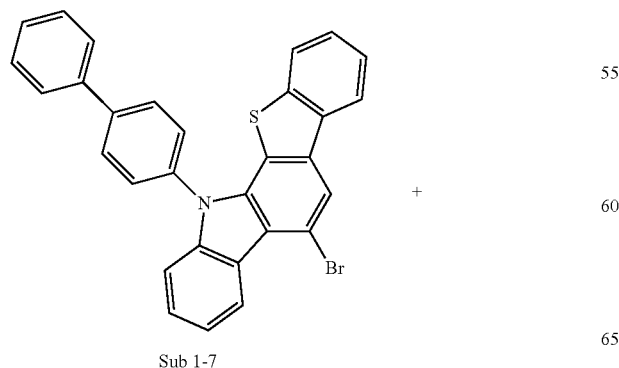

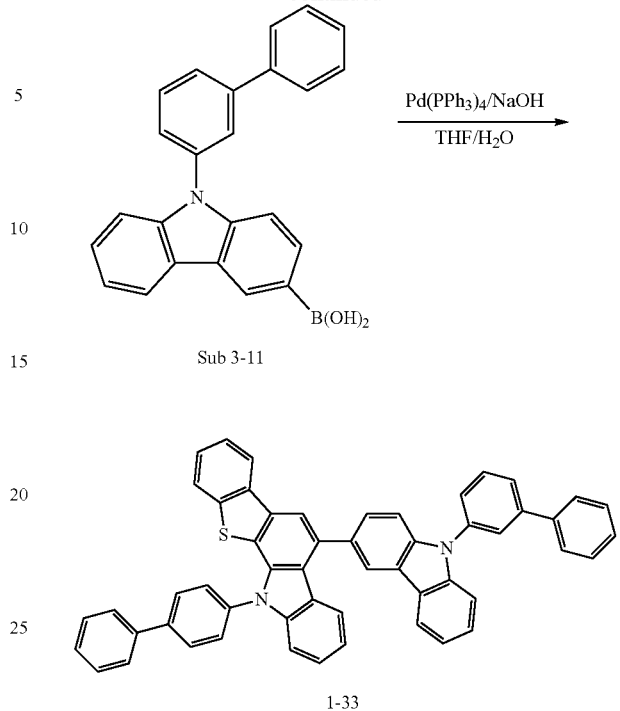

Sub 1-7 (10 g, 20 mmol), Sub 3-11 (7.3 g, 20 mmol), Pd(PPh$_3$)$_4$ (0.9 g, 0.8 mmol), NaOH (2.4 g, 59 mmol) and THF (40 mL)/H$_2$O (20 mL) were used in the same manner as described above for the synthesis of compound 1-2 to obtain the product 1-33 (13.5 g, 91%).

Synthesis of Compound 1-51

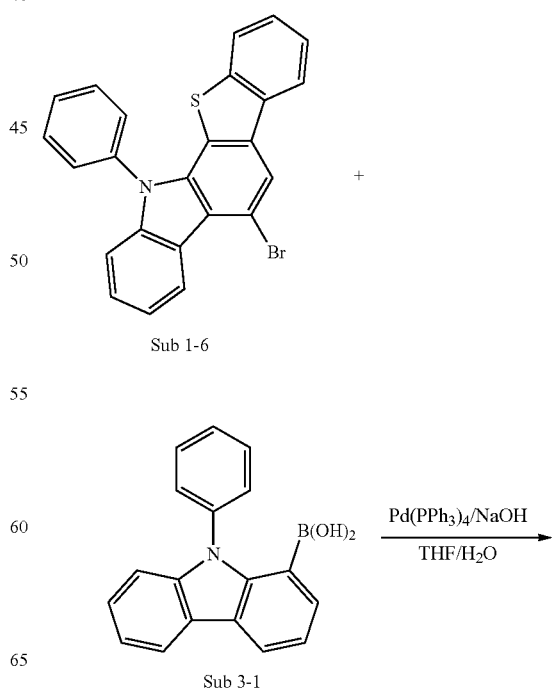

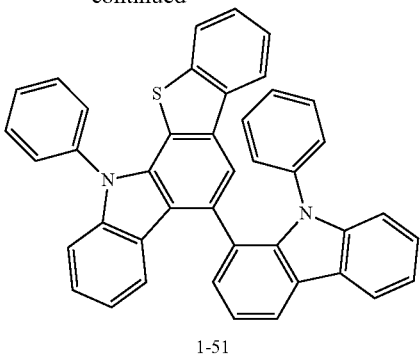

1-51

Sub 1-6 (5 g, 11.5 mmol), Sub 3-1 (3.9 g, 11.5 mmol), Pd(PPh$_3$)$_4$ (0.5 g, 0.5 mmol), NaOH (1.4 g, 35 mmol) were THF (30 mL)/H$_2$O (15 mL) were used in the same manner as described above for the synthesis of compound 1-2 to obtain the product 1-51 (3.5 g, 51%).

Synthesis of Compound 1-52

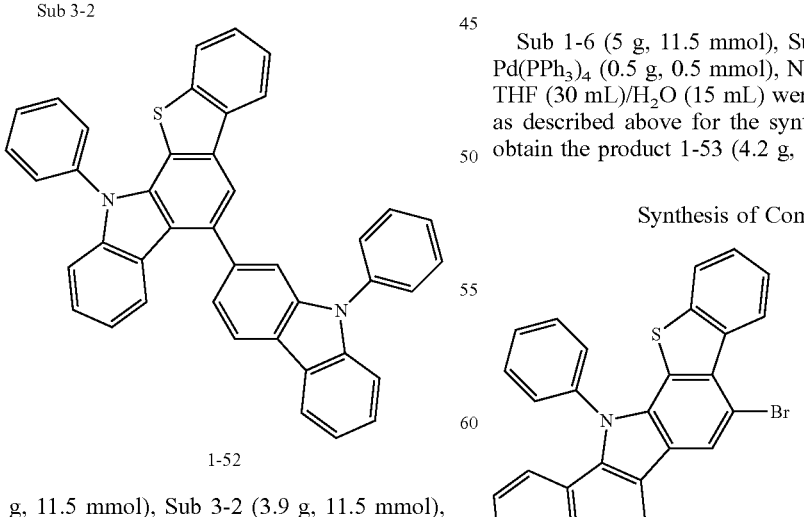

1-52

Sub 1-6 (5 g, 11.5 mmol), Sub 3-2 (3.9 g, 11.5 mmol), Pd(PPh$_3$)$_4$ (0.5 g, 0.5 mmol), NaOH (1.4 g, 35 mmol) and THF (30 mL)/H$_2$O (15 mL) were used in the same manner as described above for the synthesis of compound 1-2 to obtain the product 1-52 (3.8 g, 56%).

Synthesis of Compound 1-53

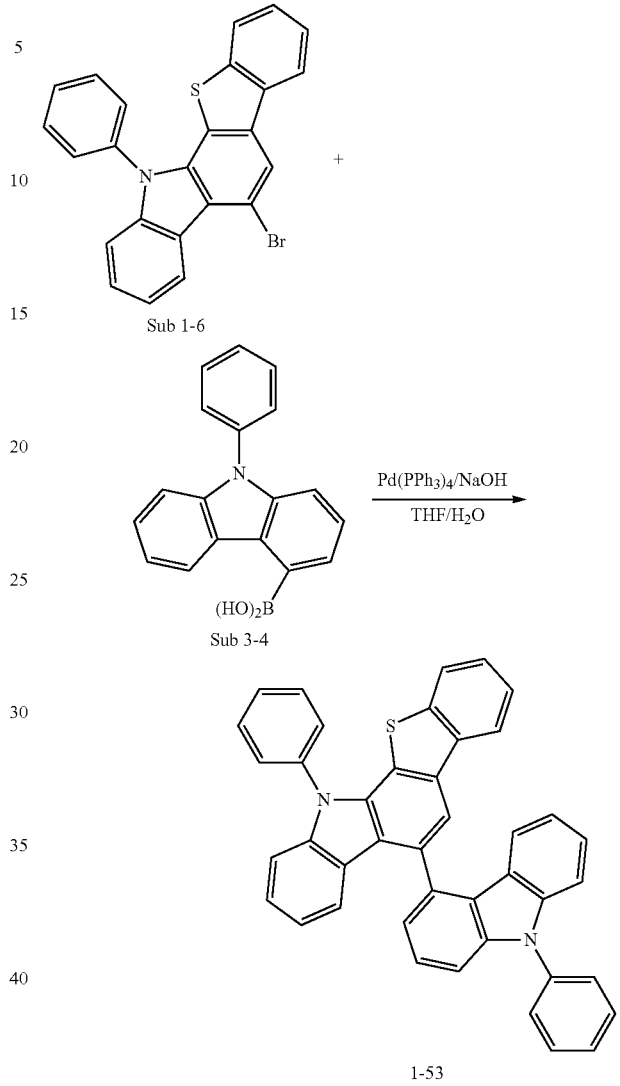

1-53

Sub 1-6 (5 g, 11.5 mmol), Sub 3-4 (3.9 g, 11.5 mmol), Pd(PPh$_3$)$_4$ (0.5 g, 0.5 mmol), NaOH (1.4 g, 35 mmol) and THF (30 mL)/H$_2$O (15 mL) were used in the same manner as described above for the synthesis of compound 1-2 to obtain the product 1-53 (4.2 g, 62%).

Synthesis of Compound 1-66

-continued

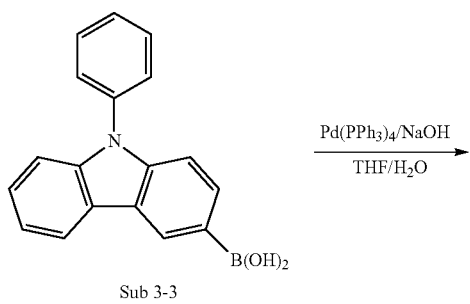
Sub 3-3

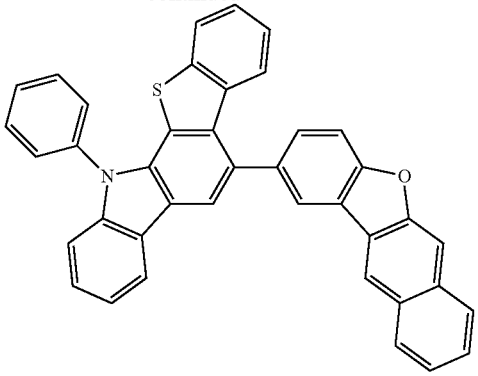
1-71

To a round bottom flask were added Sub 1-1 (5 g, 11.5 mmol), Sub 3-46 (3.0 g, 11.5 mmol), Pd(PPh₃)₄ (0.5 g, 0.5 mmol), NaOH (1.4 g, 35 mmol) and THF (30 mL)/H₂O (15 mL)), and then the product 1-71 (4.7 g, 73%) was obtained by using the same manner as described above for the synthesis of compound Sub 1-2.

Synthesis of Compound 1-78

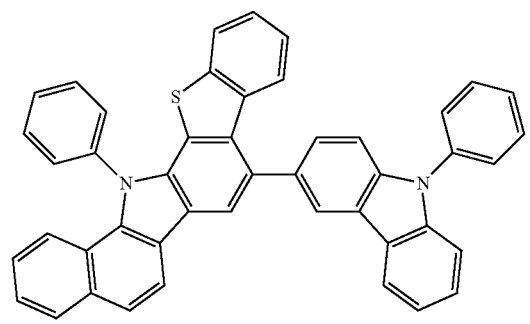
1-66

Sub 1-14 (10 g, 21 mmol), Sub 3-3 (7.6 g, 21 mmol), Pd(PPh₃)₄ (1 g, 0.8 mmol), NaOH (2.5 g, 63 mmol) and THF (40 mL)/H₂O (20 mL) were used in the same manner as described above for the synthesis of compound 1-2 to obtain the product 1-66 (8.5 g, 63%).

Synthesis of Compound 1-71

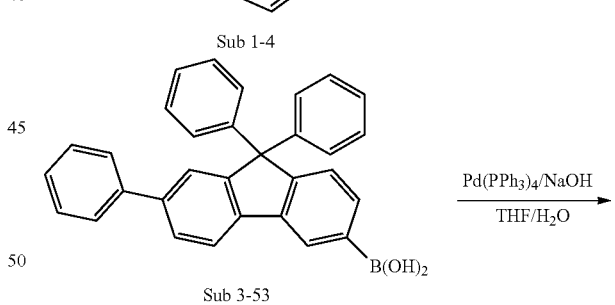
Sub 1-4

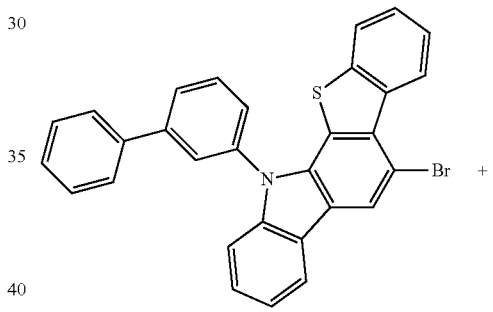
Sub 3-53

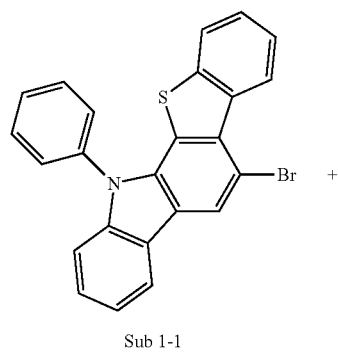
Sub 1-1

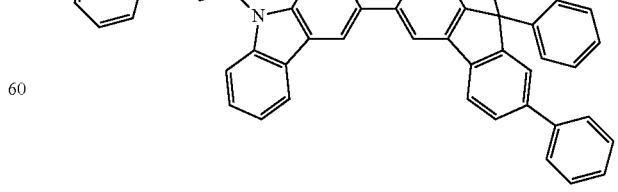
1-78

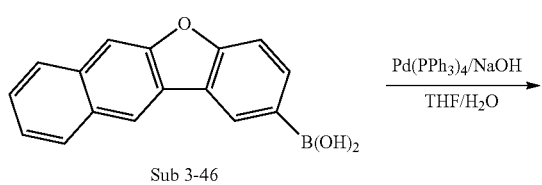
Sub 3-46

To a round bottom flask were added Sub 1-4 (5 g, 9.9 mmol), Sub 3-53 (4.3 g, 9.9 mmol), Pd(PPh₃)₄ (0.5 g, 0.4 mmol), NaOH (1.2 g, 29.7 mmol) and THF (40 mL)/H₂O (20 mL), and then the product 1-78 (5.3 g, 65%) was obtained by using the same manner as described above for the synthesis of compound Sub 1-2.

Synthesis of Compound 1-90

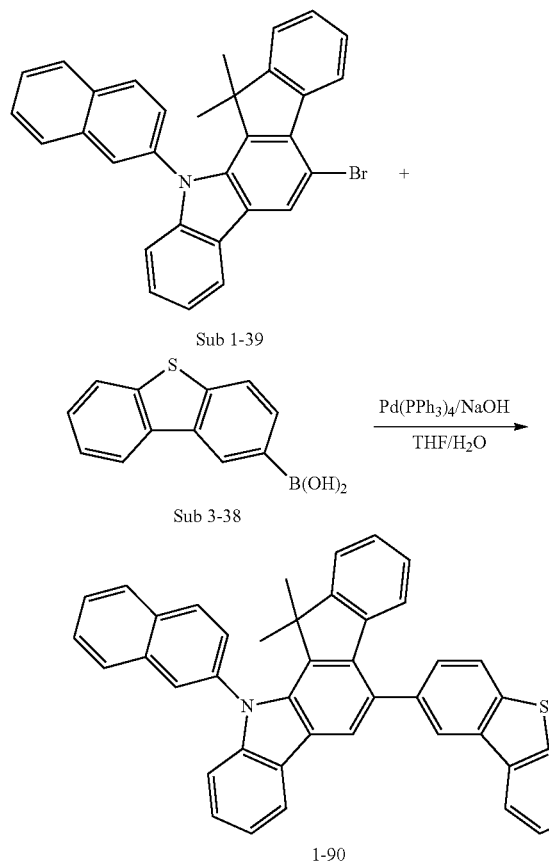

To a round bottom flask were added Sub 1-39 (10 g, 20.5 mmol), Sub 3-38 (5.9 g, 20.5 mmol), Pd(PPh₃)₄ (1 g, 0.8 mmol), NaOH (2.5 g, 61 mmol) and THF (40 mL)/H₂O (20 mL), and then the product 1-90 (5.8 g, 48%) was obtained by using the same manner as described above for the synthesis of compound Sub 1-2.

Synthesis of Compound 2-1

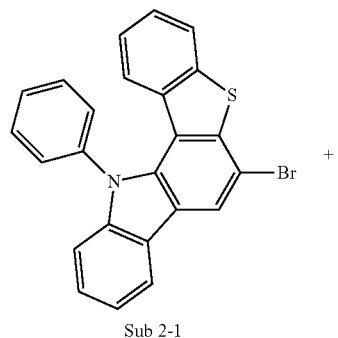

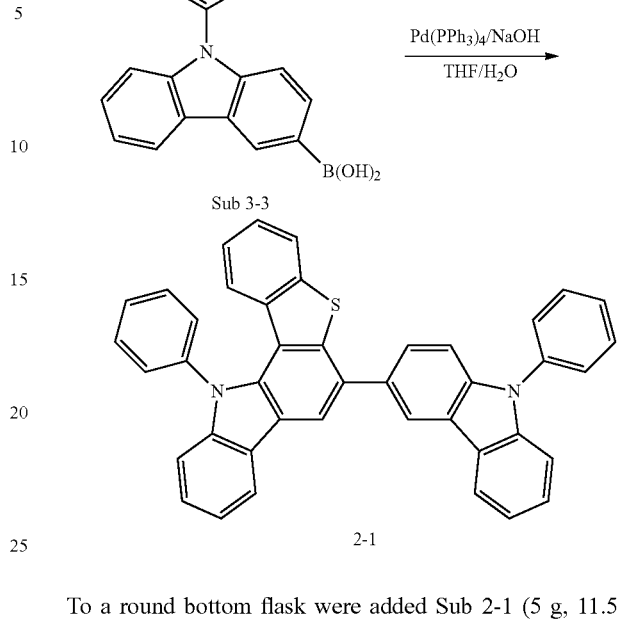

To a round bottom flask were added Sub 2-1 (5 g, 11.5 mmol), Sub 3-3 (3.9 g, 11.5 mmol), Pd(PPh₃)₄ (0.5 g, 0.5 mmol), NaOH (1.4 g, 35 mmol) and THF (30 mL)/H₂O (15 mL), and then the product 2-1 (5.5 g, 81%) was obtained by using the same manner as described above for the synthesis of compound Sub 1-2.

Synthesis of Compound 2-2

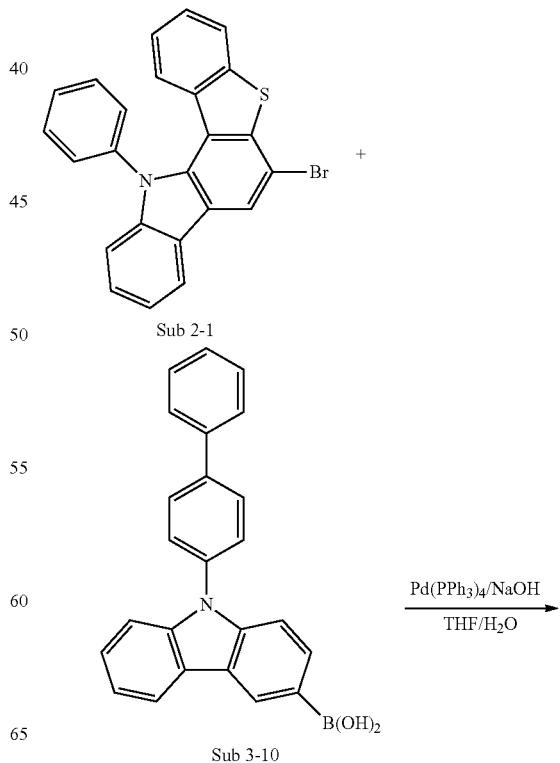

Synthesis of Compound 2-6

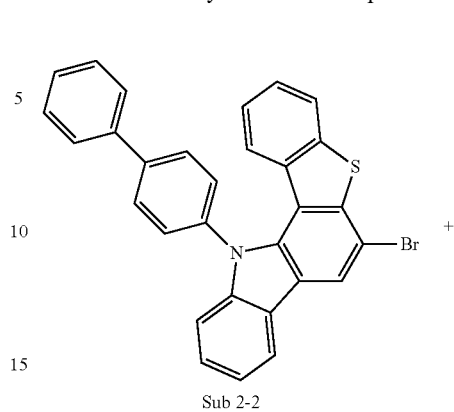

Sub 2-2

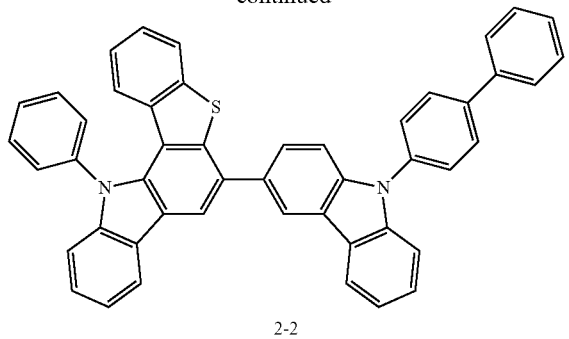

2-2

To a round bottom flask were added Sub 2-1 (5 g, 11.5 mmol), Sub 3-10 (4.2 g, 11.5 mmol), Pd(PPh$_3$)$_4$ (0.5 g, 0.5 mmol), NaOH (1.4 g, 35 mmol) and THF (30 mL)/H$_2$O (15 mL), and then the product 2-2 (6.1 g, 80%) was obtained by using the same manner as described above for the synthesis of compound Sub 1-2.

Synthesis of Compound 2-3

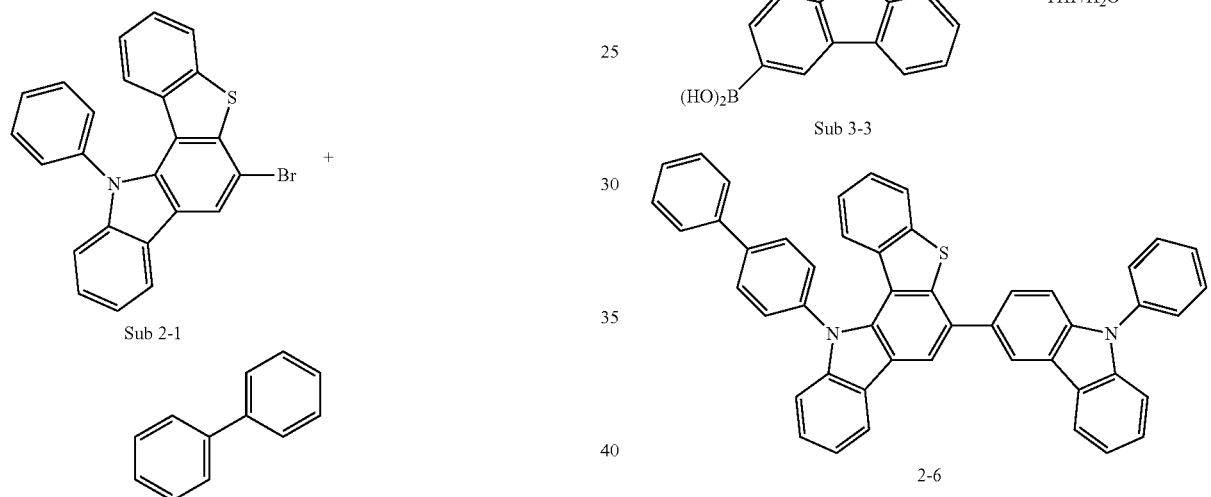

Sub 2-1

Sub 3-11

2-3

To a round bottom flask were added Sub 2-1 (5 g, 11.5 mmol), Sub 3-11 (4.2 g, 11.5 mmol), Pd(PPh$_3$)$_4$ (0.5 g, 0.5 mmol), NaOH (1.4 g, 35 mmol) and THF (30 mL)/H$_2$O (15 mL), and then the product 2-3 (5.8 g, 76%) was obtained by using the same manner as described above for the synthesis of compound Sub 1-2.

Sub 3-3

2-6

To a round bottom flask were added Sub 2-2 (10 g, 20 mmol), Sub 3-3 (5.7 g, 20 mmol), Pd(PPh$_3$)$_4$ (0.9 g, 0.8 mmol), NaOH (2.4 g, 59 mmol) and THF (40 mL)/H$_2$O (20 mL), and then the product 2-6 (10.3 g, 81%) was obtained by using the same manner as described above for the synthesis of compound Sub 1-2.

Synthesis of Compound 2-7

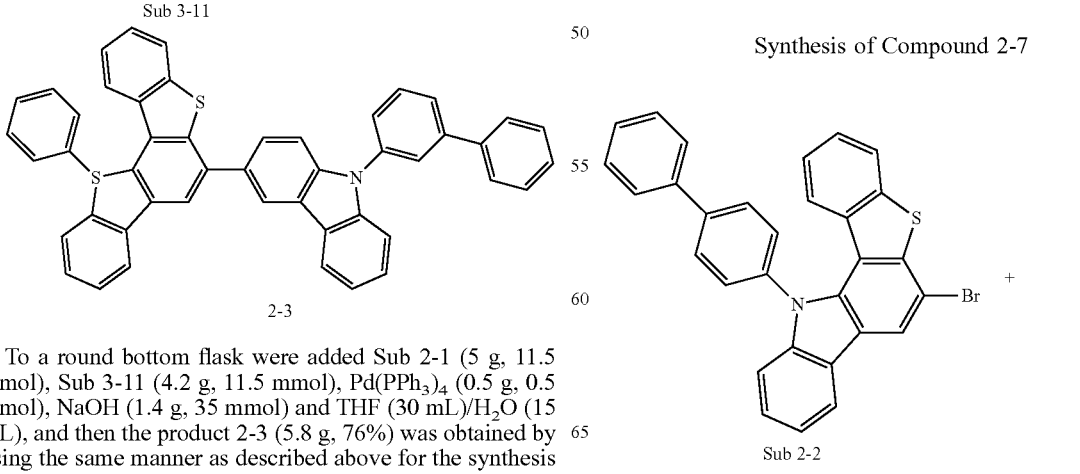

Sub 2-2

-continued

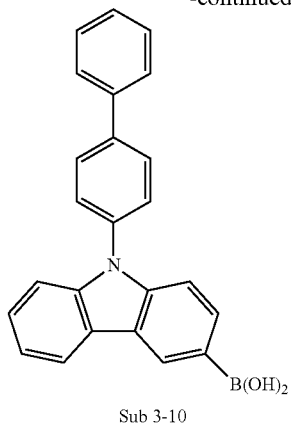
Sub 3-10

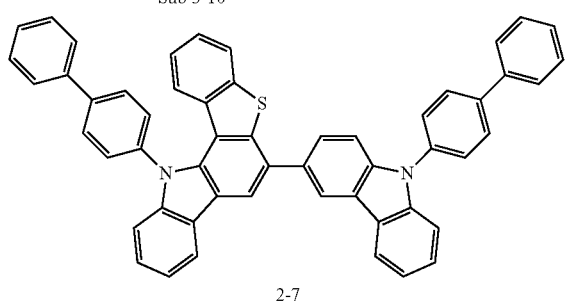
2-7

To a round bottom flask were added Sub 2-2 (10 g, 20 mmol), Sub 3-10 (7.3 g, 20 mmol), Pd(PPh$_3$)$_4$ (0.9 g, 0.8 mmol), NaOH (2.4 g, 59 mmol) and THF (40 mL)/H$_2$O (20 mL), and then the product 2-7 (11 g, 74%) was obtained by using the same manner as described above for the synthesis of compound Sub 1-2.

Synthesis of Compound 2-8

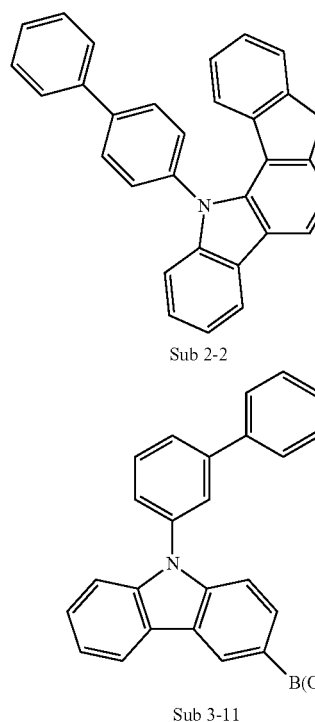
Sub 2-2

Sub 3-11

-continued

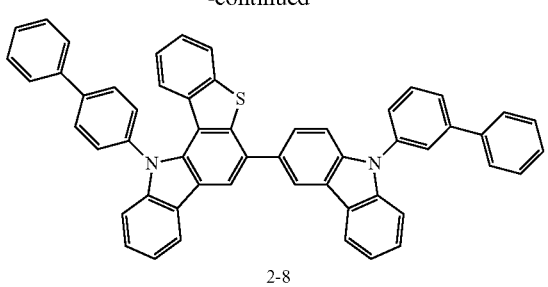
2-8

To a round bottom flask were added Sub 2-2 (10 g, 20 mmol), Sub 3-11 (7.3 g, 20 mmol), Pd(PPh$_3$)$_4$ (0.9 g, 0.8 mmol), NaOH (2.4 g, 59 mmol) and THF (40 mL)/H$_2$O (20 mL), and then the product 2-8 (12 g, 81%) was obtained by using the same manner as described above for the synthesis of compound Sub 1-2.

Synthesis of Compound 2-33

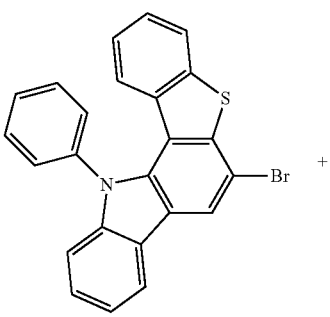
Sub 2-1

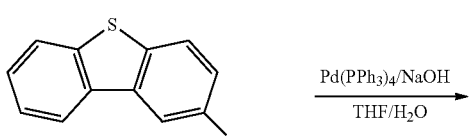
Sub 3-38

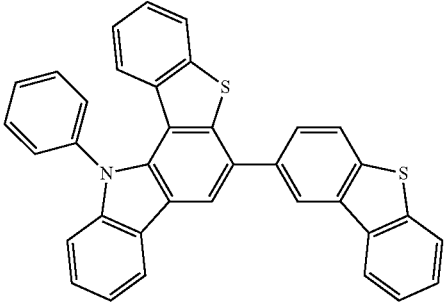
2-33

To a round bottom flask were added Sub 2-1 (5 g, 11.5 mmol), Sub 3-38 (2.6 g, 11.5 mmol), Pd(PPh$_3$)$_4$ (0.5 g, 0.5 mmol), NaOH (1.4 g, 35 mmol) and THF (30 mL)/H$_2$O (15 mL), and then the product 2-1 (5.0 g, 82%) was obtained by using the same manner as described above for the synthesis of compound Sub 1-2.

Synthesis of 2-38

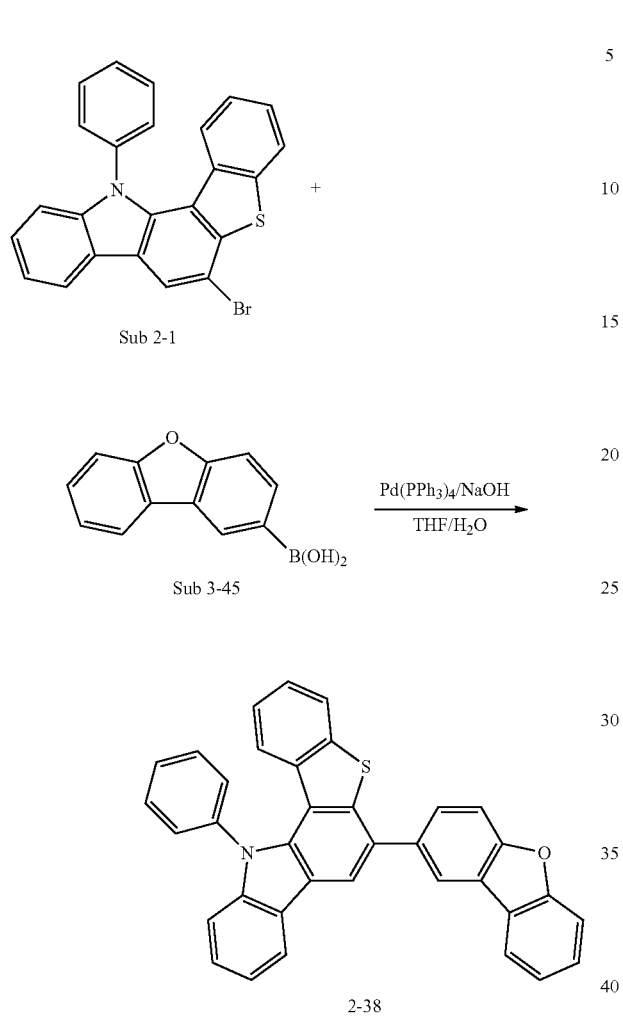

To a round bottom flask were added Sub 2-1 (5 g, 11.5 mmol), Sub 3-45 (2.4 g, 11.5 mmol), Pd(PPh₃)₄ (0.5 g, 0.5 mmol), NaOH (1.4 g, 35 mmol) and THF (30 mL)/H₂O (15 mL), and then the product 2-1 (4.4 g, 74%) was obtained by using the same manner as described above for the synthesis of compound Sub 1-2.

Synthesis of Compound 2-133

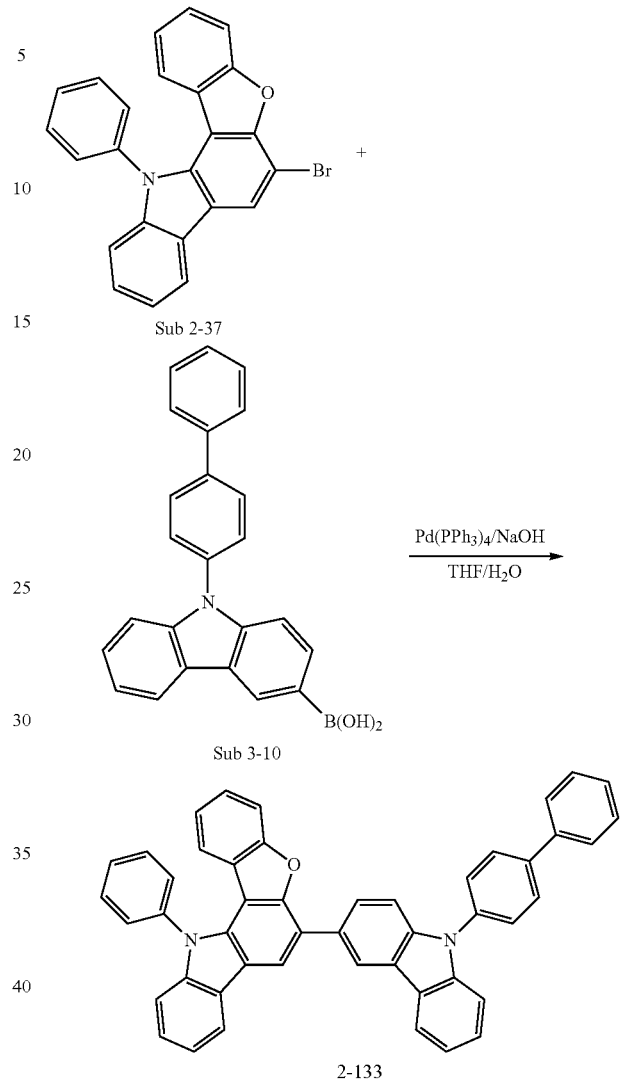

To a round bottom flask were added Sub 2-37 (5 g, 12 mmol), Sub 3-10 (4.4 g, 12 mmol), Pd(PPh₃)₄ (0.6 g, 0.5 mmol), NaOH (1.5 g, 36 mmol) and THF (30 mL)/H₂O (15 mL), and then the product 2-133 (5.6 g, 72%) was obtained by using the same manner as described above for the synthesis of compound Sub 1-2.

TABLE 4

| compound | FD-MS | compound | FD-MS |
|---|---|---|---|
| 1-1 | m/z = 690.21($C_{50}H_{30}N_2S$ = 690.85) | 1-2 | m/z = 590.18($C_{42}H_{26}N_2S$ = 590.73) |
| 1-3 | m/z = 666.21($C_{48}H_{30}N_2S$ = 666.83) | 1-4 | m/z = 666.21($C_{48}H_{30}N_2S$ = 666.83) |
| 1-5 | m/z = 640.20($C_{46}H_{28}N_2S$ = 640.79) | 1-6 | m/z = 640.20($C_{46}H_{28}N_2S$ = 640.79) |
| 1-7 | m/z = 666.21($C_{48}H_{30}N_2S$ = 666.83) | 1-8 | m/z = 742.24($C_{54}H_{34}N_2S$ = 742.93) |
| 1-9 | m/z = 742.24($C_{54}H_{34}N_2S$ = 742.93) | 1-10 | m/z = 716.23($C_{52}H_{32}N_2S$ = 716.89) |
| 1-11 | m/z = 716.23($C_{52}H_{32}N_2S$ = 716.89) | 1-12 | m/z = 666.21($C_{48}H_{30}N_2S$ = 666.83) |
| 1-13 | m/z = 640.20($C_{46}H_{28}N_2S$ = 640.79) | 1-14 | m/z = 716.23($C_{52}H_{32}N_2S$ = 716.89) |
| 1-15 | m/z = 716.23($C_{52}H_{32}N_2S$ = 716.89) | 1-16 | m/z = 690.21 ($C_{50}H_{30}N_2S$ = 690.85) |
| 1-17 | m/z = 690.21($C_{50}H_{30}N_2S$ = 690.85) | 1-18 | m/z = 640.20($C_{46}H_{28}N_2S$ = 640.79) |
| 1-19 | m/z = 716.23($C_{52}H_{32}N_2S$ = 716.89) | 1-20 | m/z = 716.23($C_{52}H_{32}N_2S$ = 716.89) |
| 1-21 | m/z = 690.21($C_{50}H_{30}N_2S$ = 690.85) | 1-22 | m/z = 690.21($C_{50}H_{30}N_2S$ = 690.85) |
| 1-23 | m/z = 590.18($C_{42}H_{26}N_2S$ = 590.73) | 1-24 | m/z = 590.18($C_{42}H_{26}N_2S$ = 590.73) |
| 1-25 | m/z = 590.18($C_{42}H_{26}N_2S$ = 590.73) | 1-26 | m/z = 590.18($C_{42}H_{26}N_2S$ = 590.73) |
| 1-27 | m/z = 666.21($C_{48}H_{30}N_2S$ = 666.83) | 1-28 | m/z = 666.21($C_{48}H_{30}N_2S$ = 666.83) |
| 1-29 | m/z = 640.20($C_{46}H_{28}N_2S$ = 640.79) | 1-30 | m/z = 640.20($C_{46}H_{28}N_2S$ = 640.79) |

TABLE 4-continued

| compound | FD-MS | compound | FD-MS |
| --- | --- | --- | --- |
| 1-31 | m/z = 666.21($C_{48}H_{30}N_2S$ = 666.83) | 1-32 | m/z = 742.24($C_{54}H_{34}N_2S$ = 742.93) |
| 1-33 | m/z = 742.24($C_{54}H_{34}N_2S$ = 742.93) | 1-34 | m/z = 716.23($C_{52}H_{32}N_2S$ = 716.89) |
| 1-35 | m/z = 716.23($C_{52}H_{32}N_2S$ = 716.89) | 1-36 | m/z = 666.21($C_{48}H_{30}N_2S$ = 666.83) |
| 1-37 | m/z = 742.24($C_{54}H_{34}N_2S$ = 742.93) | 1-38 | m/z = 742.24($C_{54}H_{34}N_2S$ = 742.93) |
| 1-39 | m/z = 716.23($C_{52}H_{32}N_2S$ = 716.89) | 1-40 | m/z = 716.23($C_{52}H_{32}N_2S$ = 716.89) |
| 1-41 | m/z = 640.20($C_{46}H_{28}N_2S$ = 640.79) | 1-42 | m/z = 716.23($C_{52}H_{32}N_2S$ = 716.89) |
| 1-43 | m/z = 716.23($C_{52}H_{32}N_2S$ = 716.89) | 1-44 | m/z = 690.21($C_{50}H_{30}N_2S$ = 690.85) |
| 1-45 | m/z = 690.21($C_{50}H_{30}N_2S$ = 690.85) | 1-46 | m/z = 640.20($C_{46}H_{28}N_2S$ = 640.79) |
| 1-47 | m/z = 716.23($C_{52}H_{32}N_2S$ = 716.89) | 1-48 | m/z = 716.23($C_{52}H_{32}N_2S$ = 716.89) |
| 1-49 | m/z = 690.21($C_{50}H_{30}N_2S$ = 690.85) | 1-50 | m/z = 690.21($C_{50}H_{30}N_2S$ = 690.85) |
| 1-51 | m/z = 590.18($C_{42}H_{26}N_2S$ = 590.73) | 1-52 | m/z = 590.18($C_{42}H_{26}N_2S$ = 590.73) |
| 1-53 | m/z = 590.18($C_{42}H_{26}N_2S$ = 590.73) | 1-54 | m/z = 531.11($C_{36}H_{21}NS_2$ = 531.69) |
| 1-55 | m/z = 531.11($C_{36}H_{21}NS_2$ = 531.69) | 1-56 | m/z = 515.13($C_{36}H_{21}NOS$ = 515.62) |
| 1-57 | m/z = 744.23($C_{52}H_{32}N_4S$ = 743.90) | 1-58 | m/z = 870.28($C_{62}H_{38}N_4S$ = 871.06) |
| 1-59 | m/z = 768.23($C_{54}H_{32}N_4S$ = 768.92) | 1-60 | m/z = 718.22($C_{50}H_{30}N_4S$ = 718.87) |
| 1-61 | m/z = 931.30($C_{68}H_{41}N_3S$ = 932.14) | 1-62 | m/z = 808.25($C_{56}H_{32}N_4OS$ = 808.94) |
| 1-63 | m/z = 850.22($C_{58}H_{34}N_4S_2$ = 851.05) | 1-64 | m/z = 831.32($C_{57}H_{25}D_{10}N_5S$ = 832.05) |
| 1-65 | m/z = 768.23($C_{54}H_{32}N_4S$ = 768.92) | 1-66 | m/z = 640.20($C_{46}H_{28}N_2S$ = 640.79) |
| 1-67 | m/z = 531.11($C_{36}H_{21}NS_2$ = 531.69) | 1-68 | m/z = 708.17($C_{49}H_{28}N_2S_2$ = 708.89) |
| 1-69 | m/z = 733.19($C_{52}H_{31}NS_2$ = 733.94) | 1-70 | m/z = 708.17($C_{49}H_{28}N_2S_2$ = 708.89) |
| 1-71 | m/z = 565.15($C_{40}H_{23}NOS$ = 565.68) | 1-72 | m/z = 822.25($C_{57}H_{34}N_4OS$ = 822.97) |
| 1-73 | m/z = 809.21($C_{56}H_{31}N_3O_2S$ = 809.93) | 1-74 | m/z = 781.13($C_{53}H_{31}NSSe$ = 780.83) |
| 1-75 | m/z = 681.08($C_{42}H_{23}N_3SSe$ = 680.68) | 1-76 | m/z = 585.19($C_{40}H_{31}NSSi$ = 585.83) |
| 1-77 | m/z = 809.23($C_{56}H_{35}N_3SSi$ = 810.05) | 1-78 | m/z = 817.28($C_{61}H_{39}NS$ = 818.03) |
| 1-79 | m/z = 817.26($C_{59}H_{35}N_3S$ = 817.99) | 1-80 | m/z = 742.28($C_{50}H_{30}N_4OS$ = 742.93) |
| 1-81 | m/z = 574.20($C_{42}H_{26}N_2O$ = 574.67) | 1-82 | m/z = 624.22($C_{46}H_{28}N_2O$ = 624.73) |
| 1-83 | m/z = 852.29($C_{66}H_{36}N_4O$ = 852.98) | 1-84 | m/z = 834.25($C_{58}H_{34}N_4OS$ = 834.98) |
| 1-85 | m/z = 649.24($C_{49}H_{31}NO$ = 649.78) | 1-86 | m/z = 829.24($C_{61}H_{35}NOS$ = 830.00) |
| 1-87 | m/z = 665.22($C_{48}H_{31}NOSi$ = 665.85) | 1-88 | m/z = 563.08($C_{36}H_{21}NOSe$ = 562.52) |
| 1-89 | m/z = 600.26($C_{45}H_{32}N_2$ = 600.75) | 1-90 | m/z = 591.20($C_{43}H_{29}NS$ = 591.76) |
| 1-91 | m/z = 525.21($C_{39}H_{27}NO$ = 525.64) | 1-92 | m/z = 551.26($C_{42}H_{33}N$ = 551.72) |
| 1-93 | m/z = 616.23($C_{44}H_{32}N_2Si$ = 616.82) | 1-94 | m/z = 541.19($C_{38}H_{27}NOSi$ = 541.71) |
| 1-95 | m/z = 557.16($C_{38}H_{27}NSSi$ = 557.78) | 1-96 | m/z = 638.13($C_{42}H_{26}N_2Se$ = 637.63) |
| 1-97 | m/z = 563.08($C_{35}H_{21}NOSe$ = 562.52) | 1-98 | m/z = 589.13($C_{39}H_{27}NSe$ = 588.60) |
| 2-1 | m/z = 590.18($C_{42}H_{26}N_2S$ = 590.73) | 2-2 | m/z = 666.21($C_{48}H_{30}N_2S$ = 666.83) |
| 2-3 | m/z = 666.21($C_{48}H_{30}N_2S$ = 666.83) | 2-4 | m/z = 640.20($C_{46}H_{28}N_2S$ = 640.79) |
| 2-5 | m/z = 640.20($C_{46}H_{28}N_2S$ = 640.79) | 2-6 | m/z = 666.21($C_{48}H_{30}N_2S$ = 666.83) |
| 2-7 | m/z = 742.24($C_{54}H_{34}N_2S$ = 742.93) | 2-8 | m/z = 742.24($C_{54}H_{34}N_2S$ = 742.93) |
| 2-9 | m/z = 716.23($C_{52}H_{32}N_2S$ = 716.89) | 2-10 | m/z = 716.23($C_{52}H_{32}N_2S$ = 716.89) |
| 2-11 | m/z = 666.21($C_{48}H_{30}N_2S$ = 666.83) | 2-12 | m/z = 742.24($C_{54}H_{34}N_2S$ = 742.93) |
| 2-13 | m/z = 742.24($C_{54}H_{34}N_2S$ = 742.93) | 2-14 | m/z = 716.23($C_{52}H_{32}N_2S$ = 716.89) |
| 2-15 | m/z = 716.23($C_{52}H_{32}N_2S$ = 716.89) | 2-16 | m/z = 716.23($C_{52}H_{32}N_2S$ = 716.89) |
| 2-17 | m/z = 716.23($C_{52}H_{32}N_2S$ = 716.89) | 2-18 | m/z = 716.23($C_{52}H_{32}N_2S$ = 716.89) |
| 2-19 | m/z = 690.21($C_{50}H_{30}N_2S$ = 690.85) | 2-20 | m/z = 690.21($C_{50}H_{30}N_2S$ = 690.85) |
| 2-21 | m/z = 640.20($C_{46}H_{28}N_2S$ = 640.79) | 2-22 | m/z = 716.23($C_{52}H_{32}N_2S$ = 716.89) |
| 2-23 | m/z = 716.23($C_{52}H_{32}N_2S$ = 716.89) | 2-24 | m/z = 690.21($C_{50}H_{30}N_2S$ = 690.85) |
| 2-25 | m/z = 742.24($C_{54}H_{34}N_2S$ = 742.93) | 2-26 | m/z = 742.24($C_{54}H_{34}N_2S$ = 742.93) |
| 2-27 | m/z = 716.23($C_{52}H_{32}N_2S$ = 716.89) | 2-28 | m/z = 716.23($C_{52}H_{32}N_2S$ = 716.89) |
| 2-29 | m/z = 746.28($C_{54}H_{38}N_2S$ = 746.96) | 2-30 | m/z = 796.25($C_{57}H_{36}N_2OS$ = 796.97) |
| 2-31 | m/z = 780.26($C_{57}H_{36}N_2S$ = 780.97) | 2-32 | m/z = 743.24($C_{53}H_{33}N_3S$ = 743.91) |
| 2-33 | m/z = 531.11($C_{36}H_{21}NS_2$ = 531.69) | 2-34 | m/z = 607.14($C_{42}H_{25}NS_2$ = 607.78) |
| 2-35 | m/z = 607.14($C_{42}H_{25}NS_2$ = 607.78) | 2-36 | m/z = 581.13($C_{40}H_{23}NS_2$ = 581.75) |
| 2-37 | m/z = 581.13($C_{40}H_{23}NS_2$ = 581.75) | 2-38 | m/z = 515.13($C_{36}H_{21}NOS$ = 515.62) |
| 2-39 | m/z = 591.17($C_{42}H_{25}NOS$ = 591.72) | 2-40 | m/z = 591.17($C_{42}H_{25}NOS$ = 591.72) |
| 2-41 | m/z = 565.15($C_{40}H_{23}NOS$ = 565.68) | 2-42 | m/z = 565.15($C_{40}H_{23}NOS$ = 565.68) |
| 2-43 | m/z = 541.19($C_{39}H_{27}NS$ = 541.70) | 2-44 | m/z = 617.21($C_{45}H_{31}NS$ = 617.80) |
| 2-45 | m/z = 617.21($C_{45}H_{31}NS$ = 617.80) | 2-46 | m/z = 591.20($C_{43}H_{29}NS$ = 591.76) |
| 2-47 | m/z = 591.20($C_{43}H_{29}NS$ = 591.76) | 2-48 | m/z = 590.18($C_{42}H_{26}N_2S$ = 590.73) |
| 2-49 | m/z = 590.18($C_{42}H_{26}N_2S$ = 590.73) | 2-50 | m/z = 590.18($C_{42}H_{26}N_2S$ = 590.73) |
| 2-51 | m/z = 590.18($C_{42}H_{26}N_2S$ = 590.73) | 2-52 | m/z = 666.21($C_{48}H_{30}N_2S$ = 666.83) |
| 2-53 | m/z = 666.21($C_{48}H_{30}N_2S$ = 666.83) | 2-54 | m/z = 640.20($C_{46}H_{28}N_2S$ = 640.79) |
| 2-55 | m/z = 640.20($C_{46}H_{28}N_2S$ = 640.79) | 2-56 | m/z = 666.21($C_{48}H_{30}N_2S$ = 666.83) |
| 2-57 | m/z = 742.24($C_{54}H_{34}N_2S$ = 742.93) | 2-58 | m/z = 742.24($C_{54}H_{34}N_2S$ = 742.93) |
| 2-59 | m/z = 716.23($C_{52}H_{32}N_2S$ = 716.89) | 2-60 | m/z = 716.23($C_{52}H_{32}N_2S$ = 716.89) |
| 2-61 | m/z = 666.21($C_{48}H_{30}N_2S$ = 666.83) | 2-62 | m/z = 742.24($C_{54}H_{34}N_2S$ = 742.93) |
| 2-63 | m/z = 742.24($C_{54}H_{34}N_2S$ = 742.93) | 2-64 | m/z = 716.23($C_{52}H_{32}N_2S$ = 716.89) |
| 2-65 | m/z = 716.23($C_{52}H_{32}N_2S$ = 716.89) | 2-66 | m/z = 640.20($C_{46}H_{28}N_2S$ = 640.79) |
| 2-67 | m/z = 716.23($C_{52}H_{32}N_2S$ = 716.89) | 2-68 | m/z = 716.23($C_{52}H_{32}N_2S$ = 716.89) |
| 2-69 | m/z = 690.21($C_{50}H_{30}N_2S$ = 690.85) | 2-70 | m/z = 690.21($C_{50}H_{30}N_2S$ = 690.85) |
| 2-71 | m/z = 640.20($C_{46}H_{28}N_2S$ = 640.79) | 2-72 | m/z = 716.23($C_{52}H_{32}N_2S$ = 716.89) |
| 2-73 | m/z = 716.23($C_{52}H_{32}N_2S$ = 716.89) | 2-74 | m/z = 690.21($C_{50}H_{30}N_2S$ = 690.85) |
| 2-75 | m/z = 690.21($C_{50}H_{30}N_2S$ = 690.85) | 2-76 | m/z = 590.18($C_{42}H_{26}N_2S$ = 590.73) |
| 2-77 | m/z = 590.18($C_{42}H_{26}N_2S$ = 590.73) | 2-78 | m/z = 590.18($C_{42}H_{26}N_2S$ = 590.73) |
| 2-79 | m/z = 581.13($C_{40}H_{23}NS_2$ = 581.75) | 2-80 | m/z = 581.13($C_{40}H_{23}NS_2$ = 581.75) |

TABLE 4-continued

| compound | FD-MS | compound | FD-MS |
|---|---|---|---|
| 2-81 | m/z = 515.13($C_{36}H_{21}NOS$ = 515.62) | 2-82 | m/z = 591.17($C_{42}H_{25}NOS$ = 591.72) |
| 2-83 | m/z = 591.17($C_{42}H_{25}NOS$ = 591.72) | 2-84 | m/z = 565.15($C_{40}H_{23}NOS$ = 565.68) |
| 2-85 | m/z = 565.15($C_{40}H_{23}NOS$ = 565.68) | 2-86 | m/z = 541.19($C_{39}H_{27}NS$ = 541.70) |
| 2-87 | m/z = 617.21($C_{45}H_{31}NS$ = 617.80) | 2-88 | m/z = 617.21($C_{45}H_{31}NS$ = 617.80) |
| 2-89 | m/z = 531.11($C_{36}H_{21}NS_2$ = 531.69) | 2-90 | m/z = 607.14($C_{42}H_{25}NS_2$ = 607.78) |
| 2-91 | m/z = 607.14($C_{42}H_{25}NS_2$ = 607.78) | 2-92 | m/z = 591.20($C_{43}H_{29}NS$ = 591.76) |
| 2-93 | m/z = 591.20($C_{43}H_{29}NS$ = 591.76) | 2-94 | m/z = 745.23($C_{51}H_{31}N_5S$ = 745.89) |
| 2-95 | m/z = 744.23($C_{52}H_{32}N_4S$ = 744.90) | 2-96 | m/z = 744.23($C_{52}H_{32}N_4S$ = 744.90) |
| 2-97 | m/z = 744.23($C_{52}H_{32}N_4S$ = 744.90) | 2-98 | m/z = 718.22($C_{50}H_{30}N_4S$ = 718.87) |
| 2-99 | m/z = 745.23($C_{51}H_{31}N_5S$ = 745.89) | 2-100 | m/z = 744.23($C_{52}H_{32}N_4S$ = 744.90) |
| 2-101 | m/z = 744.23($C_{52}H_{32}N_4S$ = 744.90) | 2-102 | m/z = 744.23($C_{52}H_{32}N_4S$ = 744.90) |
| 2-103 | m/z = 718.22($C_{50}H_{30}N_4S$ = 718.87) | 2-104 | m/z = 768.24($C_{54}H_{32}N_4S$ = 768.92) |
| 2-105 | m/z = 834.25($C_{58}H_{34}N_4OS$ = 834.98) | 2-106 | m/z = 900.24($C_{62}H_{36}N_4S_2$ = 901.11) |
| 2-107 | m/z = 844.27($C_{60}H_{36}N_4S$ = 845.02) | 2-108 | m/z = 847.25($C_{60}H_3FN_3S$ = 848.00) |
| 2-109 | m/z = 745.23($C_{51}H_{31}N_5S$ = 745.89) | 2-110 | m/z = 909.32($C_{67}H_{35}D_5N_2S$ = 910.14) |
| 2-111 | m/z = 747.18($C_{51}H_{29}N_3S_2$ = 747.93) | 2-112 | m/z = 762.29($C_{54}H_{30}D_5N_3S$ = 762.97) |
| 2-113 | m/z = 789.25($C_{59}H_{35}NS$ = 789.98) | 2-114 | m/z = 860.26($C_{60}H_{36}N_4OS$ = 861.02) |
| 2-115 | m/z = 515.13($C_{36}H_{21}NOS$ = 515.62) | 2-116 | m/z = 717.21($C_{52}H_{31}NOS$ = 717.87) |
| 2-117 | m/z = 770.21($C_{53}H_{30}N_4S$ = 770.90) | 2-118 | m/z = 845.25($C_{60}H_{35}N_3OS$ = 846.00) |
| 2-119 | m/z = 699.14($C_{46}H_{25}N_3S_2$ = 699.84) | 2-120 | m/z = 581.13($C_{40}H_{23}NS_2$ = 581.75) |
| 2-121 | m/z = 785.20($C_{54}H_{31}N_3S_2$ = 785.97) | 2-122 | m/z = 824.20($C_{57}H_{32}N_2OS_2$ = 825.01) |
| 2-123 | m/z = 697.19($C_{49}H_{31}NS_2$ = 697.91) | 2-124 | m/z = 624.04($C_{36}H_{20}N_2O_2SSe$ = 623.58) |
| 2-125 | m/z = 666.21($C_{48}H_{30}N_2S$ = 666.83) | 2-126 | m/z = 640.20($C_{46}H_{28}N_2S$ = 640.79) |
| 2-127 | m/z = 640.20($C_{46}H_{28}N_2S$ = 640.79) | 2-128 | m/z = 671.24($C_{48}H_{25}D_5N_2S$ = 671.86) |
| 2-129 | m/z = 671.24($C_{48}H_{25}D_5N_2S$ = 671.86) | 2-130 | m/z = 557.16($C_{38}H_{27}NSSi$ = 557.78) |
| 2-131 | m/z = 579.06($C_{36}H_{21}NSSe$ = 579.58) | 2-132 | m/z = 681.19($C_{48}H_{31}NSSi$ = 681.92) |
| 2-133 | m/z = 574.20($C_{42}H_{26}N_2O$ = 574.67) | 2-134 | m/z = 650.24($C_{48}H_{30}N_2O$ = 650.76) |
| 2-135 | m/z = 664.22($C_{48}H_{28}N_2O_2$ = 664.75) | 2-136 | m/z = 818.27($C_{58}H_{34}N_4O_2$ = 818.92) |
| 2-137 | m/z = 758.21($C_{52}H_{30}N_4OS$ = 758.89) | 2-138 | m/z = 702.24($C_{50}H_{30}N_4O$ = 702.80) |
| 2-139 | m/z = 729.25($C_{51}H_{31}N_5O$ = 729.82) | 2-140 | m/z = 759.23($C_{53}H_{33}N_3OS$ = 759.91) |
| 2-141 | m/z = 697.24($C_{53}H_{31}NO$ = 697.82) | 2-142 | m/z = 739.23($C_{54}H_{33}NOSi$ = 739.93) |
| 2-143 | m/z = 739.14($C_{50}H_{29}NOSe$ = 738.73) | 2-144 | m/z = 650.27($C_{49}H_{34}N_2$ = 650.81) |
| 2-145 | m/z = 591.20($C_{43}H_{29}NO$ = 591.76) | 2-146 | m/z = 525.21($C_{39}H_{27}NO$ = 525.64) |
| 2-147 | m/z = 551.26($C_{42}H_{33}$ = 551.72) | 2-148 | m/z = 616.23($C_{44}H_{32}N_2Si$ = 616.82) |
| 2-149 | m/z = 557.16($C_{38}H_{27}NSSi$ = 557.78) | 2-150 | m/z = 541.19($C_{38}H_{27}NOSi$ = 541.71) |
| 2-151 | m/z = 583.22($C_{40}H_{33}NSi_2$ = 583.87) | 2-152 | m/z = 638.13($C_{42}H_{25}N_2Se$ = 637.63) |
| 2-153 | m/z = 579.06($C_{36}H_{21}NSSe$ = 578.58) | 2-154 | m/z = 589.13($C_{39}H_{27}NSe$ = 588.60) |

Fabrication and Evaluation of Organic Electronic Element

Example 1

Green OLED (Phosphorescent Host)

First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter abbreviated as "2-TNATA") was vacuum-deposited on the ITO layer to form a hole injection layer with a thickness of 60 nm. Then, 4,4-bis[N-(1-naphthyl)-N-phenylamino]biphenyl (hereinafter abbreviated as "NPD") was vacuum-deposited on the hole injection layer to form a hole transfer layer with a thickness of 60 nm.

Subsequently, a light emitting layer with a thickness of 30 nm was deposited on the hole transport layer by doping the hole transport layer with the compound 1-1 of the present invention as a host material and tris(2-phenylpyridine)-iridium (hereinafter abbreviated as "Ir(ppy)$_3$") as a dopant material in a weight ratio of 95:5.

Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode.

[Example 2] to [Example 80]

The OLEDs were manufactured in the same manner as described in Example 1, except that any one of the compounds of the present invention in the Table 4 below was used as the green host material of the light emitting layer, instead of the inventive compound 1-1.

[Comparative Example 1] to [Comparative Example 7]

OLEDs were manufactured in the same manner as described in Example 1, except that any one of comparative compounds 1 to 7 in Table 5 below was used as the host material of the light emitting layer, instead of the inventive compound 1-1.

<comp.com. 1>

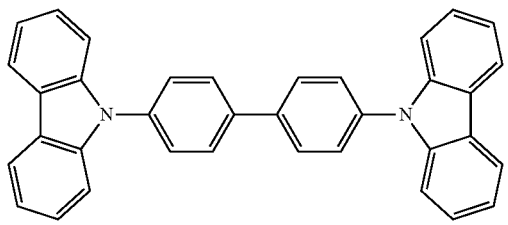

<comp.com. 2>

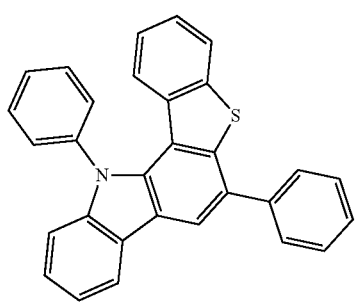

<comp.com. 3>

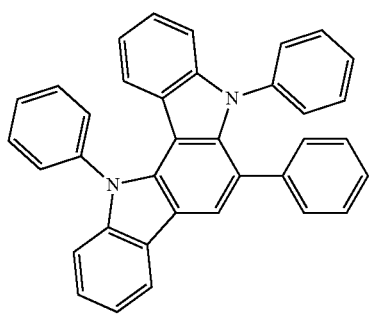

<comp.com. 4>

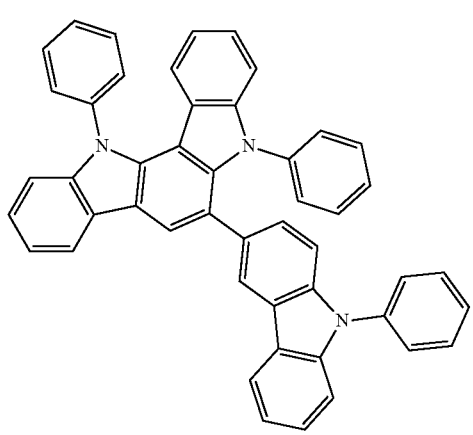

<comp.com. 5>

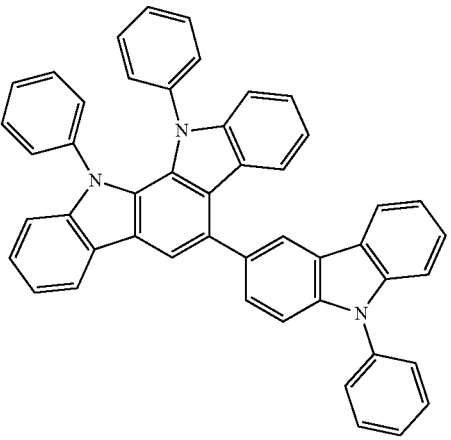

<comp.com. 6>

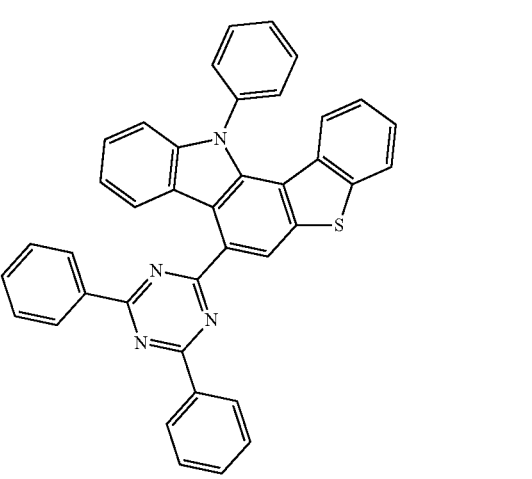

<comp.com. 7>

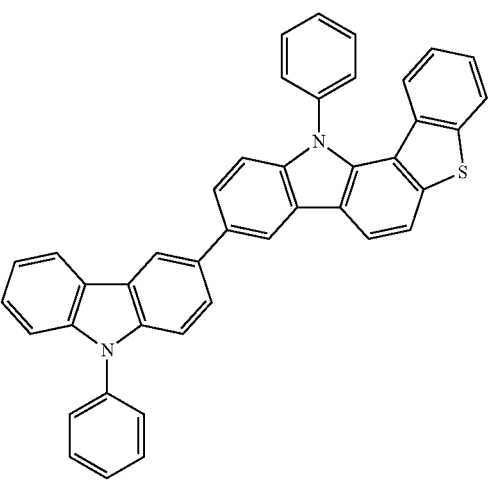

A forward bias DC voltage was applied to each of the OLEDs manufactured through the Examples 1 to 80 and Comparative Example 1 to 7, and electro-luminescence (EL) characteristics of the OLED were measured by PR-650 (Photo research). T95 life span was measured by life span measuring equipment (Mc science) at reference brightness of 5000 cd/m². Table 5 below shows evaluation results.

TABLE 5

| | compound | Voltage (V) | Current Density (mA/cm$^2$) | Brightness (cd/m$^2$) | Efficiency (cd/A) | Lifetime T(95) | CIE X | CIE Y |
|---|---|---|---|---|---|---|---|---|
| comp. Ex(1) | comp. Com 1 | 6.7 | 22.2 | 5000 | 22.5 | 63.5 | 0.33 | 0.61 |
| comp. Ex(2) | comp. Com 2 | 6.3 | 17.7 | 5000 | 28.2 | 84.2 | 0.33 | 0.62 |
| comp. Ex(3) | comp. Com 3 | 6.5 | 20.3 | 5000 | 24.6 | 75.8 | 0.32 | 0.62 |
| comp. Ex(4) | comp. Com 4 | 6.4 | 16.9 | 5000 | 29.5 | 90.3 | 0.32 | 0.62 |
| comp. Ex(5) | comp. Com 5 | 6.4 | 17.2 | 5000 | 29.1 | 88.6 | 0.32 | 0.62 |
| comp. Ex(6) | comp. Com 6 | 6.2 | 15.1 | 5000 | 33.2 | 98.4 | 0.32 | 0.62 |
| comp. Ex(7) | comp. Com 7 | 6.2 | 16.1 | 5000 | 31.1 | 96.5 | 0.32 | 0.62 |
| Ex. (1) | Com. (1-1) | 5.1 | 9.7 | 5000 | 51.6 | 141.0 | 0.32 | 0.62 |
| Ex. (2) | Com. (1-2) | 5.1 | 9.5 | 5000 | 52.4 | 141.9 | 0.32 | 0.62 |
| Ex. (3) | Com. (1-3) | 5.1 | 9.5 | 5000 | 52.5 | 142.3 | 0.32 | 0.62 |
| Ex. (4) | Com. (1-5) | 4.9 | 9.6 | 5000 | 52.3 | 141.2 | 0.33 | 0.61 |
| Ex. (5) | Com. (1-7) | 5.1 | 9.5 | 5000 | 52.5 | 142.3 | 0.33 | 0.61 |
| Ex. (6) | Com. (1-9) | 4.9 | 9.7 | 5000 | 51.6 | 142.4 | 0.33 | 0.61 |
| Ex. (7) | Com. (1-11) | 5.0 | 9.6 | 5000 | 52.3 | 141.0 | 0.33 | 0.62 |
| Ex. (8) | Com. (1-13) | 4.9 | 9.6 | 5000 | 51.9 | 141.1 | 0.33 | 0.61 |
| Ex. (9) | Com. (1-19) | 5.0 | 9.7 | 5000 | 51.6 | 142.5 | 0.33 | 0.62 |
| Ex. (10) | Com. (1-23) | 5.0 | 10.2 | 5000 | 49.0 | 140.3 | 0.33 | 0.61 |
| Ex. (11) | Com. (1-25) | 5.1 | 10.4 | 5000 | 47.9 | 139.1 | 0.33 | 0.61 |
| Ex. (12) | Com. (1-26) | 5.2 | 10.5 | 5000 | 47.4 | 140.3 | 0.33 | 0.61 |
| Ex. (13) | Com. (1-29) | 5.2 | 10.6 | 5000 | 47.3 | 140.5 | 0.33 | 0.62 |
| Ex. (14) | Com. (1-31) | 5.3 | 10.9 | 5000 | 45.8 | 139.6 | 0.33 | 0.62 |
| Ex. (15) | Com. (1-35) | 5.2 | 10.7 | 5000 | 46.8 | 140.9 | 0.33 | 0.61 |
| Ex. (16) | Com. (1-37) | 5.2 | 10.9 | 5000 | 45.8 | 140.8 | 0.33 | 0.62 |
| Ex. (17) | Com. (1-55) | 5.4 | 11.4 | 5000 | 43.7 | 135.4 | 0.33 | 0.61 |
| Ex. (18) | Com. (1-57) | 5.1 | 11.0 | 5000 | 45.5 | 138.0 | 0.33 | 0.62 |
| Ex. (19) | Com. (1-58) | 5.2 | 11.0 | 5000 | 45.3 | 138.2 | 0.33 | 0.61 |
| Ex. (20) | Com. (1-64) | 5.4 | 11.6 | 5000 | 43.1 | 135.3 | 0.33 | 0.61 |
| Ex. (21) | Com. (1-67) | 5.3 | 11.1 | 5000 | 45.1 | 139.1 | 0.33 | 0.61 |
| Ex. (22) | Com. (1-72) | 5.2 | 11.6 | 5000 | 43.1 | 136.0 | 0.33 | 0.62 |
| Ex. (23) | Com. (1-74) | 5.3 | 11.4 | 5000 | 44.0 | 136.4 | 0.33 | 0.62 |
| Ex. (24) | Com. (1-78) | 5.3 | 11.3 | 5000 | 44.1 | 136.8 | 0.33 | 0.61 |
| Ex. (25) | Com. (1-81) | 5.1 | 10.2 | 5000 | 49.2 | 138.5 | 0.33 | 0.61 |
| Ex. (26) | Com. (1-85) | 5.1 | 10.7 | 5000 | 46.7 | 140.8 | 0.33 | 0.62 |
| Ex. (27) | Com. (1-87) | 5.3 | 11.7 | 5000 | 42.8 | 135.0 | 0.33 | 0.61 |
| Ex. (28) | Com. (1-88) | 5.2 | 11.3 | 5000 | 44.2 | 137.4 | 0.33 | 0.62 |
| Ex. (29) | Com. (1-89) | 5.3 | 10.8 | 5000 | 46.2 | 138.3 | 0.33 | 0.62 |
| Ex. (30) | Com. (1-87) | 5.3 | 11.5 | 5000 | 43.3 | 137.1 | 0.33 | 0.62 |
| Ex. (31) | Com. (1-88) | 5.3 | 11.4 | 5000 | 43.9 | 137.2 | 0.33 | 0.62 |
| Ex. (32) | Com. (1-89) | 5.3 | 10.7 | 5000 | 46.7 | 139.7 | 0.33 | 0.61 |
| Ex. (33) | Com. (1-93) | 5.2 | 10.9 | 5000 | 45.9 | 138.1 | 0.33 | 0.61 |
| Ex. (34) | Com. (1-96) | 5.2 | 10.9 | 5000 | 46.0 | 139.8 | 0.33 | 0.61 |
| Ex. (35) | Com. (2-1) | 4.7 | 9.1 | 5000 | 55.1 | 144.9 | 0.33 | 0.61 |
| Ex. (36) | Com. (2-2) | 4.8 | 9.3 | 5000 | 53.5 | 144.1 | 0.33 | 0.61 |
| Ex. (37) | Com. (2-3) | 4.8 | 9.3 | 5000 | 53.9 | 143.6 | 0.33 | 0.61 |
| Ex. (38) | Com. (2-5) | 5.0 | 9.2 | 5000 | 54.4 | 144.9 | 0.33 | 0.61 |
| Ex. (39) | Com. (2-11) | 5.0 | 9.2 | 5000 | 54.2 | 144.5 | 0.33 | 0.61 |
| Ex. (40) | Com. (2-12) | 4.8 | 9.2 | 5000 | 54.6 | 144.2 | 0.33 | 0.62 |
| Ex. (41) | Com. (2-13) | 4.8 | 9.4 | 5000 | 53.1 | 143.8 | 0.33 | 0.62 |
| Ex. (42) | Com. (2-16) | 4.8 | 9.2 | 5000 | 54.2 | 143.1 | 0.33 | 0.62 |
| Ex. (43) | Com. (2-24) | 4.8 | 9.3 | 5000 | 53.8 | 144.0 | 0.33 | 0.61 |
| Ex. (44) | Com. (2-26) | 4.8 | 9.4 | 5000 | 53.2 | 144.7 | 0.33 | 0.62 |
| Ex. (45) | Com. (2-27) | 4.8 | 9.3 | 5000 | 53.6 | 143.4 | 0.33 | 0.62 |
| Ex. (46) | Com. (2-33) | 4.9 | 9.5 | 5000 | 52.4 | 142.5 | 0.33 | 0.62 |
| Ex. (47) | Com. (2-37) | 5.0 | 9.6 | 5000 | 52.3 | 141.9 | 0.33 | 0.62 |
| Ex. (48) | Com. (2-38) | 5.0 | 10.2 | 5000 | 49.1 | 140.2 | 0.33 | 0.61 |
| Ex. (49) | Com. (2-39) | 5.2 | 10.3 | 5000 | 48.5 | 138.9 | 0.33 | 0.61 |
| Ex. (50) | Com. (2-46) | 5.1 | 10.7 | 5000 | 46.8 | 140.3 | 0.33 | 0.62 |
| Ex. (51) | Com. (2-48) | 4.9 | 9.6 | 5000 | 51.9 | 141.1 | 0.33 | 0.61 |
| Ex. (52) | Com. (2-51) | 4.9 | 9.6 | 5000 | 52.2 | 141.2 | 0.33 | 0.62 |
| Ex. (53) | Com. (2-57) | 5.0 | 9.5 | 5000 | 52.4 | 142.2 | 0.33 | 0.62 |
| Ex. (54) | Com. (2-64) | 5.0 | 9.7 | 5000 | 51.6 | 141.0 | 0.33 | 0.61 |
| Ex. (55) | Com. (2-66) | 5.0 | 9.6 | 5000 | 52.3 | 141.3 | 0.33 | 0.62 |
| Ex. (56) | Com. (2-77) | 5.0 | 10.0 | 5000 | 49.8 | 139.3 | 0.33 | 0.61 |
| Ex. (57) | Com. (2-79) | 5.1 | 10.3 | 5000 | 48.5 | 138.6 | 0.33 | 0.61 |
| Ex. (58) | Com. (2-81) | 5.1 | 10.8 | 5000 | 46.1 | 138.2 | 0.33 | 0.61 |
| Ex. (59) | Com. (2-86) | 5.4 | 11.5 | 5000 | 43.6 | 136.2 | 0.33 | 0.62 |
| Ex. (60) | Com. (2-94) | 5.0 | 9.6 | 5000 | 51.8 | 141.8 | 0.33 | 0.62 |
| Ex. (61) | Com. (2-95) | 5.0 | 9.6 | 5000 | 51.9 | 142.1 | 0.33 | 0.62 |
| Ex. (62) | Com. (2-96) | 5.0 | 9.7 | 5000 | 51.7 | 141.5 | 0.33 | 0.61 |
| Ex. (63) | Com. (2-97) | 5.0 | 9.7 | 5000 | 51.6 | 141.1 | 0.33 | 0.61 |
| Ex. (64) | Com. (2-99) | 4.9 | 9.6 | 5000 | 51.8 | 142.1 | 0.33 | 0.62 |
| Ex. (65) | Com. (2-100) | 5.1 | 9.5 | 5000 | 52.4 | 142.5 | 0.33 | 0.61 |
| Ex. (66) | Com. (2-101) | 5.0 | 9.5 | 5000 | 52.5 | 142.0 | 0.33 | 0.62 |
| Ex. (67) | Com. (2-115) | 5.0 | 9.7 | 5000 | 51.8 | 142.4 | 0.33 | 0.62 |
| Ex. (68) | Com. (2-120) | 5.1 | 9.7 | 5000 | 51.6 | 142.4 | 0.33 | 0.61 |

TABLE 5-continued

| | compound | Voltage (V) | Current Density (mA/cm²) | Brightness (cd/m²) | Efficiency (cd/A) | Lifetime T(95) | CIE X | CIE Y |
|---|---|---|---|---|---|---|---|---|
| Ex. (69) | Com. (2-128) | 4.9 | 9.6 | 5000 | 52.3 | 141.3 | 0.33 | 0.61 |
| Ex. (70) | Com. (2-129) | 4.9 | 9.6 | 5000 | 52.1 | 141.8 | 0.33 | 0.61 |
| Ex. (71) | Com. (2-130) | 5.3 | 11.9 | 5000 | 41.9 | 133.5 | 0.33 | 0.62 |
| Ex. (72) | Com. (2-131) | 5.3 | 11.8 | 5000 | 42.3 | 132.7 | 0.33 | 0.62 |
| Ex. (73) | Com. (2-133) | 5.0 | 9.6 | 5000 | 52.2 | 141.1 | 0.33 | 0.61 |
| Ex. (74) | Com. (2-134) | 5.0 | 9.5 | 5000 | 52.4 | 141.8 | 0.33 | 0.61 |
| Ex. (75) | Com. (2-135) | 5.0 | 9.7 | 5000 | 51.8 | 142.1 | 0.33 | 0.61 |
| Ex. (76) | Com. (2-139) | 4.9 | 9.7 | 5000 | 51.6 | 141.2 | 0.33 | 0.61 |
| Ex. (77) | Com. (2-141) | 5.3 | 11.5 | 5000 | 43.4 | 136.6 | 0.33 | 0.61 |
| Ex. (78) | Com. (2-146) | 5.2 | 10.8 | 5000 | 46.2 | 138.3 | 0.33 | 0.61 |
| Ex. (79) | Com. (2-148) | 5.3 | 12.2 | 5000 | 41.1 | 134.5 | 0.33 | 0.61 |
| Ex. (80) | Com. (2-152) | 5.3 | 12.2 | 5000 | 41.1 | 133.3 | 0.33 | 0.61 |

As noted from the above table 5, driving voltage, luminous efficiency and lifespan and the like were remarkably improved when the compound of the present invention according to Examples 1 to 80 was used as green phosphorescent host material compared with Comparative examples 1 to 7.

It is confirmed that efficiency and lifespan of OLEDs according to Comparative examples 2 and 3 are improved compared with Comparative example 1. This is because charge mobility and thermal properties of comparative compounds 2 and 3 of which benzene in the middle of 5-rings heterocycle is substituted by phenyl group are increased due to 5-rings hetero-core. Also, from the results of Comparative examples 2 and 3, it's noted that properties are changed depending on the hetero-atom type in 5-rings hetero cyclic ring compound. That is, it's confirmed that N-S type rather than N-N type hetero-atom showed better results. To show the differences of two types, properties data of comparative compounds 4 and the compound 2-1 of the present invention are compared in the following table 6.

From the above table 6, it is confirmed that closer look of LUMO electron cloud of the present invention 2-1 and comparative compound 4 shows that the electron cloud is separated and spread in carbazole group in case of 5-rings heterocycle is N-N type (comparative compound 4) while the electron cloud is spread in of backbone of 5-rings heterocycle in case N-S type, the present invention 2-1.

This resulted from the characteristic difference of hetero-atom in molecules. It shows that hetero-atom in the core is a decisive factor of HOMO/LUMO level of core, band gap energy and T1 value. If two materials are compared, it's noted that there are huge difference in the energy level of HOMO and LUMO. In addition, as T1 value of the compound of the present invention 2-1 is lower than that of comparative compound 4, probability of reverse transfer from dopant to host of exciton after exciton at host moved to dopant has decreased considerably, which result in higher probability of luminous efficiency of the element. The compound of the present invention 2-1 has deep HOMO

TABLE 6

Figure 2:
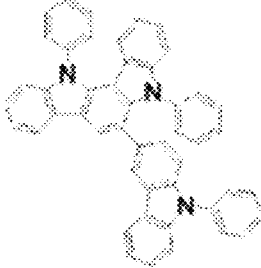
FIG. 2 illustrates HOMO/LUMO electron cloud of the present compound 2-1 and comparative compound 4 in the comparative properties data of Table 6.
Figure 2:
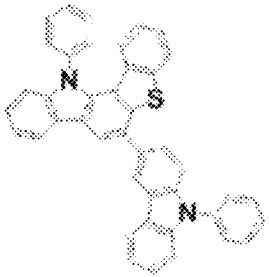
Figure 2:
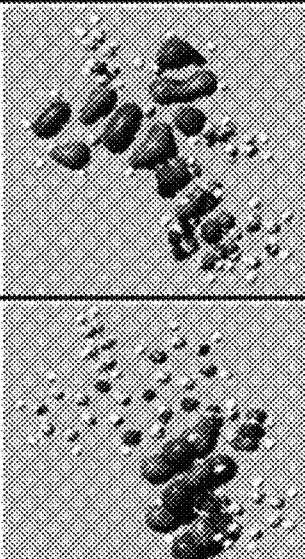
Figure 2:
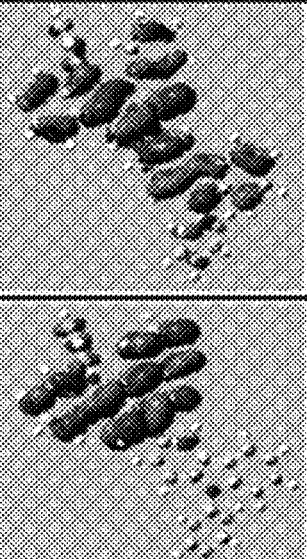
Figure 2:
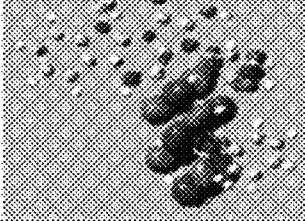
Figure 2:
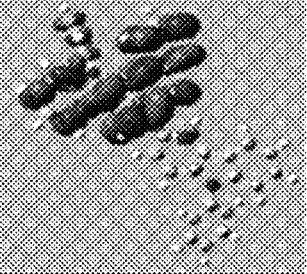

| | Comparative compound 4 | The present invention Com. 2-1 |
|---|---|---|
| Structure | 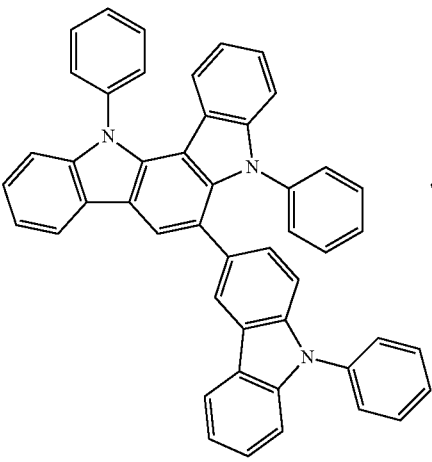 [SMILES: c1ccc(-n2c3ccccc3c3cc(-c4cc5c6ccccc6n(-c6ccccc6)c5c5c6ccccc6n(-c6ccccc6)c45)ccc32)cc1] | 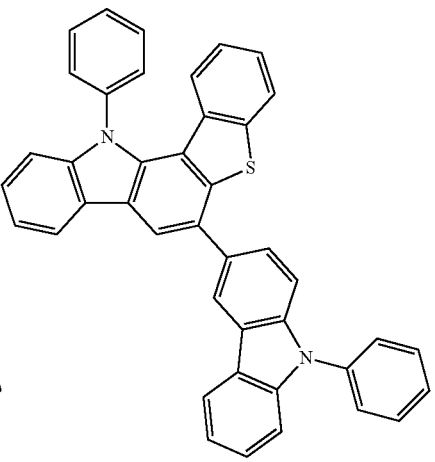 [SMILES: c1ccc(-n2c3ccccc3c3cc(-c4cc5c6ccccc6n(-c6ccccc6)c5c5c4sc4ccccc45)ccc32)cc1] |
| HOMO (electron cloud) | Refer to FIG.2 | Refer to FIG.2 |
| LUMO (electron cloud) | Refer to FIG.2 | Refer to FIG.2 |
| HOMO (eV) | −4.88 | −5.13 |
| LUMO (eV) | −0.71 | −0.91 |
| Eg (eV) | 4.17 | 4.23 |
| T1 (nm) | 2.92 | 2.88 | value, which enhances hole capping capacity making efficient charge balance inside light emitting layer and decreases excessive polaron created inside light emitting layer, resulting in improving efficiency and lifespan.

Even though benzene ring in the middle of heterocycle consisting of 5-rings is substituted with carbazole, there's no big difference in element properties comparing element properties of comparative compounds 4 and 5 which have 5-rings of N-N type. This confirmed that there are no significant differences depending on the orientation of the heteroatom. Furthermore, comparing element data of comparative compound 6 and the compounds of the present invention, wherein the comparative compound 6 has a substituent of triazine derivative belong to a general heteroaryl group, it's found that efficiency and lifespan are increased only when specific type hetero-aryl group to be bonded like the compounds of the present invention, not when a general hetero-aryl group is bonded to the benzene ring in the middle.

In addition, comparing the comparative compound 7 of the Comparative example 7 and the compound of the present invention, wherein the comparative compound 7 substituents such as carbazole, dibenzofuran, and dibenzothiophen bonded to 5-rings cycle does not bond to a middle benzene ring but bond at the side position, as predicted, the compound of the present invention has wider band gap energy due to its own feature of deep HOMO energy level so that hole is transported from hole transport layer to light emitting layer more smoothly and it functions to prevent light emission leakage as exciton is not blocked inside light emitting layer. As a result, charge balance in light emitting layer is increased and alteration of lighting material is decreased by reducing excessive polaron in light emitting layer. In the end, it's assumed that color purity, lifespan and efficiency are improved.

Like this, seeing the result of above table 5, it implies that efficiency and lifespan will be dependent on the kind and arrangement of hetero atom which is contained in 5-rings cycle compound. Depending on the position and kind of substituent to be bonded, band gap, electric properties, and interface properties are changed considerably. Especially, in case of phosphorescent host, interrelation between hole transport layer and dopant should be analyzed. Therefore, even though similar core is used, it will be very difficult to infer the excellent electric properties as shown from the phosphorescent host of the compound of the present invention.

Example 81

Red OLED (Phosphorescent Host)

An ITO layer (anode) was formed on a glass substrate, and a film of "2-TNATA" was vacuum-deposited on the ITO layer to form a hole injection layer with a thickness of 60 nm. Subsequently, "NPD" was vacuum-deposited on the hole injection layer to form a hole transfer layer with a thickness of 60 nm.

Continually, a light emitting layer with a thickness of 30 nm was deposited on the hole transfer layer by doping the hole transfer layer with the inventive compound 1-59 as a host material and "(piq)$_2$Ir(acac)" as a dopant material in a weight ratio of 95:5. Next, "BAlq" was vacuum-deposited with a thickness of 10 nm on the light emitting layer to form a hole blocking layer, a film of "Alq$_3$" was formed with a thickness of 40 nm to form an electron transport layer.

Next, LiF was deposited with a thickness of 0.2 nm on the electron transport layer to form an electron injection layer, and then Al was deposited with a thickness of 150 nm on the electron injection layer to form a cathode.

[Example 82] to [Example 96]

Red OLED

The OLEDs were manufactured in the same manner as described in Example 81, except that the compounds of the present invention in the Table 7 below were used as the host material of the light emitting layer, instead of the inventive compound 1-59.

[Comparative Example 8] to [Comparative Example 14]

The OLEDs were manufactured in the same manner as described in Example 81, except that any one of comparative compounds 1 to 7 was used as the host material of the light emitting layer, instead of the inventive compound 1-59.

A forward bias DC voltage was applied to each of the OLEDs manufactured through the Examples 81 to 96 and Comparative Example 8 to 14, and electro-luminescence (EL) characteristics of the OLED were measured by PR-650 (Photo research). Also, T95 life span was measured by life span measuring equipment (Mc science) at reference brightness of 2500 cd/m$^2$. Table 7 below shows evaluation results.

TABLE 7

| | compound. | Voltage (V) | Current Density (mA/cm$^2$) | Brightness (cd/m$^2$) | Efficiency (cd/A) | Lifetime T(95) | CIE X | Y |
|---|---|---|---|---|---|---|---|---|
| comp. Ex(8) | comp. Com 1 | 6.8 | 36.2 | 2500 | 6.9 | 65.3 | 0.66 | 0.32 |
| comp. Ex(9) | comp. Com 2 | 6.5 | 35.2 | 2500 | 7.3 | 71.7 | 0.66 | 0.32 |
| comp. Ex(10) | comp. Com 3 | 6.6 | 34.2 | 2500 | 7.5 | 78.4 | 0.66 | 0.32 |
| comp. Ex(11) | comp. Com 4 | 6.4 | 32.1 | 2500 | 7.7 | 82.7 | 0.66 | 0.32 |
| comp. Ex(12) | comp. Com 5 | 6.5 | 33.8 | 2500 | 7.6 | 83.4 | 0.66 | 0.32 |
| comp. Ex(13) | comp. Com 6 | 6.4 | 35.7 | 2500 | 7.8 | 98.3 | 0.66 | 0.32 |
| comp. Ex(14) | comp. Com 7 | 6.3 | 32.5 | 2500 | 7.7 | 85.2 | 0.66 | 0.32 |
| Ex. (81) | Com. (1-59) | 5.0 | 20.0 | 2500 | 12.5 | 149.3 | 0.66 | 0.32 |
| Ex. (82) | Com. (1-60) | 4.9 | 19.1 | 2500 | 13.1 | 149.7 | 0.66 | 0.32 |
| Ex. (83) | Com. (1-63) | 4.9 | 20.0 | 2500 | 12.5 | 148.8 | 0.66 | 0.32 |
| Ex. (84) | Com. (1-65) | 4.8 | 18.4 | 2500 | 13.6 | 151.4 | 0.66 | 0.32 |

TABLE 7-continued

| compound. | Voltage (V) | Current Density (mA/cm²) | Brightness (cd/m²) | Efficiency (cd/A) | Lifetime T(95) | CIE X | CIE Y |
|---|---|---|---|---|---|---|---|
| Ex. (85) Com. (1-66) | 4.9 | 18.9 | 2500 | 13.0 | 149.7 | 0.66 | 0.32 |
| Ex. (86) Com. (1-73) | 5.1 | 20.3 | 2500 | 12.3 | 146.2 | 0.66 | 0.32 |
| Ex. (87) Com. (1-84) | 5.1 | 19.7 | 2500 | 12.7 | 150.1 | 0.66 | 0.32 |
| Ex. (88) Com. (2-103) | 4.8 | 17.5 | 2500 | 14.3 | 153.1 | 0.66 | 0.32 |
| Ex. (89) Com. (2-104) | 4.8 | 18.4 | 2500 | 13.6 | 152.2 | 0.66 | 0.32 |
| Ex. (90) Com. (2-105) | 4.9 | 17.5 | 2500 | 14.3 | 154.6 | 0.66 | 0.32 |
| Ex. (91) Com. (2-106) | 4.8 | 18.6 | 2500 | 13.4 | 151.1 | 0.66 | 0.32 |
| Ex. (92) Com. (2-107) | 4.8 | 18.9 | 2500 | 13.2 | 151.8 | 0.66 | 0.32 |
| Ex. (93) Com. (2-119) | 4.9 | 18.9 | 2500 | 13.2 | 151.8 | 0.66 | 0.32 |
| Ex. (94) Com. (2-137) | 5.0 | 19.4 | 2500 | 12.9 | 148.5 | 0.66 | 0.32 |
| Ex. (95) Com. (2-138) | 5.1 | 19.6 | 2500 | 12.8 | 150 | 0.66 | 0.32 |
| Ex. (96) Com. (2-140) | 5.0 | 20.3 | 2500 | 12.3 | 146.3 | 0.66 | 0.32 |

As noted from the above table 7, it's confirmed that luminous efficiency and lifespan have enhanced much higher when compounds of the present invention were used as phosphorescent red host material, too. Compounds of the present invention used in the above table 7 are 1-59~60, 1-63, 1-65, 1-73, 1-84, 2-103~107, 2-119, 2-137~138, and 2-140, wherein these compounds has a quinazoline derivative used widely as a secondary substituents of red phosphorescent host, and compound 1-66, wherein the compound 66 has an aryl group fused to the backbone core of 5-rings heterocyclic compound among compounds of the present invention. It shows that compounds with a specific substituent or with simply a ring-fused backbone can be useful as red and green phosphorescent host.

This is because quantity of holes moved from a hole transport layer to a light emitting layer can be balanced due to deep HOMO energy level which is an original properties of the inventive compounds, resulting in charge balance of hole and electron in the light emitting layer and prevention of deterioration on the light emitting layer interface and decrease excessive polaron. As a result, it is assumed that the lifespan of organic electric element of which compound of the present invention was used as a host material are improved.

Therefore, from the above table 5 and table 7, it is shown that efficiency and lifespan can be changed depending on the kinds of hetero-atom that 5-rings compound contains and arrangement. It's also shown that band gap, electric properties and interface properties will be changed considerably depending on the position and kind of substituent to be bonded. Especially, in case of phosphorescent host, because interrelation of hole transport layer and dopant should be analyzed, it would be very difficult to assume features shown when the compound of the present invention is used as the phosphorescent, even though similar core is used.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

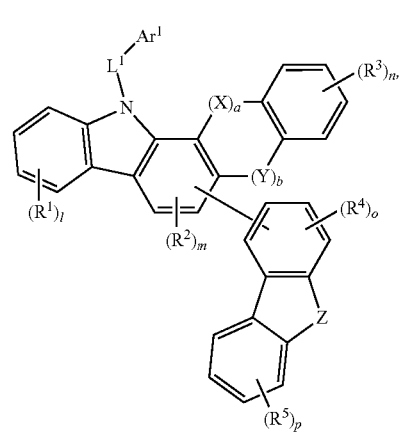

wherein:

$R^1$ to $R^5$ are each independently selected from the group consisting of deuterium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, -L'-N(R')(R''), and a combination thereof, neighboring $R^1$s, $R^3$s, $R^4$s and $R^5$s may be optionally linked to each other to form a ring, l, n, and p are each an integer of 0 to 4, m is an integer of 0 or 1, and o is an integer of 0 to 3, X and Y are each independently O, S, C($R^6$)($R^7$), Si($R^8$)($R^9$) or Se, "a" and "b" are each an integer of 0 or 1, with the proviso that at least one of "a" and "b" is an integer of 1, Z is N-($L^2$-$Ar^2$), O, S, C($R^{10}$)($R^{11}$), Si($R^{12}$)($R^{13}$), or Se, $Ar^1$ and $Ar^2$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, a $C_6$-$C_{30}$ aryloxy group, and -L'-N(R')(R''), $L^1$, $L^2$, and L' are each independently selected from the group consisting of a single bond, a $C_6$-$C_{60}$ arylene group, a fluorenylene group, a $C_2$-$C_{60}$ heterocyclic group containing at least one heteroatom selected from O, N, S, Si, and P, a fused ring group of a $C_3$-$C_{60}$ aliphatic ring and a $C_6$-$C_{60}$ aromatic ring, and a combination thereof, $R^6$ to $R^{13}$ in X, Y and Z are each independently selected from the group consisting of hydrogen, deuterium, a $C_6$-$C_{24}$ aryl group, a $C_1$-$C_{50}$ alkyl group, a $C_2$-$C_{20}$ alkenyl group, a $C_1$-$C_{30}$ alkoxyl group, and a combination thereof, $R^6$ and $R^7$, $R^8$ and $R^9$, $R^{10}$ and $R^{11}$, or $R^{12}$ and $R^{13}$ may be optionally linked to each other to form a spiro compound, R' and R'' are each independently selected from the group consisting of a 06-CM aryl group, a fluorenyl group, a $C_2$-$C_{30}$ heterocyclic group containing at least one heteroatom selected from the group consisting of O, N, S, Si, and P, a fused ring group of a $C_3$-$C_{30}$ aliphatic ring and a $C_6$-$C_{30}$ aromatic ring, a $C_1$-$C_{50}$ alkyl group, a $C_2$-$C_{20}$ alkenyl group, and a combination thereof, and when the symbols above are each the aryl group, fluorenyl group, heterocyclic group, fused ring group, alkyl group, alkenyl group, alkoxyl group, aryloxy group, arylene group, or fluorenylen group, each of the groups may be optionally substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group, arylamine group and heteroarylamine group, with the proviso that in the compound of Formula 1, both $R^4$ and $R^5$ are hydrogen, or neighboring $R^4$s or neighboring $R^5$s are linked to each other to form a ring.

2. The compound of claim 1 represented by Formula 2 or Formula 3:

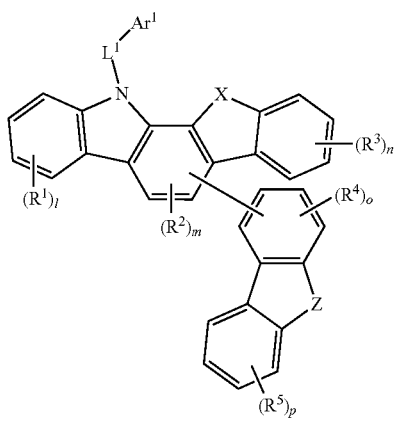

[Formula 2]

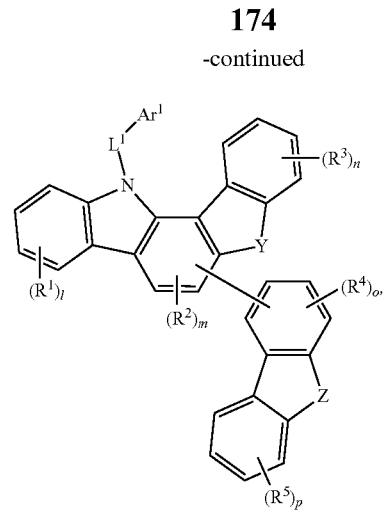

[Formula 3]

wherein each of $R^1$ to $R^5$, l, m, n, o, p, X, Y, Z, $L^1$ and $Ar^1$ is the same as defined in claim 1.

3. The compound of claim 1 represented by any one of Formula 4 to Formula 11:

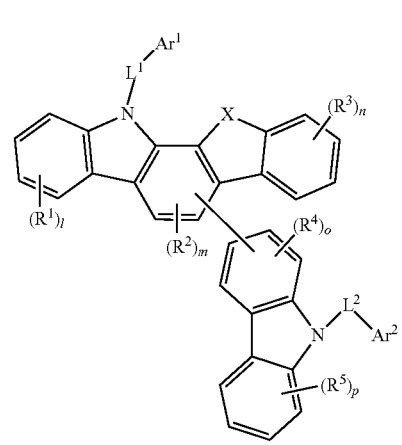

[Formula 4]

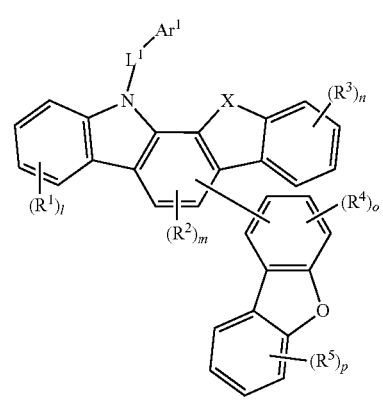

[Formula 5]

-continued
[Formula 6]
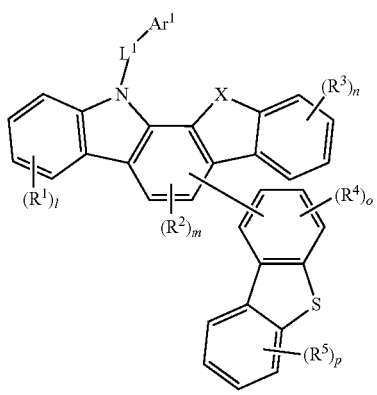
[Formula 7]
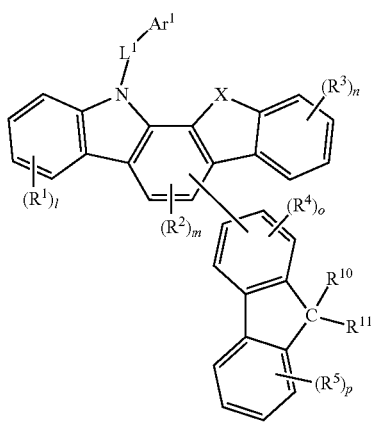
[Formula 8]
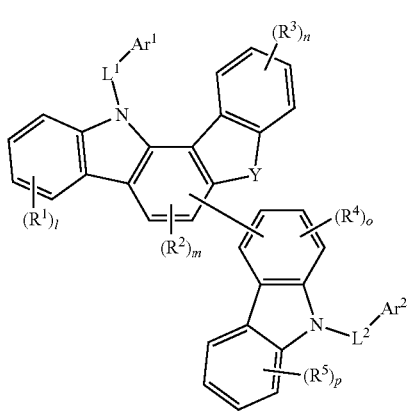
[Formula 9]
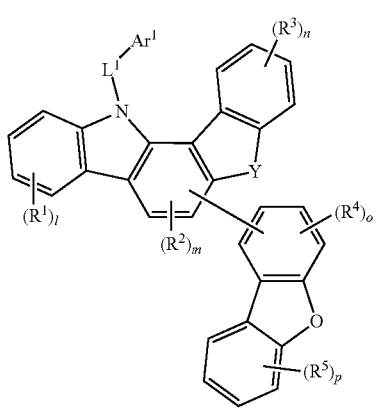
-continued
[Formula 10]
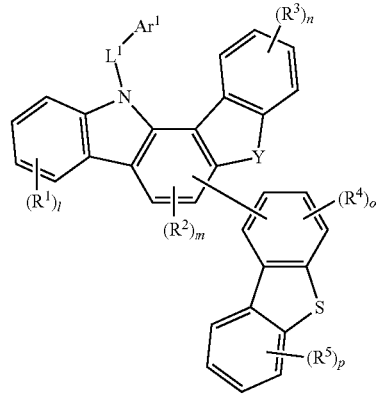
[Formula 11]
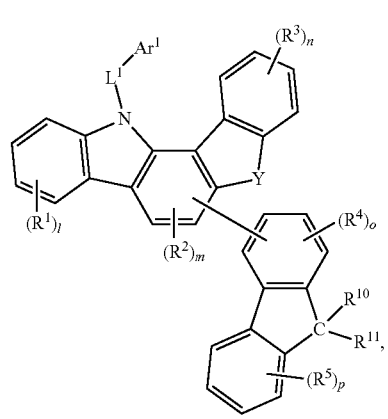
wherein each of $R^1$ to $R^5$, $R^{10}$, $R^{11}$, l, m, n, o, p, X, Y, Z, $L^1$, $L^2$, $Ar^1$, $Ar^2$ is the same as defined in claim 1.
4. The compound of claim 1, wherein all of l, m and n are 0.
5. The compound of claim 1, wherein X or Y is S or O.
6. A compound selected from the group consisting of the compounds below:
1-1
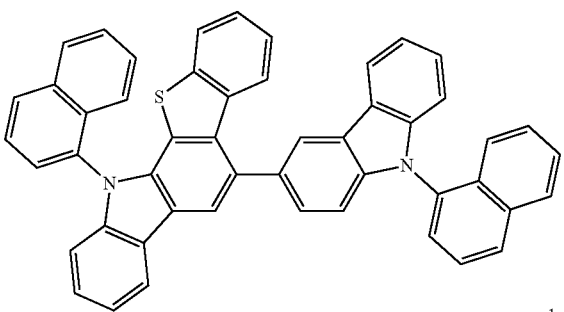
1-2
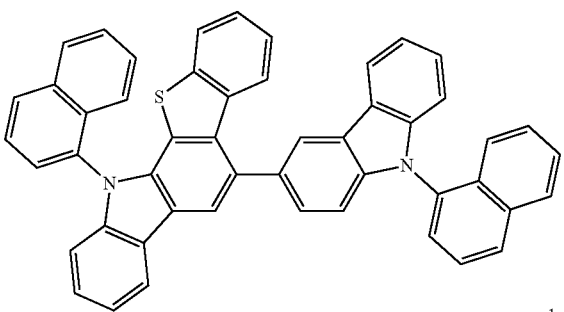

1-3
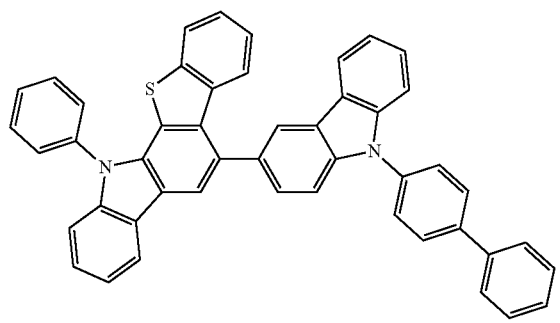
1-4
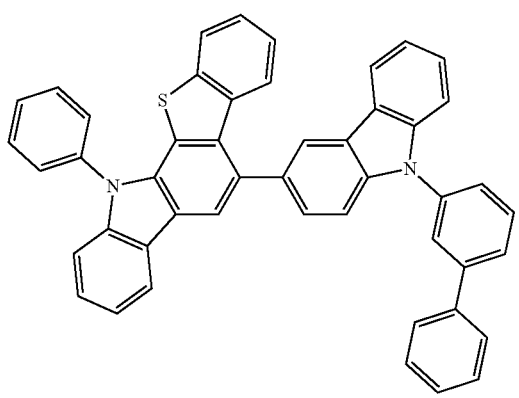
1-5
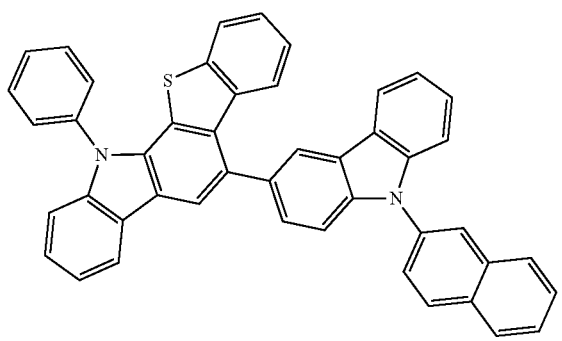
1-6
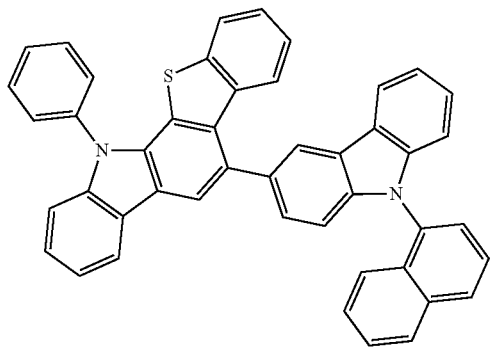
1-7
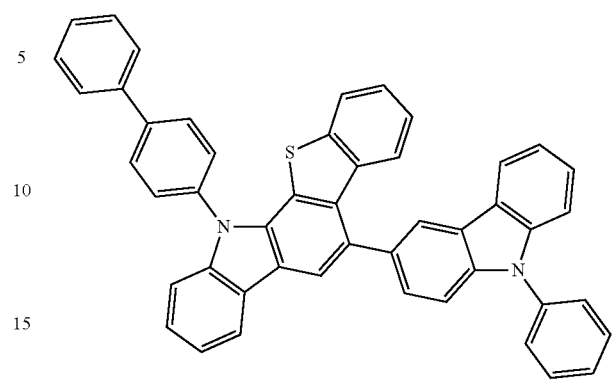
1-8
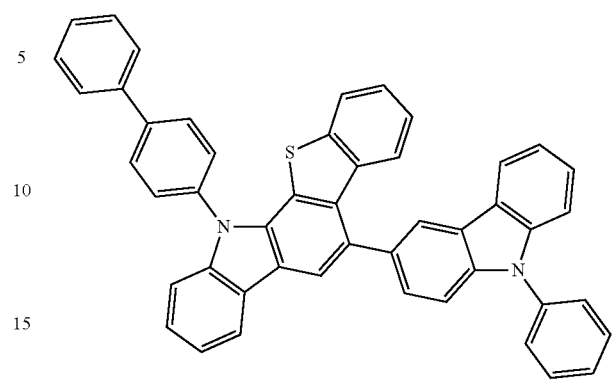
1-9
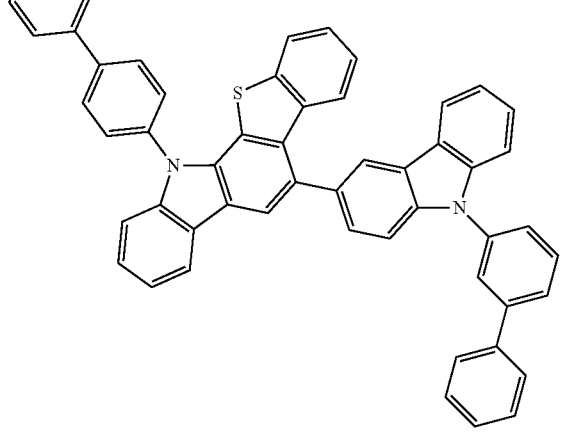

179
-continued
1-10
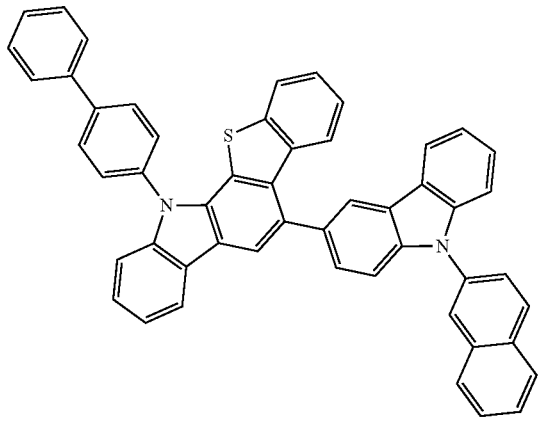
1-11
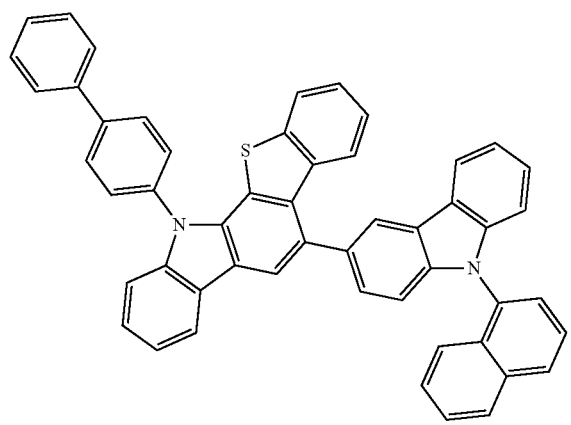
1-12
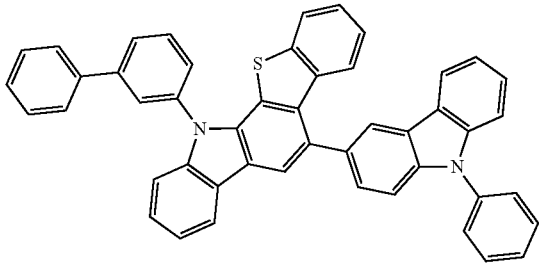
1-13
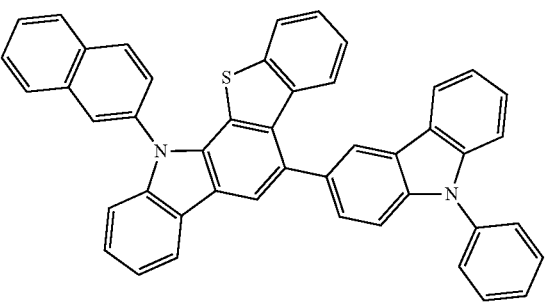
180
-continued
1-14
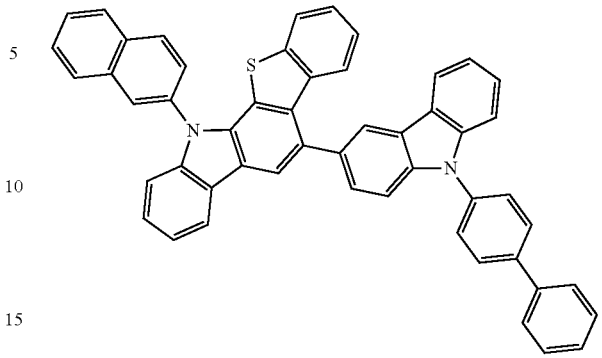
1-15
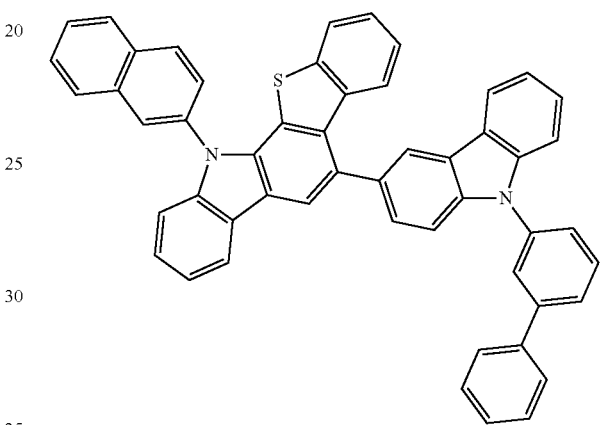
1-16
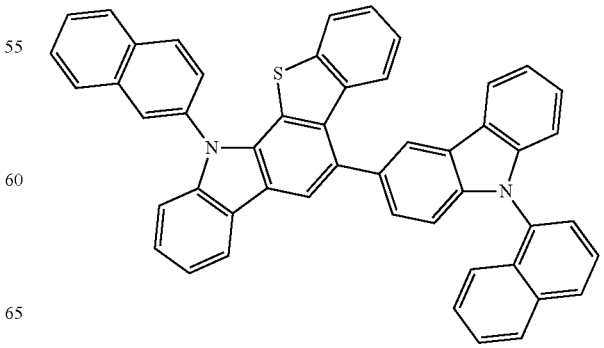
1-17

1-18
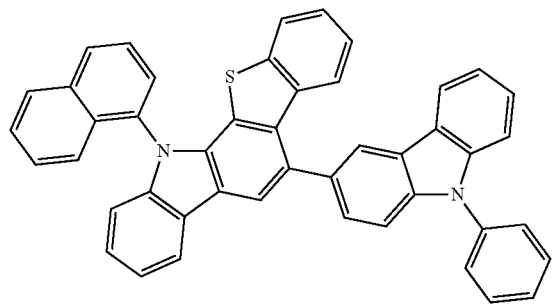
1-19
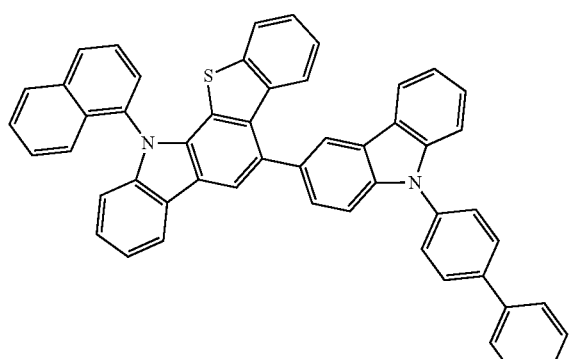
1-20
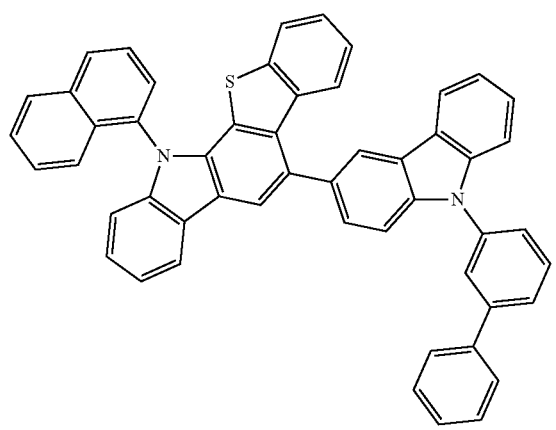
1-21
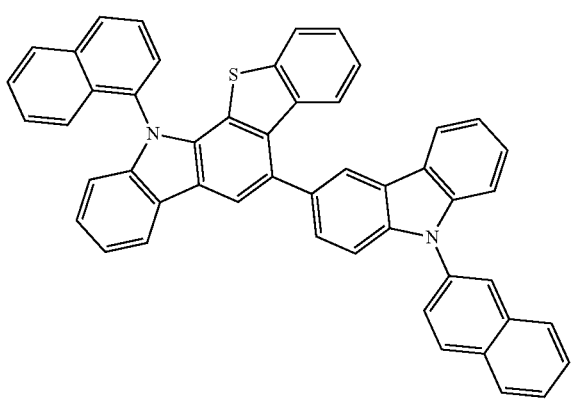
1-22
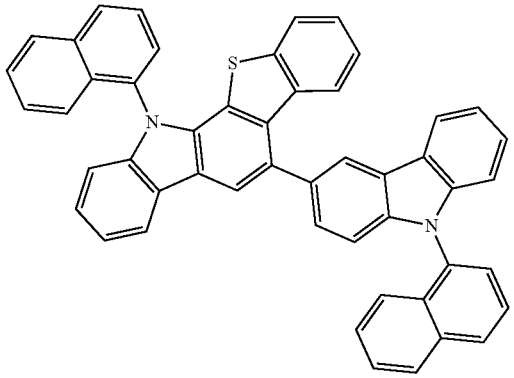
1-23
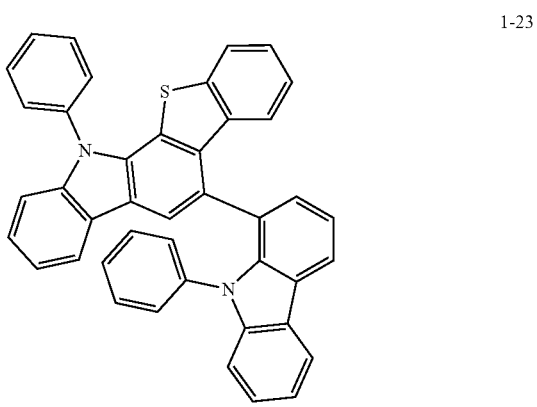
1-24
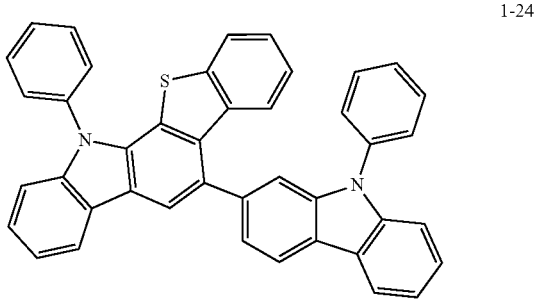
1-25
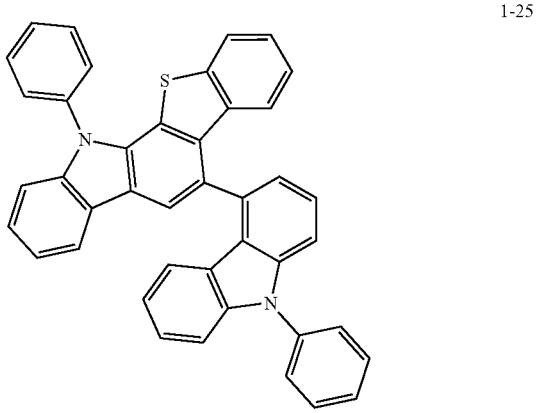

1-26
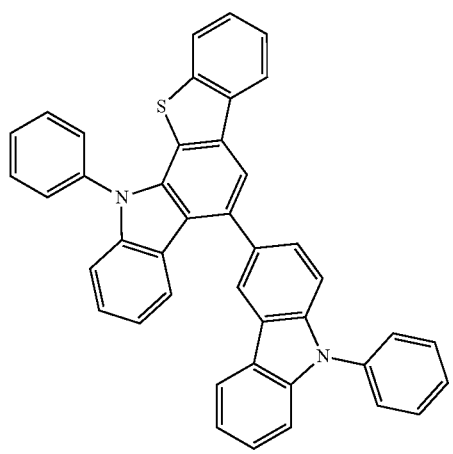
1-27
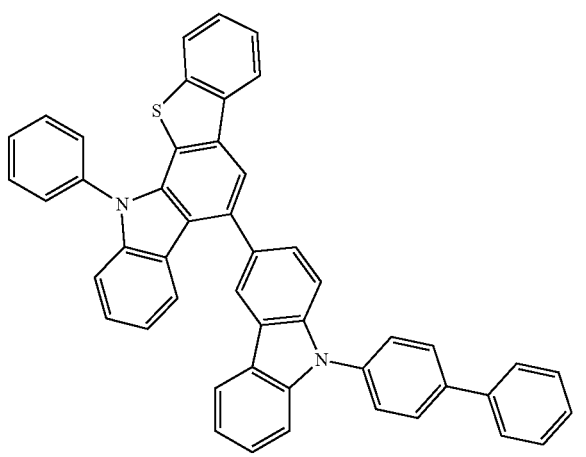
1-28
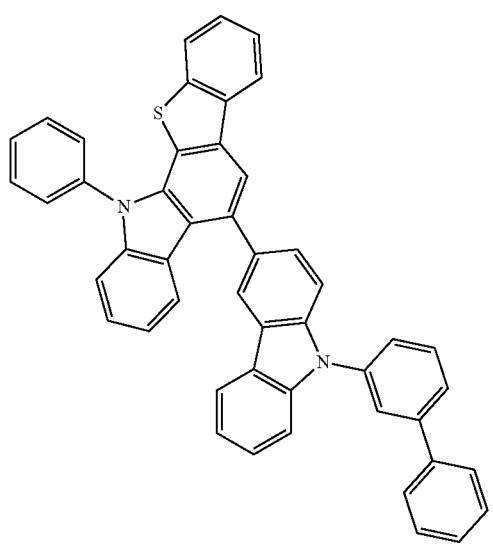
1-29
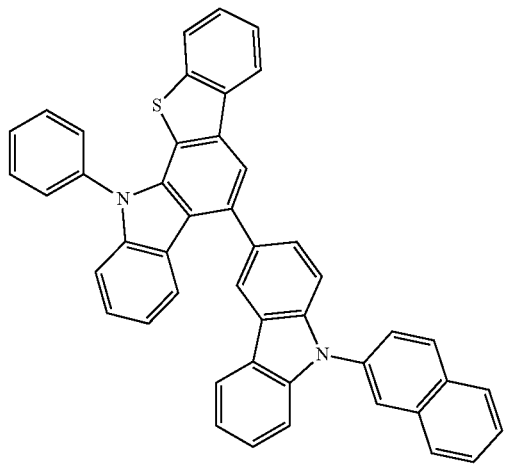
1-30
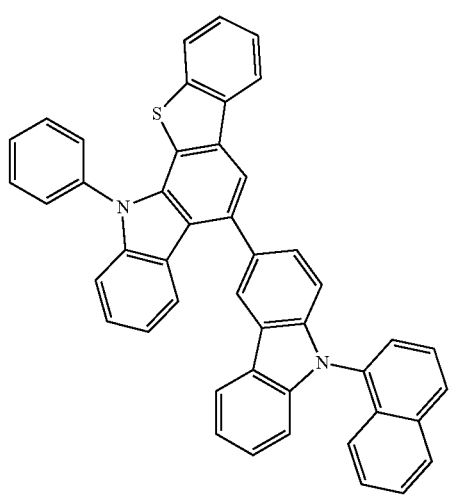
1-31
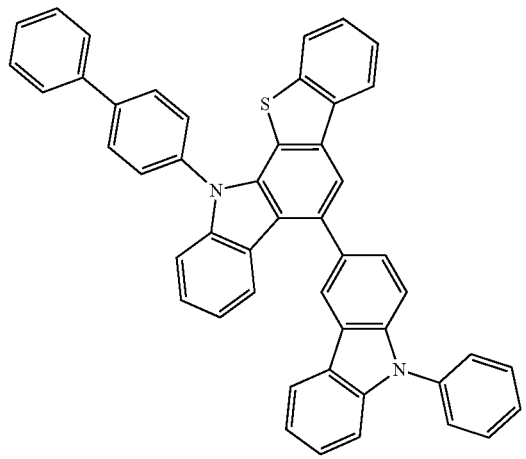

1-32
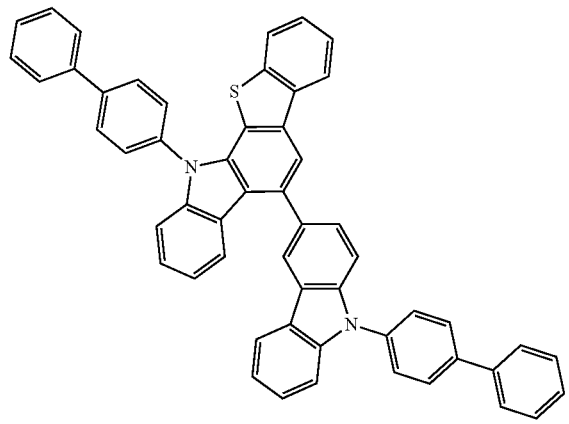
1-33
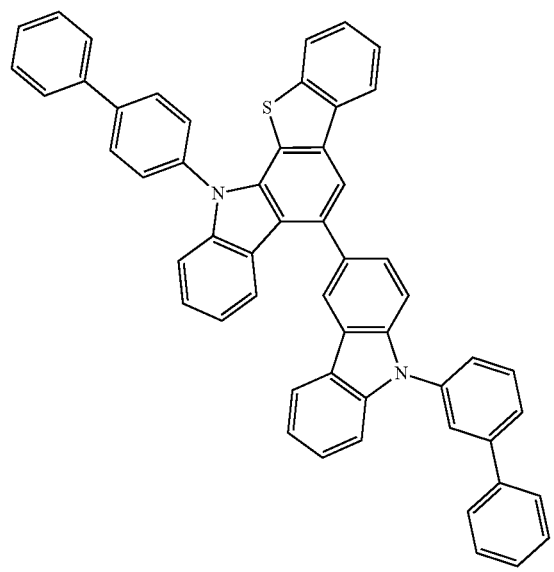
1-34
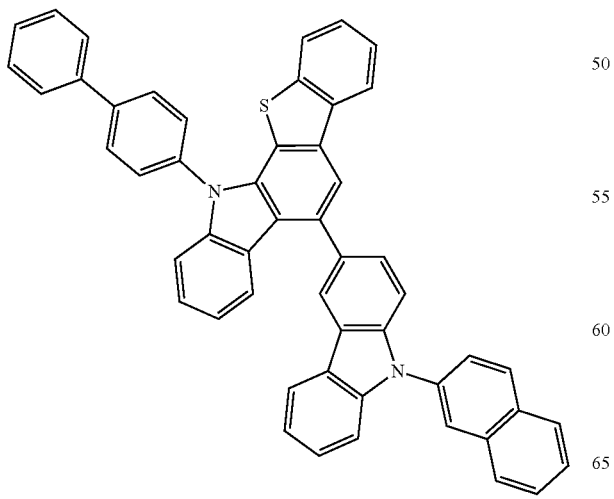
1-35
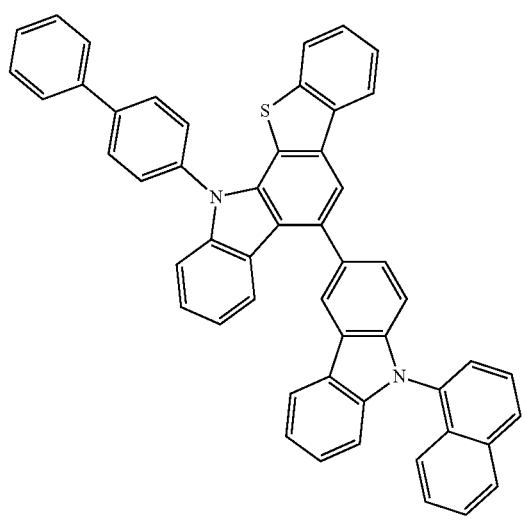
1-36
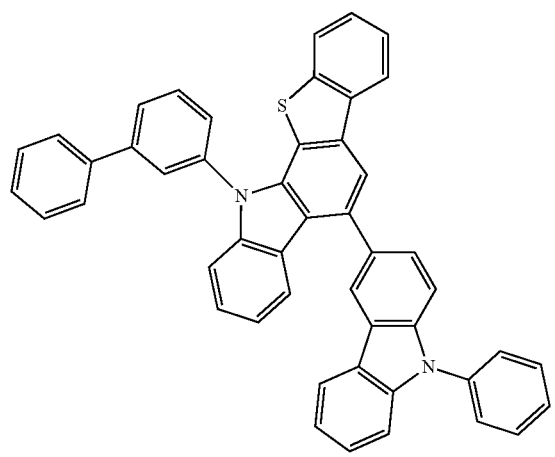
1-37
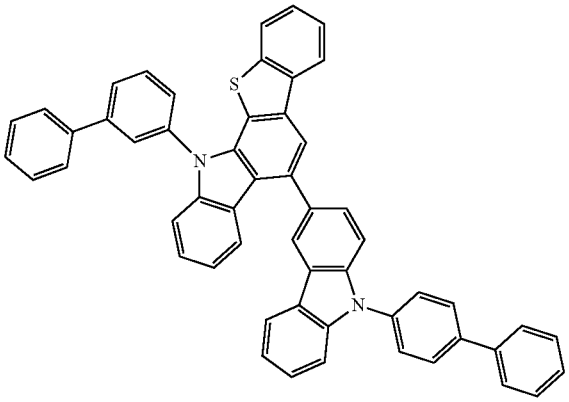

1-38
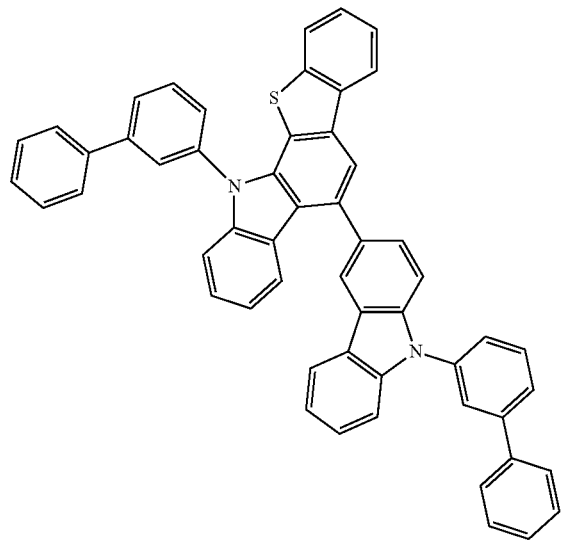
1-39
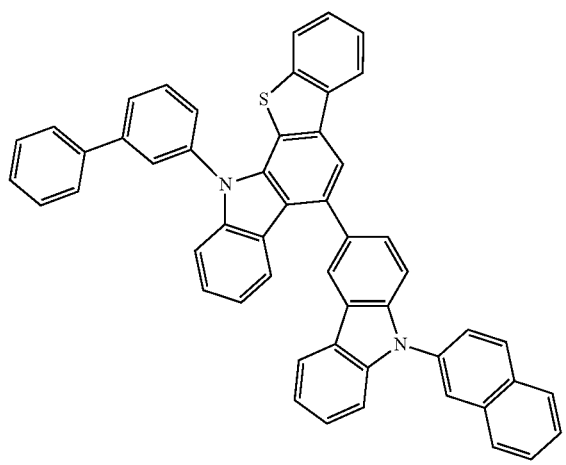
1-40
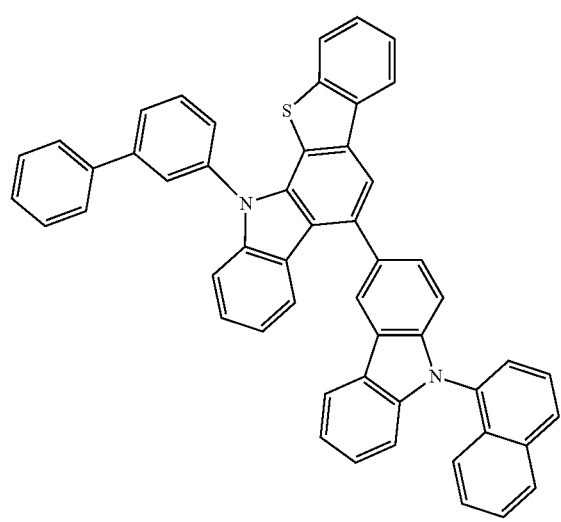
1-41
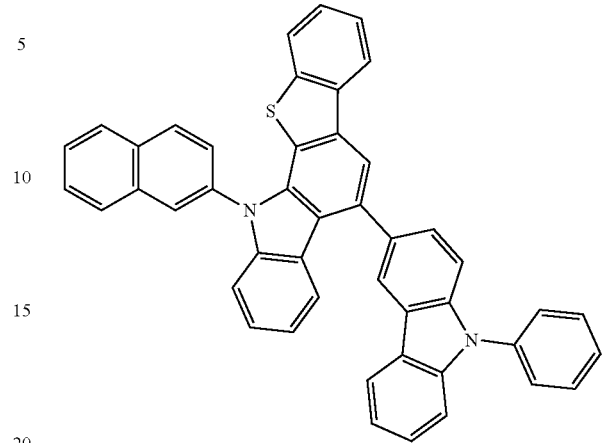
1-42
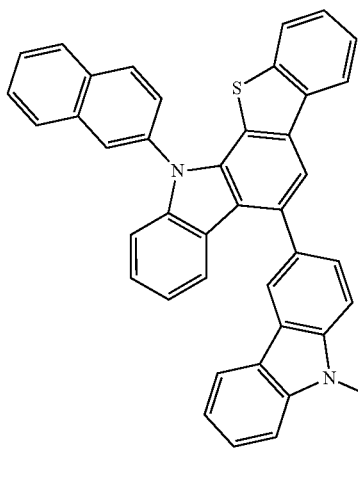
1-43
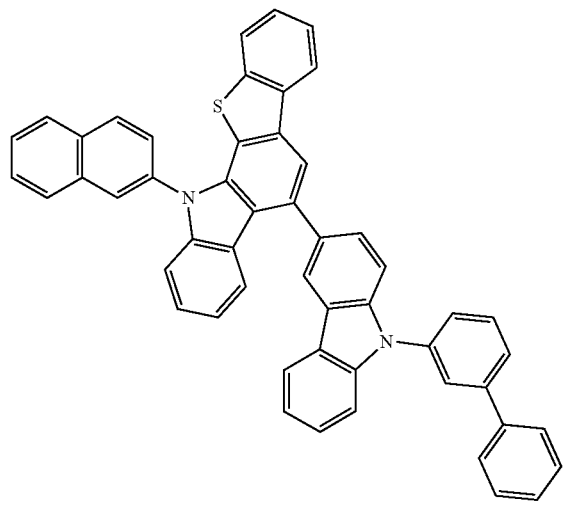

1-44
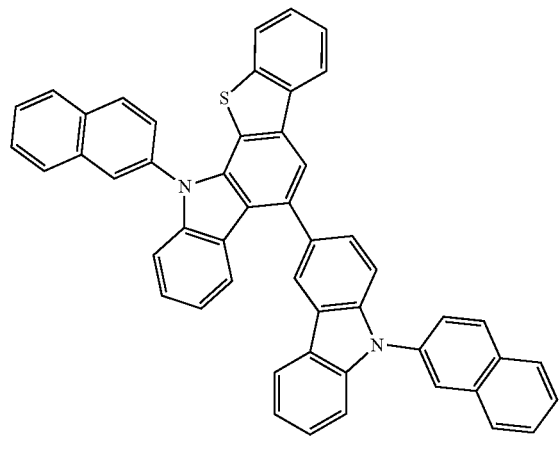
1-45
1-47
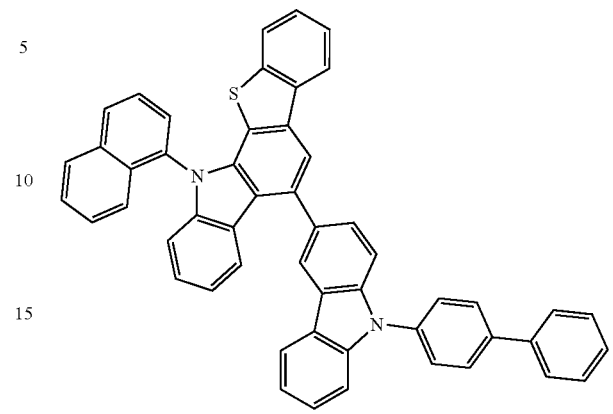
1-48
1-46
1-49
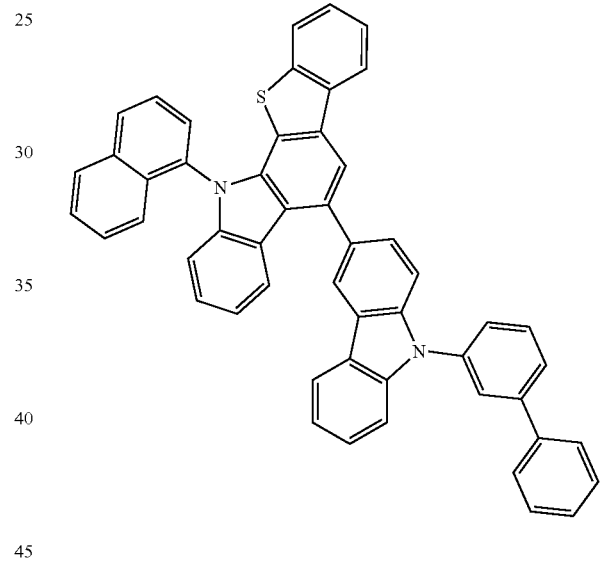
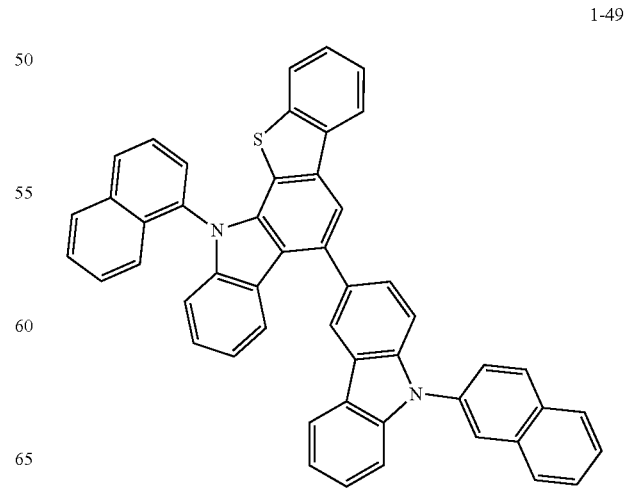

-continued
1-50
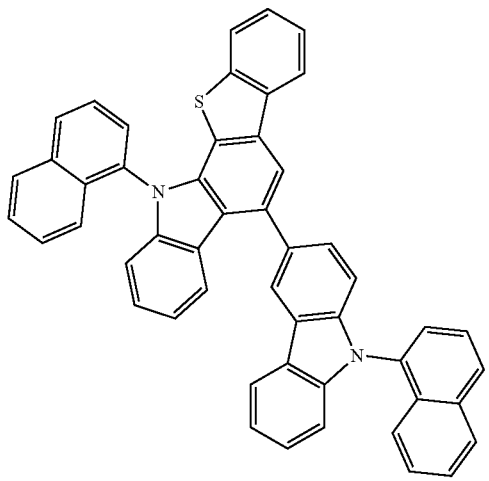
1-51
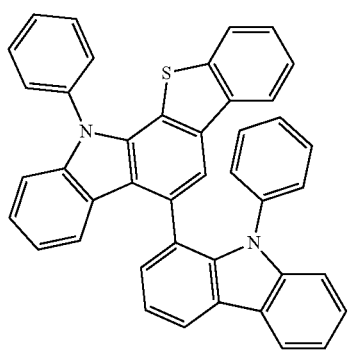
1-52
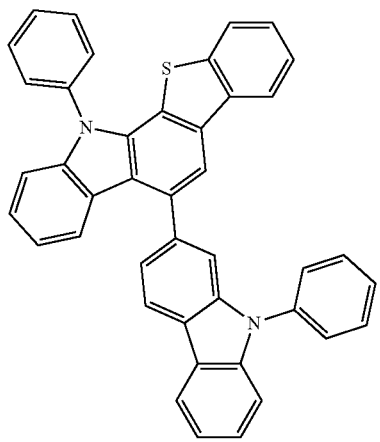
-continued
1-53
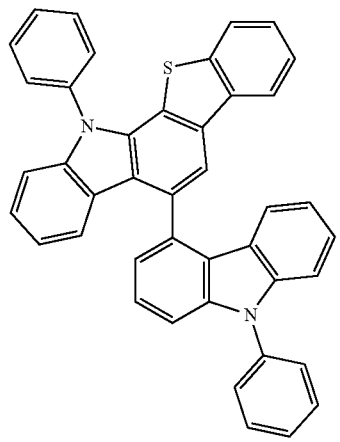
1-54
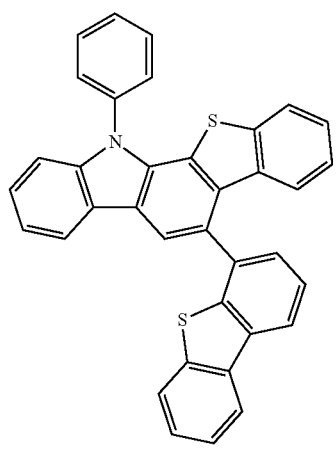
1-55
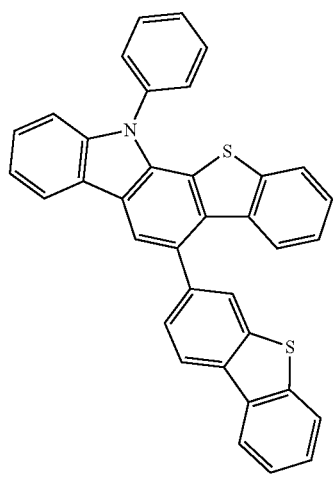

1-56
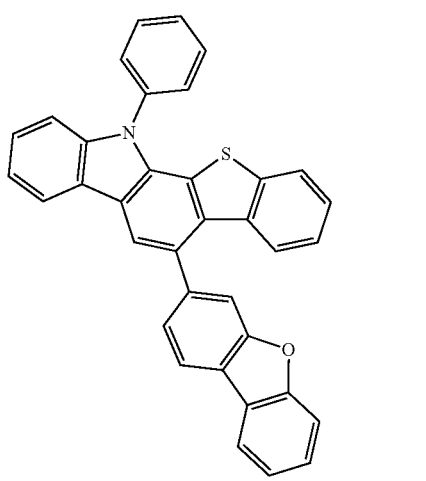
1-57
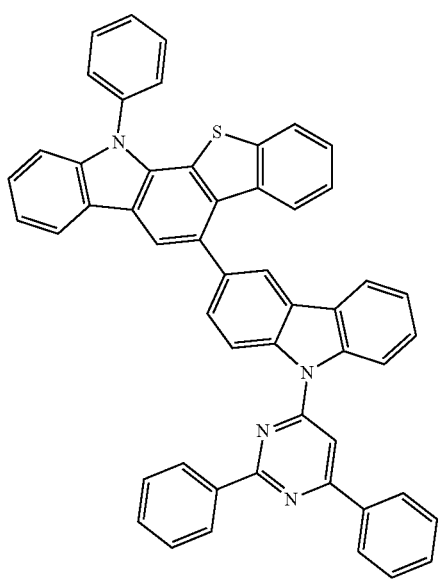
1-58
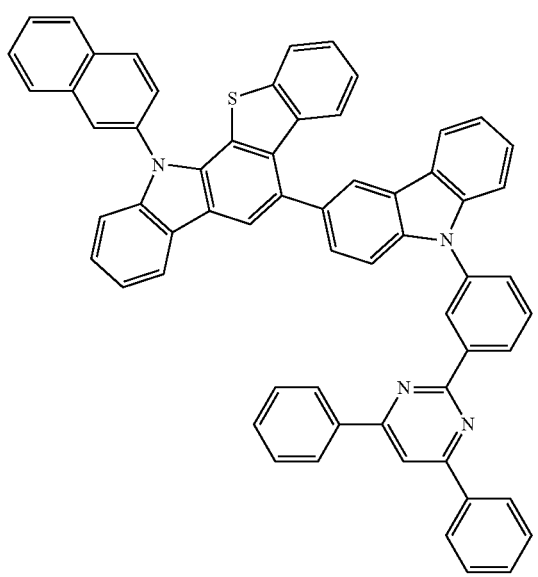
1-59
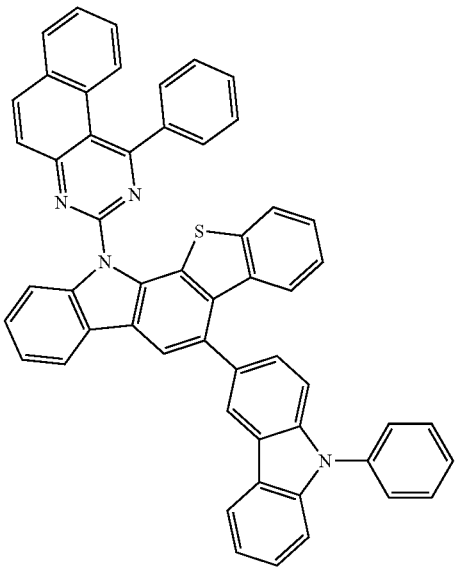
1-60
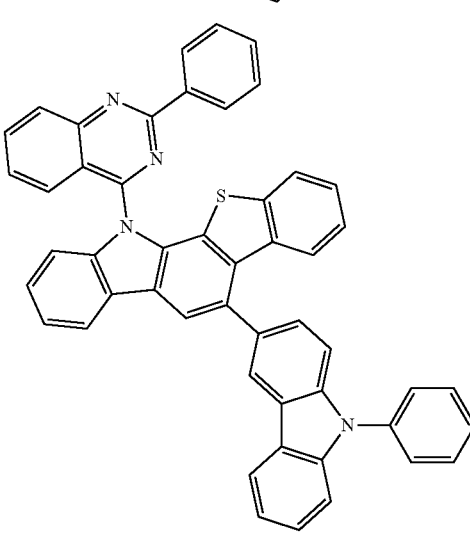
1-61
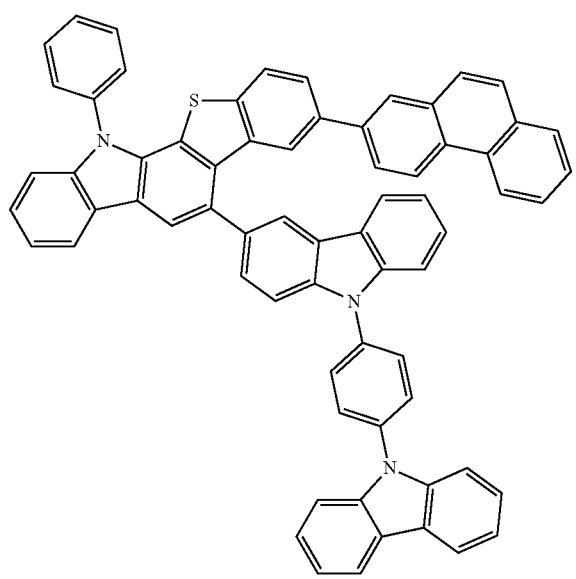

195
-continued
1-62
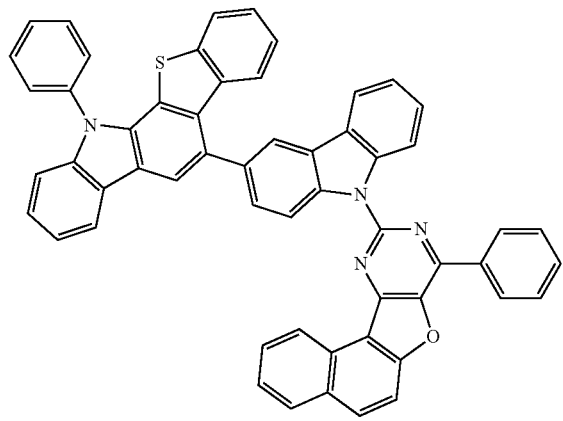
1-63
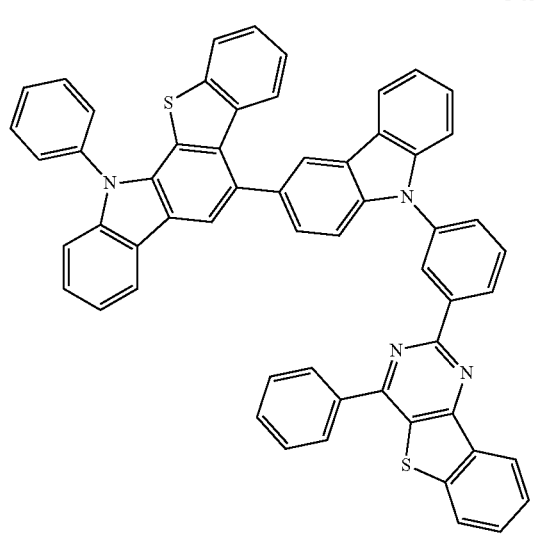
1-64
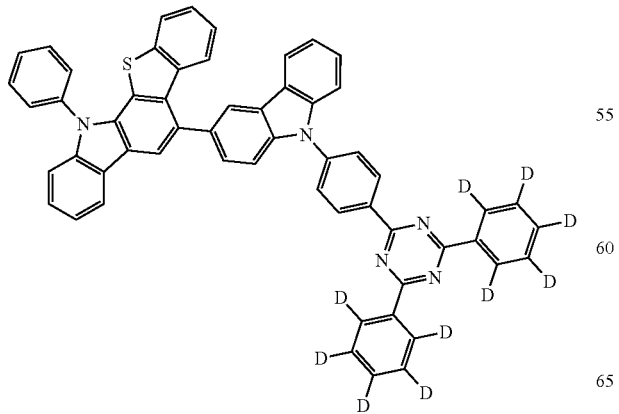
196
-continued
1-65
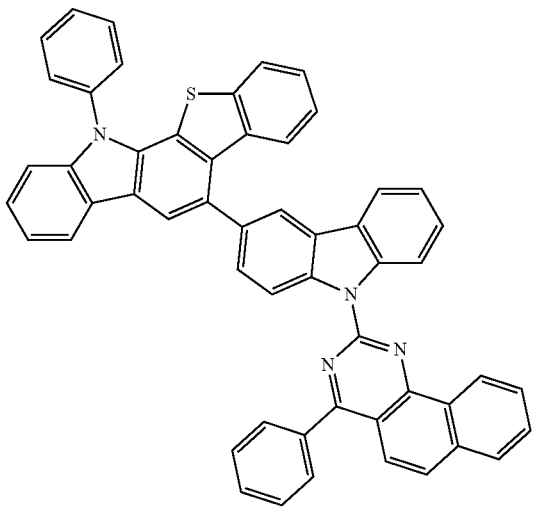
1-66
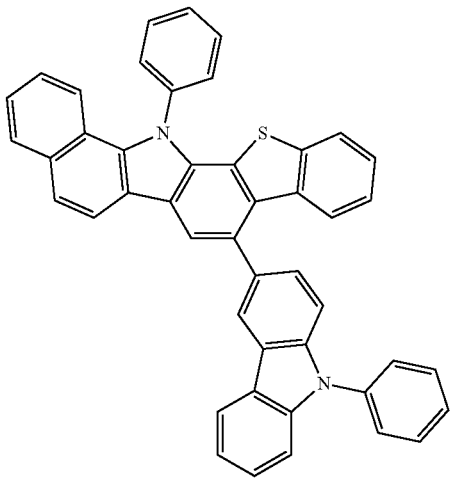
1-67
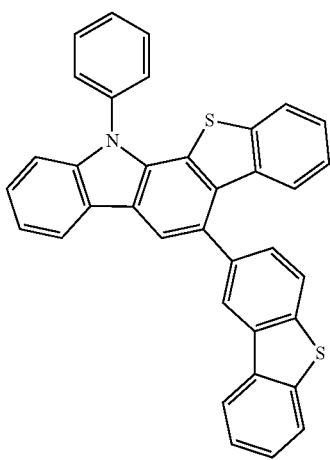

197
-continued
1-68
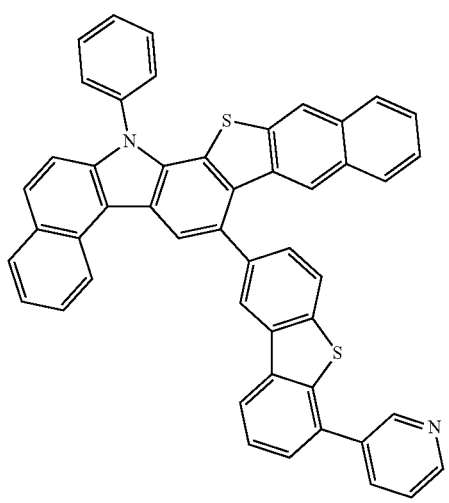
1-69
198
-continued
1-70
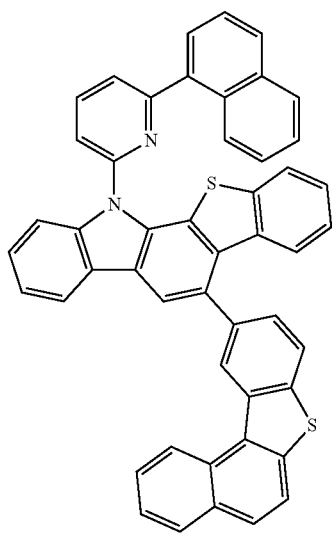
1-71
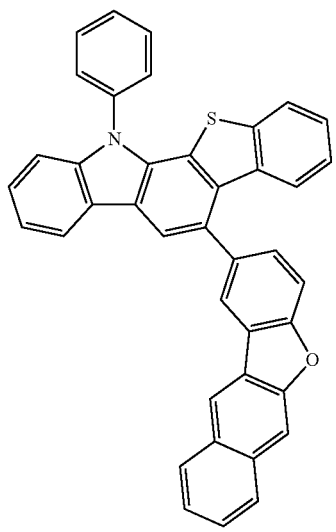

199
-continued
1-72
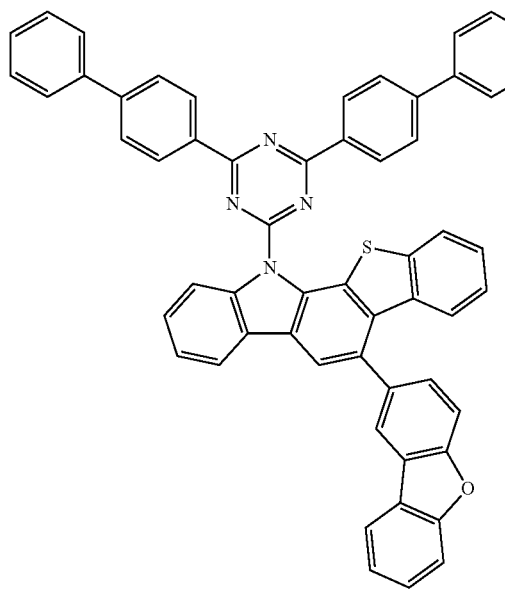
1-73
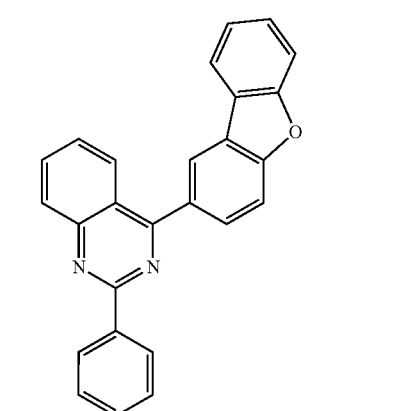
1-74
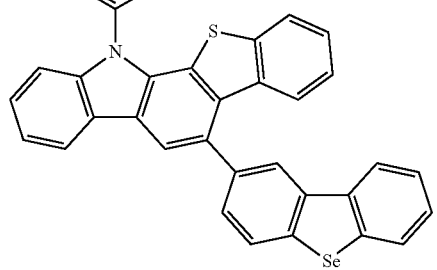
200
-continued
1-75
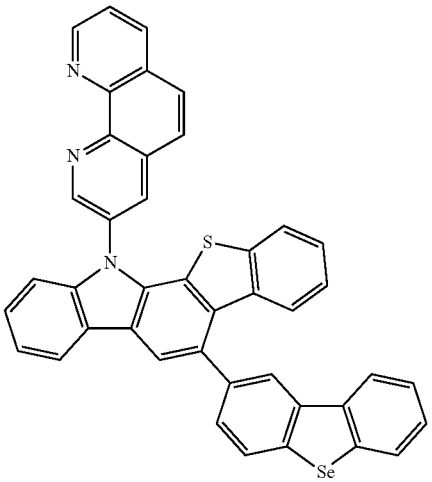
1-76
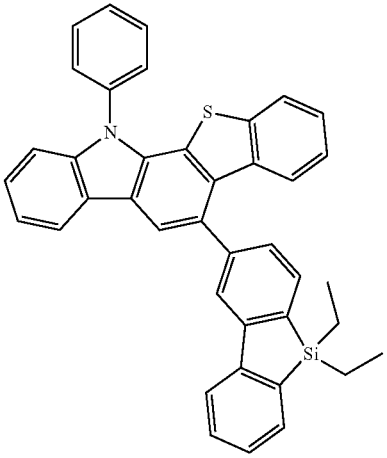
1-77
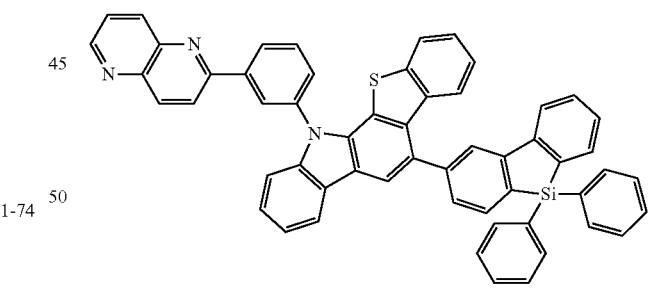
1-78
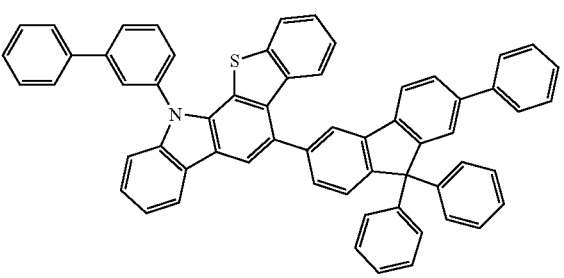

201
-continued
1-79
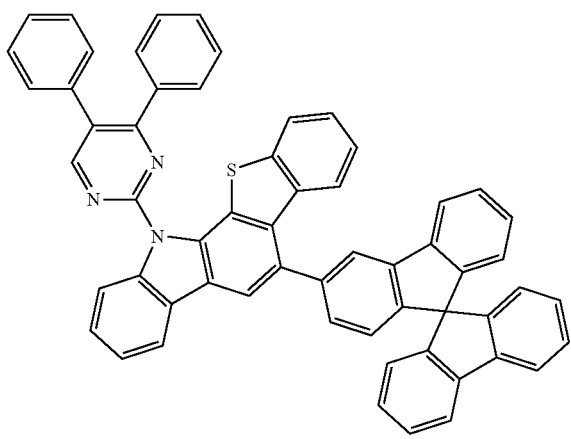
1-80
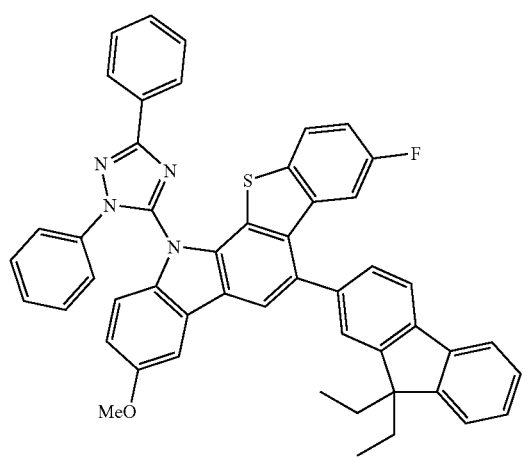
1-81
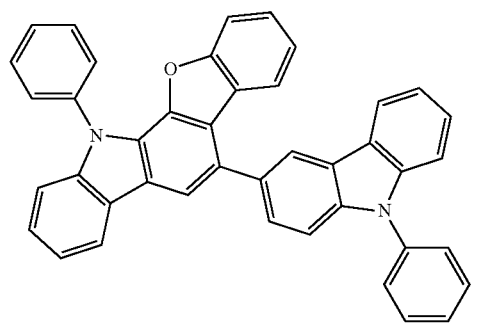
1-82
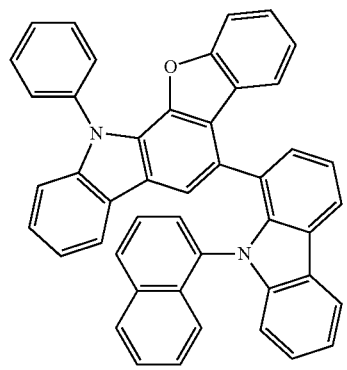
202
-continued
1-83
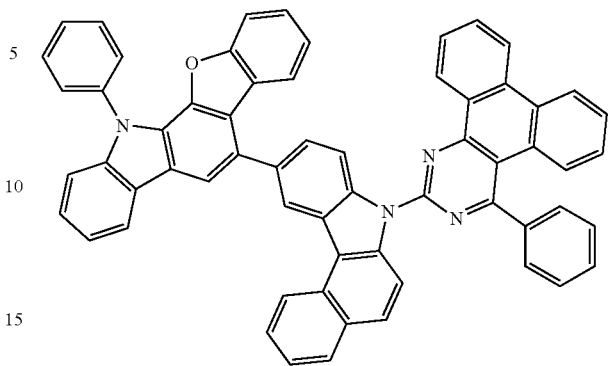
1-84
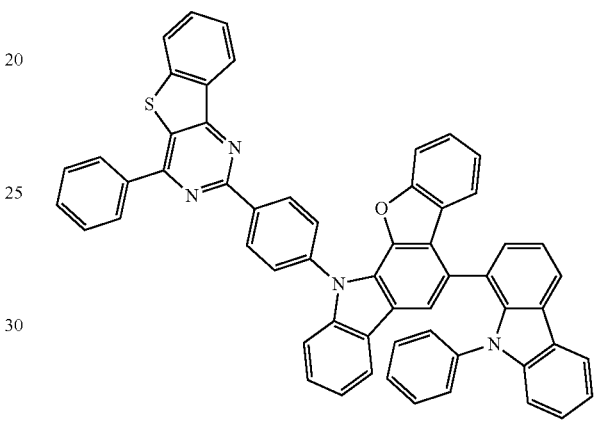
1-85
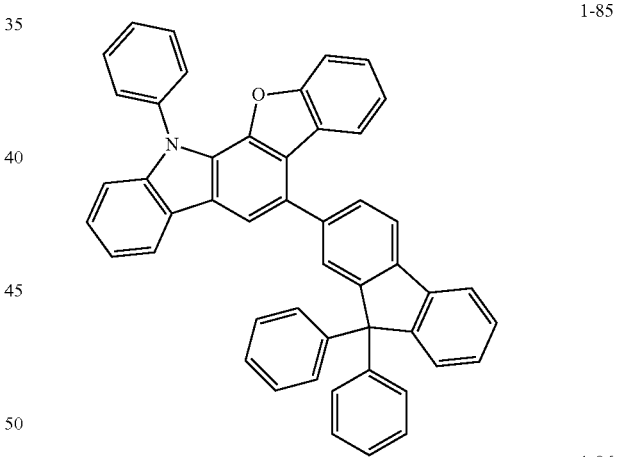
1-86
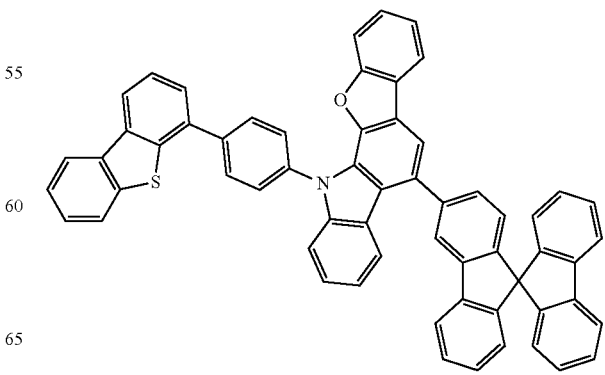

1-87
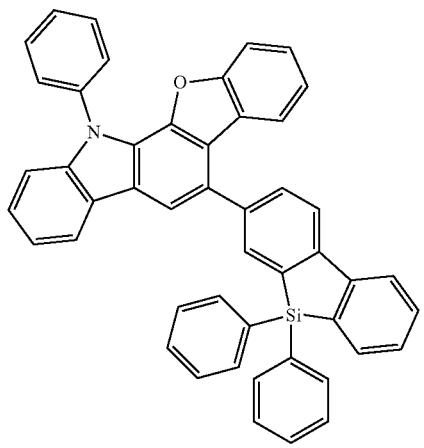
1-88
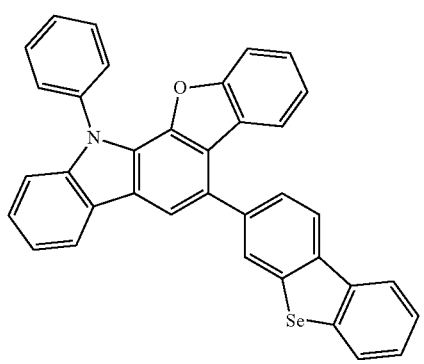
1-89
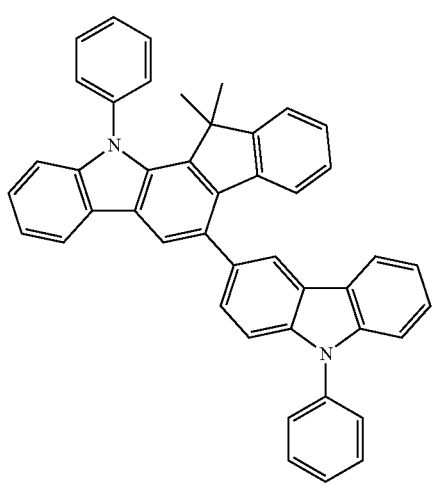
1-90
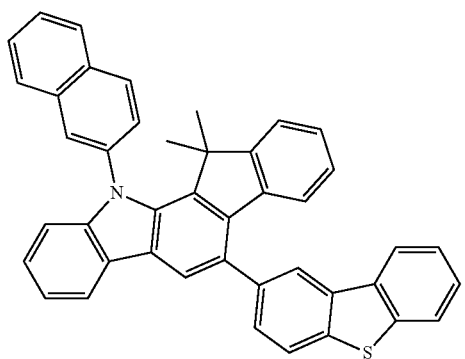
1-91
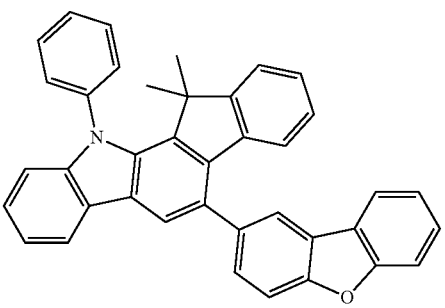
1-92
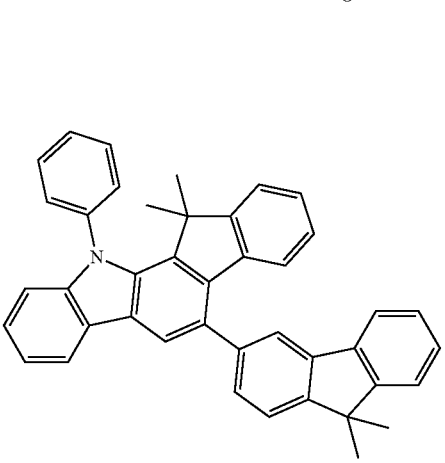
1-93
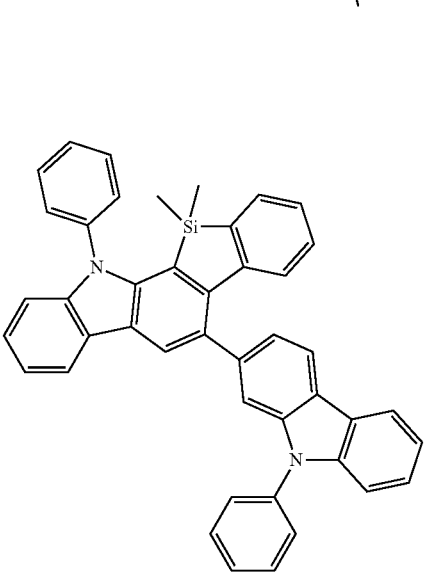
1-94
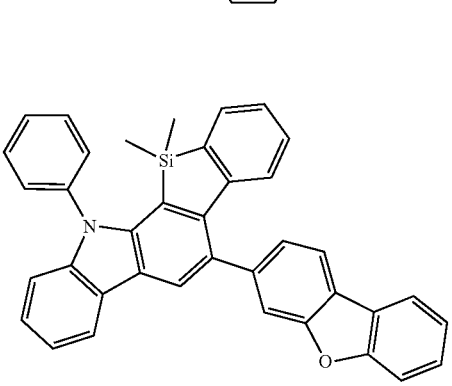

1-95
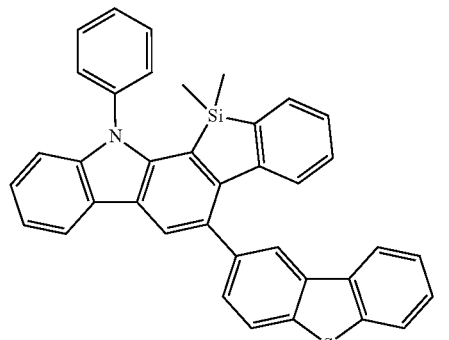
1-96
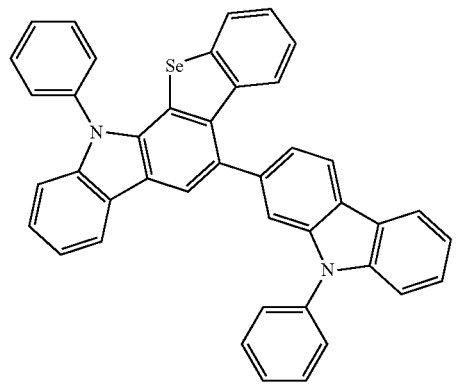
1-97
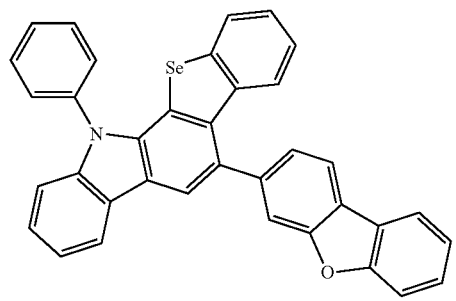
1-98
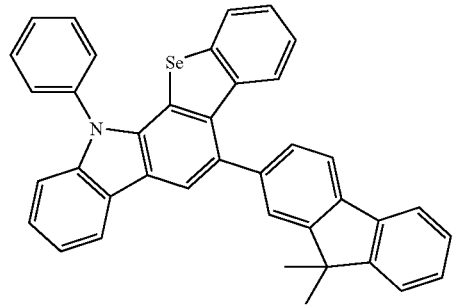
2-1
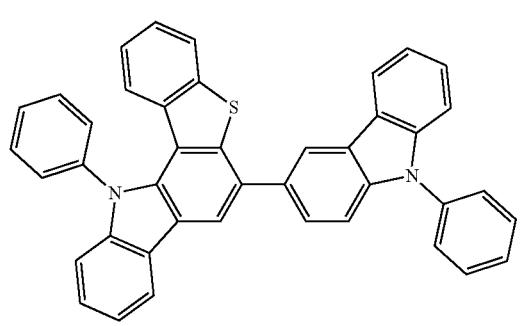
2-2
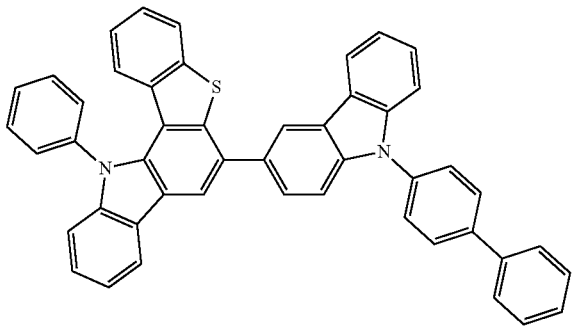
2-3
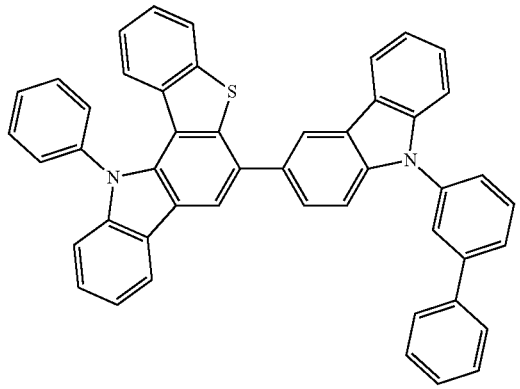
2-4
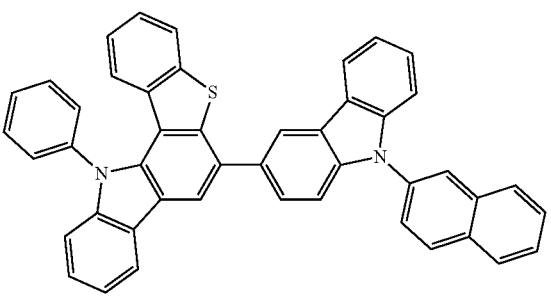
2-5
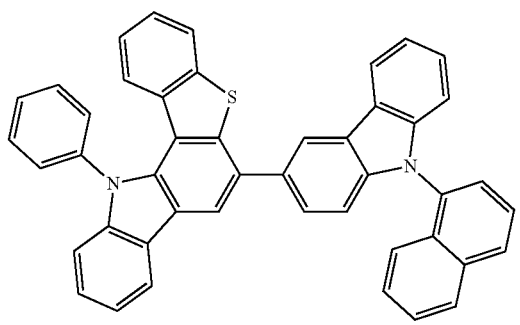

2-6
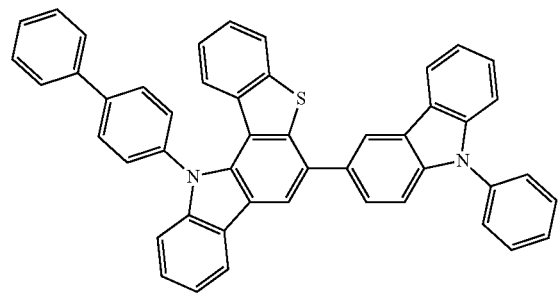
2-7
2-8
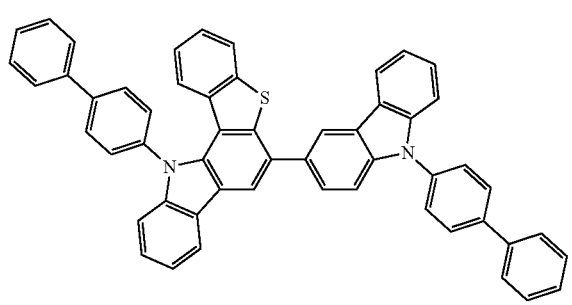
2-9
2-10
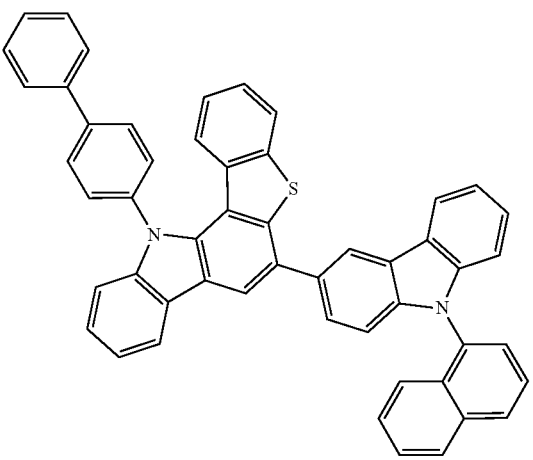
2-11
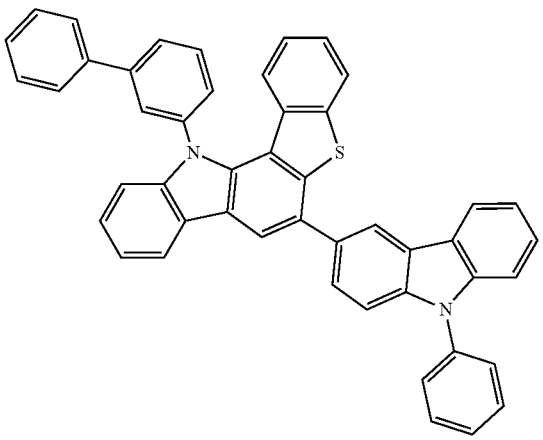
2-12
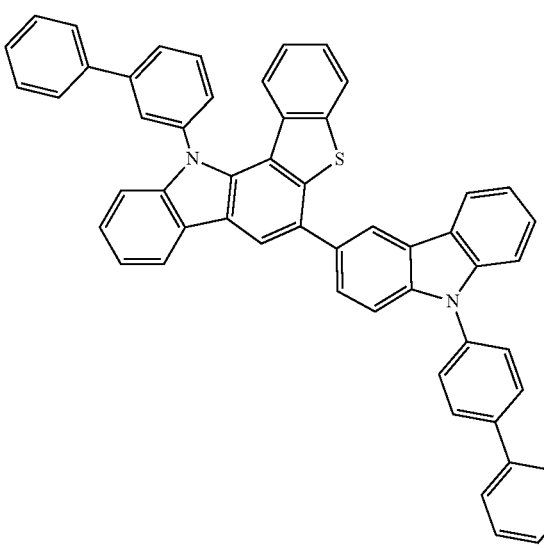

2-13
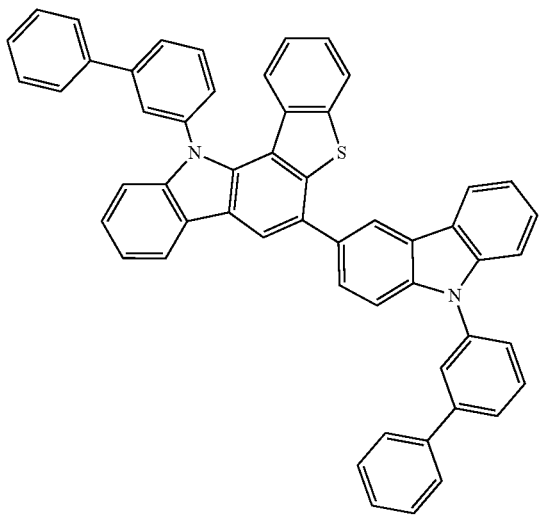
2-14
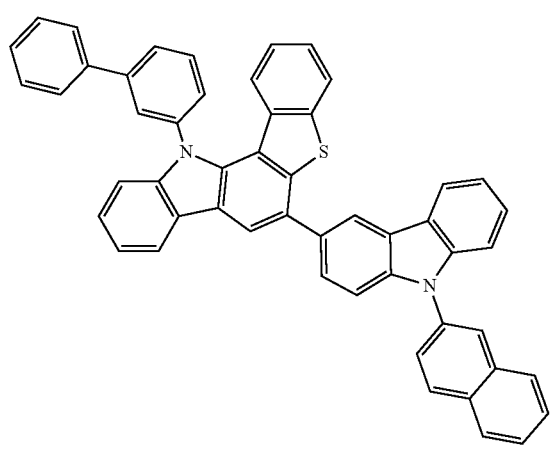
2-15
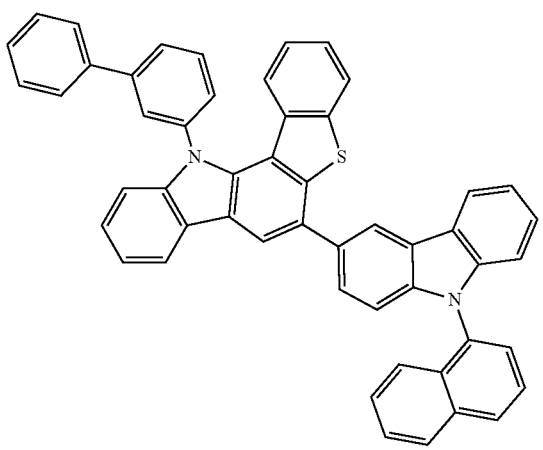
2-16
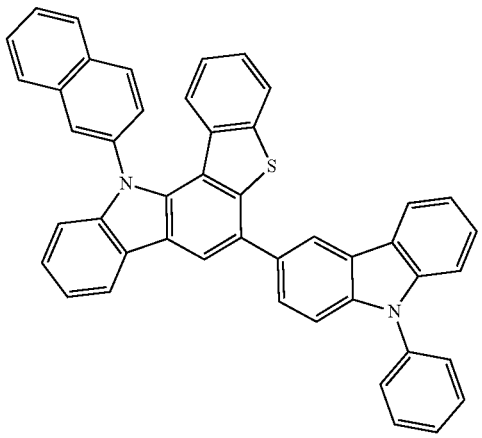
2-17
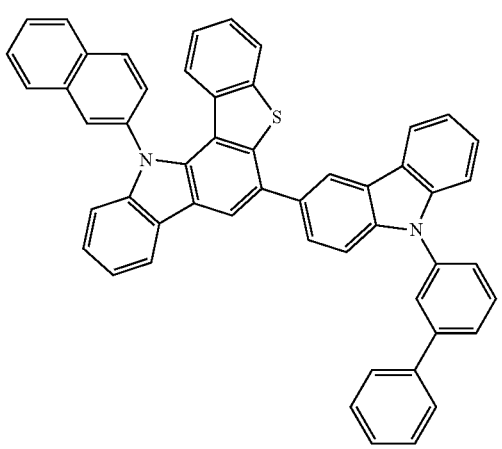
2-18

211
-continued
2-19
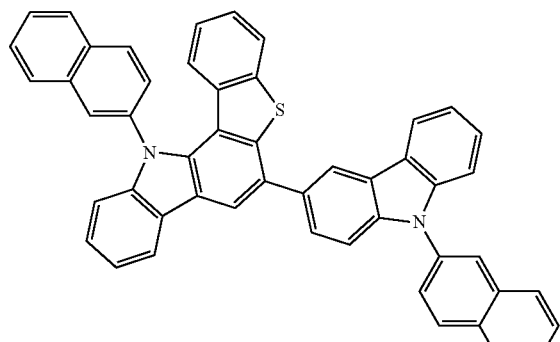
2-20
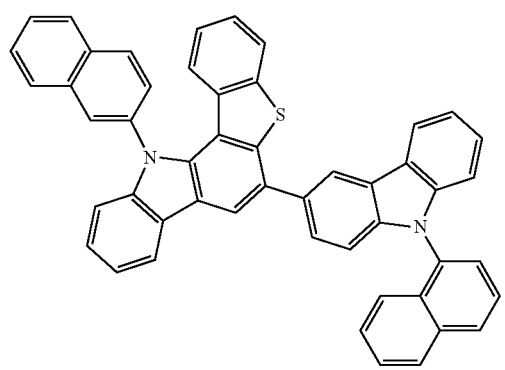
2-21
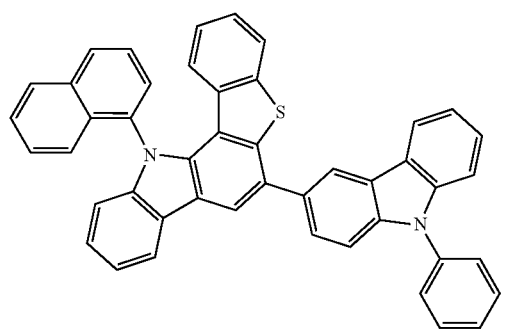
2-22
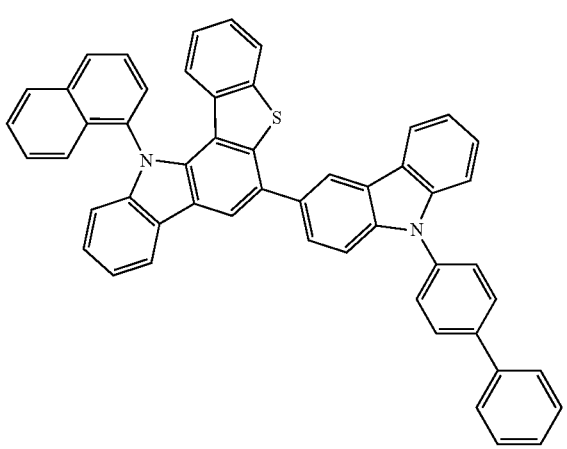
212
-continued
2-23
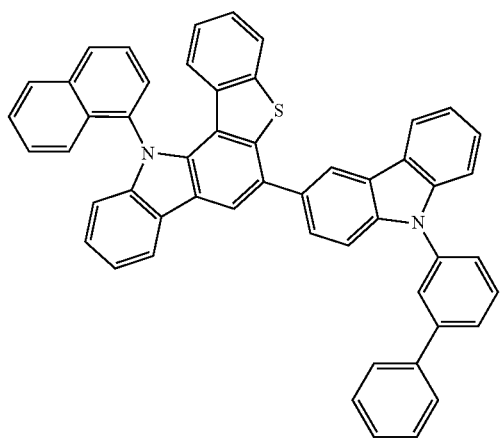
2-24
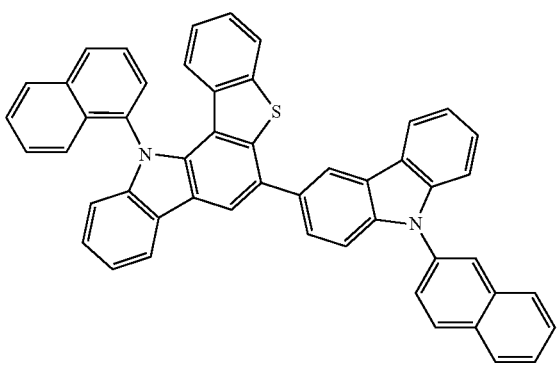
2-25
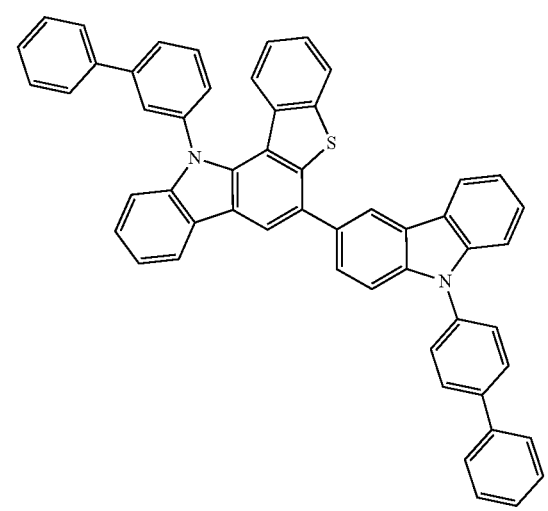

213
-continued
2-26
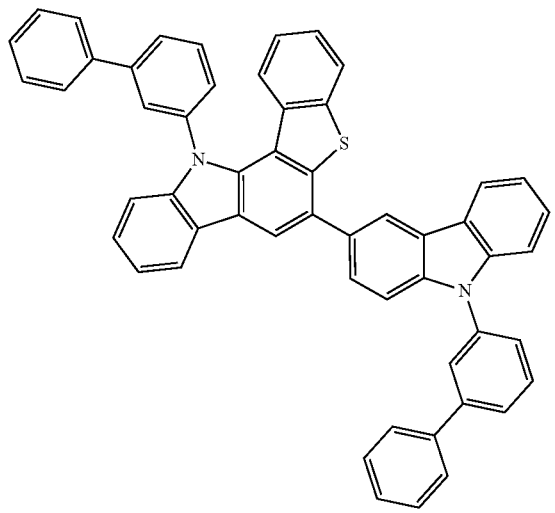
2-27
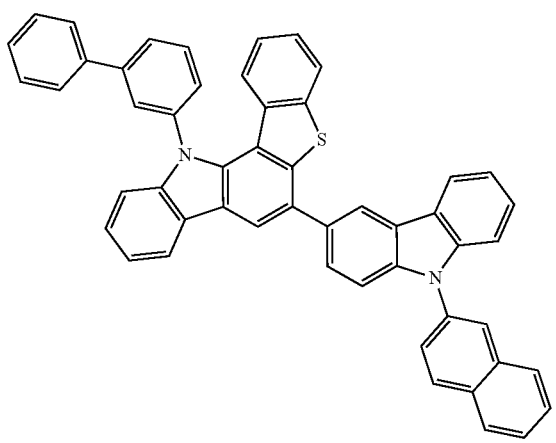
2-28
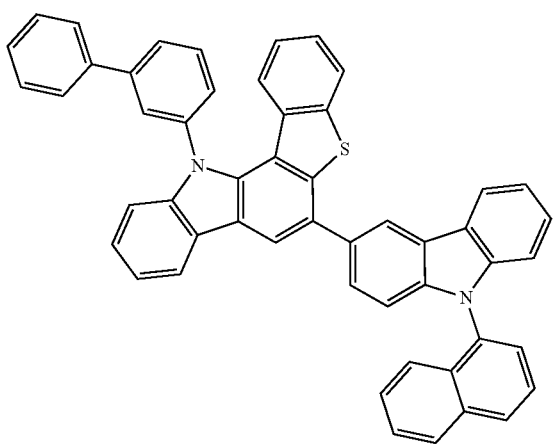
214
-continued
2-29
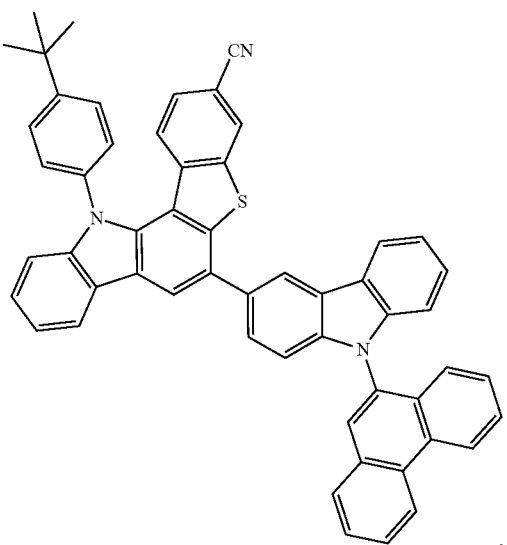
2-30
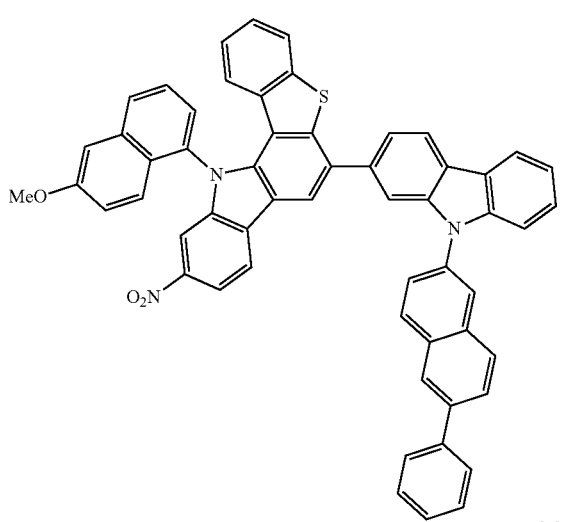
2-31
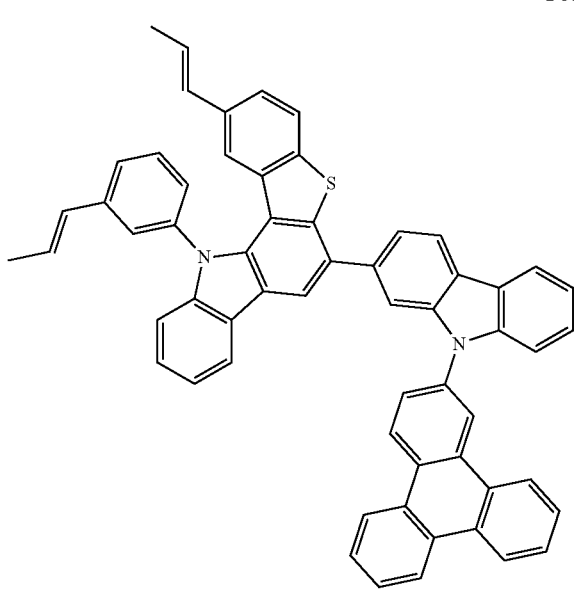

2-32
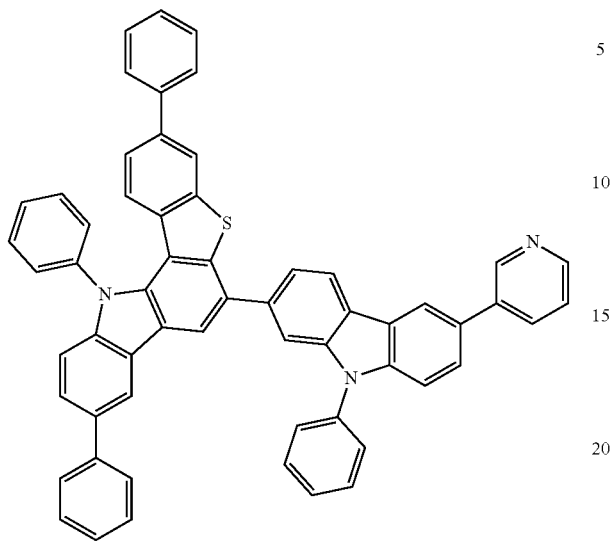
2-33
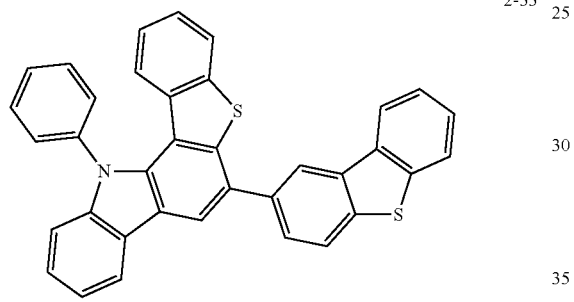
2-34
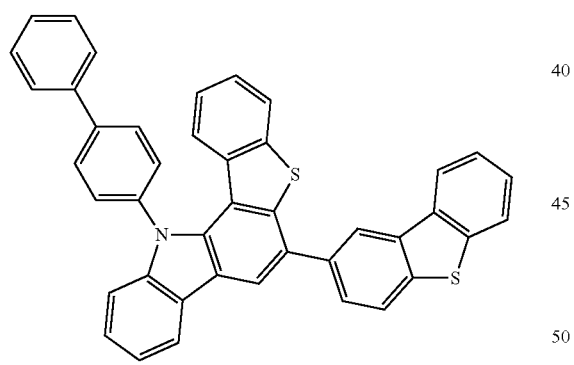
2-35
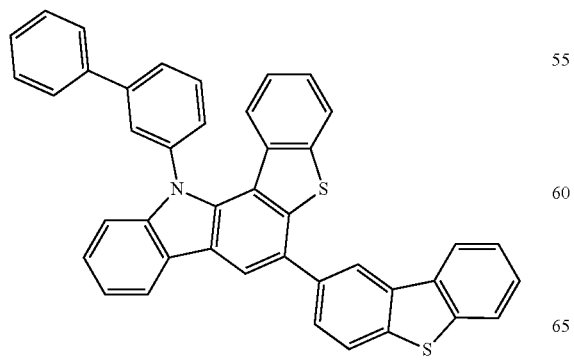
2-36
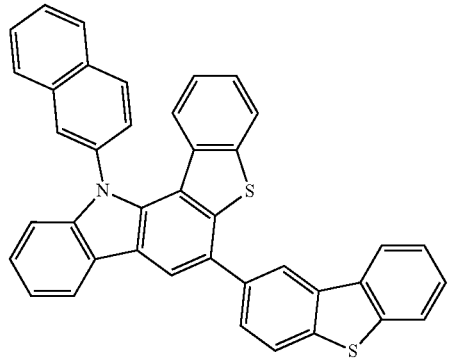
2-37
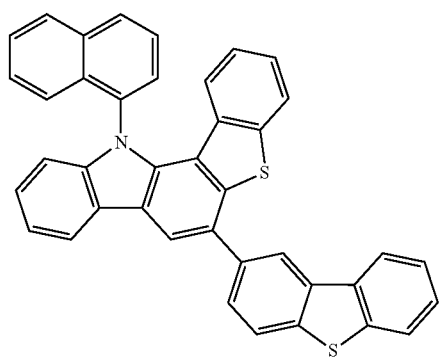
2-38
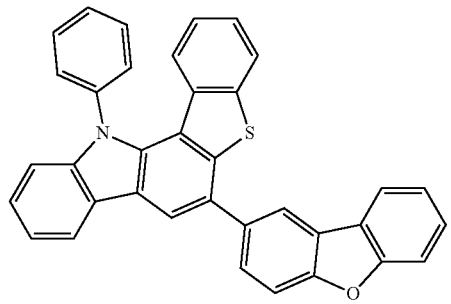
2-39
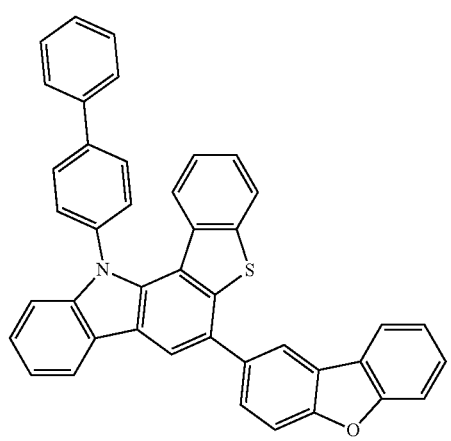

2-40
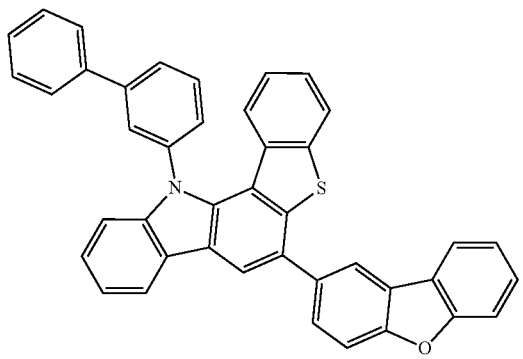
2-41
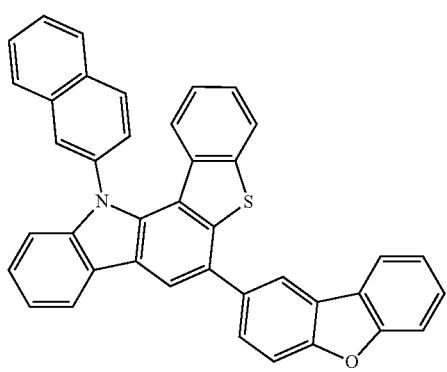
2-44
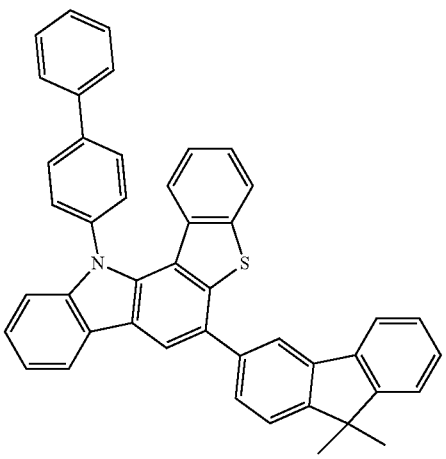
2-45
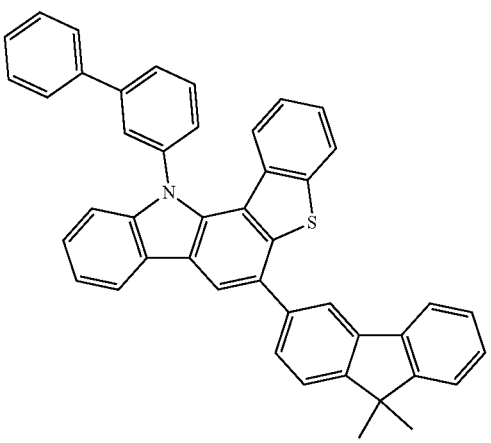
2-46
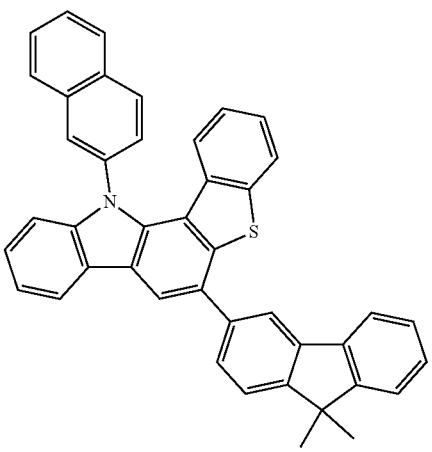

2-47
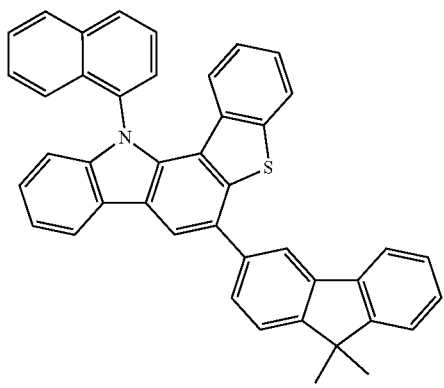
2-51
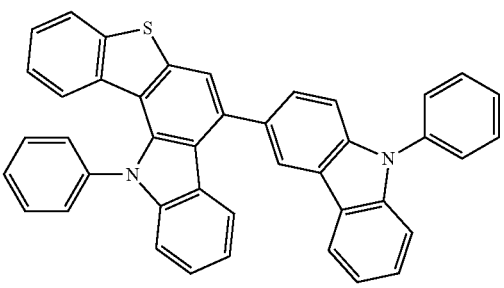
2-48
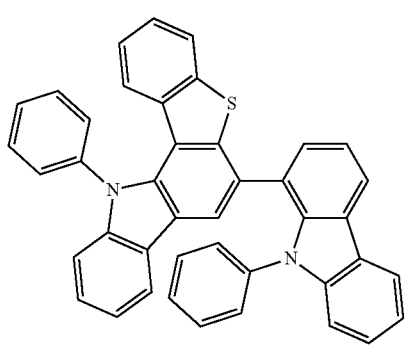
2-52
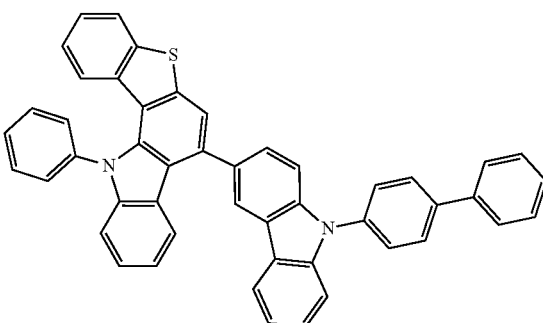
2-49
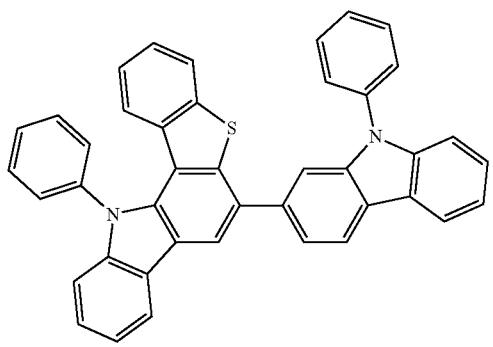
2-53
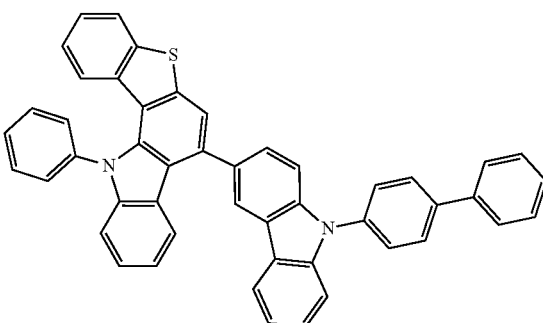
2-50
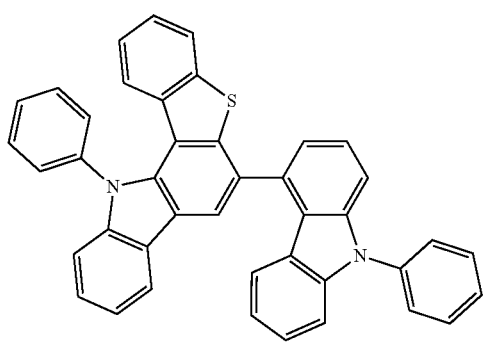
2-54
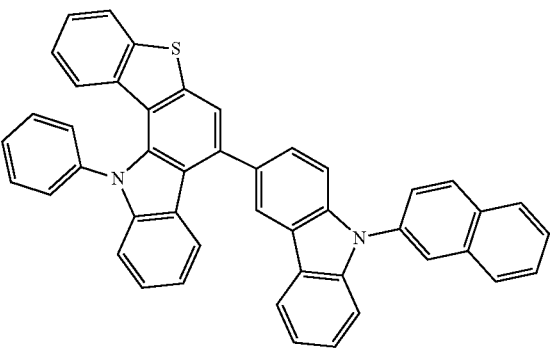

2-55
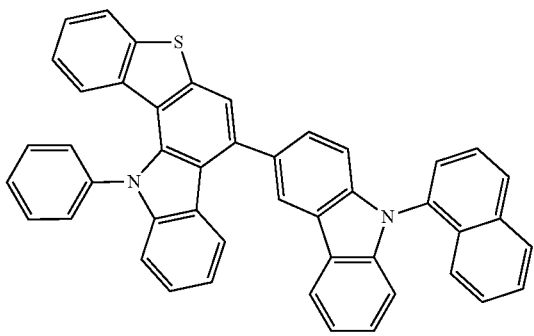
2-56
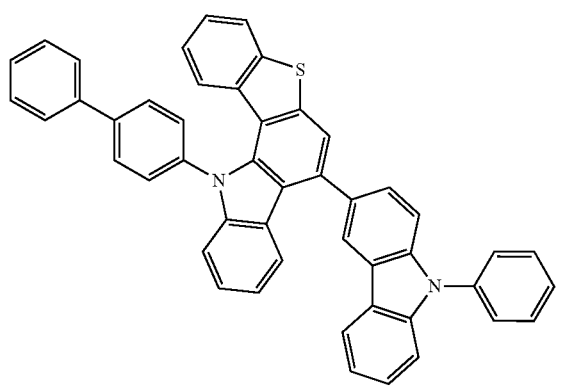
2-57
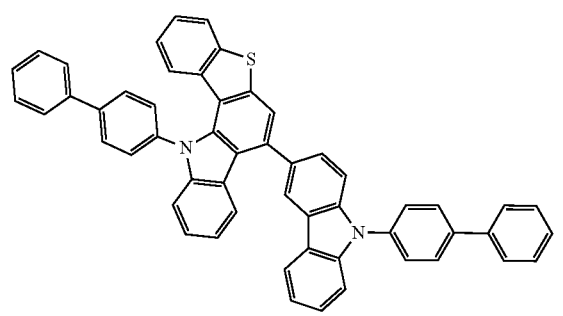
2-58
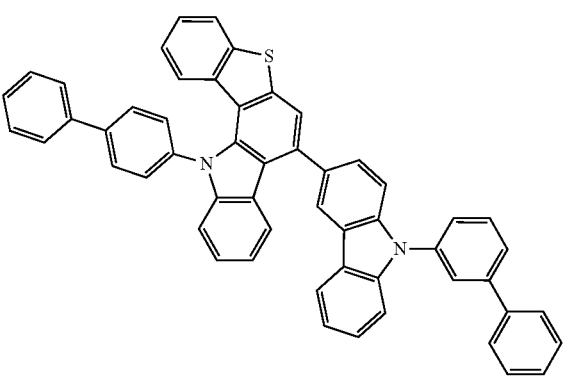
2-59
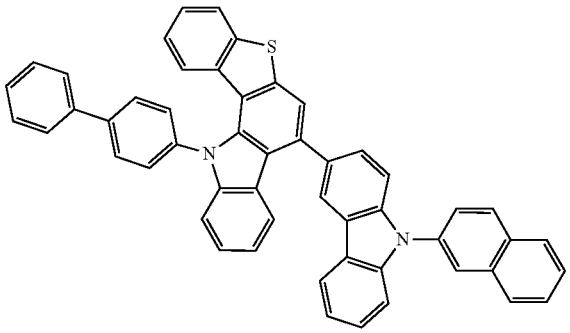
2-60
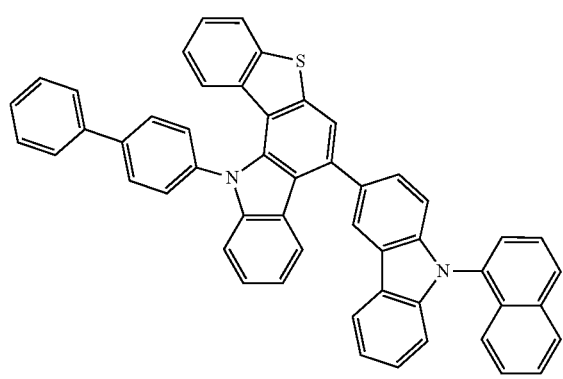
2-61
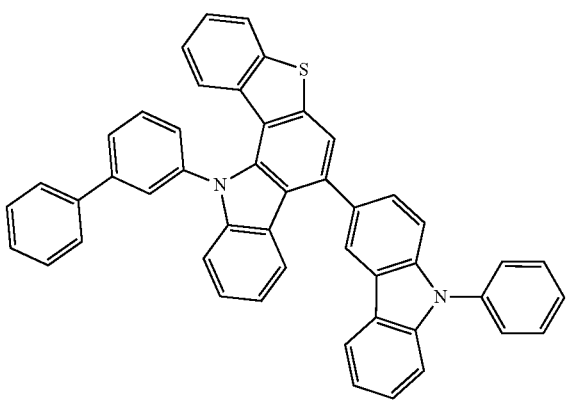
2-62
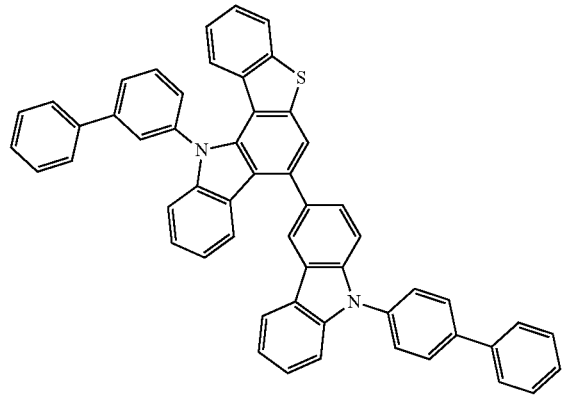

2-63
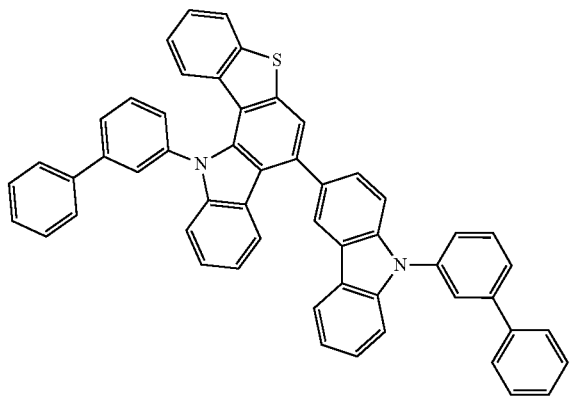
2-64
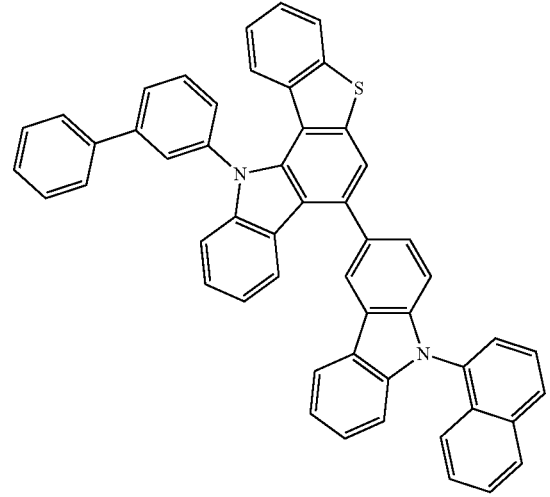
2-65
2-66
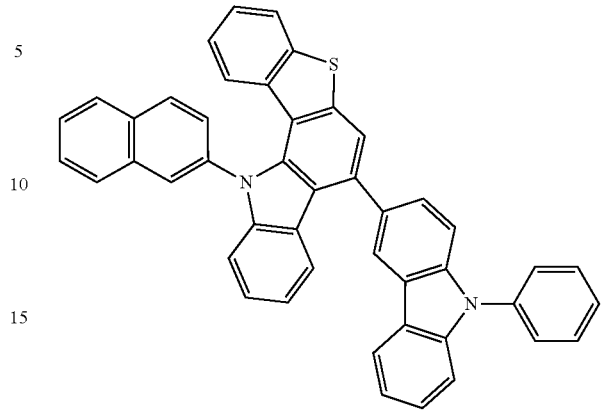
2-67
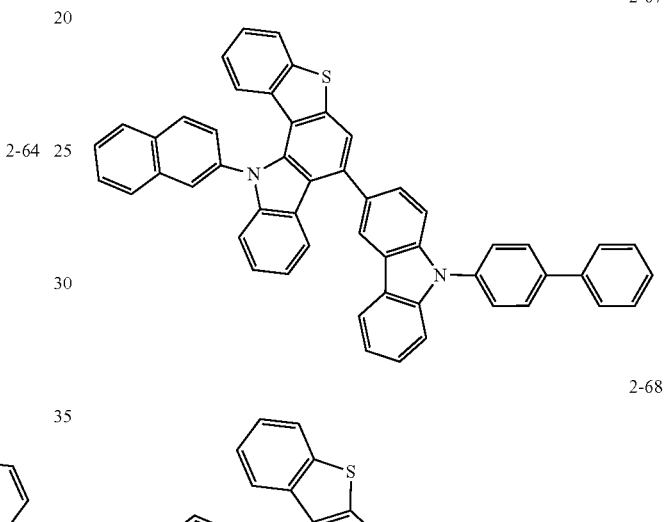
2-68
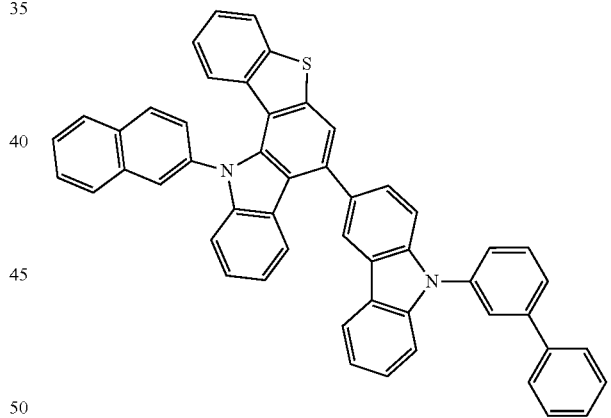
2-69
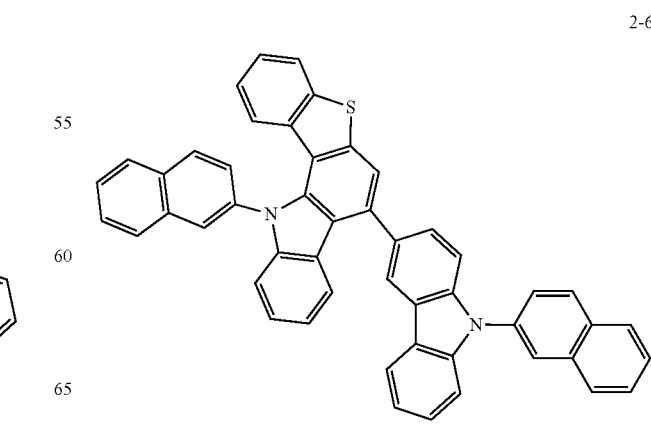

2-70
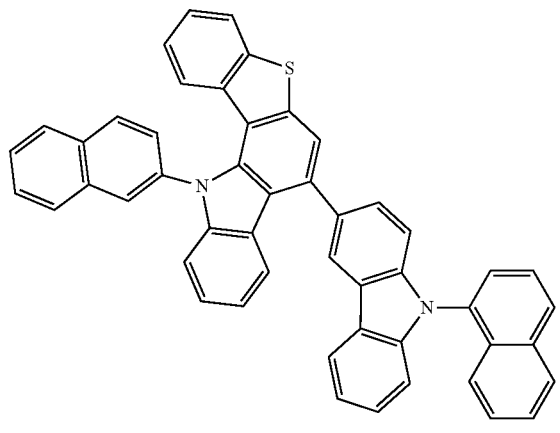
2-71
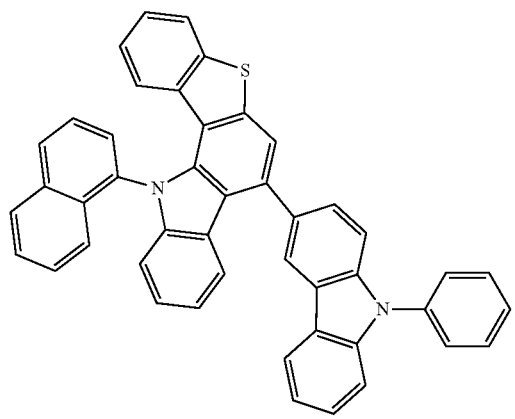
2-72
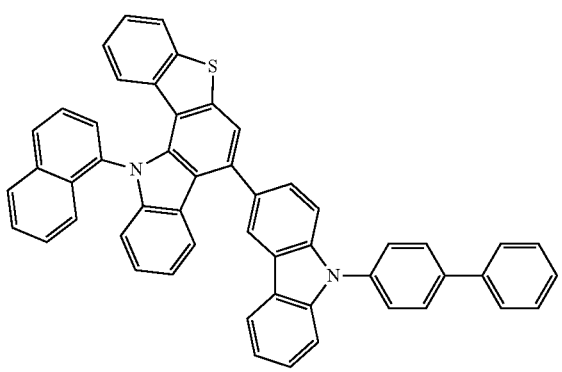
2-73
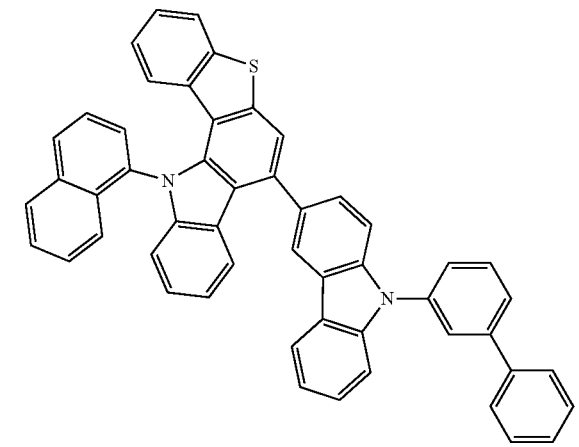
2-74
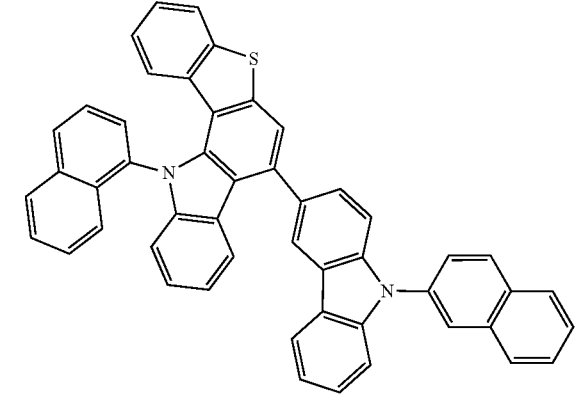
2-75
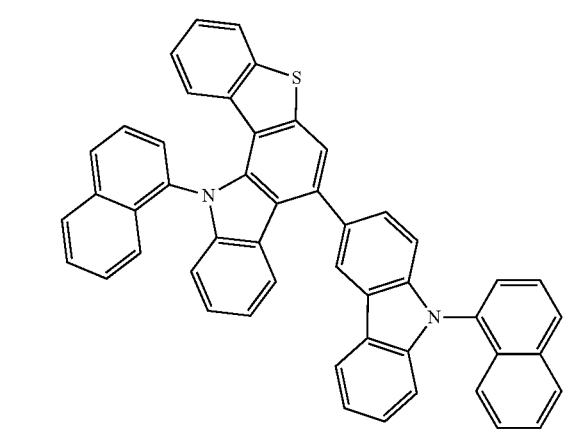

-continued
2-76
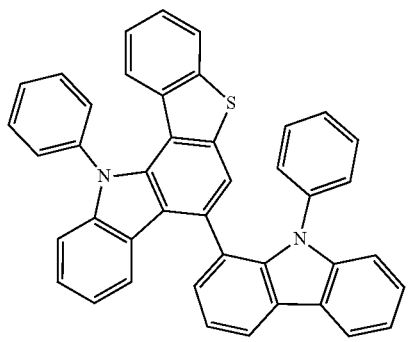
2-77
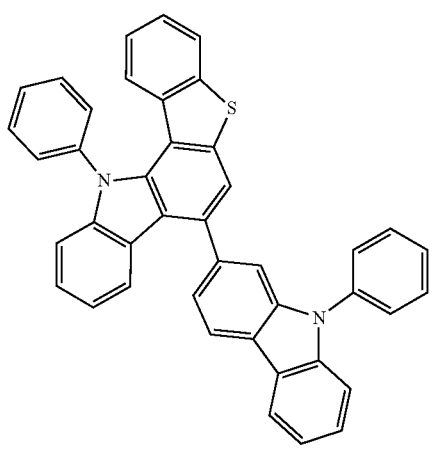
2-78
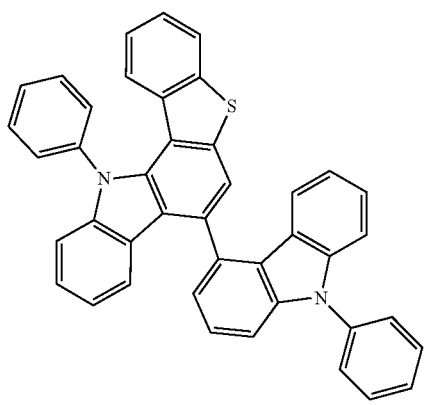
2-79
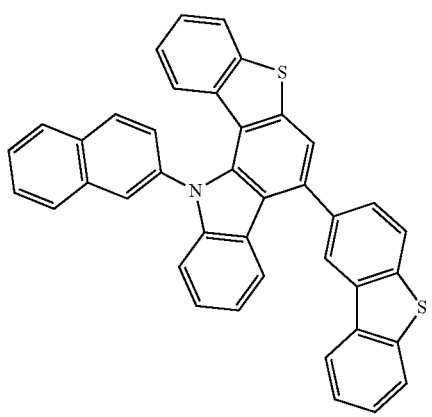
-continued
2-80
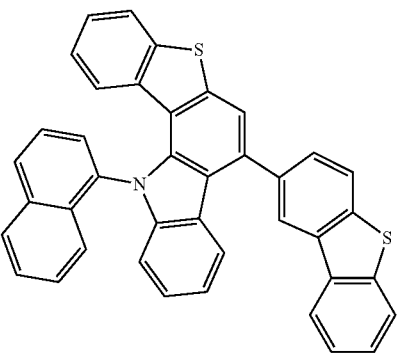
2-81
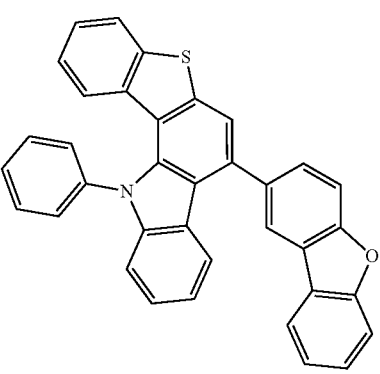
2-82
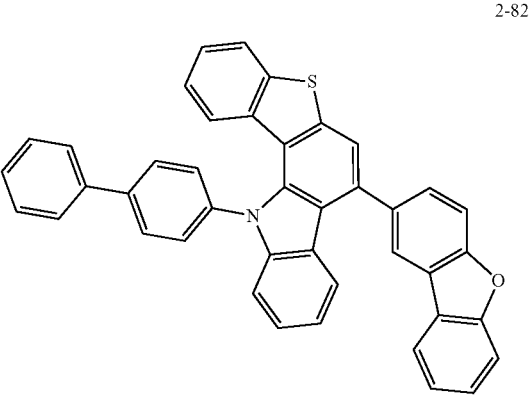
2-83
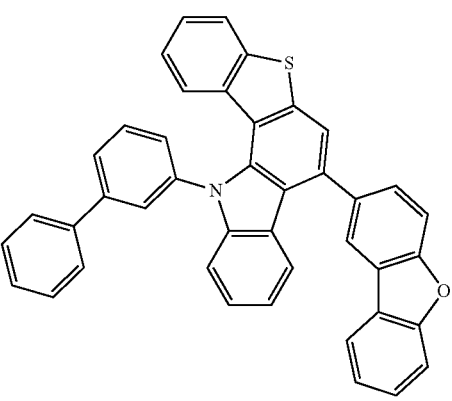

-continued
2-84
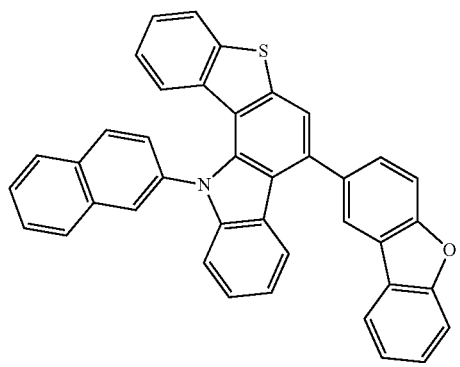
2-85
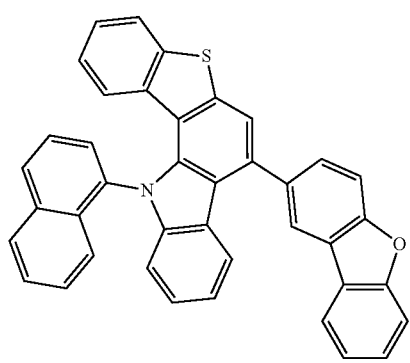
2-86
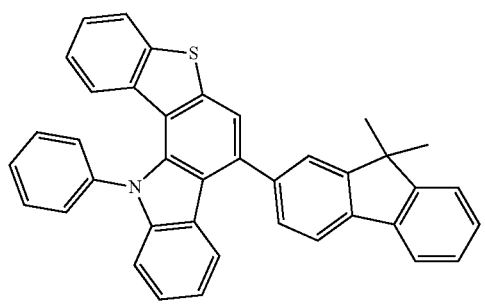
2-87
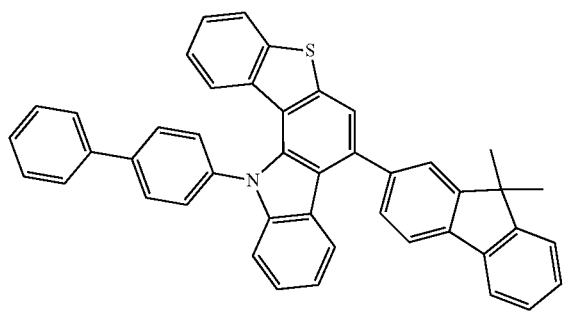
-continued
2-88
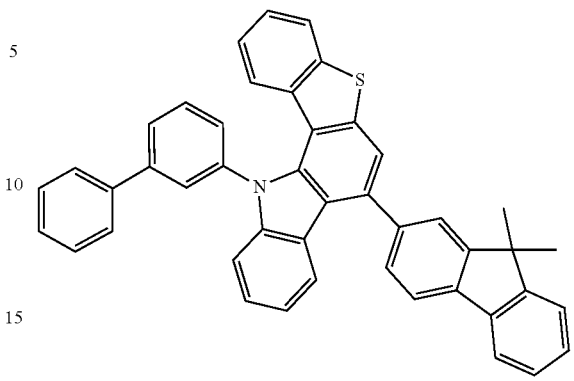
2-89
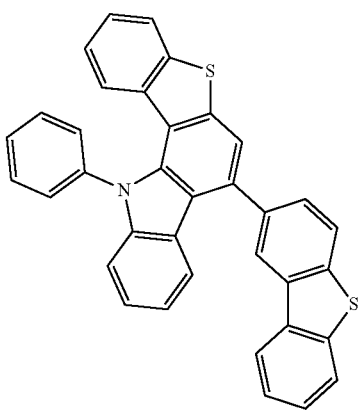
2-90
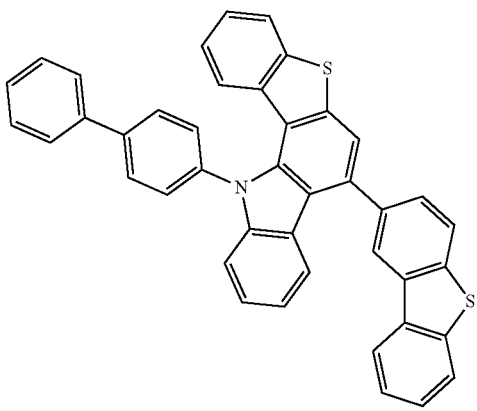
2-91
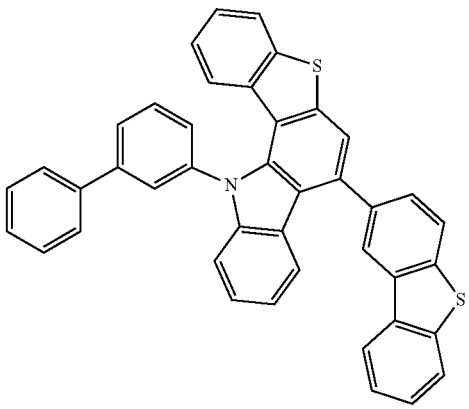

-continued
2-92
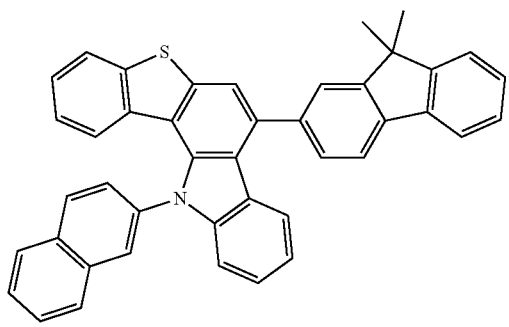
2-93
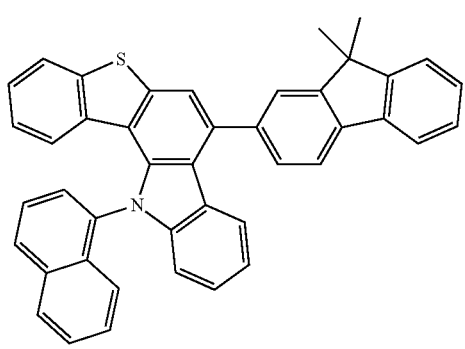
2-94
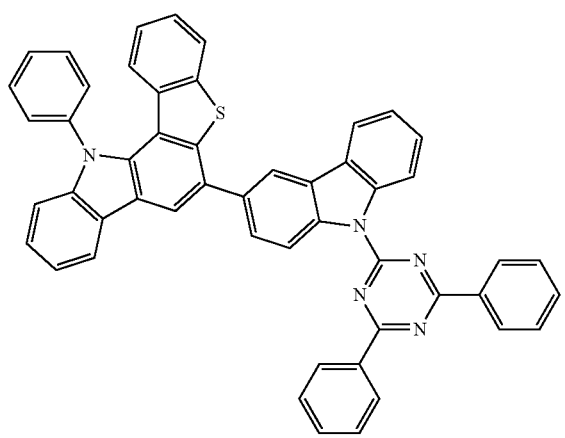
2-95
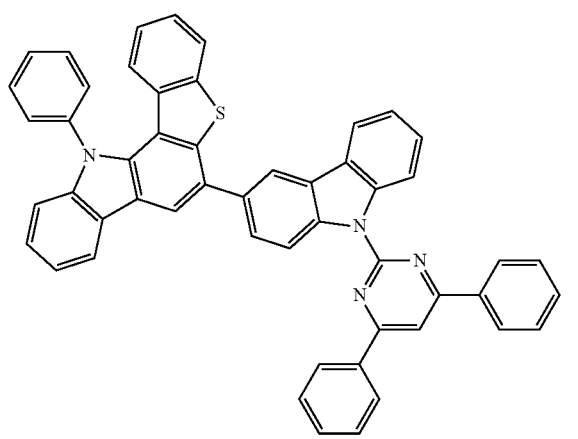
-continued
2-96
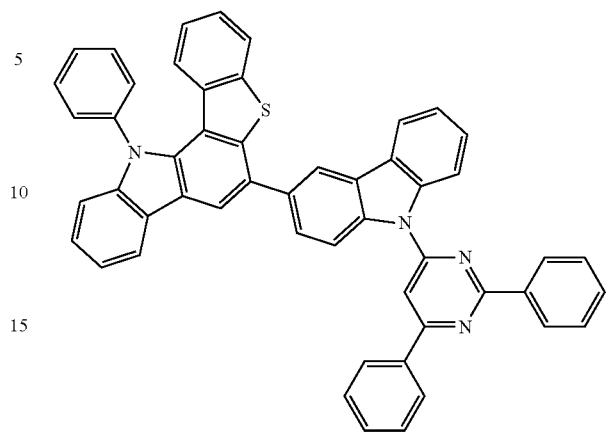
2-97
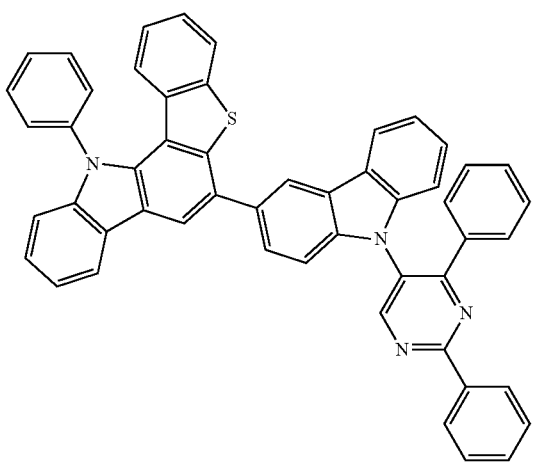
2-98
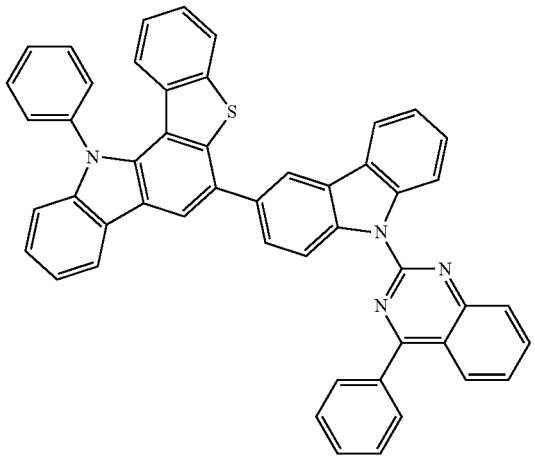

2-99
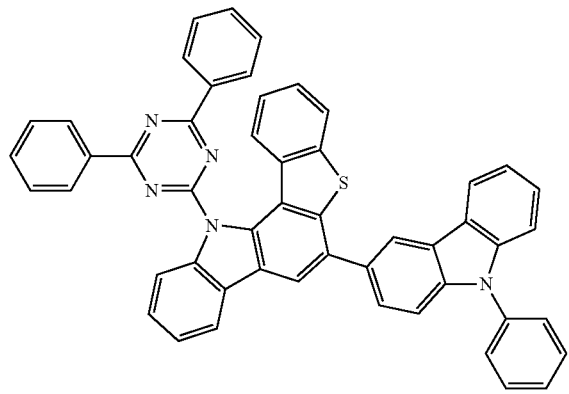
2-100
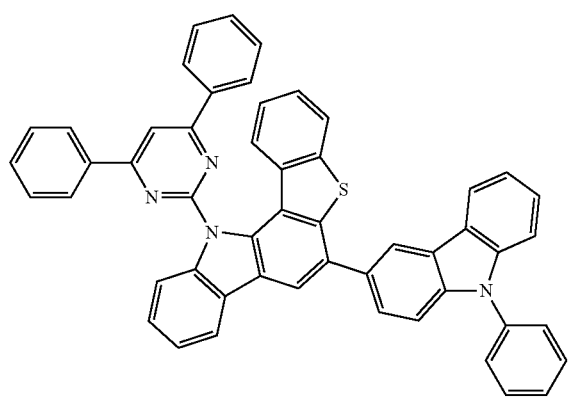
2-101
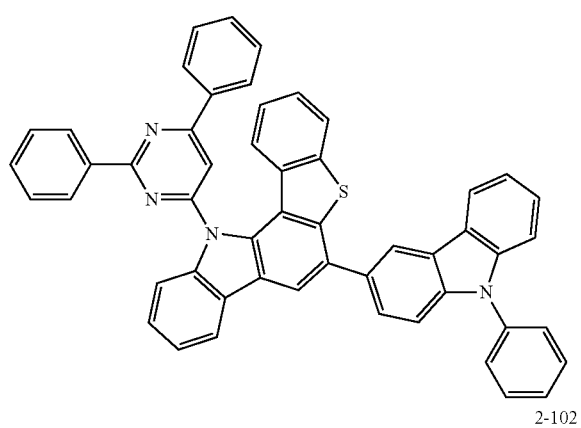
2-102
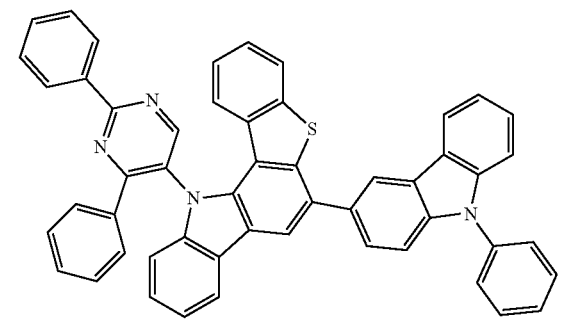
2-103
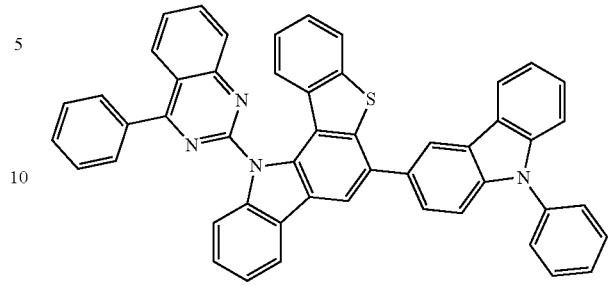
2-104
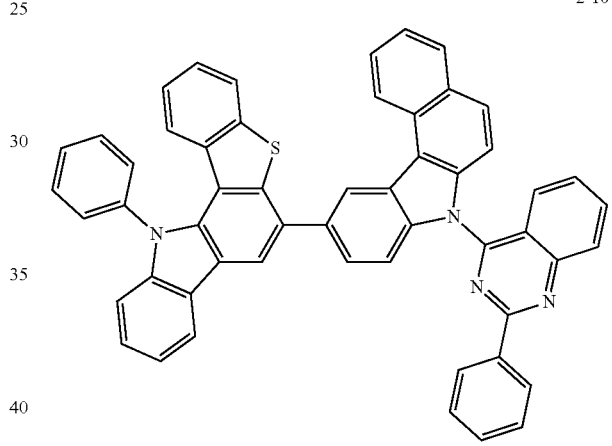
2-105
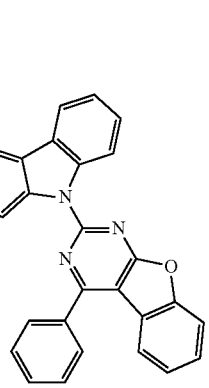

-continued
2-106
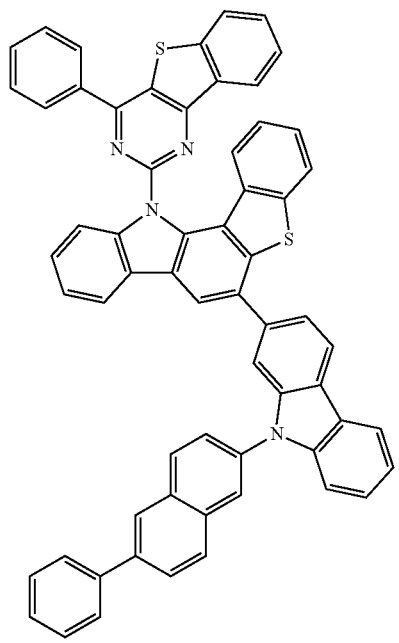
2-107
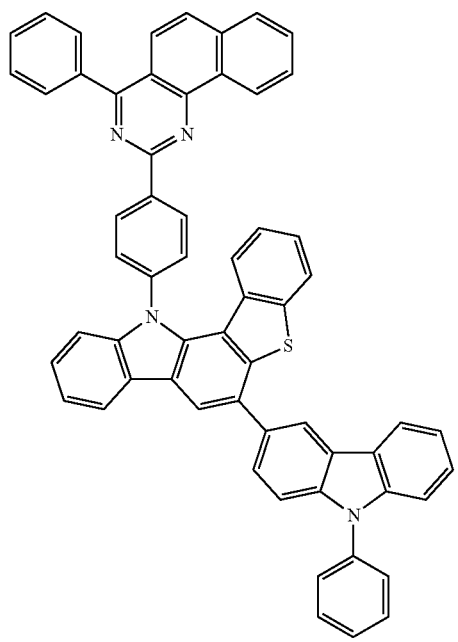
-continued
2-108
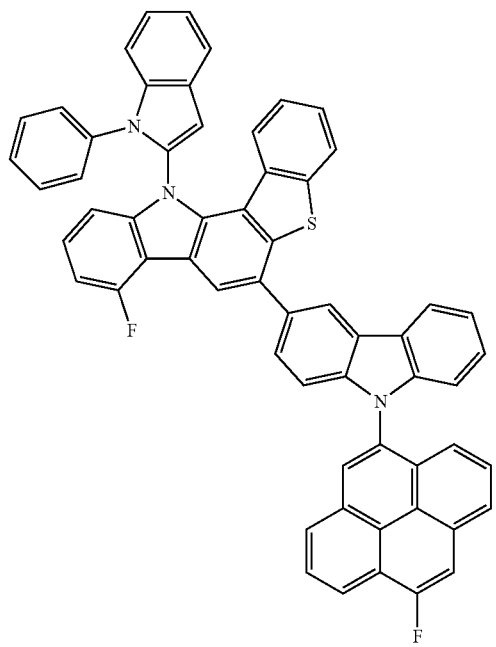
2-109
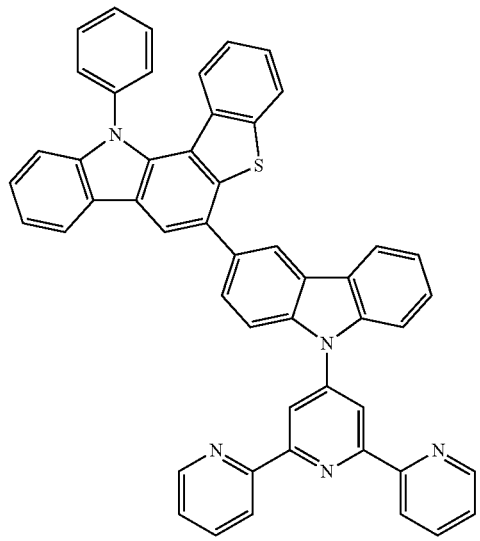

2-110
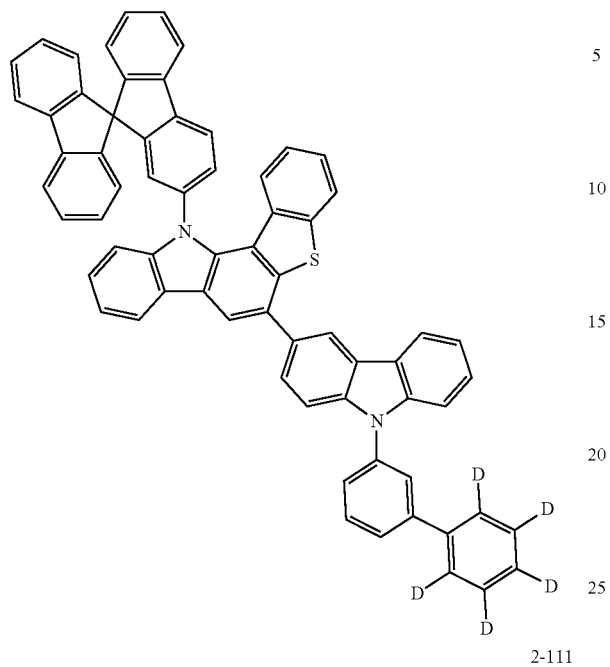
2-111
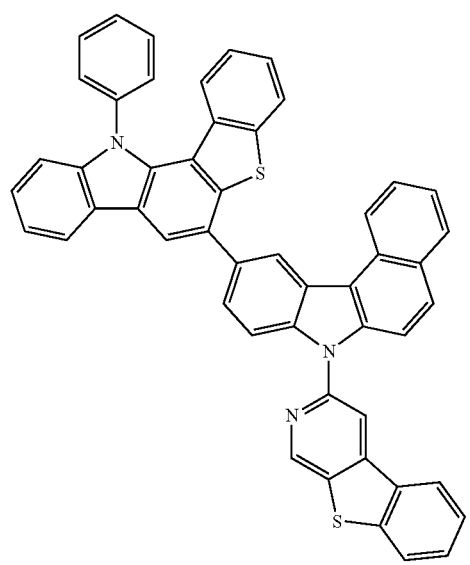
2-112
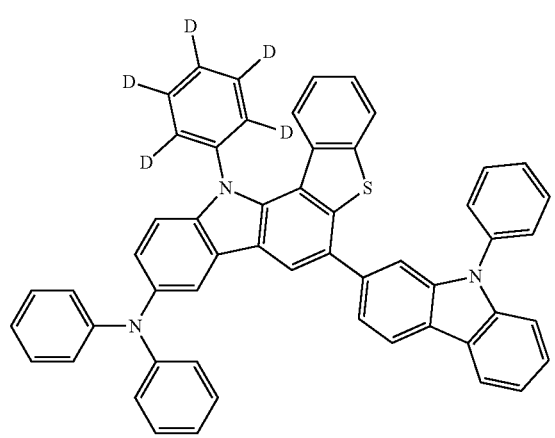
2-113
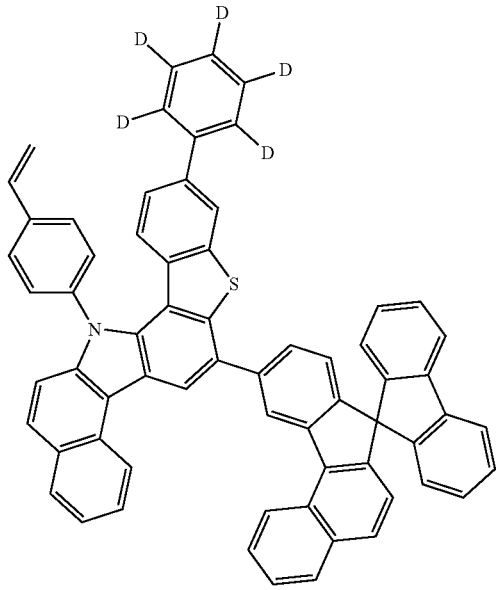
2-114
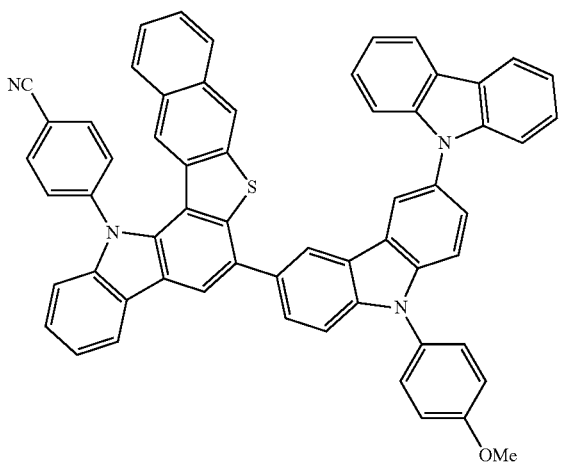
2-115
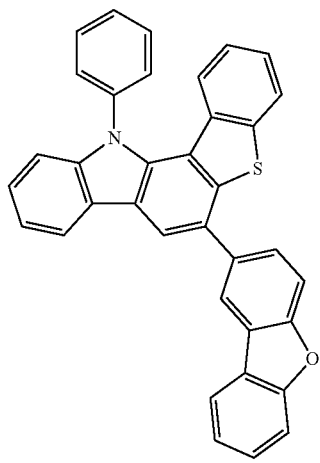

-continued
2-116
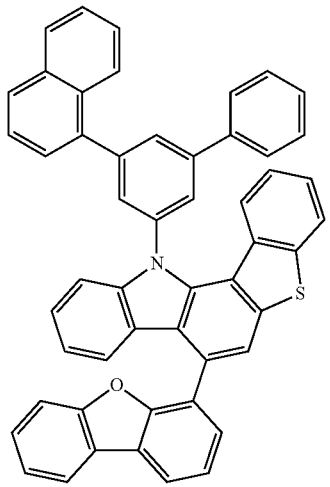
2-117
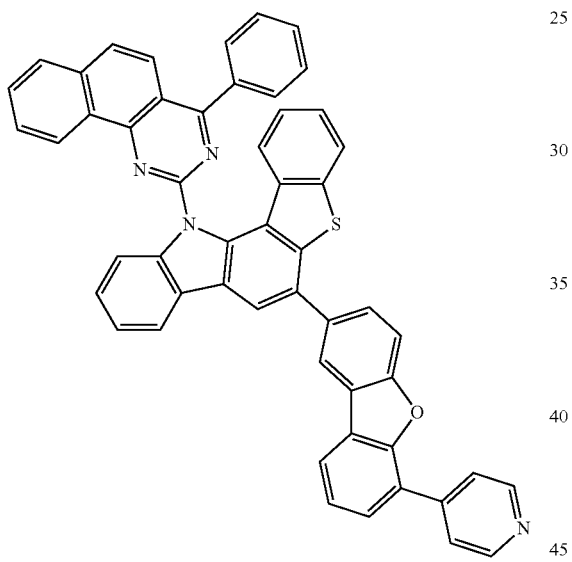
2-118
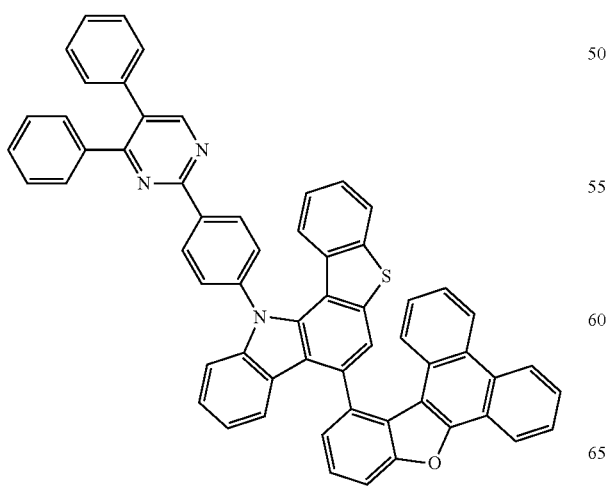
-continued
2-119
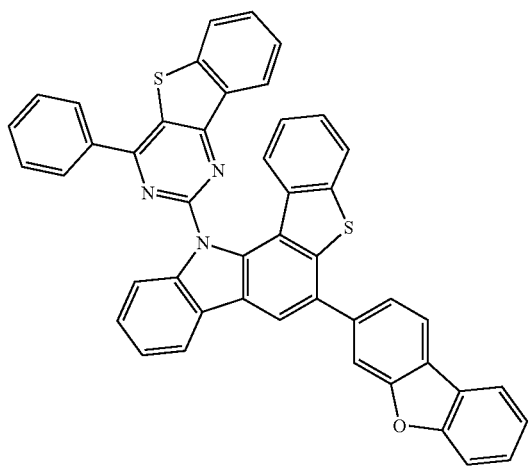
2-120
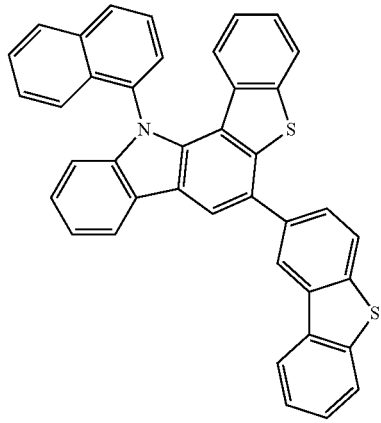
2-121
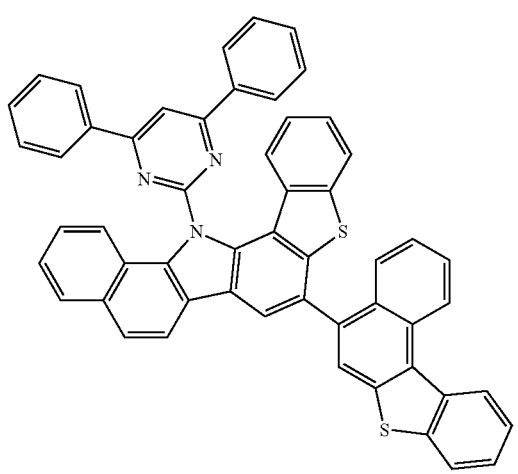

2-122
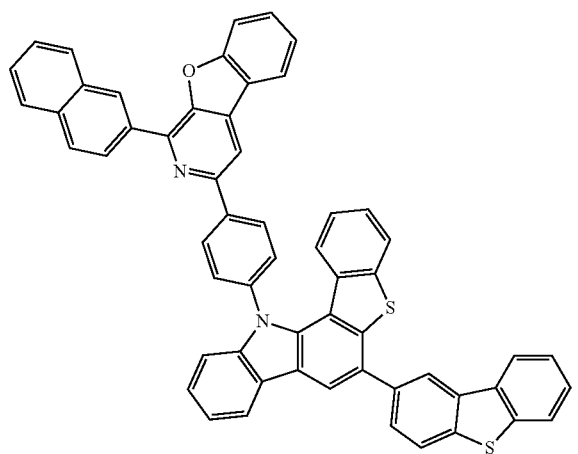
2-125
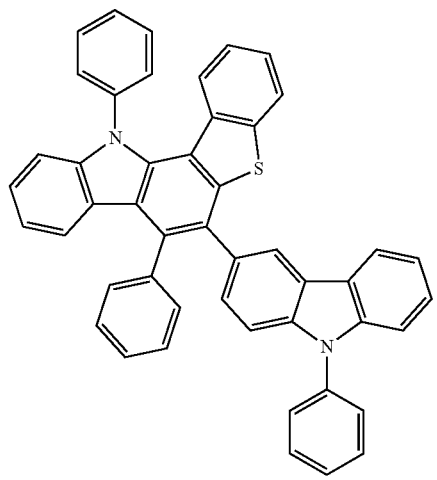
2-123
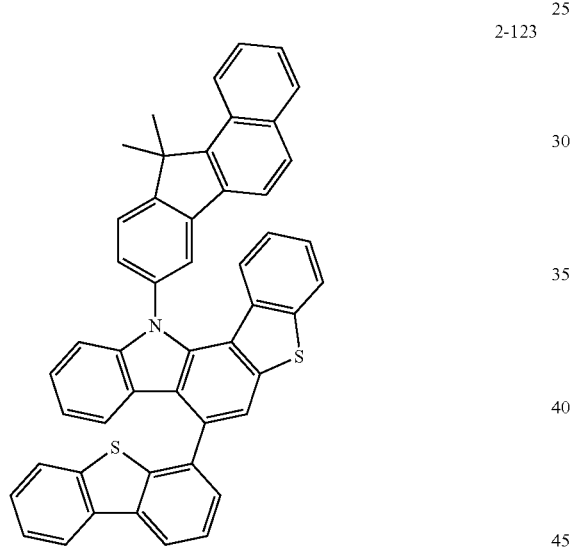
2-126
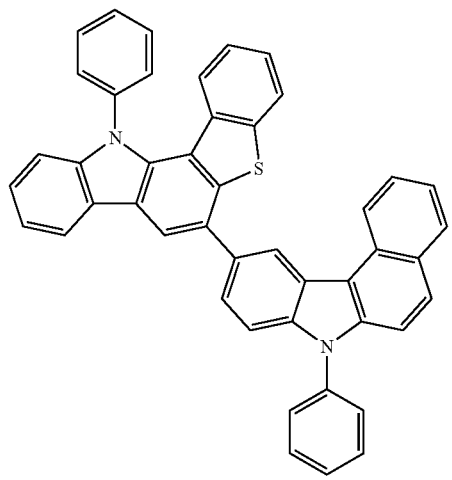
2-124
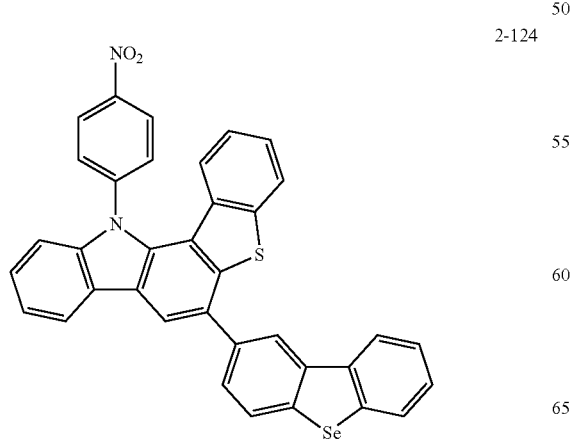
2-127
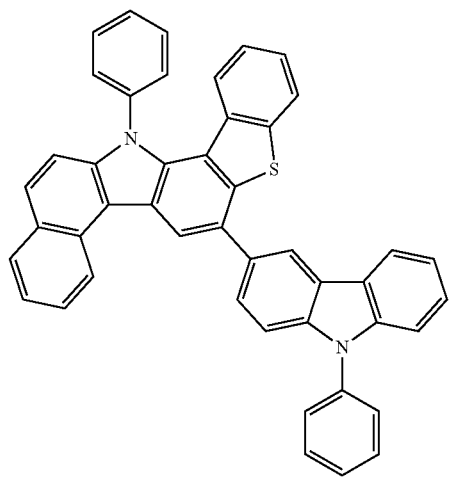

2-128
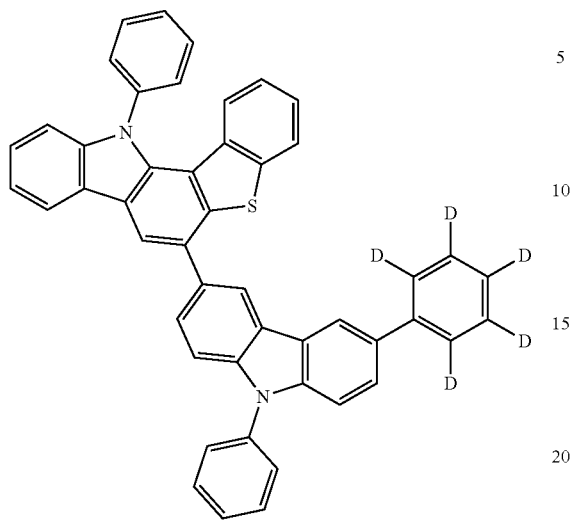
2-131
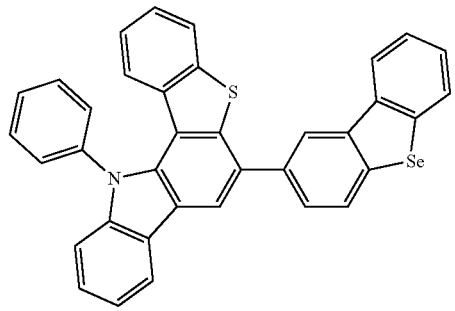
2-129
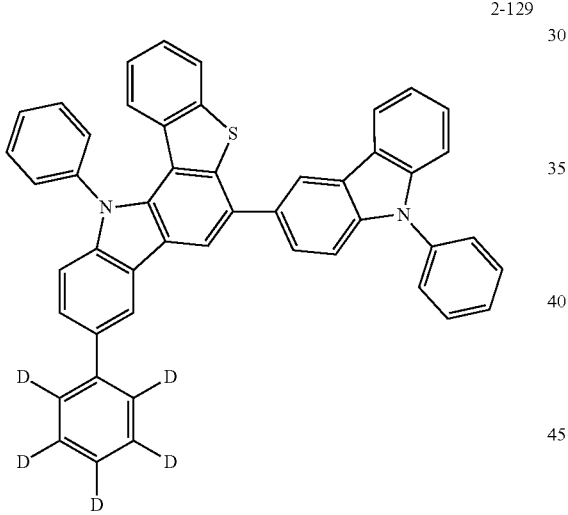
2-132
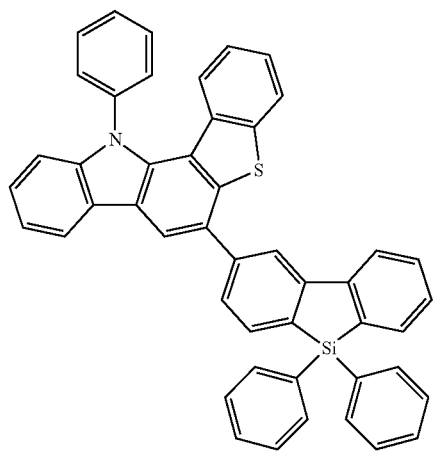
2-130
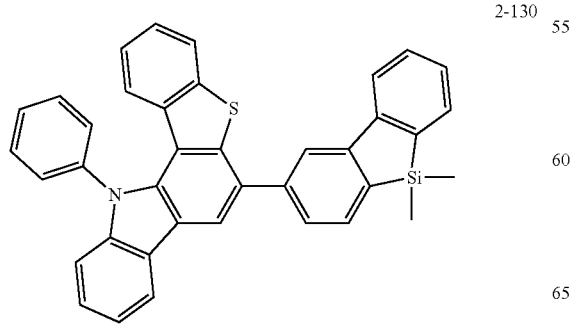
2-133
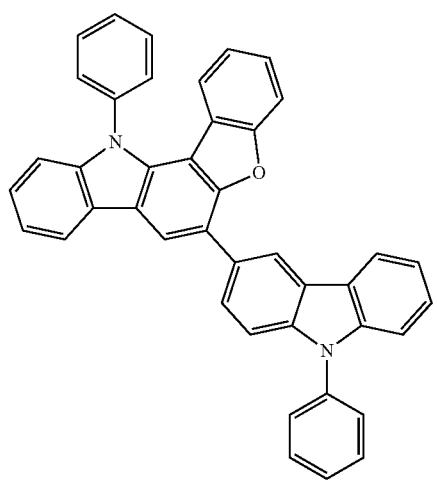

2-134
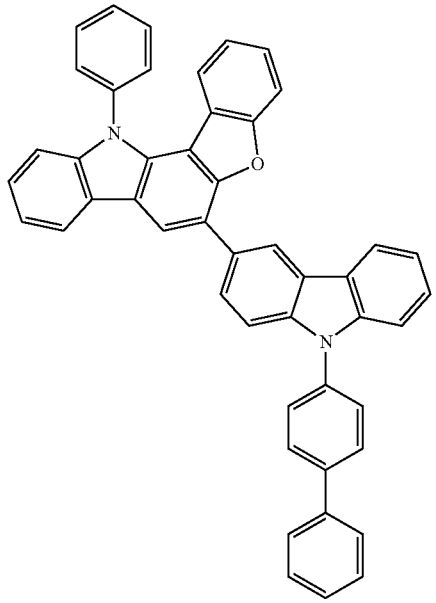
2-135
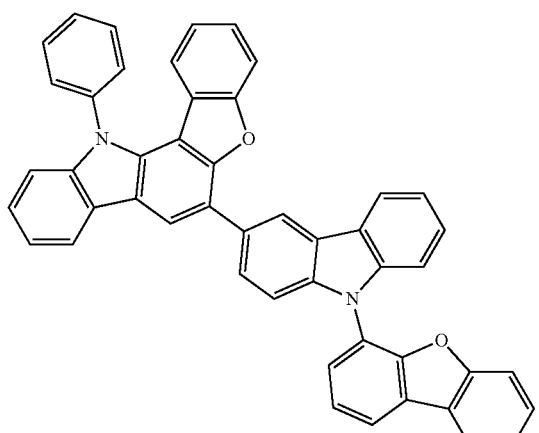
2-136
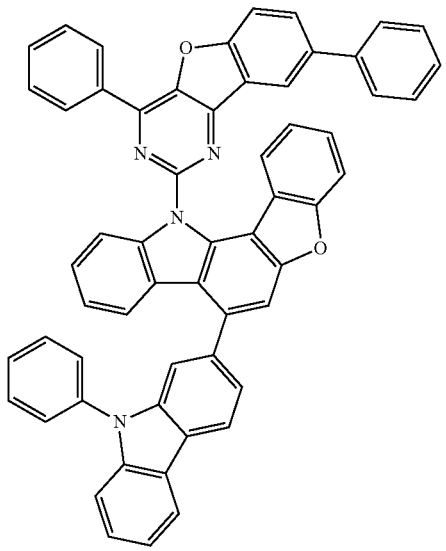
2-137
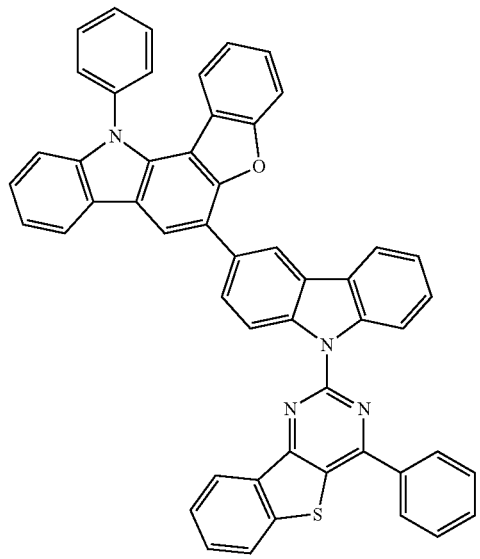
2-138
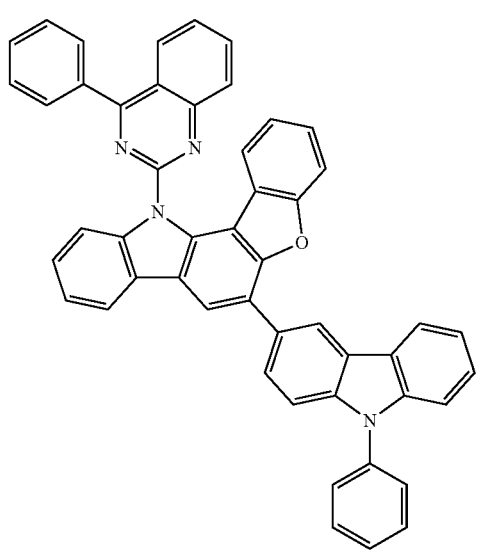
2-139
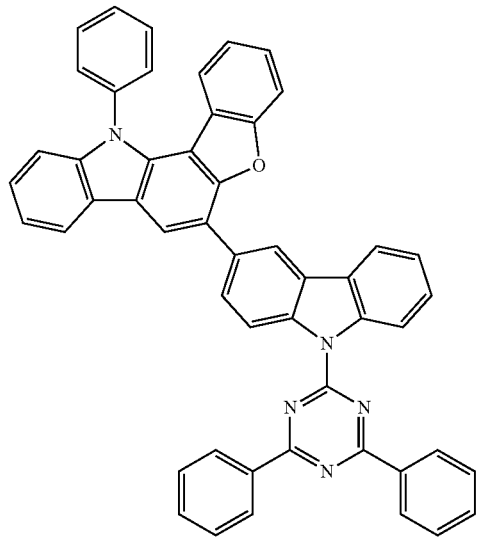

2-140
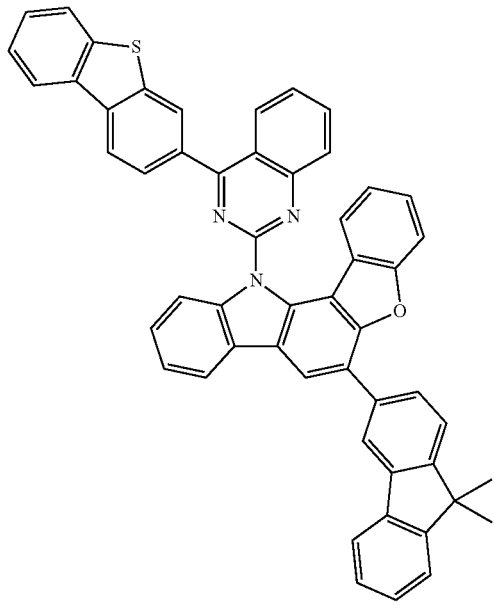
2-141
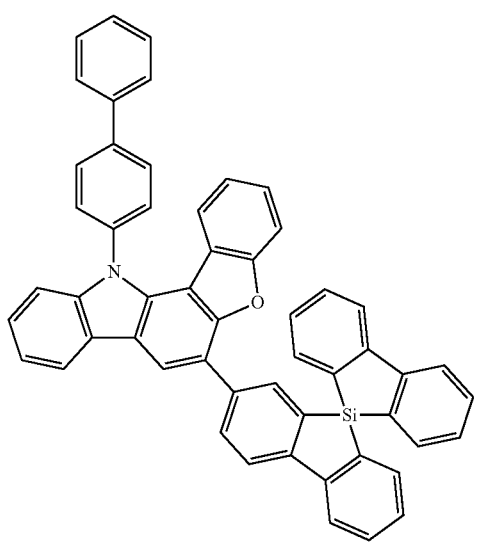
2-142
2-143
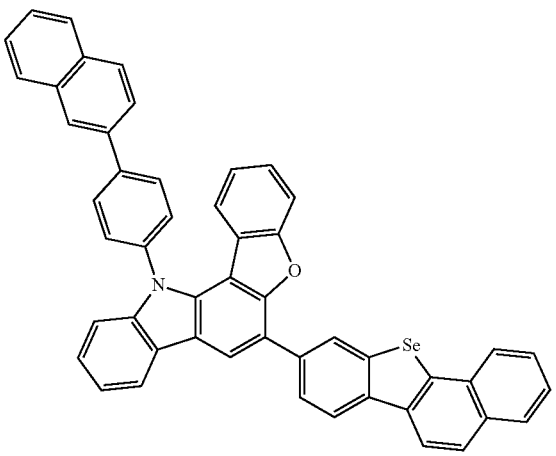
2-144
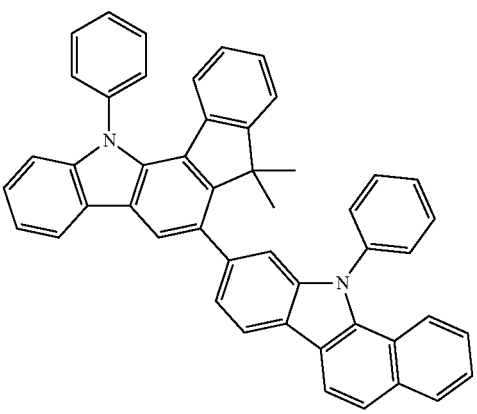
2-145
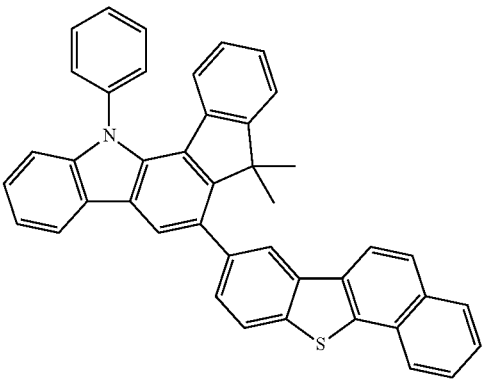
2-146
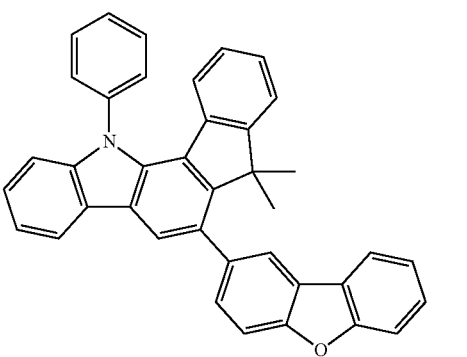

2-147 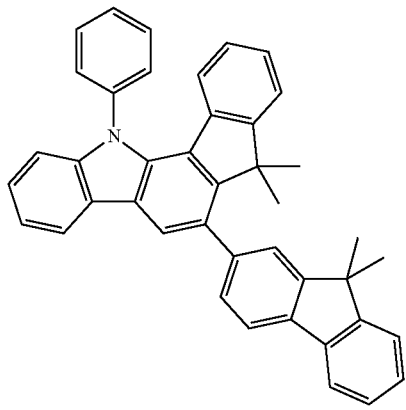

2-148 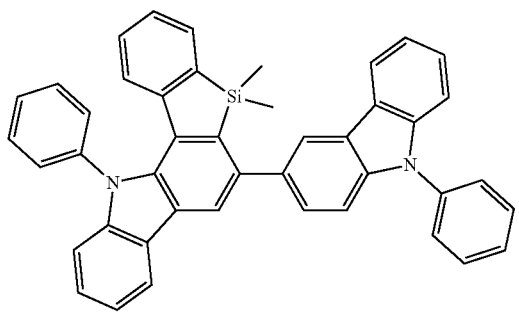

2-149 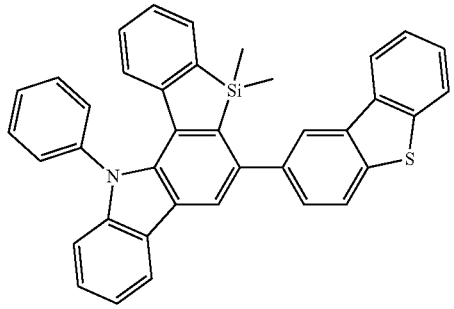

2-150 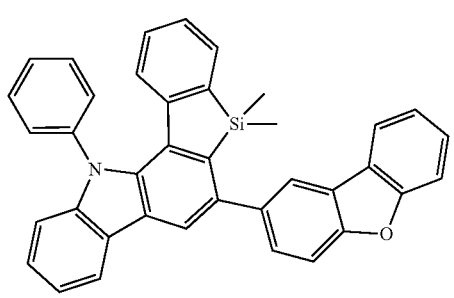

2-151 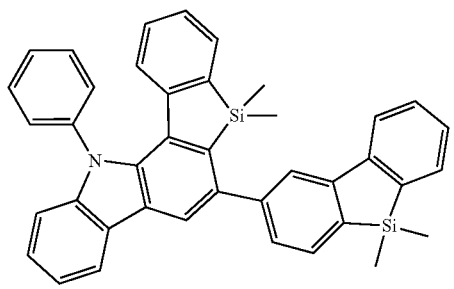

2-152 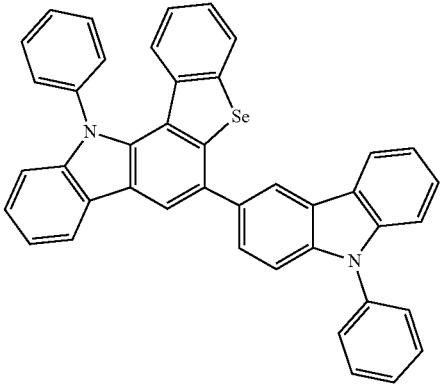

2-153 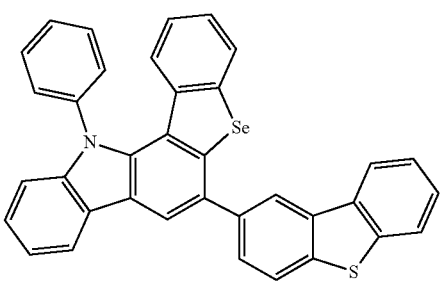

2-154 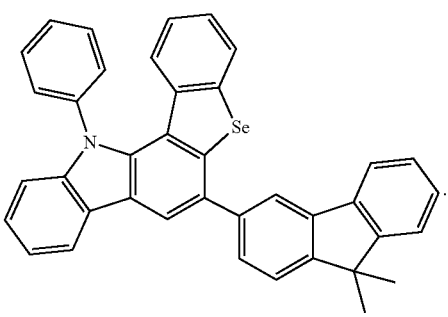

7. An organic electric element comprising a first electrode, a second electrode, and an organic material layer formed between the first electrode and the second electrode, wherein the organic material layer comprises the compound of claim 1.

8. The organic electric element of claim 7, wherein the compound is comprised in at least one layer of a hole injection layer, a hole transport layer, an emission-auxiliary layer, an light emitting layer, an electron transport-auxiliary layer, an electron transport layer and an electron injection layer, and the compound is comprised as a single compound or a mixture of two or more different kinds.

9. The organic electric element of claim 7, wherein the organic electric element further comprises layer(s) to improve luminescence efficiency, formed on at least one of the sides of the first and second electrodes opposite to the organic material layer.

10. The organic electric element of claim 7, wherein the organic material layer is formed by any one of the processes of spin coating, nozzle printing, inkjet printing, slot coating, dip coating or roll-to-roll.

11. An electronic device comprising a display device and a control unit for driving the display device, wherein the display device comprises the organic electric element of claim 7.

12. The electronic device of claim 11, wherein the organic electric element is at least one of an organic light emitting diode, an organic solar cell, an organic photo conductor, an organic transistor, and an element for monochromatic or white illumination.

13. An organic electric element comprising a first electrode, a second electrode, and an organic material layer formed between the first electrode and the second electrode, wherein the organic material layer comprises the compound of claim 6.

14. An electronic device comprising a display device and a control unit for driving the display device, wherein the display device comprises the organic electric element of claim 13.

* * * * *